(12) United States Patent
Stoessel et al.

(10) Patent No.: US 10,158,083 B2
(45) Date of Patent: Dec. 18, 2018

(54) MATERIALS FOR ELECTRONIC DEVICES

(71) Applicant: Merck Patent GmbH, Darmstadt (DE)

(72) Inventors: Philipp Stoessel, Frankfurt am Main (DE); Irina Martynova, Griesheim (DE); Elvira Montenegro, Weinheim (DE); Teresa Mujica-Fernaud, Darmstadt (DE); Frank Voges, Bad Duerkheim (DE); Jonas V. Kroeber, Frankfurt am Main (DE); Frank Stieber, Einhausen (DE)

(73) Assignee: Merck Patent GmbH (DE)

( * ) Notice: Subject to any disclaimer, the term of this patent is extended or adjusted under 35 U.S.C. 154(b) by 0 days.

(21) Appl. No.: 15/103,075

(22) PCT Filed: Nov. 18, 2014

(86) PCT No.: PCT/EP2014/003072
§ 371 (c)(1),
(2) Date: Jun. 9, 2016

(87) PCT Pub. No.: WO2015/086108
PCT Pub. Date: Jun. 18, 2015

(65) Prior Publication Data
US 2016/0308129 A1 Oct. 20, 2016

(30) Foreign Application Priority Data
Dec. 12, 2013 (EP) ..................... 13005800

(51) Int. Cl.
| | | |
|---|---|---|
| *C07C 211/61* | (2006.01) | |
| *C09K 11/06* | (2006.01) | |
| *H01L 51/50* | (2006.01) | |
| *H01L 51/00* | (2006.01) | |
| *C07C 209/60* | (2006.01) | |
| *C07D 209/80* | (2006.01) | |
| *C07D 209/86* | (2006.01) | |
| *C07D 219/02* | (2006.01) | |
| *C07D 307/91* | (2006.01) | |
| *C07D 333/76* | (2006.01) | |
| *C09K 11/02* | (2006.01) | |

(52) U.S. Cl.
CPC .......... *H01L 51/006* (2013.01); *C07C 209/60* (2013.01); *C07C 211/61* (2013.01); *C07D 209/80* (2013.01); *C07D 209/86* (2013.01); *C07D 219/02* (2013.01); *C07D 307/91* (2013.01); *C07D 333/76* (2013.01); *C09K 11/02* (2013.01); *C09K 11/06* (2013.01); *H01L 51/0056* (2013.01); *H01L 51/0059* (2013.01); *H01L 51/0061* (2013.01); *H01L 51/0072* (2013.01); *H01L 51/0073* (2013.01); *H01L 51/0074* (2013.01); *C07C 2603/97* (2017.05); *C09K 2211/1007* (2013.01); *C09K 2211/1011* (2013.01); *C09K 2211/1014* (2013.01); *C09K 2211/1029* (2013.01); *C09K 2211/1088* (2013.01); *C09K 2211/1092* (2013.01); *H01L 51/0058* (2013.01); *H01L 51/506* (2013.01); *H01L 51/5016* (2013.01); *H01L 51/5056* (2013.01); *H01L 51/5064* (2013.01); *H01L 51/5088* (2013.01); *Y02E 10/549* (2013.01)

(58) Field of Classification Search
None
See application file for complete search history.

(56) References Cited

U.S. PATENT DOCUMENTS

| | | | |
|---|---|---|---|
| 2004/0023060 A1 | 2/2004 | Kim et al. | |
| 2006/0127592 A1* | 6/2006 | Spreitzer ............... | C09K 11/06 427/469 |
| 2012/0126179 A1 | 5/2012 | Parham et al. | |

FOREIGN PATENT DOCUMENTS

| | | | |
|---|---|---|---|
| CN | 1338499 A | * | 3/2002 |
| JP | 2012-532902 A | | 12/2012 |
| WO | WO-2010/050779 A1 | | 5/2010 |
| WO | WO-2011136484 A1 | | 11/2011 |
| WO | WO-2013120577 A1 | | 8/2013 |

OTHER PUBLICATIONS

Machine Translation of CN1338499A. Mar. 6, 2002. (Year: 2002).*
International Search Report for PCT/EP2014/003072 dated Mar. 23, 2015.

* cited by examiner

*Primary Examiner* — Stephen E Rieth
(74) *Attorney, Agent, or Firm* — Drinker Biddle & Reath LLP

(57) ABSTRACT

The present invention relates to compounds of the formula (1), which are suitable for use in electronic devices, in particular in organic electroluminescent devices.

13 Claims, No Drawings

MATERIALS FOR ELECTRONIC DEVICES

CROSS-REFERENCE TO RELATED APPLICATIONS

This application is a national stage application (under 35 U.S.C. § 371) of PCT/EP2014/003072, filed Nov. 18, 2014, which claims benefit of European Application No. 13005800.1, filed Dec. 12, 2013, both of which are incorporated herein by reference in their entirety.

The present invention relates to materials for use in electronic devices, in particular in organic electroluminescent devices, and to electronic devices comprising these materials.

The development of functional compounds for use in electronic devices is currently the subject of intensive research. The aim here is, in particular, the development of compounds with which improved properties of the electronic devices in one or more relevant points can be achieved, such as, for example, power efficiency, lifetime or colour coordinates of the emitted light.

In accordance with the present invention, the term electronic device is taken to mean, inter alia, organic integrated circuits (OICs), organic field-effect transistors (OFETs), organic thin-film transistors (OTFTs), organic light-emitting transistors (OLETs), organic solar cells (OSCs), organic optical detectors, organic photoreceptors, organic field-quench devices (OFQDs), organic light-emitting electrochemical cells (OLECs), organic laser diodes (O-lasers) and organic electroluminescent devices (OLEDs).

Of particular interest is the provision of compounds for use in the last-mentioned electronic devices, called OLEDs. The general structure and the functional principle of OLEDs in which organic semiconductors are employed as functional materials are known to the person skilled in the art and is described, inter alia, in U.S. Pat. No. 4,539,507, U.S. Pat. No. 5,151,629, EP 0676461 and WO 1998/27136. The emitting materials employed here are increasingly organometallic complexes which exhibit phosphorescence instead of fluorescence (M. A. Baldo et al., Appl. Phys. Lett. 1999, 75, 4-6).

In accordance with the prior art, the hole-transport materials used in the hole-transport layer or in the hole-injection layer are, in particular, triarylamine derivatives which contain either at least two triarylamino groups or at least one triarylamino group and at least one carbazole group. These compounds are frequently derived from diarylamino-substituted triphenylamines (TPA type), from diarylamino-substituted biphenyl derivatives (TAD type) or combinations of these basic compounds. Furthermore, use is made, for example, of spirobifluorene derivatives which are substituted by two or four diarylamino groups (for example in accordance with EP 676461 or U.S. Pat. No. 7,714,145). In the case of these compounds, there continues to be a need for improvement both in the case of fluorescent and in the case of phosphorescent OLEDs, in particular with respect to efficiency, lifetime and operating voltage on use in an organic electroluminescent device and with respect to the thermal stability on sublimation.

The object of the present invention is the provision of compounds which are suitable for use in a fluorescent or phosphorescent OLED, in particular a phosphorescent OLED, for example as hole-transport material in a hole-transport or exciton-blocking layer or as matrix material in an emitting layer.

Surprisingly, it has been found that certain compounds described in greater detail below achieve this object and result in significant improvements in the organic electroluminescent device, in particular with respect to the lifetime, the efficiency and the operating voltage. This applies to phosphorescent and fluorescent electroluminescent devices, especially on use of the compounds according to the invention as hole-transport material or as matrix material. The materials generally have high thermal stability and can therefore be sublimed without decomposition and in a residue-free manner. The present invention therefore relates to these materials and to electronic devices which contain compounds of this type.

The specification WO 02/088274 A1 shows the synthesis of dispiro[fluoren-9,9'-anthracene-10',9''-fluorene]derivatives which are substituted, in particular, on the anthracene unit.

For clarity, the numbering of the dispiro[fluoren-9,9'-anthracene-10',9''-fluorene]skeleton is depicted below:

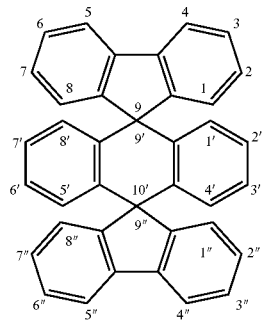

The present invention therefore relates to a compound of the formula (1), formula (1)

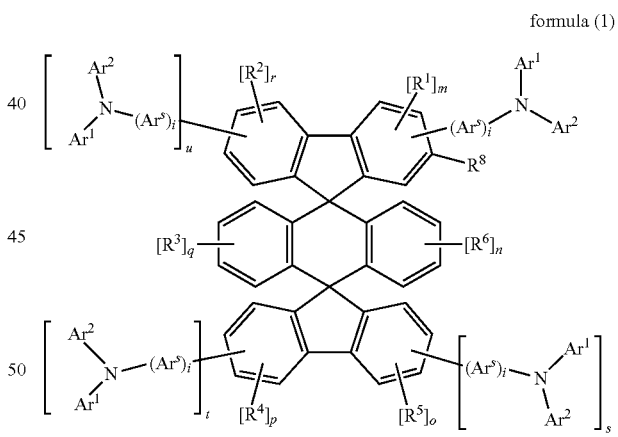

where the following applies to the symbols and indices occurring:

$Ar^S$ is, identically or differently on each occurrence, an aromatic or heteroaromatic ring system having 6 to 60 C atoms, which may in each case also be substituted by one or more radicals $R^7$; $Ar^S$ here may be connected to $Ar^1$ and/or to $Ar^2$ by a group E;

$Ar^1$, $Ar^2$ are, identically or differently on each occurrence, an aromatic or heteroaromatic ring system having 6 to 60 aromatic ring atoms, which may in each case also be substituted by one or more radicals $R^7$; $Ar^1$ and $Ar^2$ here may be connected to one another and/or $Ar^1$ may be connected to $Ar^S$ and/or $Ar^2$ may be connected to $Ar^S$ by a group E;

E is selected, identically or differently on each occurrence, from the group consisting of $C(R^7)_2$, O, S and $NR^7$;

$R^1$, $R^2$, $R^3$, $R^4$, $R^5$, $R^6$ are selected on each occurrence, identically or differently, from the group consisting of H, D, F, Cl, Br, I, CN, $Si(R^9)_3$, a straight-chain alkyl, alkoxy or thioalkyl group having 1 to 40 C atoms or a branched or cyclic alkyl, alkoxy or thioalkyl group having 3 to 40 C atoms, each of which may be substituted by one or more radicals $R^9$, where in each case one or more non-adjacent $CH_2$ groups may be replaced by $Si(R^9)_2$, $C=NR^9$, $P(=O)(R^9)$, SO, $SO_2$, $NR^9$, O, S or $CONR^9$ and where one or more H atoms may be replaced by D, F, Cl, Br or I, an aromatic or heteroaromatic ring system having 6 to 60 aromatic ring atoms, which may in each case be substituted by one or more radicals $R^9$, an aryloxy group or heteroaryloxy group having 5 to 60 aromatic ring atoms, which may be substituted by one or more radicals $R^9$, or an aralkyl group or heteroaralkyl group having 5 to 60 aromatic ring atoms, which may in each case be substituted by one or more radicals $R^9$, where two or more adjacent substituents $R^1$ or two or more adjacent substituents $R^2$ or two or more adjacent substituents $R^3$ or two or more adjacent substituents $R^4$ or two or more adjacent substituents $R^5$ or two or more adjacent substituents $R^6$ may optionally form a mono- or polycyclic, aliphatic or aromatic ring system, which may be substituted by one or more radicals $R^9$;

$R^7$ is selected on each occurrence, identically or differently, from the group consisting of H, D, F, Cl, Br, I, CN, $Si(R^9)_3$, $N(R^9)_2$, a straight-chain alkyl, alkoxy or thioalkyl group having 1 to 40 C atoms or a branched or cyclic alkyl, alkoxy or thioalkyl group having 3 to 40 C atoms, each of which may be substituted by one or more radicals $R^9$, where in each case one or more non-adjacent $CH_2$ groups may be replaced by $Si(R^9)_2$, $C=NR^9$, $P(=O)(R^9)$, SO, $SO_2$, $NR^9$, O, S or $CONR^9$ and where one or more H atoms may be replaced by D, F, Cl, Br or I, an aromatic or heteroaromatic ring system having 6 to 60 aromatic ring atoms, which may in each case be substituted by one or more radicals $R^9$, an aryloxy group or heteroaryloxy group having 5 to 60 aromatic ring atoms, which may be substituted by one or more radicals $R^9$, or an aralkyl group or heteroaralkyl group having 5 to 60 aromatic ring atoms, which may in each case be substituted by one or more radicals $R^9$, where two or more adjacent substituents $R^7$ may optionally form a mono- or polycyclic, aliphatic or aromatic ring system, which may be substituted by one or more radicals $R^9$;

$R^8$ is selected from the group consisting of H, D, F, Cl, Br, I, CN, $Si(R^9)_3$, a straight-chain alkyl, alkoxy or thioalkyl group having 1 to 40 C atoms or a branched or cyclic alkyl, alkoxy or thioalkyl group having 3 to 40 C atoms, each of which may be substituted by one or more radicals $R^9$, where in each case one or more non-adjacent $CH_2$ groups may be replaced by $Si(R^9)_2$, $C=NR^9$, $P(=O)(R^9)$, SO, $SO_2$, $NR^9$, O, S or $CONR^9$ and where one or more H atoms may be replaced by D, F, Cl, Br or I, an aromatic or heteroaromatic ring system having 6 to 60 aromatic ring atoms, which may in each case be substituted by one or more radicals $R^9$, an aryloxy group or heteroaryloxy group having 5 to 60 aromatic ring atoms, which may be substituted by one or more radicals $R^9$, or an aralkyl group or heteroaralkyl group having 5 to 60 aromatic ring atoms, which may in each case be substituted by one or more radicals $R^9$, where a substituent $R^8$ and an adjacent substituent $R^1$ may optionally form a mono- or polycyclic, aliphatic or aromatic ring system, which may be substituted by one or more radicals $R^9$;

$R^9$ is selected on each occurrence, identically or differently, from the group consisting of H, D, F, Cl, Br, I, $Si(R^{10})_3$, a straight-chain alkyl, alkoxy or thioalkyl group having 1 to 40 C atoms or a branched or cyclic alkyl, alkoxy or thioalkyl group having 3 to 40 C atoms, each of which may be substituted by one or more radicals $R^{10}$, where one or more non-adjacent $CH_2$ groups may be replaced by $Si(R^{10})_2$, $C=NR^{10}$, $P(=O)(R^{10})$, SO, $SO_2$, $NR^{10}$, O, S or $CONR^{10}$ and where one or more H atoms may be replaced by D, F, Cl, Br or I, an aromatic or heteroaromatic ring system having 6 to 60 aromatic ring atoms, which may in each case be substituted by one or more radicals $R^{10}$, an aryloxy group or heteroaryloxy group having 5 to 60 aromatic ring atoms, which may be substituted by one or more radicals $R^{10}$, or an aralkyl group or heteroaralkyl group having 5 to 60 aromatic or heteroaromatic ring atoms, which may be substituted by one or more radicals $R^{10}$, where two or more adjacent substituents $R^9$ may optionally form a mono- or polycyclic, aliphatic ring system, which may be substituted by one or more radicals $R^{10}$;

$R^{10}$ is selected from the group consisting of H, D, F, an aliphatic hydrocarbon radical having 1 to 20 C atoms, an aromatic ring system having 6 to 30 C atoms, in which one or more H atoms may be replaced by D or F, where two or more adjacent substituents $R^{10}$ may form a mono- or polycyclic, aliphatic ring system with one another;

i is on each occurrence 0, 1 or 2;

m is 0, 1 or 2;

n, o, p, q, r are on each occurrence, identically or differently, 0, 1, 2, 3 or 4;

s, t, u are on each occurrence, identically or differently, 0, 1 or 2;

where $s+o \leq 4$, $p+t \leq 4$ and $r+u \leq 4$;

and furthermore $u+t+s \leq 2$.

An aryl group in the sense of this invention contains 6 to 60 aromatic ring atoms; a heteroaryl group in the sense of this invention contains in principle 5 to 60 aromatic ring atoms, at least one of which is a heteroatom. The heteroatoms are preferably selected from N, O and/or S. This represents the basic definition. If other preferences are indicated in the description of the present invention, such as, for example, with respect to the number of aromatic ring atoms or the heteroatoms present, these apply.

An aryl group here is taken to mean either a simple aromatic ring, i.e. benzene, or a condensed (annellated) aromatic or heteroaromatic polycycle, for example naphthalene, anthracene, phenanthrene, quinoline, isoquinoline or carbazole. A condensed (annellated) aromatic polycycle in the sense of the present application consists of two or more simple aromatic rings condensed with one another. Aromatic rings which are linked to one another by a single bond, such as, for example, biphenyl or fluorene, are, by contrast, not referred to as an aryl or heteroaryl group, but instead as an aromatic ring system.

A heteroaryl group in the sense of this invention contains at least one heteroatom in the aromatic ring or polycycle, preferably a heteroatom selected from N, O or S. A heteroaryl group is, for example, a simple heteroaromatic ring, for example pyridine, pyrimidine, thiophene, etc., or a condensed (annelated) heteroaromatic polycycle, for example carbazole or quinoline.

An aryloxy group in accordance with the definition of the present invention is taken to mean an aryl group, as defined above, which is bonded via an oxygen atom. An analogous definition applies to heteroaryloxy groups.

An aromatic ring system in the sense of this invention contains 6 to 60 aromatic ring atoms in the ring system. A heteroaromatic ring system in the sense of this invention contains 5 to 60 aromatic ring atoms, at least one of which is a heteroatom. The heteroatoms are preferably selected from N, O and/or S. An aromatic or heteroaromatic ring system in the sense of this invention is intended to be taken to mean a system which does not necessarily contain only aryl or heteroaryl groups, but instead in which, in addition, a plurality of aryl or heteroaryl groups may be connected by a non-aromatic unit (preferably less than 10% of the atoms other than H), such as, for example, an $sp^3$-hybridised C, Si or O atom, an $sp^2$-hybridised C atom or an sp-hybridised C atom. Thus, for example, systems such as 9,9'-spirobifluorene, 9,9'-diarylfluorene, diaryl ether, stilbene, etc., are also intended to be taken to be aromatic ring systems in the sense of this invention, as are systems in which two or more aryl groups are connected, for example, by a linear or cyclic alkyl, alkenyl or alkynyl group or by a silyl group. Furthermore, systems in which two or more aryl or heteroaryl groups are linked to one another via single bonds are also taken to be aromatic or heteroaromatic ring systems in the sense of this invention, such as, for example, systems such as biphenyl, terphenyl or quaterphenyl. The aromatic or heteroaromatic ring system here contains, by definition, no amino groups. Triarylamino groups are thus not covered by the definition of an aromatic or heteroaromatic ring system.

An aromatic or heteroaromatic ring system having 5 to 60 aromatic ring atoms, which may in each case also be substituted by radicals as defined above and which may be linked to the aromatic or heteroaromatic group via any desired positions, is taken to mean, in particular, groups derived from benzene, naphthalene, anthracene, benzanthracene, phenanthrene, benzophenanthrene, pyrene, chrysene, perylene, fluoranthene, naphthacene, pentacene, benzopyrene, biphenyl, biphenylene, terphenyl, terphenylene, quaterphenyl, fluorene, spirobifluorene, dihydrophenanthrene, dihydropyrene, tetrahydropyrene, cis- or trans-indenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, indolocarbazole, indenocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole, or combinations of these groups.

For the purposes of the present invention, a straight-chain alkyl group having 1 to 40 C atoms or a branched or cyclic alkyl group having 3 to 40 C atoms or an alkenyl or alkynyl group having 2 to 40 C atoms, in which, in addition, individual H atoms or $CH_2$ groups may be substituted by the groups mentioned above under the definition of the radicals, is preferably taken to mean the radicals methyl, ethyl, n-propyl, i-propyl, n-butyl, i-butyl, s-butyl, t-butyl, 2-methylbutyl, n-pentyl, s-pentyl, cyclopentyl, neopentyl, n-hexyl, cyclohexyl, neohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl. An alkoxy or thioalkyl group having 1 to 40 C atoms is preferably taken to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy, 2,2,2-trifluoroethoxy, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio.

The formulation that two or more radicals may form a ring with one another is, for the purposes of the present description, intended to be taken to mean, inter alia, that the two radicals are linked to one another by a chemical bond. This is illustrated by the following scheme:

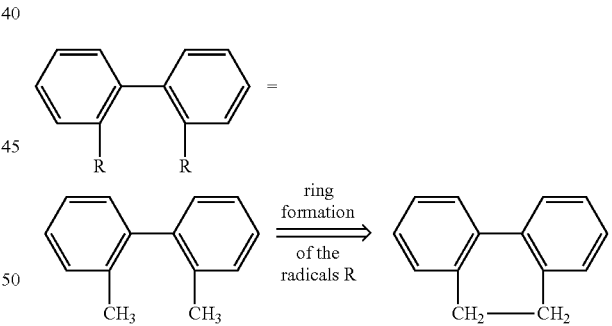

Furthermore, however, the above-mentioned formulation is also intended to be taken to mean that, in the case where one of the two radicals represents hydrogen, the second radical is bonded at the position to which the hydrogen atom was bonded, with formation of a ring. This is illustrated by the following scheme:

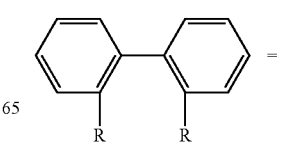

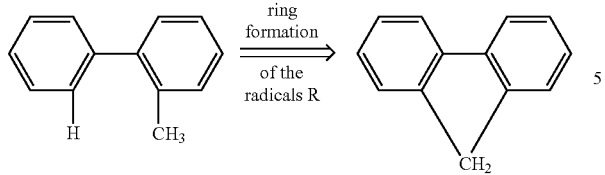

In a preferred embodiment of the invention, s+t+u is equal to 0 or 1. The compound then contains one or two diarylamino groups.

In a further preferred embodiment of the invention, m, n, o, p, q, r are, identically or differently, 0 or 1, preferably m, o, p, r are equal to 0, very particularly preferably m, o, p, r are equal to 0 and n, q are equal to 0 or 1.

In a further preferred embodiment of the invention, all indices i in the formula (1) are identical on each occurrence, i.e. all indices i have, for example, the value 0. If i is equal to 0, the nitrogen atom is bonded directly to the basic structure.

In a further preferred embodiment of the invention, at least one group —$(Ar^5)_i NAr^1 Ar^2$ contains in total at least 18 aromatic ring atoms, particularly preferably at least 18 and less than 50 aromatic ring atoms.

In a preferred embodiment, the compound of the formula (1) is a compound of one of the following formulae (2) to (5):

formula (2)

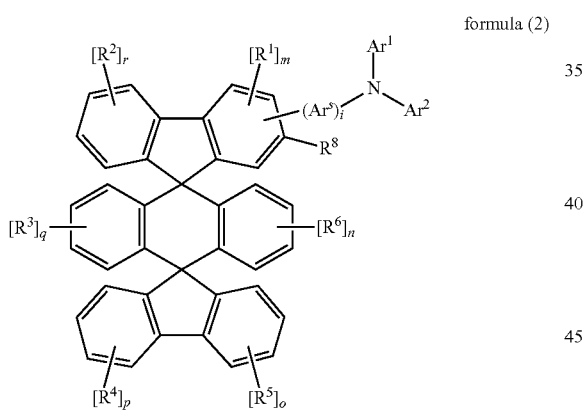

formula (3)

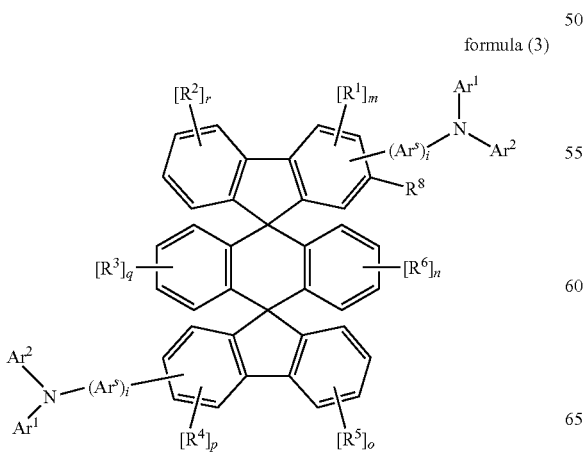

formula (4)

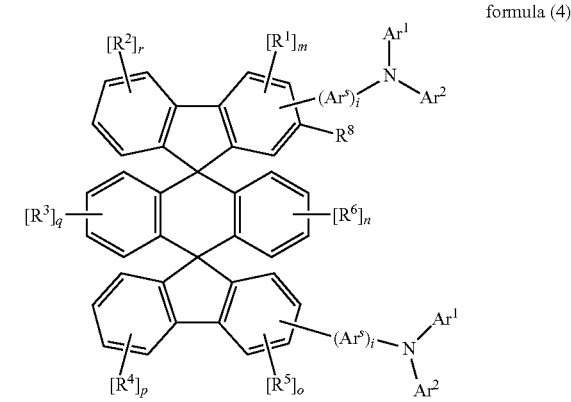

formula (5)

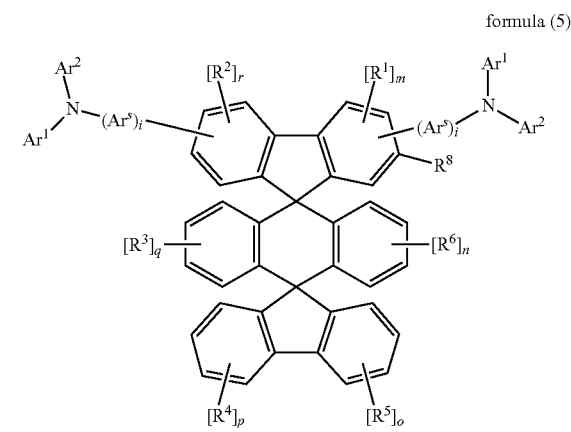

where the symbols and indices have the same meaning as for formula (1).

In a particularly preferred embodiment, the compound of the formula (1) is a compound of one of the following formulae (6) to (28):

formula (6)

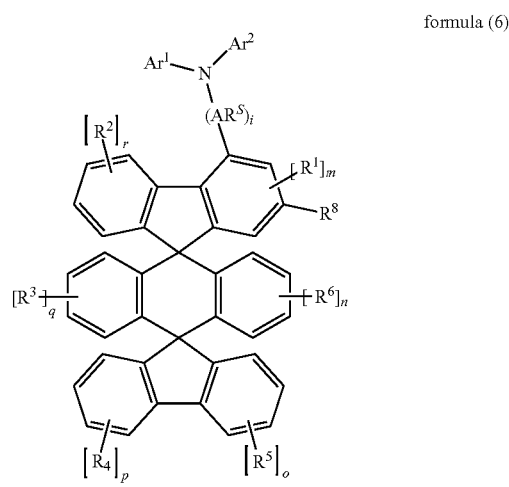

formula (7)
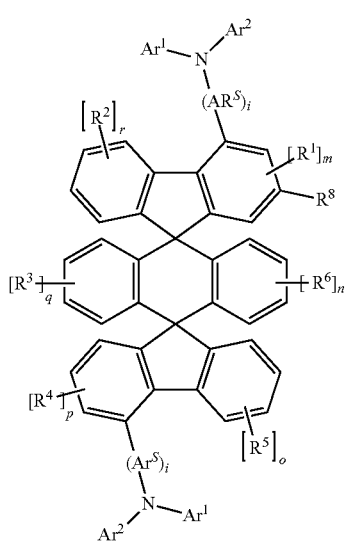
formula (8)
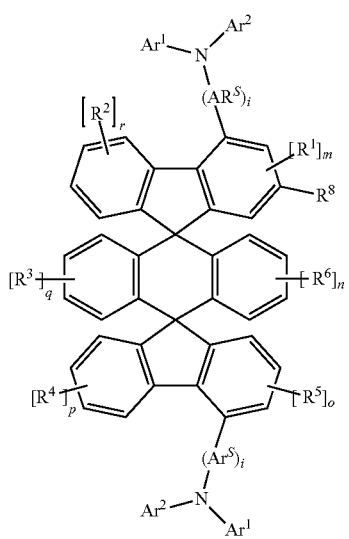
formula (9)
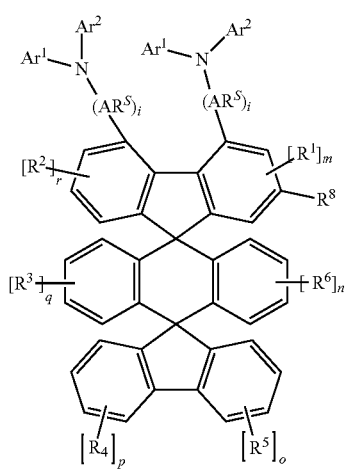
formula (10)
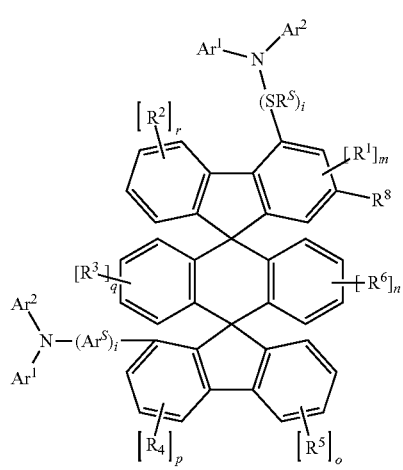
formula (11)
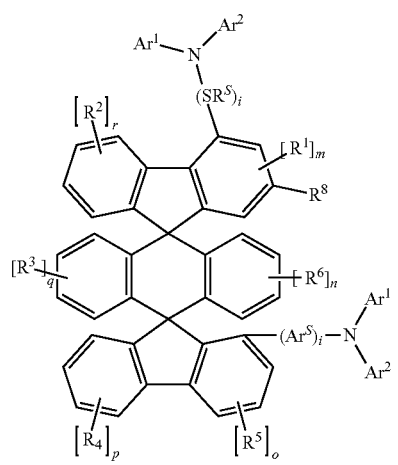
formula (12)
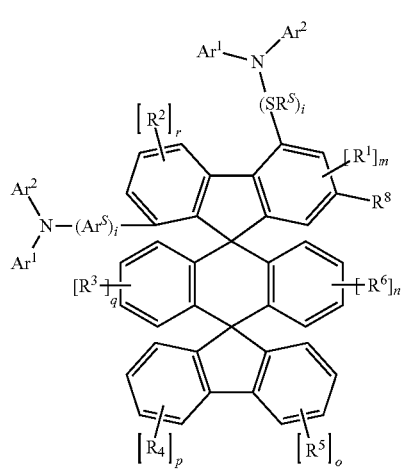

formula (13)
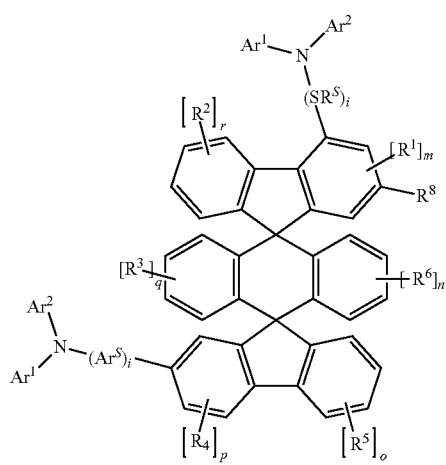
formula (14)
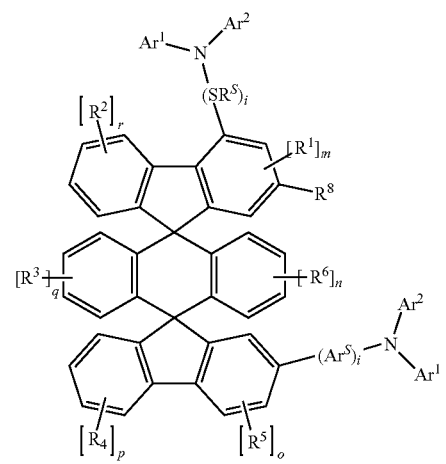
formula (15)
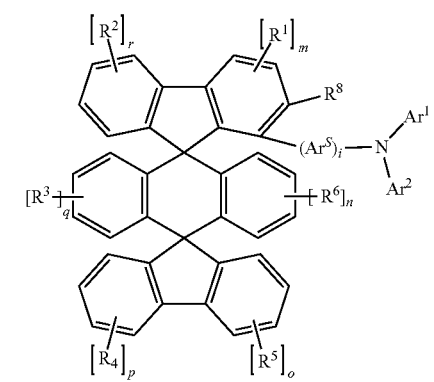
formula (16)
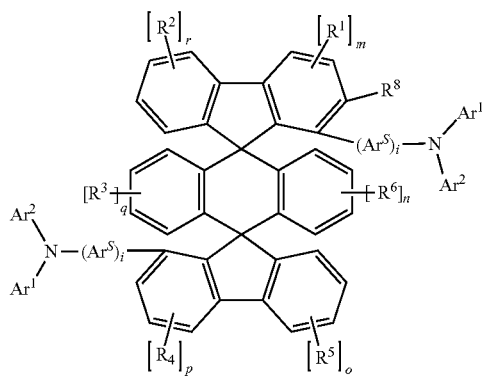
formula (17)
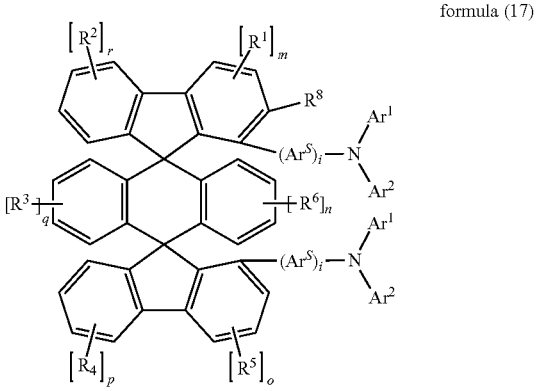
formula (18)
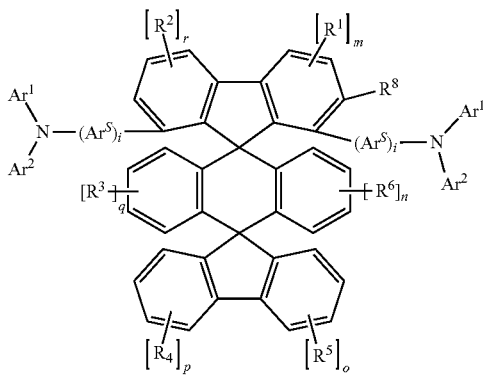
formula (20)
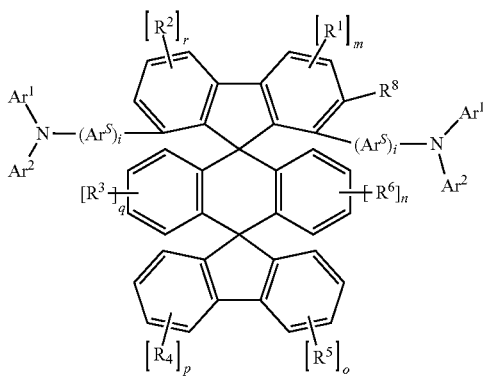

formula (20)
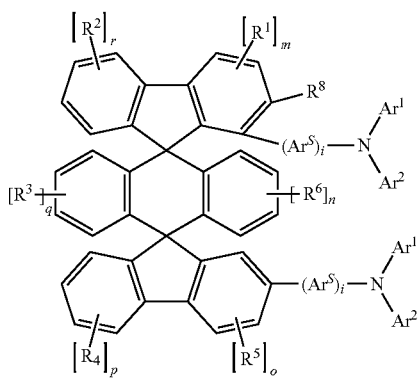
formula (21)
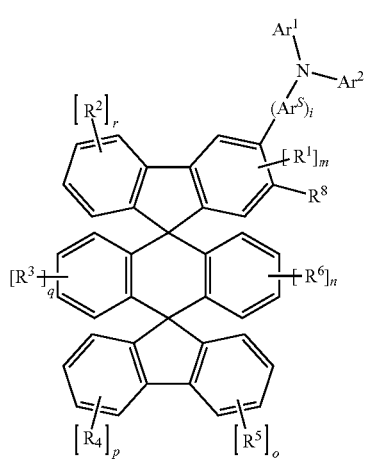
formula (22)
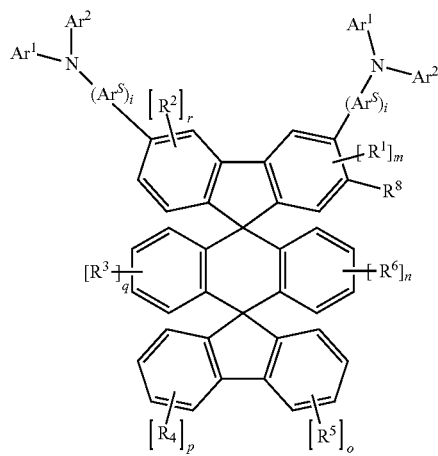
formula (23)
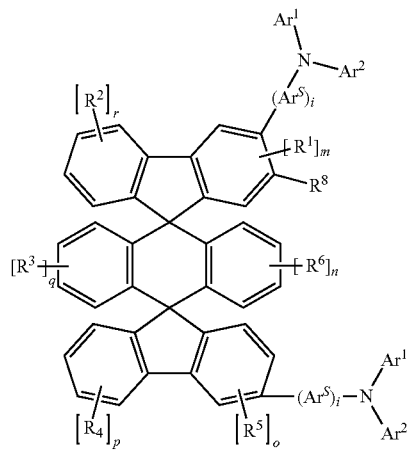
formula (24)
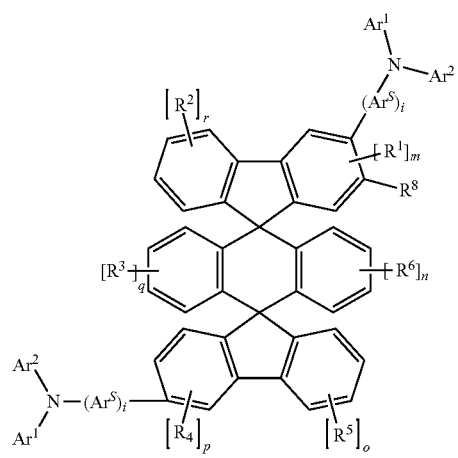
formula (25)
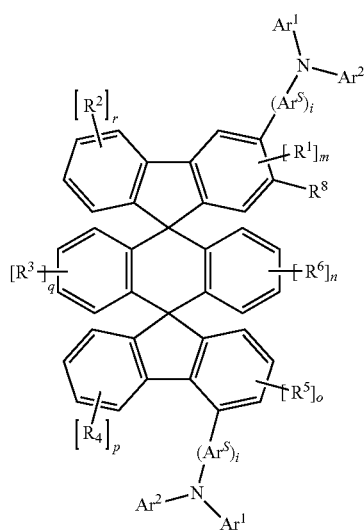

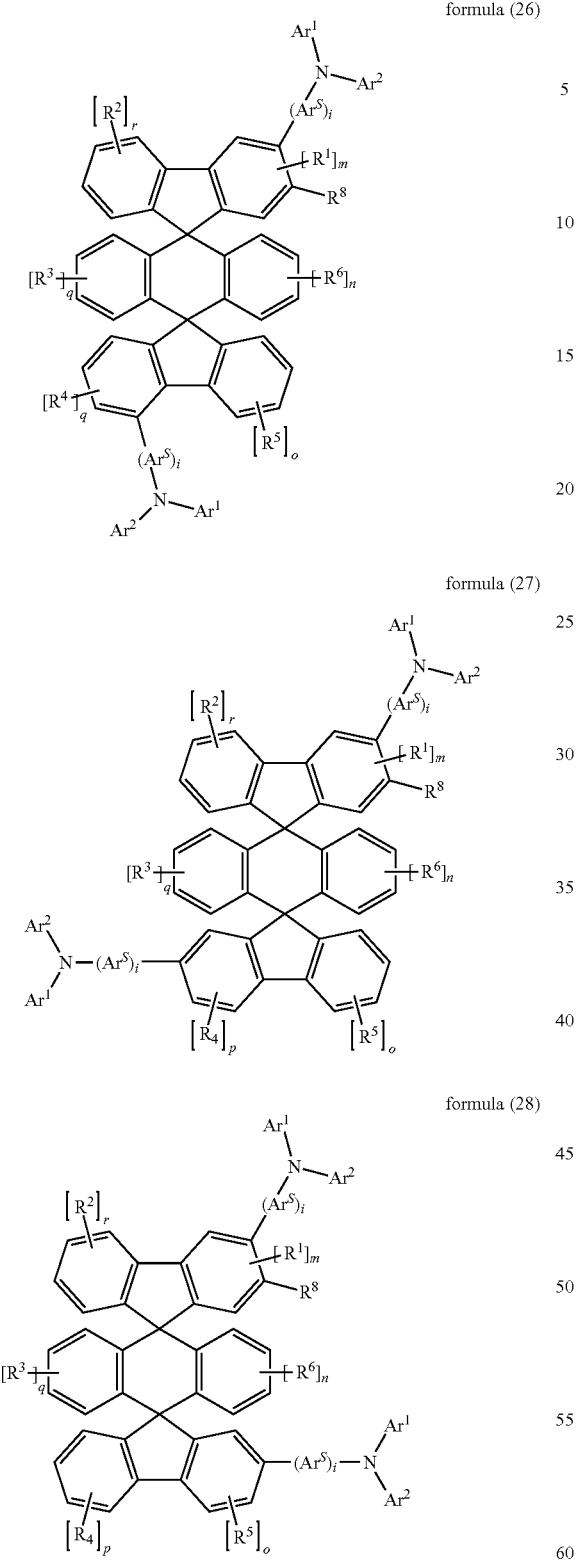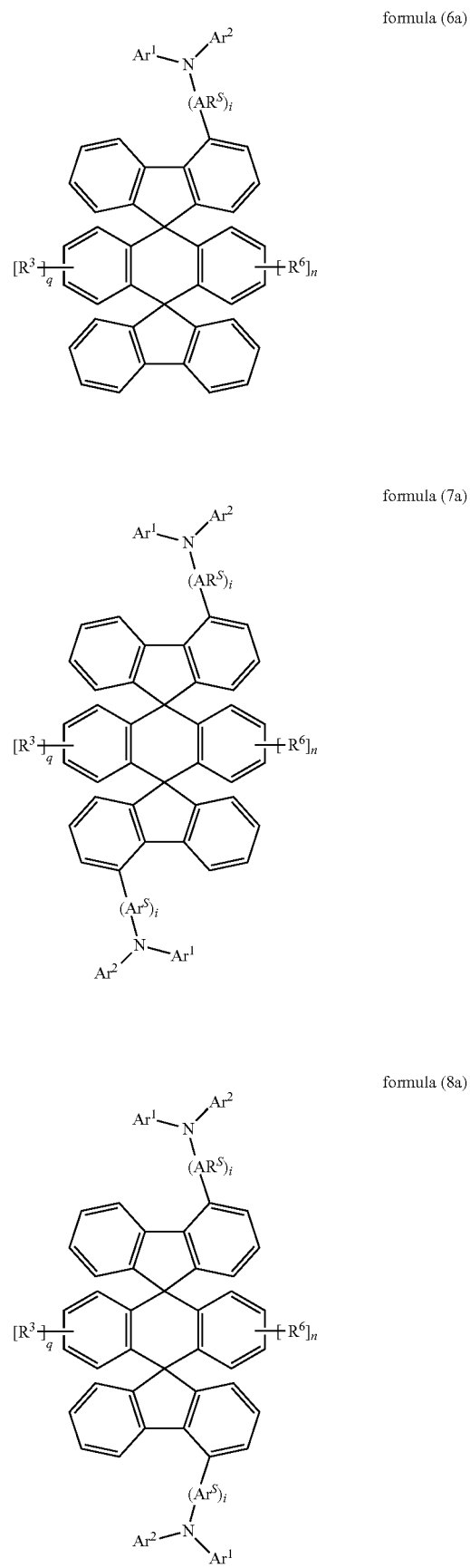
where the symbols and indices have the same meaning as for formula (1).
In a further particularly preferred embodiment, the compound of the formula (1) is a compound of one of the following formulae (6a) to (28a):

formula (9a)
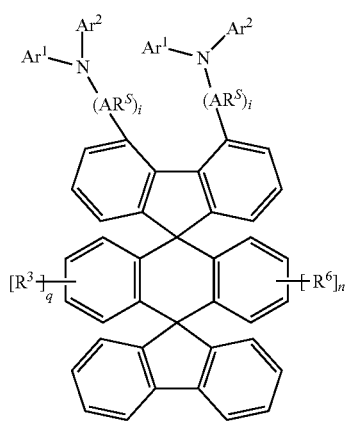
formula (10a)
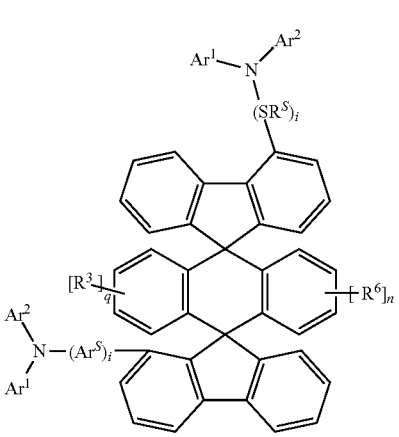
formula (11a)
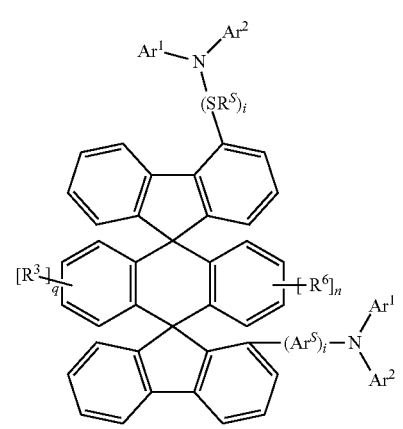
formula (12a)
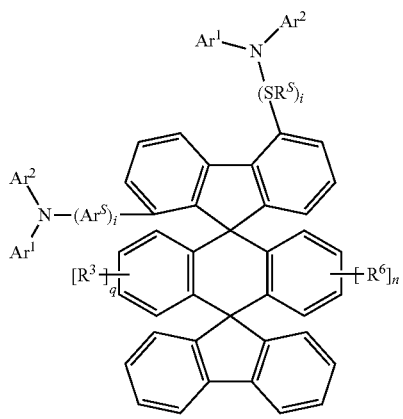
formula (13a)
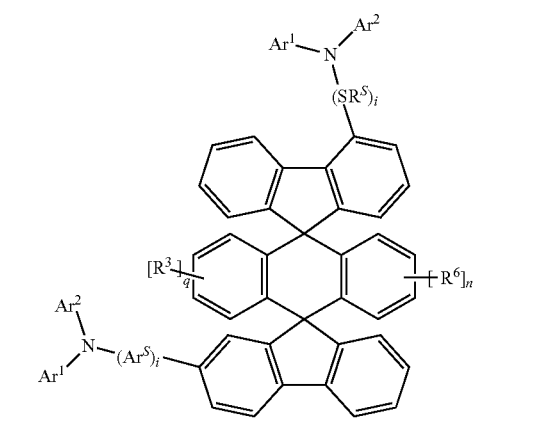
formula (14a)
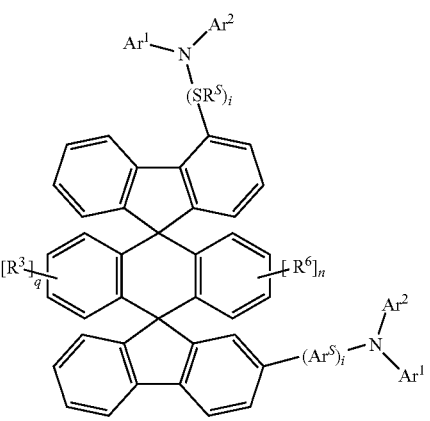
formula (15a)
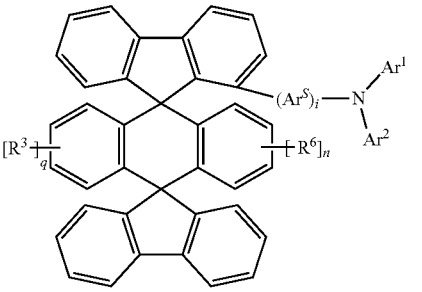

formula (16a)
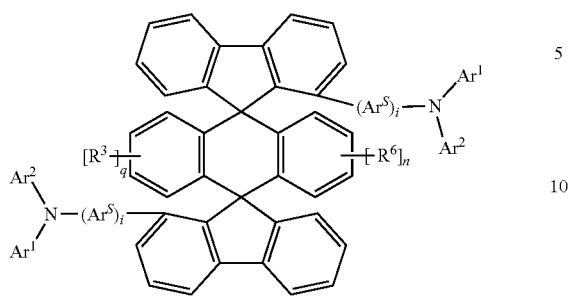
formula (17a)
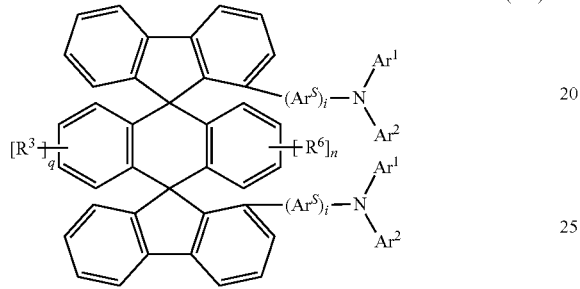
formula (18a)
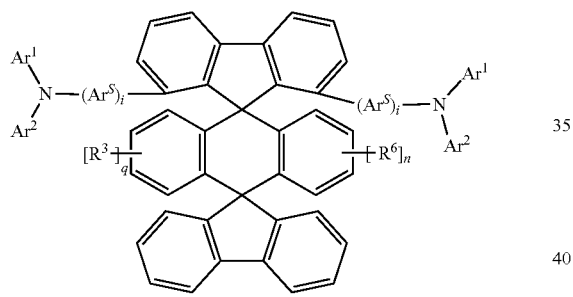
formula (20a)
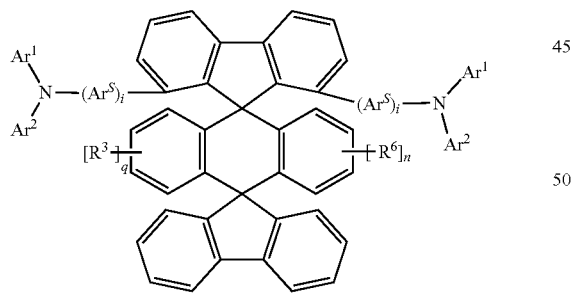
formula (20a)
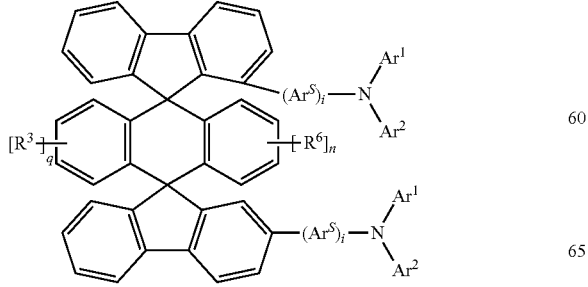
formula (21a)
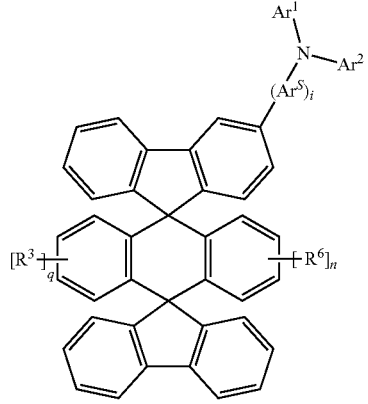
formula (22a)
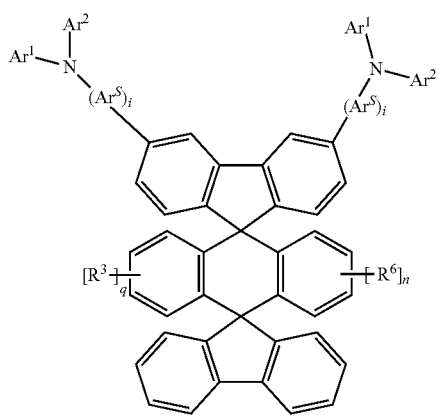
formula (23a)
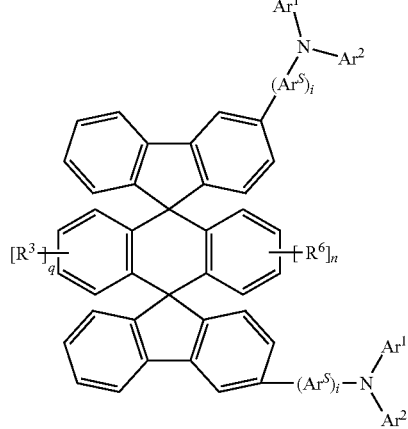

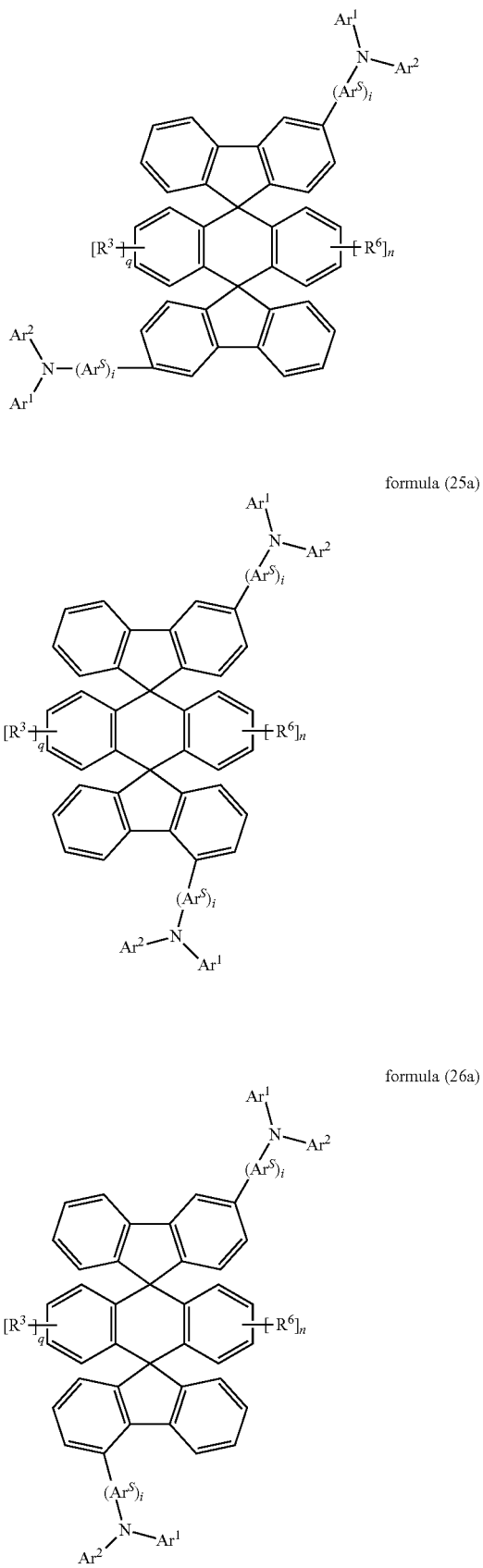

formula (24a)

formula (25a)

formula (26a)

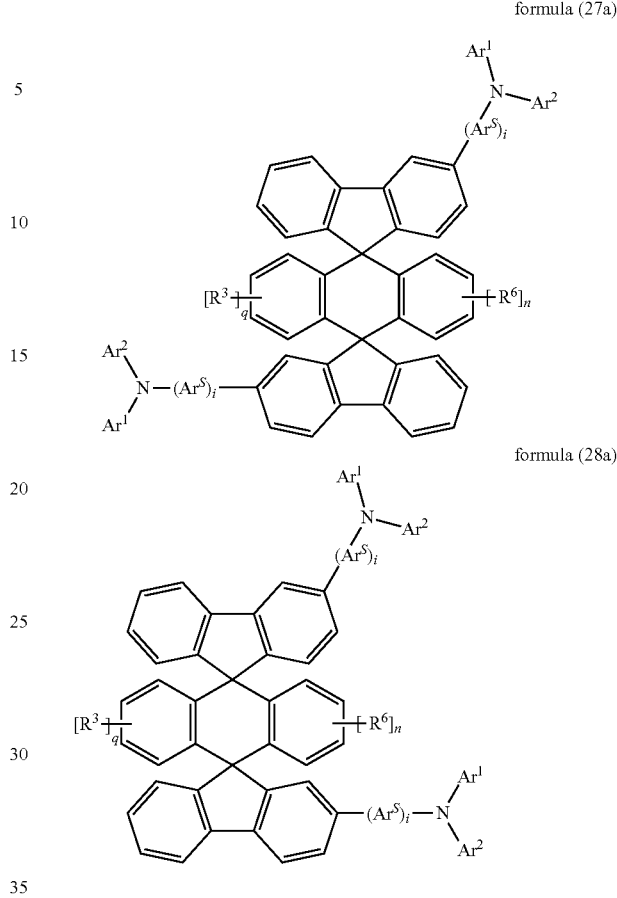

formula (27a)

formula (28a)

where the symbols and indices have the same meaning as for formula (1).

In a preferred embodiment of the invention, a group —NAr¹Ar² or (Ar$^S$)$_i$—NAr¹Ar² is arranged at position 1, 3 or 4 and, if present, at least one further group —NAr¹Ar² or (Ar$^S$)$_i$—NAr¹Ar² is arranged at one of positions 1", 2", 4", 5", 7" or 8". The two groups are particularly preferably arranged at positions 4 and 5, 4 and 4", 4 and 5", 4 and 2", 4 and 7", 3 and 4", 3 and 5", 3 and 2", 3 and 7", 1 and 4", 1 and 5", 1 and 2", 1 and 7'''. Particular preference is given to compounds containing precisely two groups —NAr¹Ar² or (Ar$^S$)$_i$—NAr¹Ar². Preference is therefore given to compounds of the formulae (6), (7), (8), (9), (10), (11), (13), (14), (15), (19), (20), (21), (25), (26), (27) and (28), particularly preferably the compounds of the formulae (6a), (7a), (8a), (9a), (10a), (11a), (13a), (14a), (15a), (19a), (20a), (21a), (25a), (26a), (27a) and (28a).

The compound according to the invention may also be in the form of a mixture of two or more substitution isomers of the formula (1). Substitution isomers are taken to mean compounds which carry the same radicals on the basic structure, but these are arranged at different positions on the basic structure. These are preferably substitution isomers which have a mutually mirror-image substitution pattern on at least one fluorene unit and/or the anthracene unit. This means that, for these compounds, the substituent at position 1' of the one compound corresponds to the substituent at position 8' of the other compound. The same also applies to the respective substituents at positions 2'/7', 3'/6', 4'/5', 5'/4', 6'/3', 2'/7', 1'/8' and/or 1"/8", 2"/7", 3"/6", 4"/5", 5"/4", 6"/3", 7"/2", 8"/1", where the first number indicates the position of the substituent of the one compound and the second number indicates the position of the substituent of the other compound. The substitution pattern at positions 1, 2, 3, 4, 5, 6, 7 and 8 of the substitution isomers is preferably identical.

Thus, for example in the case of synthesis of compound (7), a corresponding substitution isomer of the formula (8) can be obtained. If the isomers are not separated, the compound according to the invention is in the form of a mixture of substitution isomers of the formulae (7) and (8).

In the case of the presence of stereo centres, the compounds may also be in the form of an enantiomer mixture or in the form of purified enantiomers, or in the form of a mixture of diastereomers or purified diastereomers. The compound can also be employed in the form of a mixture of a plurality of compounds according to the invention.

In a further preferred embodiment of the invention, q and n are each 0 or 1. The radicals $R^3$ and $R^6$, if present, are particularly preferably arranged at positions 2', 3', 6' and/or 7'.

In a preferred embodiment of the invention, the groups $Ar^1$ and $Ar^2$ are selected on each occurrence, identically or differently, from the groups having the following formulae (Ar-1) to (Ar-33):

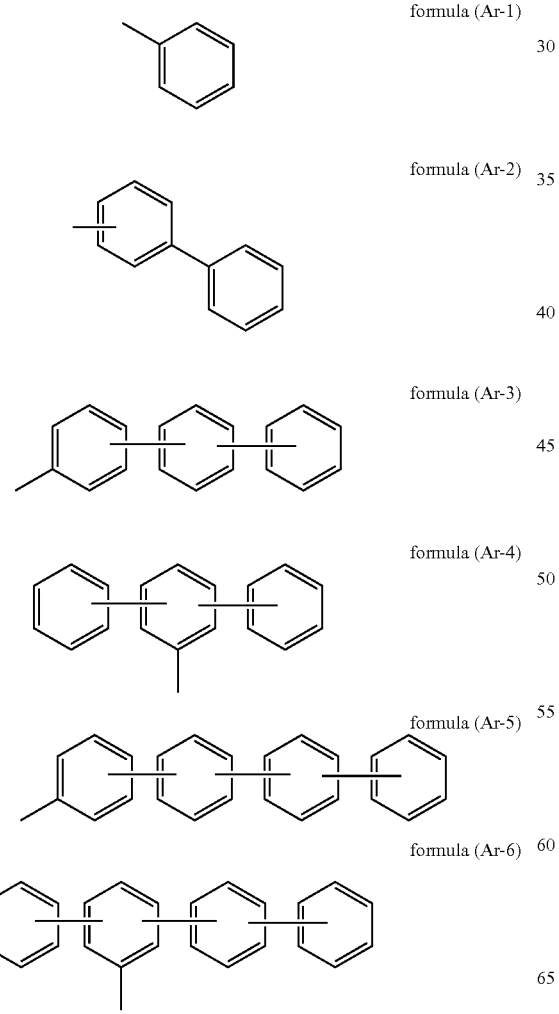

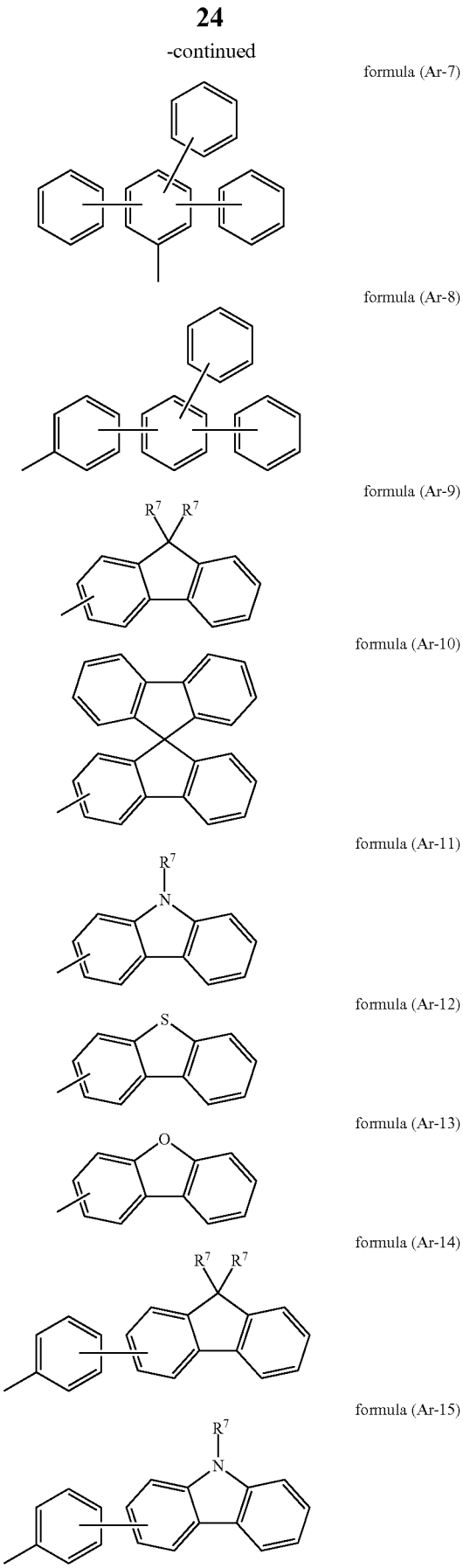

-continued
formula (Ar-16)
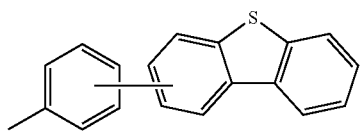
formula (Ar-17)
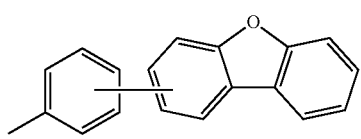
formula (Ar-18)
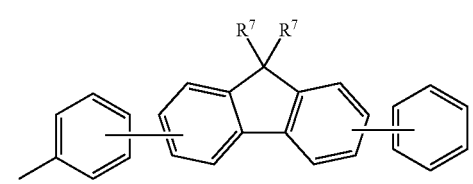
formula (Ar-19)
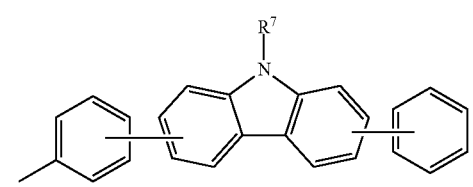
formula (Ar-20)
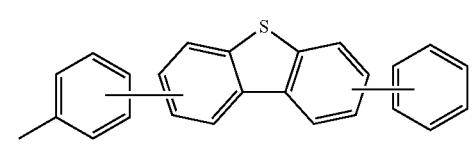
formula (Ar-21)
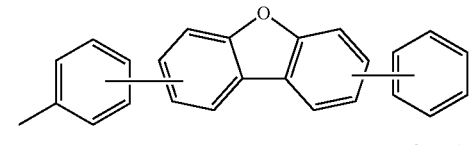
formula (Ar-22)
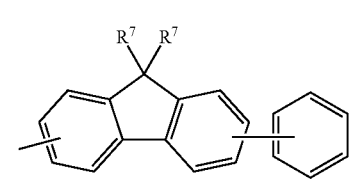
formula (Ar-23)
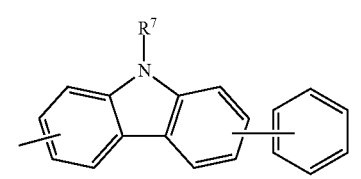
formula (Ar-24)
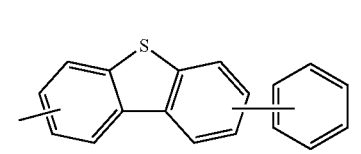
formula (Ar-25)
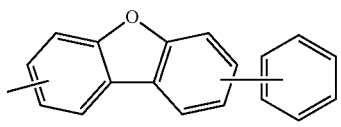
formula (Ar-26)
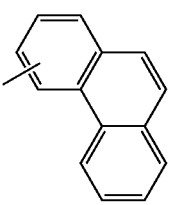
formula (Ar-27)
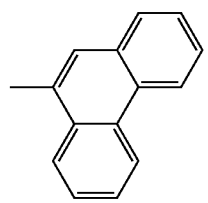
formula (Ar-28)
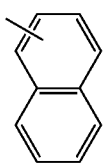
formula (Ar-29)
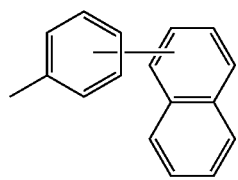
formula (Ar-30)
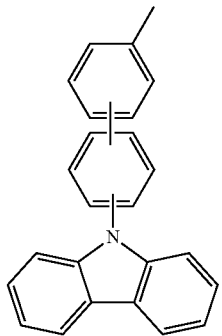

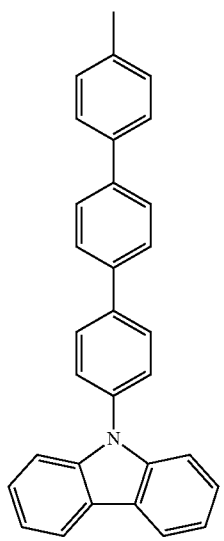
formula (Ar-31)

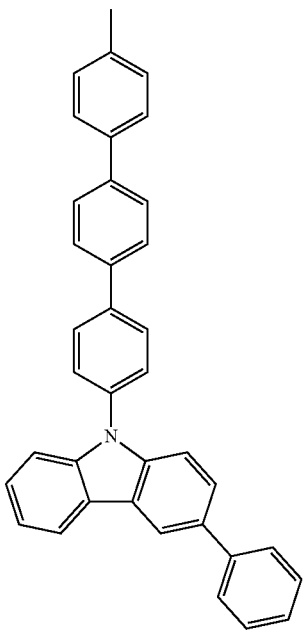
formula (Ar-33)

where the symbols used have the meanings given above and the dashed bond (or the terminal single bond) indicates the position of the bonding of the group to the nitrogen. The groups here may be substituted by $R^7$ at the free positions, but are preferably unsubstituted.

In a particularly preferred embodiment of the invention, the groups $Ar^1$ and $Ar^2$ are selected on each occurrence, identically or differently, from the groups having the structures of the formulae (Ar-1) to (Ar-33), where the general formulae are replaced by the preferred embodiments of the following formulae (Ar-1a) to (Ar-33a) (for example Ar-2 is replaced by (Ar-2a), (Ar-2b), (Ar-2c)):

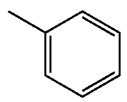
formula (Ar-1a)

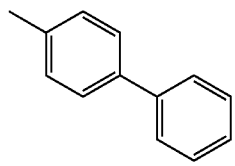
formula (Ar-2a)

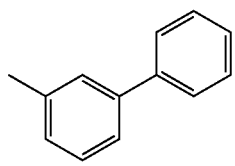
formula (Ar-2b)

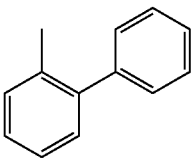
formula (Ar-2c)

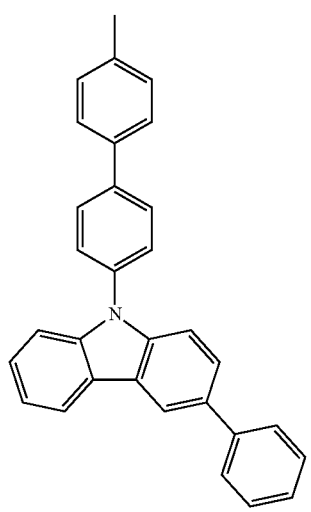
formula (Ar-32)

formula (Ar-3a)
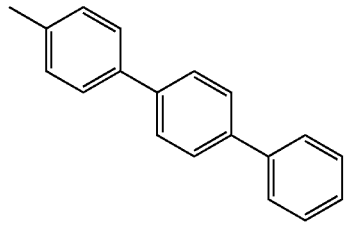
formula (Ar-3b)
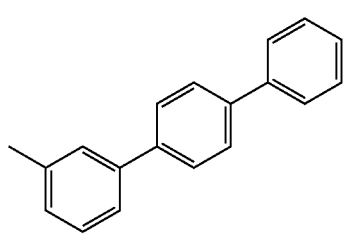
formula (Ar-3c)
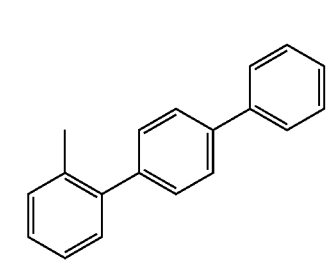
formula (Ar-3d)
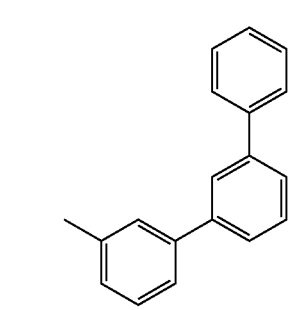
formula (Ar-3e)
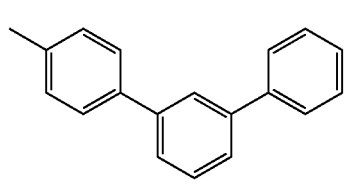
formula (Ar-3f)
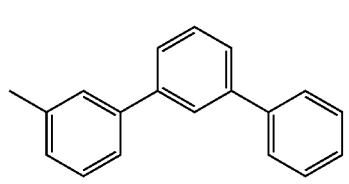
formula (Ar-3g)
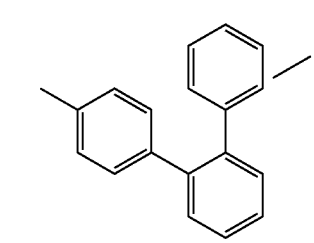
formula (Ar-3h)
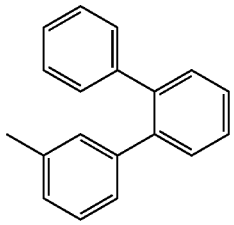
formula (Ar-3i)
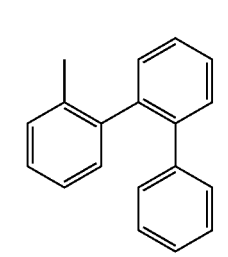
formula (Ar-4a)
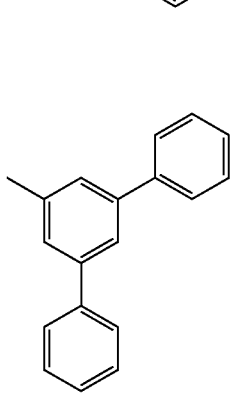
formula (Ar-4b)
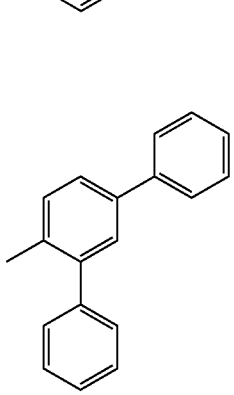
formula (Ar-5a)
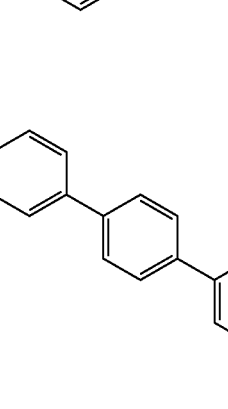

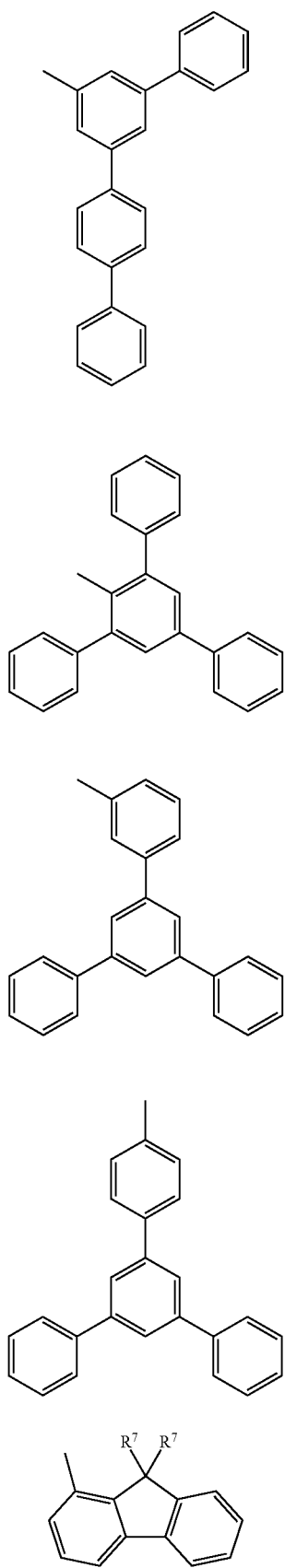

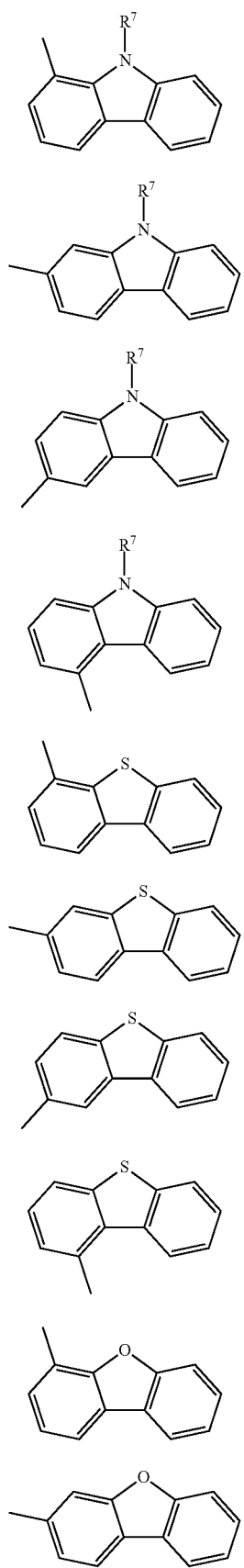
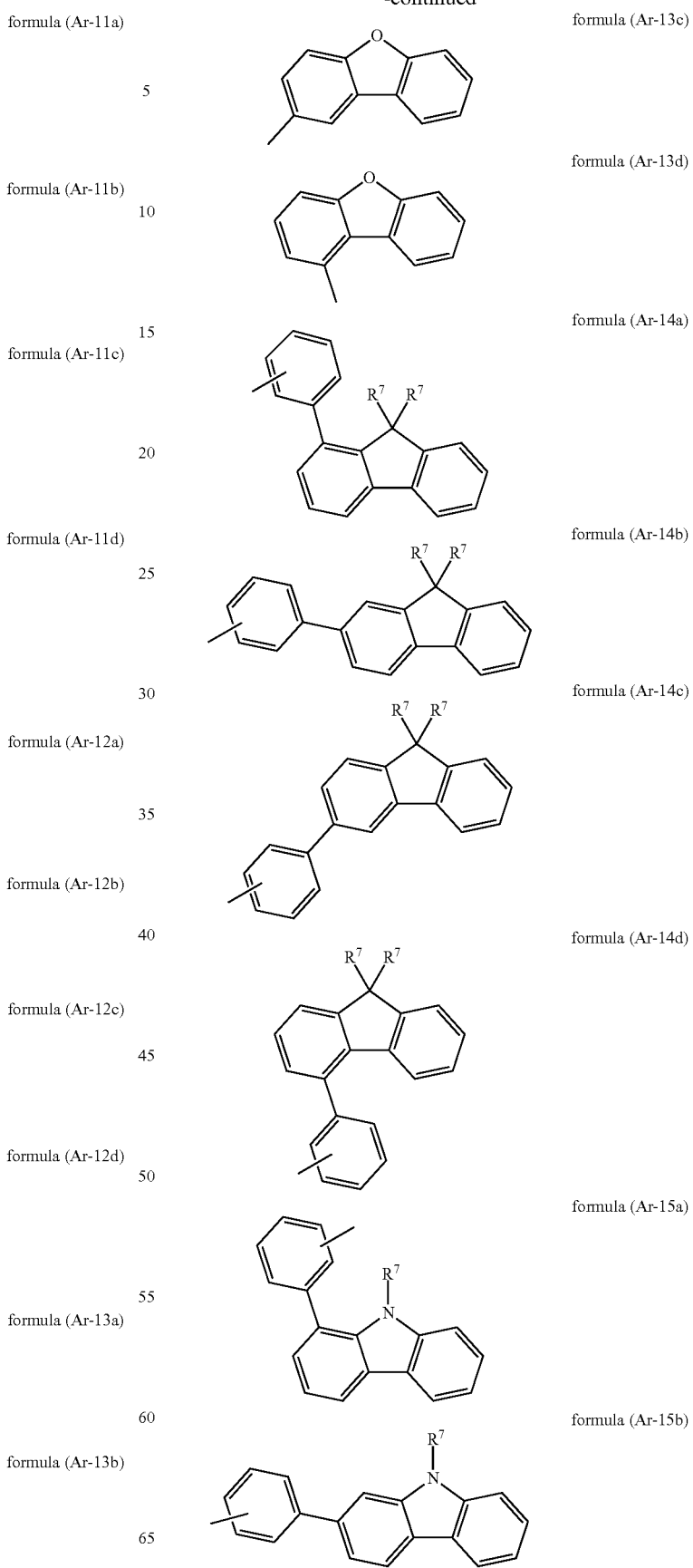

formula (Ar-15c)
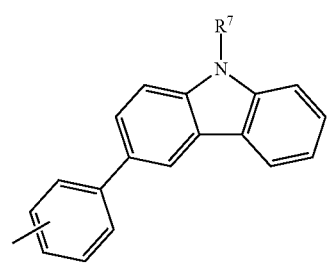
formula (Ar-15d)
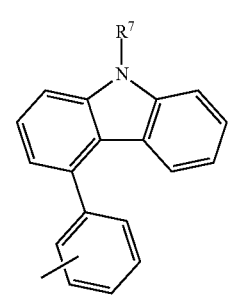
formula (Ar-16a)
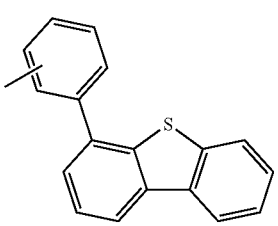
formula (Ar-16b)
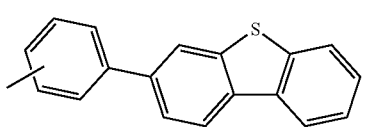
formula (Ar-16c)
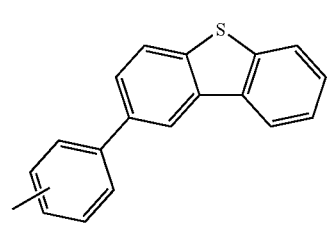
formula (Ar-16d)
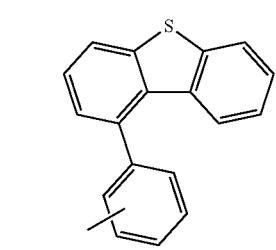
formula (Ar-17a)
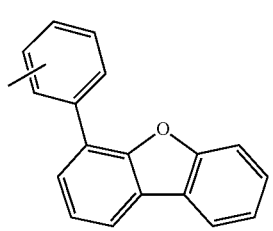
formula (Ar-17b)
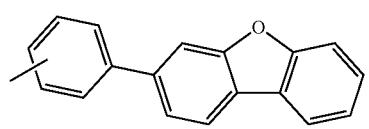
formula (Ar-17c)
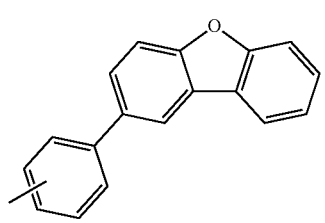
formula (Ar-17d)
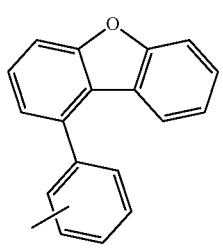
formula (Ar-19a)
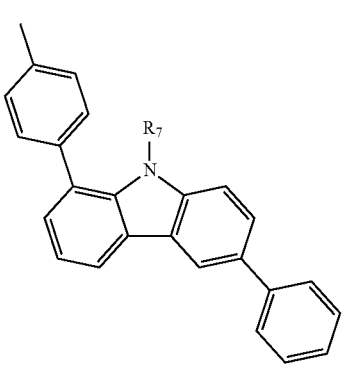
formula (Ar-19b)
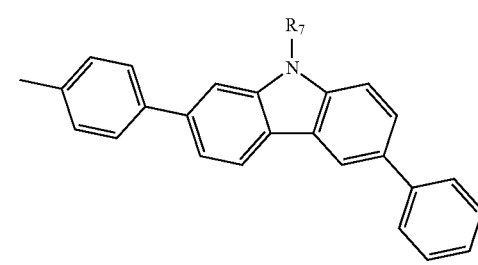
formula (Ar-19c)
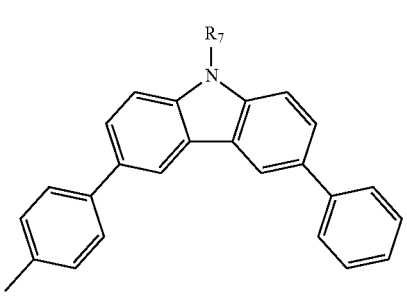

formula (Ar-19d)
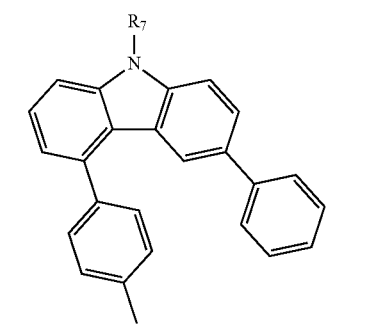
formula (Ar-22a)
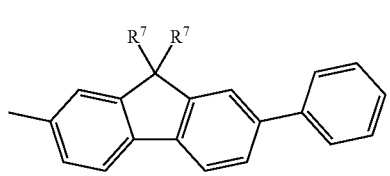
formula (Ar-23a)
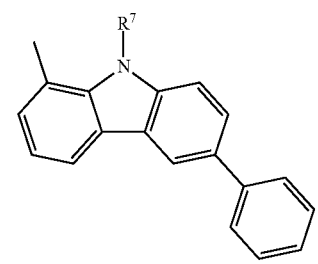
formula (Ar-23b)
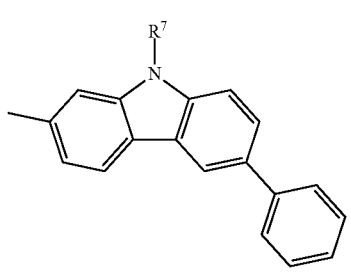
formula (Ar-23c)
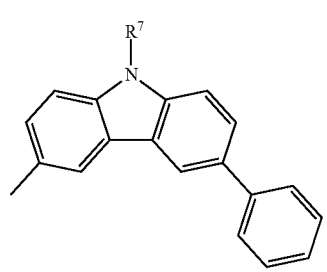
formula (Ar-23d)
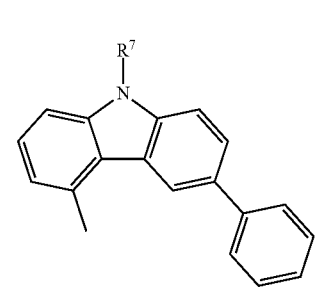
formula (Ar-26a)
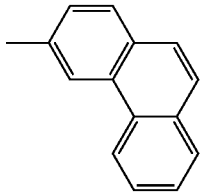
formula (Ar-26b)
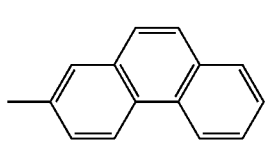
formula (Ar-27a)
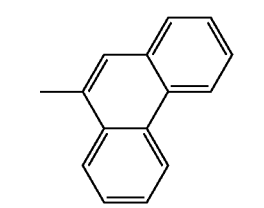
formula (Ar-28a)
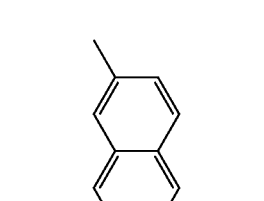
formula (Ar-28b)
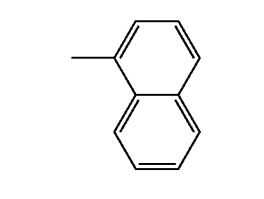
formula (Ar-29a)
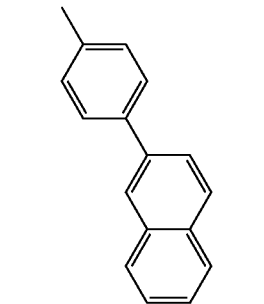
formual (Ar-29b)
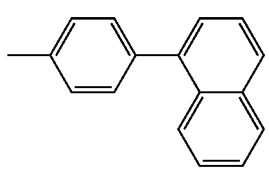

formula (Ar-30a)

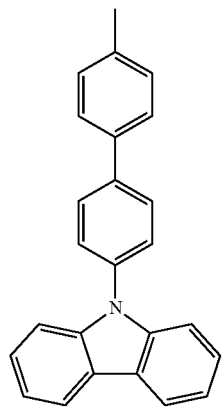

formula (Ar-30b)

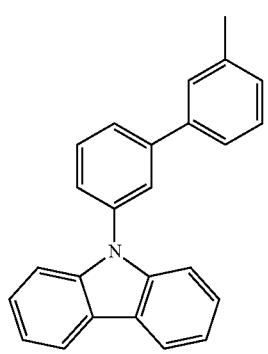

formula (Ar-31a)

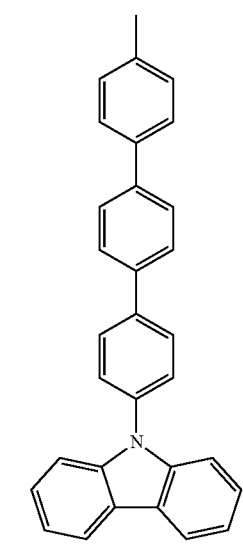

formula (Ar-32a)

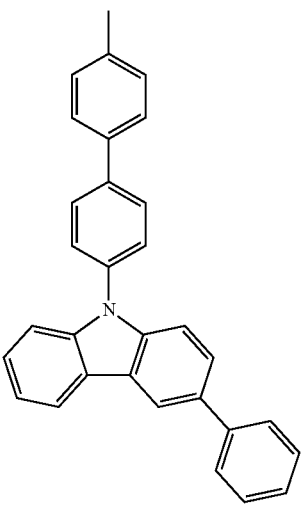

formula (Ar-33a)

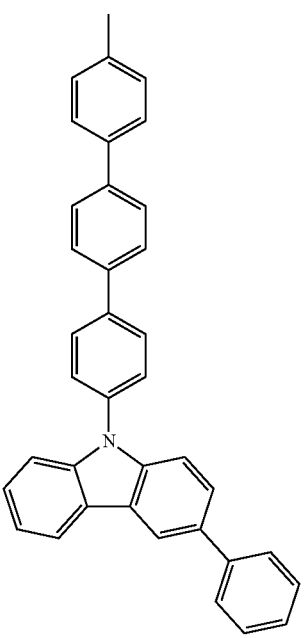

where the symbols used have the meanings given above and the dashed bond (or the terminal single bond) indicates the position of the bonding of the group to the nitrogen. The groups here may be substituted by $R^7$ at the free positions. They are preferably unsubstituted.

In a further particularly preferred embodiment of the invention, the groups $Ar^1$ and $Ar^2$ are selected on each occurrence, identically or differently, from the groups having the structures of the formulae (Ar-1a) to (Ar-33a).

A particularly preferred structure of the group of the formula (Ar-14a) is shown by the following formula (Ar-14a1). A particularly preferred structure of the group of the formula (Ar-14b) is shown by the following formula (Ar-14b). A particularly preferred structure of the group of the formula (Ar-14c) is shown by the following formula (Ar-14c1). A particularly preferred structure of the group of the formula (Ar-14d) is shown by the following formula (Ar-14d1). A particularly preferred structure of the group of the formula (Ar-15a) is shown by the following formula (Ar-15a1). A particularly preferred structure of the group of the formula (Ar-15b) is shown by the following formula (Ar-15b1). A particularly preferred structure of the group of the formula (Ar-15c) is shown by the following formula (Ar-15c1). A particularly preferred structure of the group of the formula (Ar-15d) is shown by the following formula (Ar-15d1). A particularly preferred structure of the group of the formula (Ar-16a) is shown by the following formula (Ar-16a1). A particularly preferred structure of the group of the formula (Ar-16b) is shown by the following formula (Ar-16b1). A particularly preferred structure of the group of the formula (Ar-16c) is shown by the following formula (Ar-16c1). A particularly preferred structure of the group of the formula (Ar-16d) is shown by the following formula (Ar-16d1). Particularly preferred structures of the group of the formula (Ar-17a) are shown by the following formulae (Ar-17a1), (Ar-17a2) and (Ar-17a3). A particularly preferred structure of the group of the formula (Ar-17b) is shown by the following formula (Ar-17b1). Particularly preferred structures of the group of the formula (Ar-17c) are shown by the following formulae (Ar-17c1) and (Ar-17c2). A particularly preferred structure of the group of the formula (Ar-17d) is shown by the following formula (Ar-17d1).

formula (Ar-14a1)

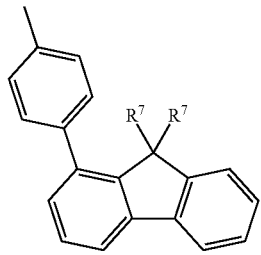

formula (Ar-14b1)

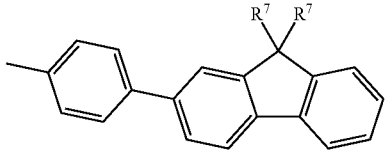

formula (Ar-14c1)

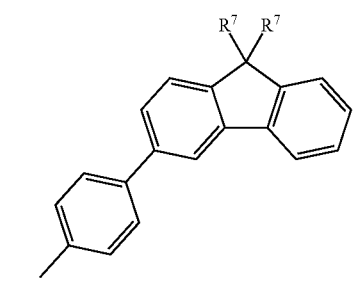

formula (Ar-14d1)

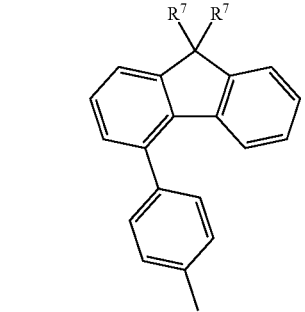

-continued formula (Ar-15a1)

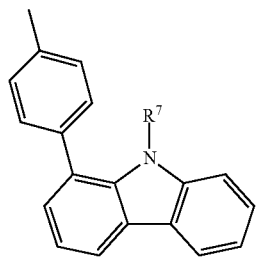

formula (Ar-15b1)

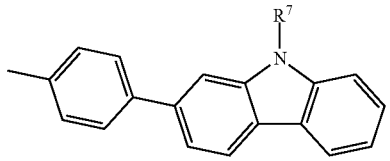

formula (Ar-15c1)

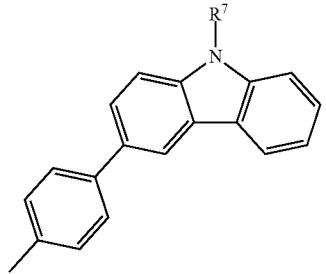

formula (Ar-15d1)

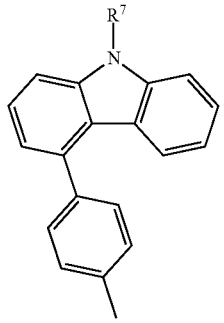

formula (Ar-16a1)

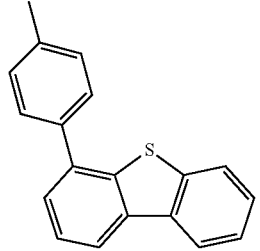

formula (Ar-16b1)

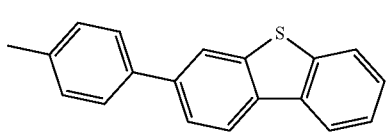

formula (Ar-16c1)

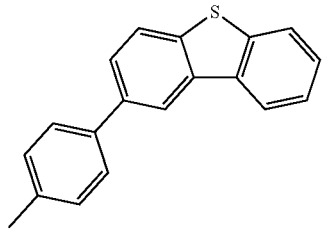

formula (Ar-16d1)

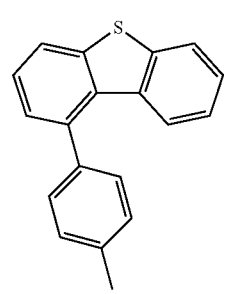

formula (Ar-17a1)

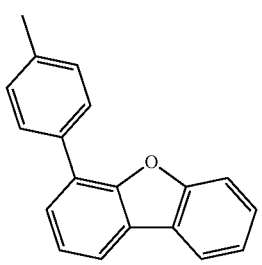

formula (Ar-17a2)

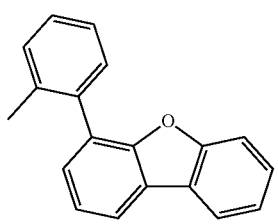

formula (Ar-17a3)

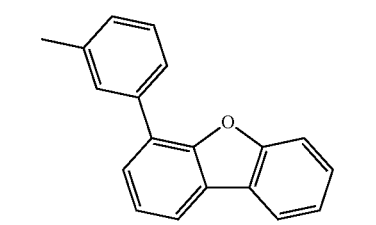

formula (Ar-17b1)

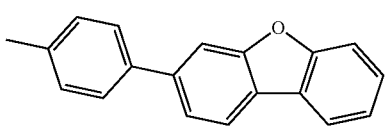

formula (Ar-17c1)

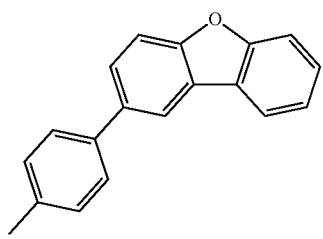

formula (Ar-17c2)

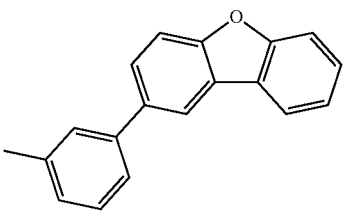

formula (Ar-17d1)

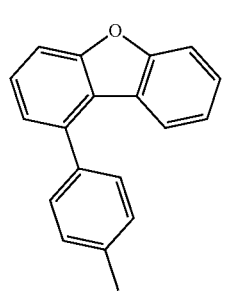

where the symbols used have the meanings given above and the dashed bond (or the terminal single bond) indicates the position of the bonding of the group to the nitrogen. The groups here may be substituted by $R^7$ at the free positions. They are preferably unsubstituted.

The two groups $Ar^1$ and $Ar^2$ of the formulae (Ar-1) to (Ar-33) shown above can be combined with one another as desired. The groups of the formulae (Ar-1), (Ar-2), (Ar-3), (Ar-4), (Ar-8), (Ar-9), (Ar-10), (Ar-11), (Ar-12), (Ar-13), (Ar-14), (Ar-15), (Ar-16), (Ar-17) and (Ar-29) are particularly preferred here.

Very particularly preferred groups —$NAr^1Ar^2$ are therefore groups which have the following combination for $Ar^1$ and $Ar^2$:

| Formula for $Ar^1$ | Formula for $Ar^2$ |
|---|---|
| (Ar-2) | (Ar-1) |
| (Ar-3) | (Ar-1) |
| (Ar-4) | (Ar-1) |
| (Ar-8) | (Ar-1) |
| (Ar-9) | (Ar-1) |
| (Ar-10) | (Ar-1) |
| (Ar-11) | (Ar-1) |
| (Ar-12) | (Ar-1) |
| (Ar-13) | (Ar-1) |
| (Ar-14) | (Ar-1) |
| (Ar-15) | (Ar-1) |
| (Ar-16) | (Ar-1) |
| (Ar-17) | (Ar-1) |
| (Ar-29) | (Ar-1) |
| (Ar-2) | (Ar-2) |
| (Ar-3) | (Ar-2) |
| (Ar-4) | (Ar-2) |
| (Ar-8) | (Ar-2) |
| (Ar-9) | (Ar-2) |
| (Ar-10) | (Ar-2) |
| (Ar-11) | (Ar-2) |
| (Ar-12) | (Ar-2) |
| (Ar-13) | (Ar-2) |
| (Ar-14) | (Ar-2) |
| (Ar-15) | (Ar-2) |
| (Ar-16) | (Ar-2) |
| (Ar-17) | (Ar-2) |
| (Ar-29) | (Ar-2) |
| (Ar-3) | (Ar-3) |
| (Ar-4) | (Ar-3) |
| (Ar-8) | (Ar-3) |

| Formula for Ar¹ | Formula for Ar² |
|---|---|
| (Ar-9) | (Ar-3) |
| (Ar-10) | (Ar-3) |
| (Ar-11) | (Ar-3) |
| (Ar-12) | (Ar-3) |
| (Ar-13) | (Ar-3) |
| (Ar-14) | (Ar-3) |
| (Ar-15) | (Ar-3) |
| (Ar-16) | (Ar-3) |
| (Ar-17) | (Ar-3) |
| (Ar-29) | (Ar-3) |
| (Ar-4) | (Ar-4) |
| (Ar-8) | (Ar-4) |
| (Ar-9) | (Ar-4) |
| (Ar-10) | (Ar-4) |
| (Ar-11) | (Ar-4) |
| (Ar-12) | (Ar-4) |
| (Ar-13) | (Ar-4) |
| (Ar-14) | (Ar-4) |
| (Ar-15) | (Ar-4) |
| (Ar-16) | (Ar-4) |
| (Ar-17) | (Ar-4) |
| (Ar-29) | (Ar-4) |
| (Ar-8) | (Ar-8) |
| (Ar-9) | (Ar-8) |
| (Ar-10) | (Ar-8) |
| (Ar-11) | (Ar-8) |
| (Ar-12) | (Ar-8) |
| (Ar-13) | (Ar-8) |
| (Ar-14) | (Ar-8) |
| (Ar-15) | (Ar-8) |
| (Ar-16) | (Ar-8) |
| (Ar-17) | (Ar-8) |
| (Ar-29) | (Ar-8) |
| (Ar-9) | (Ar-9) |
| (Ar-10) | (Ar-9) |
| (Ar-11) | (Ar-9) |
| (Ar-12) | (Ar-9) |
| (Ar-13) | (Ar-9) |
| (Ar-14) | (Ar-9) |
| (Ar-15) | (Ar-9) |
| (Ar-16) | (Ar-9) |
| (Ar-17) | (Ar-9) |
| (Ar-29) | (Ar-9) |
| (Ar-10) | (Ar-10) |
| (Ar-11) | (Ar-10) |
| (Ar-12) | (Ar-10) |
| (Ar-13) | (Ar-10) |
| (Ar-14) | (Ar-10) |
| (Ar-15) | (Ar-10) |
| (Ar-16) | (Ar-10) |
| (Ar-17) | (Ar-10) |
| (Ar-29) | (Ar-10) |
| (Ar-11) | (Ar-11) |
| (Ar-12) | (Ar-11) |
| (Ar-13) | (Ar-11) |
| (Ar-14) | (Ar-11) |
| (Ar-15) | (Ar-11) |
| (Ar-16) | (Ar-11) |
| (Ar-17) | (Ar-11) |
| (Ar-29) | (Ar-11) |
| (Ar-12) | (Ar-12) |
| (Ar-13) | (Ar-12) |
| (Ar-14) | (Ar-12) |
| (Ar-15) | (Ar-12) |
| (Ar-16) | (Ar-12) |
| (Ar-17) | (Ar-12) |
| (Ar-29) | (Ar-12) |
| (Ar-13) | (Ar-13) |
| (Ar-14) | (Ar-13) |
| (Ar-15) | (Ar-13) |
| (Ar-16) | (Ar-13) |
| (Ar-17) | (Ar-13) |
| (Ar-29) | (Ar-13) |
| (Ar-14) | (Ar-14) |
| (Ar-15) | (Ar-14) |
| (Ar-16) | (Ar-14) |
| (Ar-17) | (Ar-14) |
| (Ar-29) | (Ar-14) |
| (Ar-15) | (Ar-15) |
| (Ar-16) | (Ar-15) |
| (Ar-17) | (Ar-15) |
| (Ar-29) | (Ar-15) |
| (Ar-16) | (Ar-16) |
| (Ar-17) | (Ar-16) |
| (Ar-29) | (Ar-16) |
| (Ar-17) | (Ar-17) |
| (Ar-29) | (Ar-17) |
| (Ar-29) | (Ar-29) |
| (Ar-1) | (Ar-1) |
| (Ar-9) | (Ar-30) |
| (Ar-1) | (Ar-30) |

Very preferred groups —NAr¹Ar² are groups which have the combinations from the table shown above, where, instead of formulae (Ar-1), (Ar-2), (Ar-3), (Ar-4), (Ar-8), (Ar-9), (Ar-10), (Ar-11), (Ar-12), (Ar-13), (Ar-14), (Ar-15), (Ar-16), (Ar-17) and (Ar-29), the preferred formulae of the respective formulae, for example (Ar-2a), (Ar-2b) or (Ar-2c), are in each case employed instead of (Ar-2).

If the groups Ar¹ and Ar² in the compounds of the formulae (1) to (28) or (6a) to (28a) are linked to one another by a group E, the group —NAr¹Ar² preferably has a structure of one of the following formulae (Ar1-1) to (Ar1-19):

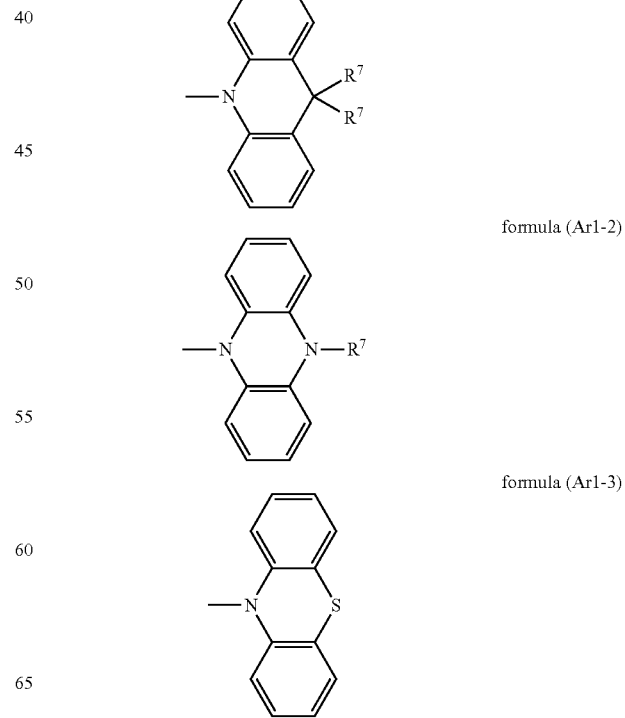

formula (Ar1-1)

formula (Ar1-2)

formula (Ar1-3)

formula (Ar1-4)
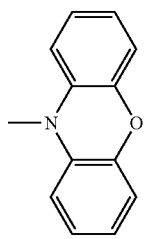
formula (Ar1-5)
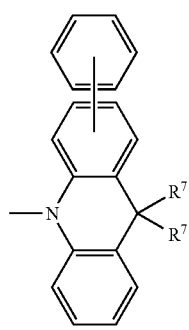
formula (Ar1-6)
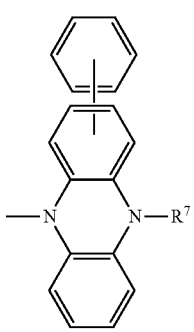
formula (Ar1-7)
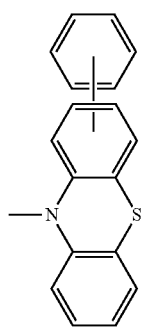
formula (Ar1-8)
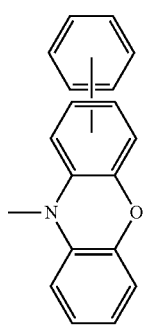
formula (Ar1-9)
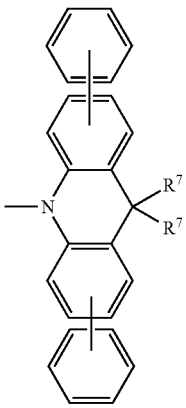
formula (Ar1-10)
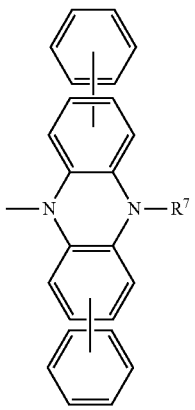
formula (Ar1-11)
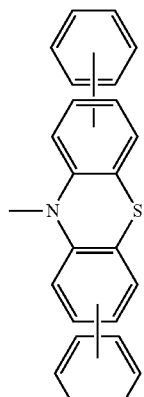
formula (Ar1-12)
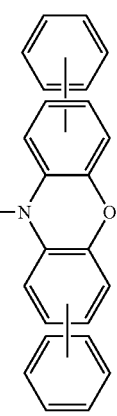

formula (Ar1-13)

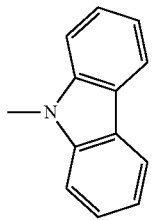

formula (Ar1-14)

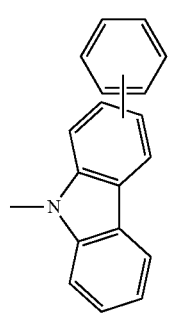

formula (Ar1-15)

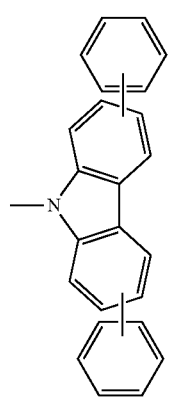

formula (Ar1-16)

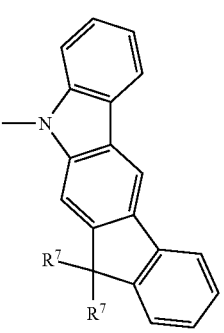

formula (Ar1-17)

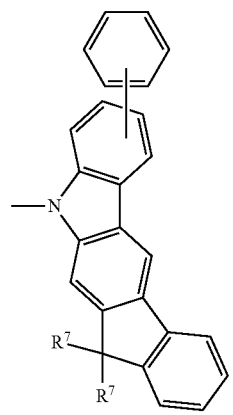

formula (Ar1-18)

formula (Ar1-19)

where the symbols used have the meanings given above and the dashed bond (or the terminal single bond) indicates the position of the bonding to the basic structure, or to $Ar^S$. The groups here may be substituted by $R^7$ at the free positions.

In a particularly preferred embodiment of the invention, the compounds of the formulae (Ar1-5), (Ar1-6), (Ar1-7), (Ar1-8), (Ar1-9), (Ar1-10), (Ar1-11), (Ar1-12), (Ar1-14), (Ar1-15) and (Ar1-17) are selected from the compounds having the following formulae:

formula (Ar1-5a)
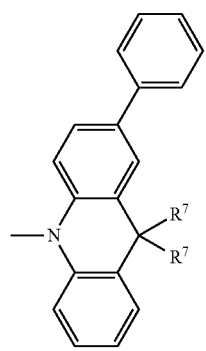
formula (Ar1-5b)
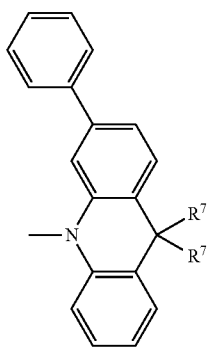
formula (Ar1-6a)
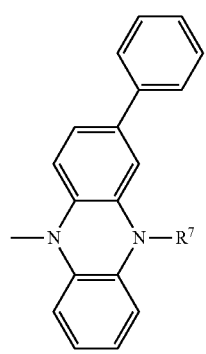
formula (Ar1-6b)
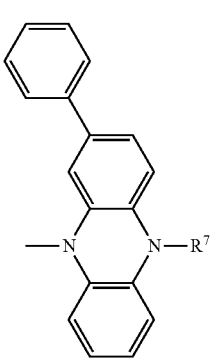
formula (Ar1-7a)
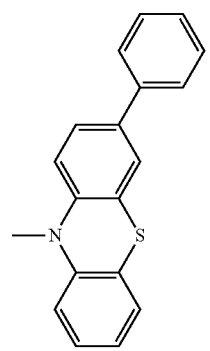
formula (Ar1-7b)
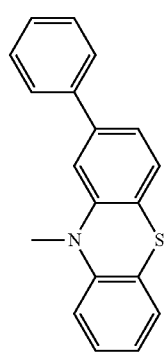
formula (Ar1-8a)
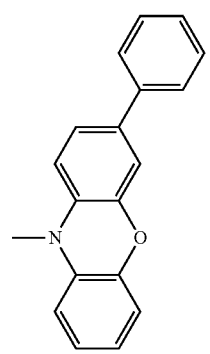
formula (Ar1-8b)
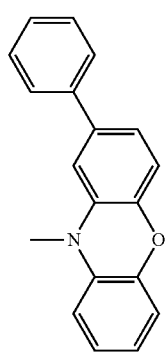

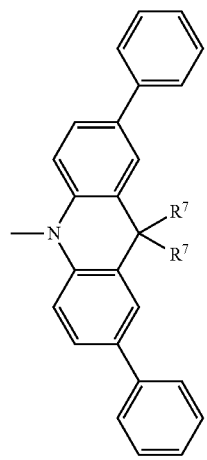
formula (Ar1-9a)
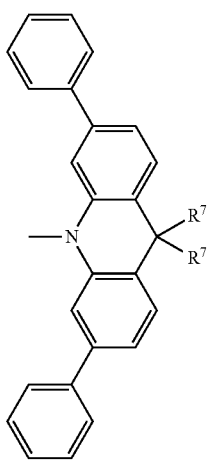
formula (Ar1-9b)
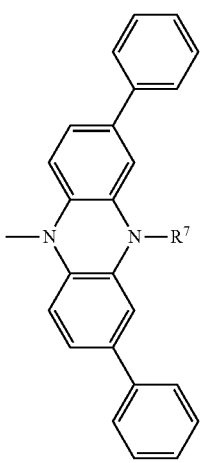
formula (Ar1-10a)
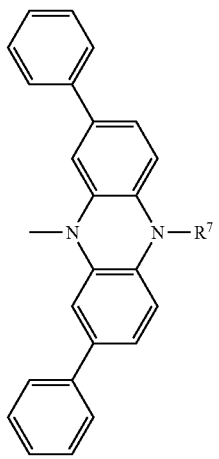
formula (Ar1-10b)
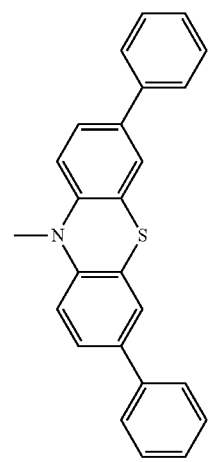
formula (Ar1-11a)
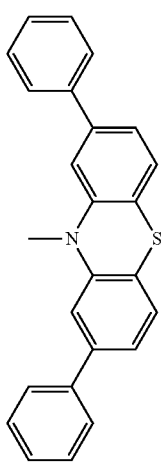
formula (Ar1-11b)

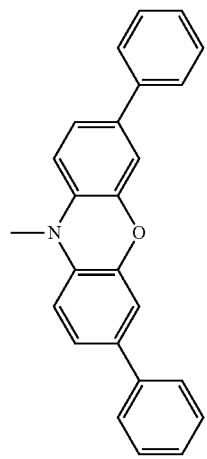
formula (Ar1-12a)
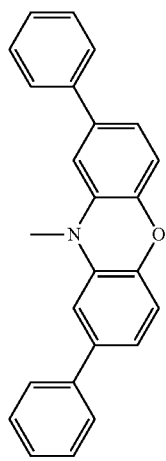
formula (Ar1-12b)
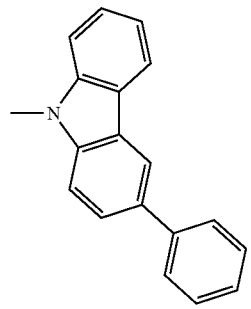
formula (Ar1-14a)
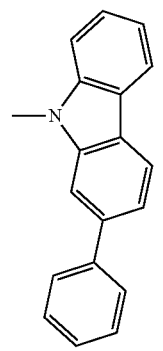
formula (Ar1014b)
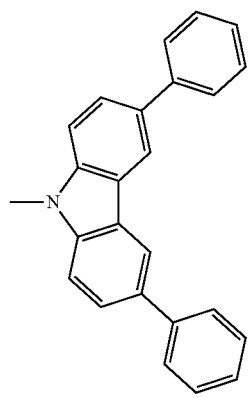
formula (Ar1015a)
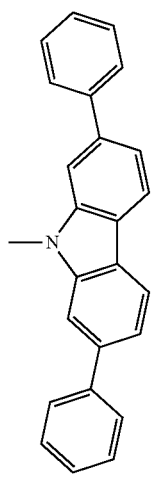
formula (Ar1-15b)
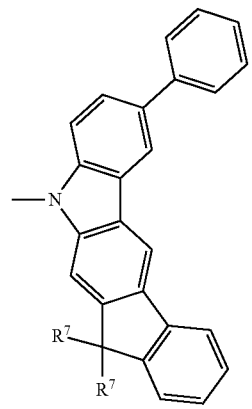
formula (Ar1-17a)

formula (Ar1-17b)

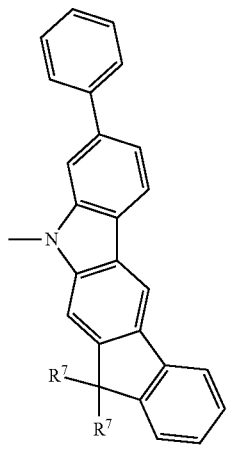

where the symbols used have the meanings given above and the dashed bond (or the terminal single bond) indicates the position of the bonding to the basic structure, or to Ar$^S$. The groups here may be substituted by R$^7$ at the free positions. They are preferably unsubstituted.

If a group Ar$^S$ in the compounds of the formulae (1) to (28) or (6a) to (28a) is linked to Ar$^1$ by a group E, the group —Ar$^S$—NAr$^1$Ar$^2$ preferably has the structure of one of the following formulae (Ar2-1) to (Ar2-9) and the dashed bond indicates the bonding to the basic structure or to the next Ar$^S$ unit. An analogous situation applies to a linking of the group Ar$^S$ to Ar$^2$.

formula (Ar2-1)

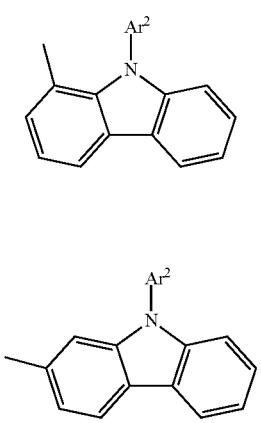

formula (Ar2-2)

formula (Ar2-3)

formula (Ar2-4)

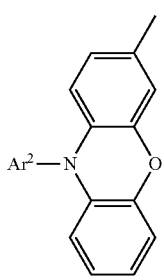

formula (Ar2-5)

formula (Ar2-6)

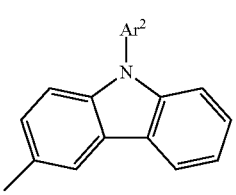

formula (Ar2-7)

formula (Ar2-8)

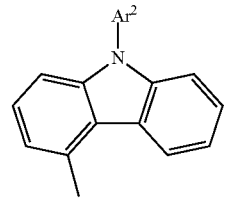

formula (Ar2-9)

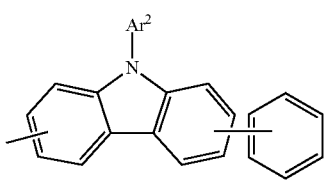

where the symbols used have the meanings given above. The groups here may be substituted by R$^7$ at the free positions. They are preferably unsubstituted.

Preferred embodiments of the formula (Ar2-9) are shown by the following formulae:

formula (Ar2-9a)
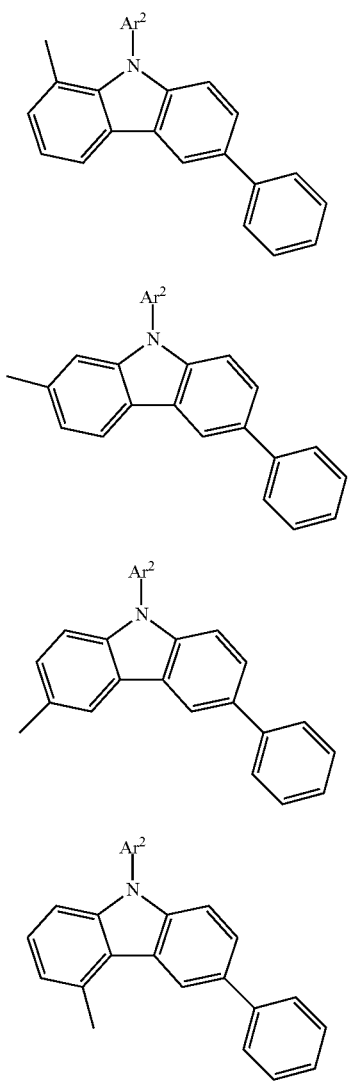
formula (Ar2-9b)

formula (Ar2-9c)

formula (Ar2-9d)

-continued formula (Ar3-3)
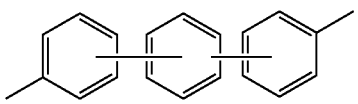

formula (Ar3-4)
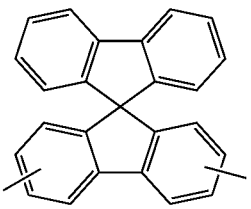

formula (Ar3-5)
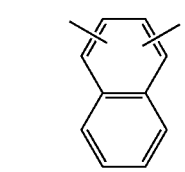

formula (Ar3-6)
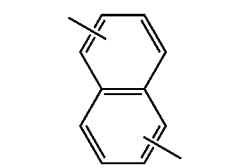

formula (Ar3-7)
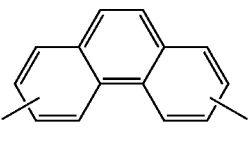

formula (Ar3-8)
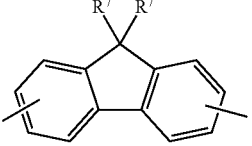

formula (Ar3-9)
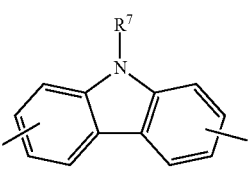

formula (Ar3-10)
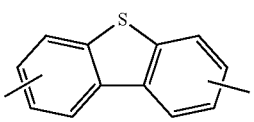

formula (Ar3-11)
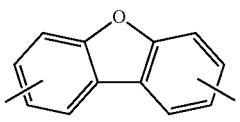

formula (Ar3-12)
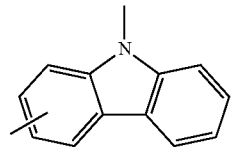

where the symbols used have the meanings given above. The groups here may be substituted by $R^7$ at the free positions. They are preferably unsubstituted.

The group $Ar^S$ is preferably, identically or differently on each occurrence, an aromatic or heteroaromatic ring system having 6 to 18 ring atoms, which may in each case be substituted by one or more radicals $R^9$.

In a further preferred embodiment of the invention, the index i is equal to 1 or 2 and the group $Ar^S$ stands for a group of one of the following formulae (Ar3-1) to (Ar3-12):

formula (Ar3-1)

formula (Ar3-2)
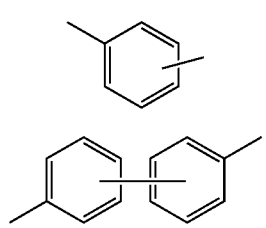

where the symbols used have the meanings given and the two dashed bonds (or terminal single bonds) represent the bonds to the adjacent groups. The groups here may be substituted by $R^7$ at the free positions. They are preferably unsubstituted.
Preferred embodiments of the formulae are shown by the following formulae (Ar3-1a) to (Ar3-12a):
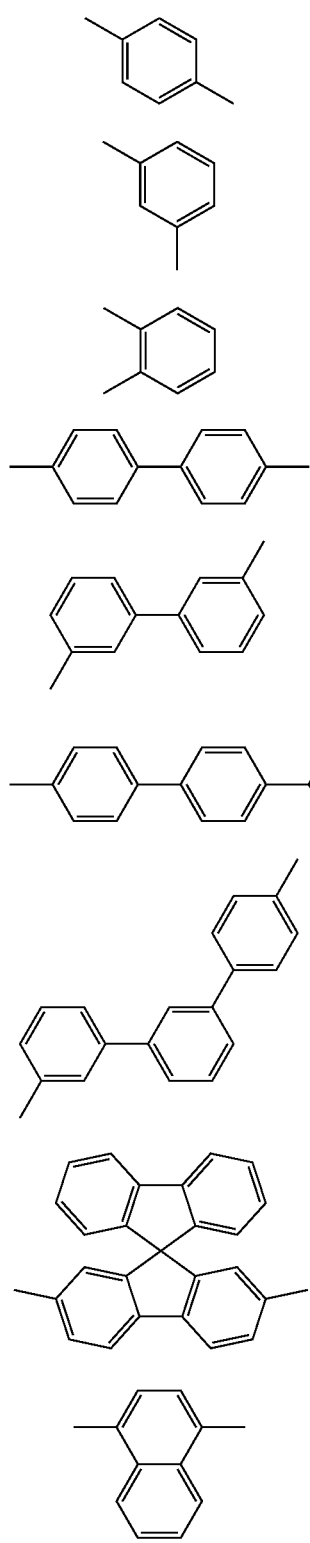
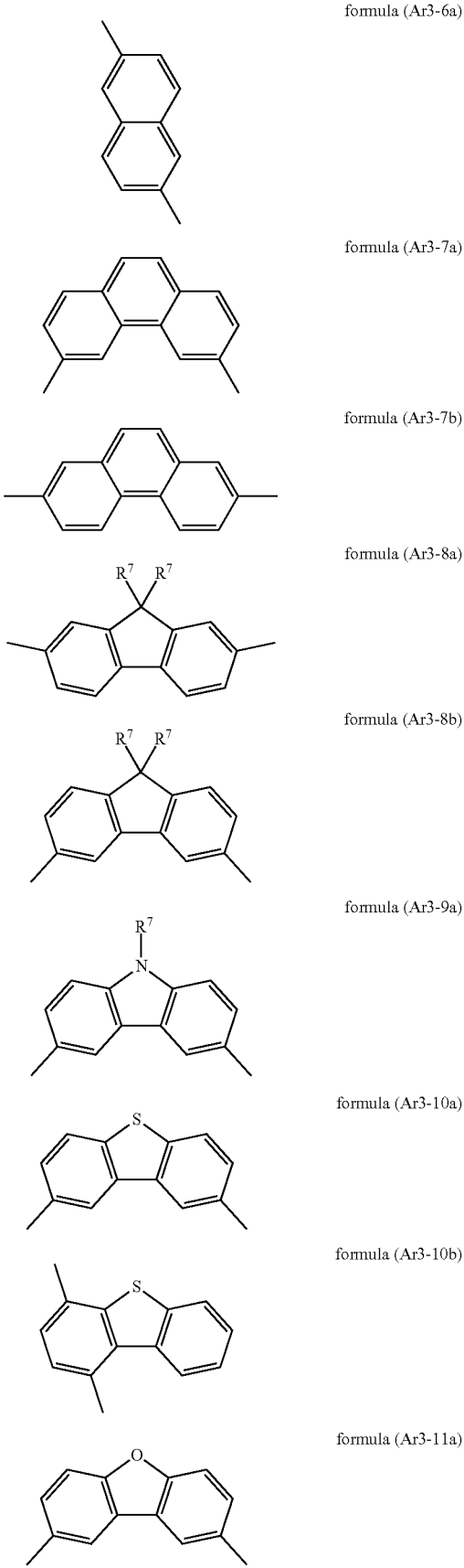

-continued

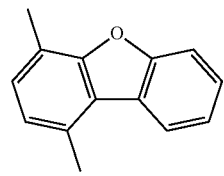
formula (Ar3-11b)

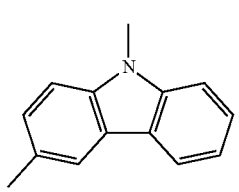
formula (Ar3-12a)

where the symbols used have the meanings given and the two dashed bonds (or terminal single bonds) represent the bonds to the adjacent groups. The groups here may be substituted by $R^7$ at the free positions. They are preferably unsubstituted.

For each group $(Ar^S)_i$, it is preferred for a maximum of one $Ar^S$ to be a group of the formula (Ar3-9), (Ar3-12), (Ar3-9a) or (Ar3-12a).

If $R^7$ stands for $N(R^7)_2$, $R^7$ preferably stands, identically or differently, for an aromatic or heteroaromatic ring system having 6 to 60 aromatic ring atoms. $R^7$ is then particularly preferably selected from the structures of the formulae (Ar-1) to (Ar-33) or their preferred embodiments, which may be substituted here by $R^9$ instead of by $R^7$.

According to a preferred embodiment, $R^7$ is selected on each occurrence, identically or differently, from the group consisting of H, D, F, Cl, Br, I, CN, $Si(R^9)_3$, a straight-chain alkyl, alkoxy or thioalkyl group having 1 to 40 C atoms or a branched or cyclic alkyl, alkoxy or thioalkyl group having 3 to 40 C atoms, each of which may be substituted by one or more radicals $R^9$, where in each case one or more non-adjacent $CH_2$ groups may be replaced by $Si(R^9)_2$, $C=NR^9$, $P(=O)(R^9)$, SO, $SO_2$, $NR^9$, O, S or $CONR^9$ and where one or more H atoms may be replaced by D, F, Cl, Br or I, an aromatic or heteroaromatic ring system having 6 to 60 aromatic ring atoms, which may in each case be substituted by one or more radicals $R^9$, an aryloxy group or heteroaryloxy group having 5 to 60 aromatic ring atoms, which may be substituted by one or more radicals $R^9$, or an aralkyl group or heteroaralkyl group having 5 to 60 aromatic ring atoms, which may in each case be substituted by one or more radicals $R^9$, where two or more adjacent substituents $R^7$ may optionally form a mono- or polycyclic, aliphatic or aromatic ring system, which may be substituted by one or more radicals $R^9$.

According to the above definition of $R^7$, a compound of the formula (1) contains no further arylamino groups apart from those explicitly indicated in the compound.

In a preferred embodiment of the invention, $R^1$, $R^2$, $R^3$, $R^4$, $R^5$, $R^6$, $R^7$, $R^8$ in the compounds of the formulae (1) to (28), or (6a) to (28a), are selected, identically or differently on each occurrence, from the group consisting of H, D, F, $Si(R^9)_3$, CN, a straight-chain alkyl or alkoxy group having 1 to 10 C atoms or a branched or cyclic alkyl or alkoxy group having 3 to 10 C atoms, each of which may be substituted by one or more radicals $R^9$, where one or more non-adjacent $CH_2$ groups may be replaced by O and where one or more H atoms may be replaced by D or F, an aromatic ring system having 6 to 60 aromatic ring atoms, which may in each case be substituted by one or more radicals $R^9$, where two or more adjacent substituents $R^1$ to $R^7$, or $R^1$ and $R^8$, may optionally form a mono- or polycyclic, aliphatic ring system, which may be substituted by one or more radicals $R^9$.

In a particularly preferred embodiment of the invention, $R^1$, $R^2$, $R^3$, $R^4$, $R^5$, $R^6$, $R^7$, $R^8$ in the compounds of the formulae (1) to (28), or (6a) to (28a), are selected, identically or differently on each occurrence, from the group consisting of H, D, a straight-chain alkyl group having 1 to 10 C atoms or a branched or cyclic alkyl group having 3 to 10 C atoms, each of which may be substituted by one or more radicals $R^9$, an aromatic ring system having 6 to 60 C atoms, which may in each case be substituted by one or more radicals $R^9$, where two or more adjacent substituents $R^1$ to $R^7$, or $R^1$ and $R^8$, may optionally form a mono- or polycyclic, aliphatic ring system, which may be substituted by one or more radicals $R^9$. In a very particularly preferred embodiment of the invention, $R^1$ to $R^6$ in the compounds of the formulae (1) to (28), or (6a) to (28a), are equal to H.

In a further preferred embodiment of the invention, the radical $R^7$ which is bonded to $Ar^1$ or $Ar^2$ or $Ar^S$ is selected, identically or differently on each occurrence, from the group consisting of H, D, a straight-chain alkyl group having 1 to 10 C atoms or a branched or cyclic alkyl group having 3 to 10 C atoms.

In a further preferred embodiment of the invention, at least one radical $R^7$ which is bonded in the ortho-position of the aryl group of $Ar^1$ or $Ar^2$ which is bonded directly to the nitrogen is not equal to hydrogen or deuterium. This applies, in particular, if a further aryl group is not already bonded in the ortho-position on the aryl group, as is the case, for example, in formula (Ar-2c).

It may furthermore be preferred for the two substituents $R^7$ in the 9-position of a fluorene together to form a cycloalkyl ring, preferably having 3 to 8 C atoms, particularly preferably having 5 or 6 C atoms.

In a further preferred embodiment, $R^7$ which is bonded to the carbon bridge in formulae (Ar1-1), (Ar1-5), (Ar1-9), (Ar1-16), (Ar1-17), (Ar1-5a), (Ar1-5b), (Ar1-9a), (Ar1-9b), (Ar1-17a), (Ar1-17b), (Ar2-1), (Ar3-8), (Ar3-8a) and (Ar3-8b) is selected, identically or differently on each occurrence, from the group consisting of a straight-chain alkyl group having 1 to 10 C atoms, a branched or cyclic alkyl group having 3 to 10 C atoms or an aromatic ring system having 6 to 30 C atoms, which is as defined above and which may be substituted by one or more radicals $R^9$. The two groups $R^7$ here may also form a ring system with one another, which may be aliphatic or, in addition to the definition of $R^7$ given above, also aromatic. A spiro system is formed by ring formation.

In a further preferred embodiment, $R^7$ which is bonded to the nitrogen bridge in formulae (Ar1-2), (Ar1-6), (Ar1-10), (Ar1-19), (Ar1-6a), (Ar1-6b), (Ar1-10a), (Ar1-10b), (Ar2-2), (Ar3-9) and (Ar3-9a) is selected from the group consisting of a straight-chain alkyl group having 1 to 10 C atoms, a branched or cyclic alkyl group having 3 to 10 C atoms or an aromatic ring system having 6 to 30 C atoms, in particular an aromatic ring system having 6 to 24 C atoms, which is as defined above, and which may be substituted by one or more radicals $R^9$.

In a further preferred embodiment, $R^3$ and $R^6$, if they include an aromatic or heteroaromatic ring system, are selected from the groups of the formulae (Ar-1) to (Ar-33), particularly preferably (Ar-1) to (Ar-10), and the preferred embodiments of these groups. The radicals $R^3$ and $R^6$ preferably do not include a heteroaromatic ring system.

For compounds which are processed by vacuum evaporation, the alkyl groups preferably have not more than four C atoms, particularly preferably not more than 1 C atom. For compounds which are processed from solution, compounds which are substituted by linear, branched or cyclic alkyl groups having up to 10 C atoms or which are substituted by oligoarylene groups, for example ortho-, meta-, para- or branched terphenyl or quaterphenyl groups, are also suitable.

In a preferred embodiment of the invention, $R^9$ is selected, identically or differently on each occurrence, from the group consisting of H, D, a straight-chain alkyl group having 1 to 10 C atoms or a branched or cyclic alkyl group having 3 to 10 C atoms or an aromatic ring system having 6 to 30 C atoms, which is as defined above and which may in each case be substituted by one or more radicals $R^{10}$.

In a particularly preferred embodiment of the invention, $R^9$ is selected, identically or differently on each occurrence, from the group consisting of H, D, a straight-chain alkyl group having 1 to 5 C atoms or a branched or cyclic alkyl group having 3 to 5 C atoms, or an aromatic ring system having 6 to 18 C atoms, which is as defined above.

In a further preferred embodiment of the invention, the radicals $R^1$ to $R^6$ do not contain any fused aryl or heteroaryl groups which contain more than 12 aromatic ring atoms.

In a further preferred embodiment of the invention, two or more adjacent radicals $R^1$ to $R^6$, and adjacent radicals $R^1$ and $R^8$, do not form a mono- or polycyclic aromatic ring system.

Preference is given to compounds of the formulae (1), (2) to (28) and (6a) to (28a) in which the above-mentioned preferred embodiments occur simultaneously. Particular preference is therefore given to compounds for which:

$Ar^S$ is, identically or differently on each occurrence, an aromatic or heteroaromatic ring system, where, for i=1 or 2, $Ar^S$ is selected from the groups of the formulae (Ar3-1) to (Ar3-12), and preferred embodiments thereof of the formulae (Ar3-1a) to (Ar3-12a), where $Ar^S$ may be connected to $Ar^1$ by a group E;

$Ar^1$, $Ar^2$ are, identically or differently on each occurrence, an aromatic or heteroaromatic ring system selected from the groups of the formulae (Ar-1) to (Ar-33), and preferred embodiments thereof; or —$NAr^1Ar^2$ stands for a group of one of the formulae (Ar1-1) to (Ar1-19), and preferred embodiments thereof; or $Ar^S$—$NAr^1Ar^2$ stands for a group of one of the formulae (Ar2-1) to (Ar2-9) and preferred embodiments thereof;

E is selected, identically or differently on each occurrence, from the group consisting of $C(R^7)_2$, O, S and $NR^7$;

$R^1$, $R^2$, $R^3$, $R^4$, $R^5$, $R^6$, $R^8$ are selected on each occurrence, identically or differently, from the group consisting of H, D, F, $Si(R^9)_3$, CN, a straight-chain alkyl or alkoxy group having 1 to 10 C atoms or a branched or cyclic alkyl or alkoxy group having 3 to 10 C atoms, each of which may be substituted by one or more radicals $R^9$, where one or more non-adjacent $CH_2$ groups may be replaced by O and where one or more H atoms may be replaced by D or F, an aromatic ring system having 6 to 60 aromatic ring atoms, which may in each case be substituted by one or more radicals $R^9$, where two or more adjacent substituents $R^1$ to $R^6$, or $R^1$ and $R^8$, may optionally form a mono- or polycyclic, aliphatic ring system, which may be substituted by one or more radicals $R^9$;

$R^7$ is selected on each occurrence, identically or differently, from the group consisting of H, D, F, $Si(R^9)_3$, CN, a straight-chain alkyl or alkoxy group having 1 to 10 C atoms or a branched or cyclic alkyl or alkoxy group having 3 to 10 C atoms, each of which may be substituted by one or more radicals $R^9$, where one or more non-adjacent $CH_2$ groups may be replaced by O and where one or more H atoms may be replaced by D or F, an aromatic ring system having 6 to 60 aromatic ring atoms, which may in each case be substituted by one or more radicals $R^9$, where two or more adjacent substituents $R^7$ may optionally form a mono- or polycyclic, aliphatic ring system, which may be substituted by one or more radicals $R^9$;

or $R^7$ which is bonded to the carbon bridge in formulae (Ar1-1), (Ar1-5), (Ar1-9), (Ar1-16), (Ar1-17), (Ar1-5a), (Ar1-5b), (Ar1-9a), (Ar1-9b), (Ar1-17a), (Ar1-17b), (Ar2-1), (Ar3-8), (Ar3-8a) and (Ar3-8b) is selected, identically or differently on each occurrence, from the group consisting of a straight-chain alkyl group having 1 to 10 C atoms, a branched or cyclic alkyl group having 3 to 10 C atoms or an aromatic ring system having 6 to 30 C atoms, which may be substituted by one or more radicals $R^9$; the two groups $R^7$ here may also form a ring system with one another, which may be aliphatic or aromatic;

or $R^7$ which is bonded to the nitrogen bridge in formulae (Ar1-2), (Ar1-6), (Ar1-10), (Ar1-19), (Ar1-6a), (Ar1-6b), (Ar1-10a), (Ar1-10b), (Ar2-2), (Ar3-9) and (Ar3-9a) is selected from the group consisting of a straight-chain alkyl group having 1 to 10 C atoms, a branched or cyclic alkyl group having 3 to 10 C atoms or an aromatic ring system having 6 to 30 C atoms, which may be substituted by one or more radicals $R^9$;

$R^9$ is selected, identically or differently on each occurrence, from the group consisting of H, D, F, a straight-chain alkyl group having 1 to 10 C atoms or a branched or cyclic alkyl group having 3 to 10 C atoms or an aromatic ring system having 6 to 30 C atoms, each of which may be substituted by one or more radicals $R^{10}$, where two or more adjacent substituents $R^9$ may form a mono- or polycyclic, aliphatic ring system with one another;

$R^{10}$ is selected from the group consisting of H, D, F, an aliphatic hydrocarbon radical having 1 to 20 C atoms, an aromatic ring system having 6 to 30 C atoms, in which one or more H atoms may be replaced by D or F, where two or more adjacent substituents $R^{10}$ may form a mono- or polycyclic, aliphatic ring system with one another;

i is on each occurrence 0, 1 or 2;

m is 0 or 1, preferably 0;

o, p, r are on each occurrence, identically or differently, 0, 1 or 2, preferably 0;

n, q are on each occurrence, identically or differently, 0, 1 or 2, preferably 0 or 1;

s, t, u are on each occurrence, identically or differently, 0 or 1;

where u+t+s≤2.

The above-mentioned compound may also be in the form of a mixture of two or more substitution isomers.

In an embodiment of the invention, the above-mentioned preferences can be combined with one another as desired.

Examples of preferred structures of the compound of the formula (1) are indicated in the following table. The compounds are based on the basic structures (6a), (7a), (8a), (10a), (15a) and (21a). Merged cells mean that the radicals are connected to one another via a group E.

| Structure | Basic structure | i ($Ar^S$) | $Ar^1$ | $Ar^2$ |
|---|---|---|---|---|
| 6a-1-1 | 6a | 0 | Ar-9b | Ar-2a |
| 6a-1-2 | 6a | 0 | Ar-29b | Ar-2a |
| 6a-1-3 | 6a | 0 | Ar-1a | Ar-2a |

| Structure | Basic structure | i (Ar⁵) | Ar¹ | Ar² |
|---|---|---|---|---|
| 6a-1-4 | 6a | 0 | Ar-2a | Ar-2a |
| 6a-1-5 | 6a | 0 | Ar-17a1 | Ar-2a |
| 6a-1-6 | 6a | 0 | Ar-12a | Ar-2a |
| 6a-1-7 | 6a | 0 | Ar-13c | Ar-2a |
| 6a-1-8 | 6a | 0 | Ar-2c | Ar-9b |
| 6a-1-9 | 6a | 0 | Ar-9b | Ar-9b |
| 6a-1-10 | 6a | 0 | Ar1-5a | |
| 6a-1-11 | 6a | 0 | Ar-2a | Ar-2a |
| 6a-1-12 | 6a | 0 | Ar-2c | Ar-9b |
| 6a-1-13 | 6a | 0 | Ar-2a | Ar-1a |
| 6a-1-14 | 6a | 0 | Ar1-14a | |
| 6a-1-15 | 6a | 0 | Ar1-15a | |
| 6a-1-16 | 6a | 0 | Ar1-15b | |
| 6a-1-17 | 6a | 0 | Ar1-16 | |
| 6a-1-18 | 6a | 0 | Ar1-17a | |
| 6a-1-19 | 6a | 0 | Ar1-18 | |
| 6a-1-20 | 6a | 0 | Ar-8b | Ar-9b |
| 6a-1-21 | 6a | 0 | Ar-8a | Ar-9b |
| 6a-1-22 | 6a | 0 | Ar-3e | Ar-9b |
| 6a-1-23 | 6a | 0 | Ar-2a | Ar-2a |
| 6a-1-24 | 6a | 0 | Ar-2a | Ar-3g |
| 6a-1-25 | 6a | 0 | Ar-2a | Ar-15c1 |
| 6a-1-26 | 6a | 0 | Ar-9b | Ar-30a |
| 6a-1-27 | 6a | 0 | Ar-28b | Ar-2a |
| 6a-1-28 | 6a | 0 | Ar-1a Ar-15c1 | |
| 6a-1-29 | 6a | 0 | Ar-1a Ar-17a1 | |
| 6a-1-30 | 6a | 0 | Ar-11c | Ar-17a1 |
| 6a-1-31 | 6a | 0 | Ar-1a | Ar-30b |
| 6a-1-32 | 6a | 0 | Ar-1a | Ar-1a |
| 6a-1-33 | 6a | 0 | Ar-1a | Ar-13a |
| 6a-2-1 | 6a | 2 (Ar3-12a; Ar3-1a) | Ar-2a | Ar-2a |
| 6a-2-2 | 6a | 2 (Ar3-12a; Ar3-1b) | Ar-2a | Ar-2a |
| 6a-2-3 | 6a | 2 (Ar3-12a; Ar3-1b) | Ar-9b | Ar-2a |
| 6a-2-4 | 6a | 1 (Ar3-1b) | Ar-2a | Ar-2a |
| 6a-2-5 | 6a | 1 (Ar3-1b) | Ar-2b | Ar-2a |
| 6a-2-6 | 6a | 1 (Ar3-1b) | Ar-2b | Ar-2a |
| 6a-2-7 | 6a | 2 (Ar-1a, Ar2-7) | | Ar-1a |
| 6a-2-8 | 6a | 2 (Ar-1a, Ar2-7) | | Ar-1a |
| 6a-2-9 | 6a | 2 (Ar-1a, Ar2-7) | | Ar-2c |
| 6a-2-10 | 6a | | 1 (Ar2-9c) | Ar-2a |
| 6a-2-11 | 6a | | 1 (Ar2-9c) | Ar-2a |
| 6a-2-12 | 6a | | 1 (Ar2-9c) | Ar-2b |
| 6a-2-13 | 6a | 1 (Ar3-1a) | Ar-2a | Ar-2a |
| 6a-2-14 | 6a | 1 (Ar3-1a) | Ar-2a | Ar-2a |
| 6a-2-15 | 6a | 1 (Ar3-1a) | Ar-2a | Ar-2b |
| 6a-2-16 | 6a | 1 (Ar3-1a) | Ar-2a | Ar-17a2 |
| 6a-2-17 | 6a | 1 (Ar3-1a) | Ar-2a | Ar-17a3 |
| 6a-2-18 | 6a | 1 (Ar3-1a) | Ar-2a | Ar-17c2 |
| 6a-2-19 | 6a | 1 (Ar3-1a) | Ar-2a | Ar-9b |
| 6a-2-20 | 6a | 1 (Ar3-1a) | Ar-2b | Ar-9b |
| 6a-2-21 | 6a | 1 (Ar3-1a) | Ar-2b | Ar-10b |
| 6a-2-22 | 6a | 2 (Ar3-1b, Ar2-7) | | Ar-1a |
| 6a-2-23 | 6a | 2 (Ar3-1b, Ar2-7) | | Ar-2a |
| 6a-2-24 | 6a | 2 (Ar3-1b, Ar2-7) | | Ar-1a |
| 7a-1-1 | 7a | 0 | Ar-2a | Ar-2a |
| 7a-1-2 | 7a | 0 | Ar-9b | Ar-2c |
| 8a-1-1 | 8a | 0 | Ar1-16 Ar1-16 | |
| 8a-1-2 | 8a | 0 | Ar1-16 Ar1-17a | |
| 8a-1-3 | 8a | 0 | Ar1-16 Ar1-14a | |
| 8a-1-4 | 8a | 0 | Ar1-14a Ar1-14a | |
| 8a-1-5 | 8a | 0 | Ar1-14a Ar1-13 | |
| 8a-1-6 | 8a | 0 | Ar1-14b Ar1-14b | |
| 10a-1-1 | 10a | 0 | Ar-2a | Ar-2a |
| 10a-2-1 | 10a | 1 (Ar3-1a) | Ar-2a | Ar-9b |
| 10a-2-2 | 10a | 1 (Ar3-1a) | Ar-2b | Ar-9b |
| 10a-2-3 | 10a | 1 (Ar3-1b) | Ar-4a | Ar-9b |
| 10a-2-4 | 10a | 1 (Ar3-1a) | Ar-2a | Ar-2a |
| 10a-2-5 | 10a | 1 (Ar3-1a) | Ar-1a | Ar-2a |
| 10a-2-6 | 10a | 1 (Ar3-1a) | Ar-2b | Ar-2a |
| 10a-2-7 | 10a | 1 (Ar3-1b) | Ar-2a | Ar-2a |
| 10a-2-8 | 10a | 1 (Ar3-1b) | Ar-2a | Ar-2a |
| 10a-2-9 | 10a | 1 (Ar3-1b) | Ar-2a | Ar-3a |
| 10a-2-10 | 10a | 2 (Ar3-1b, Ar2-7) | | Ar-1a |
| 10a-2-11 | 10a | 2 (Ar3-1b, Ar2-9c) | | Ar-1a |
| 15a-1-1 | 15a | 0 | Ar-2a | Ar-2a |
| 15a-1-2 | 15a | 0 | Ar-2a | Ar-2a |
| 15a-2-1 | 15a | 1 (Ar3-1a) | Ar-2a | Ar-2a |
| 15a-2-2 | 15a | 1 (Ar3-1a) | Ar-9b | Ar-2a |
| 15a-2-3 | 15a | 1 (Ar3-1a) | Ar-1a | Ar-2a |
| 15a-2-4 | 15a | 1 (Ar3-1b) | Ar-2a | Ar-2a |
| 15a-2-5 | 15a | 1 (Ar3-1b) | Ar-2a | Ar-9b |
| 15a-2-6 | 15a | 1 (Ar3-1a) | Ar-2a | Ar-2b |
| 15a-2-7 | 15a | 2 (Ar3-1a, Ar2-7) | | Ar-1a |
| 15a-2-8 | 15a | 2 (Ar3-1b, Ar2-7) | | Ar-1a |
| 15a-2-9 | 15a | 2 (Ar3-1b, Ar2-7) | | Ar-2b |
| 21a-1-1 | 21a | 0 | Ar-2a | Ar-2a |
| 21a-1-2 | 21a | 0 | Ar-2c | Ar-9b |
| 21a-1-3 | 21a | 0 | Ar-17a1 | Ar-2a |
| 21a-1-4 | 21a | 0 | Ar-2a | Ar-2a | n and q in the formulae here can adopt the value 0 or 1. The radicals $R^3$ and $R^6$ in the formulae are preferably selected from the groups of the formulae (Ar-1) to (Ar-33), particularly preferably from the groups of the formulae (Ar-1) to (Ar-10).

Examples of preferred compounds in accordance with the embodiments shown above, or compounds as can preferably be employed in electronic devices, are the compounds of the following structures (1) to (98):

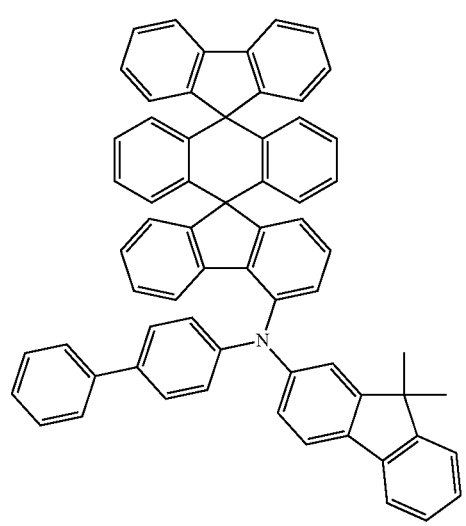

1

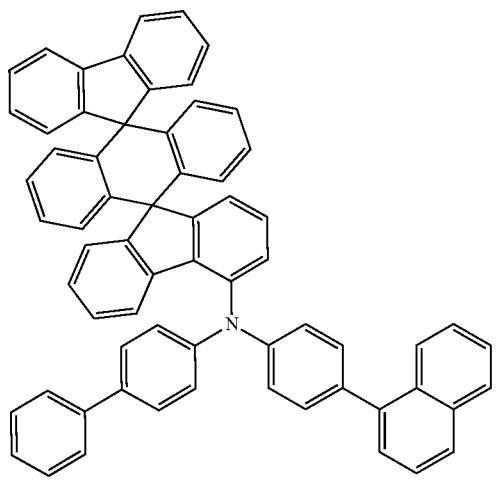
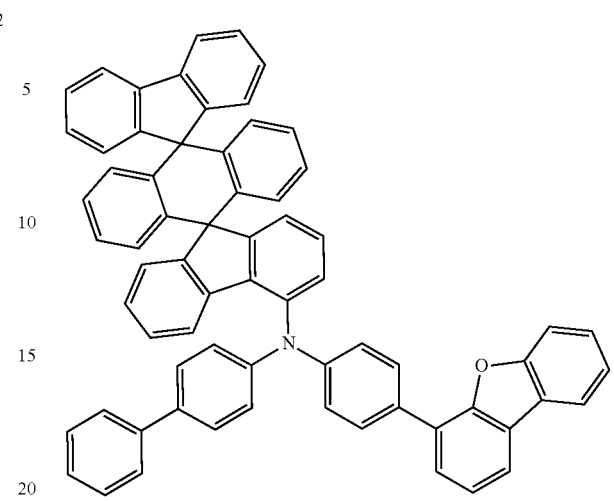
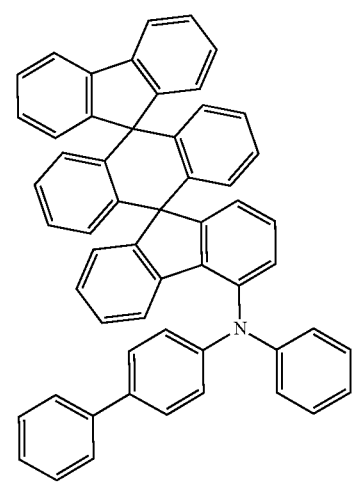
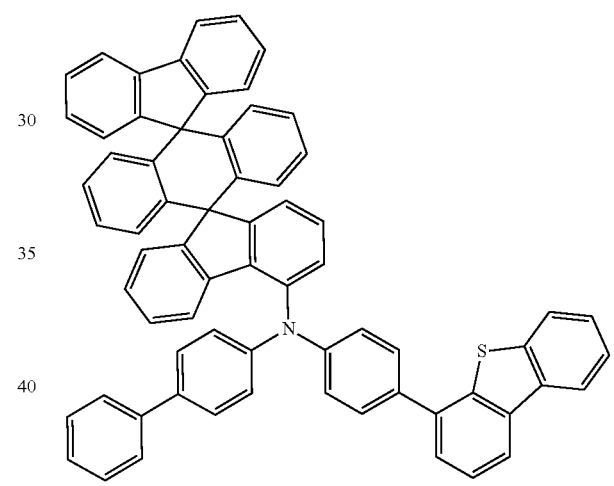
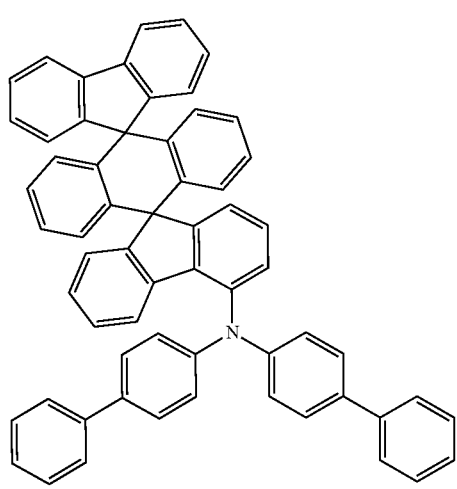
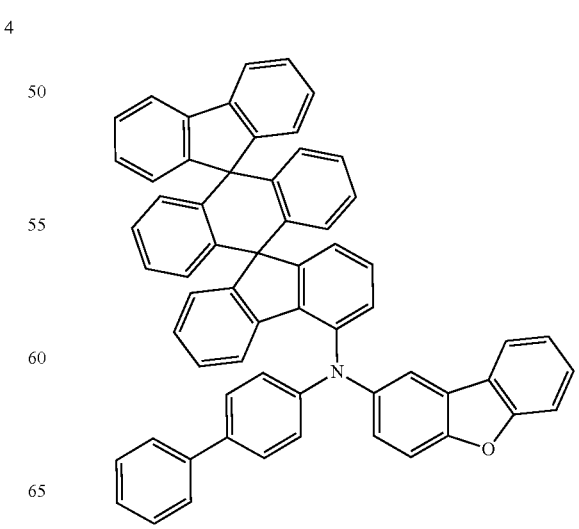

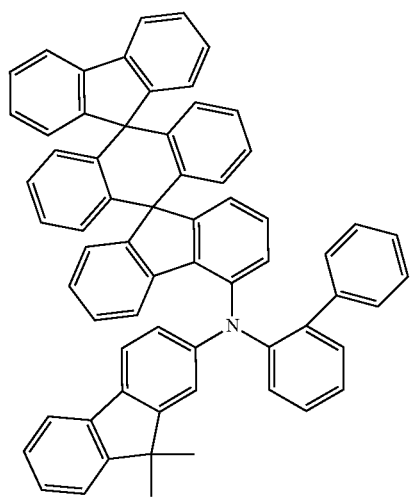
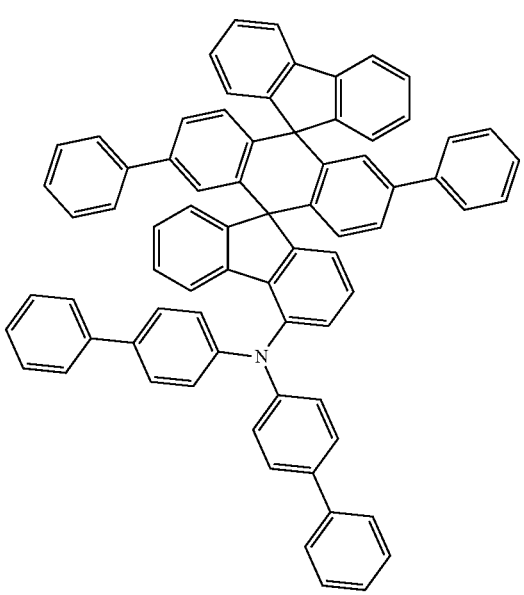
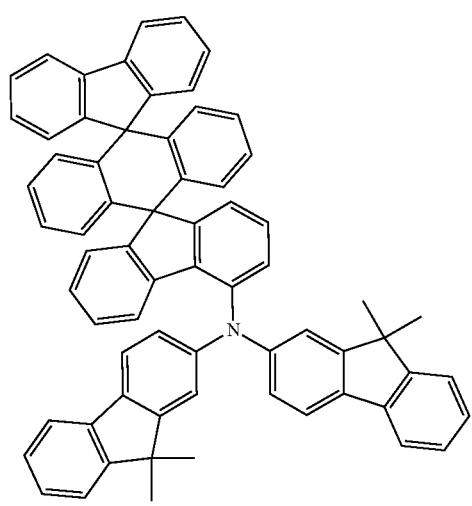
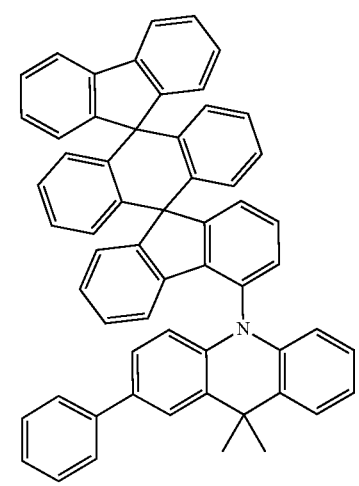
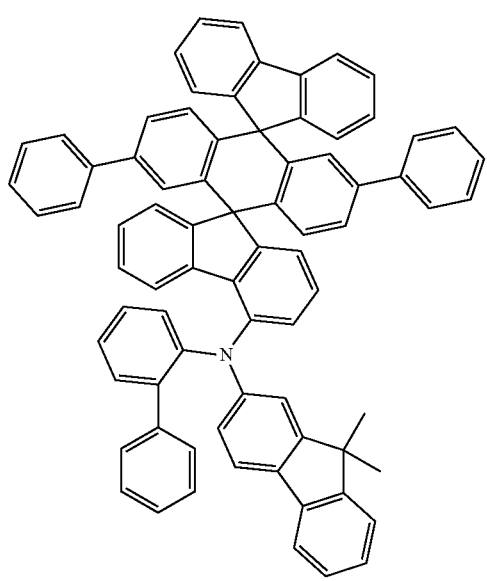

13
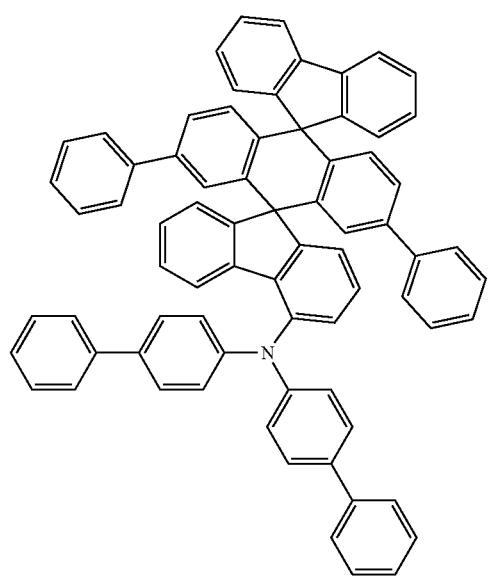
14
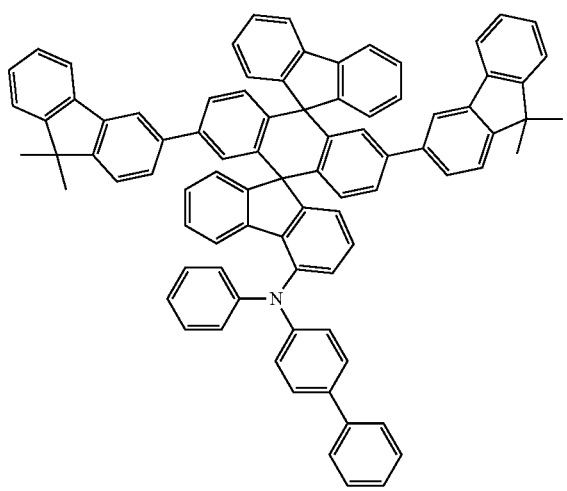
15
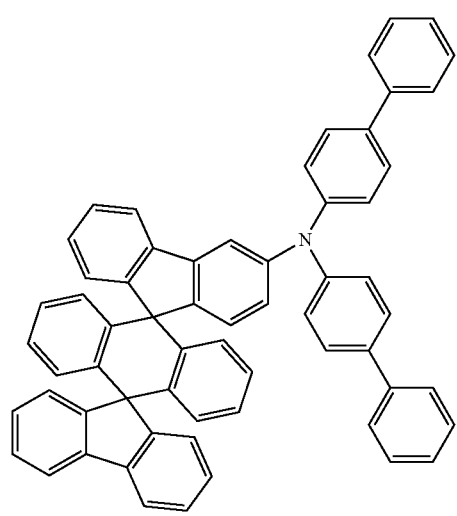
16
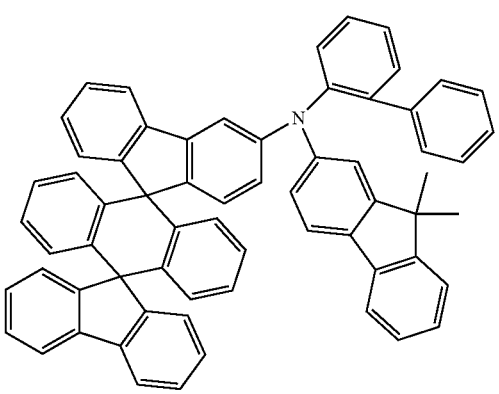
17
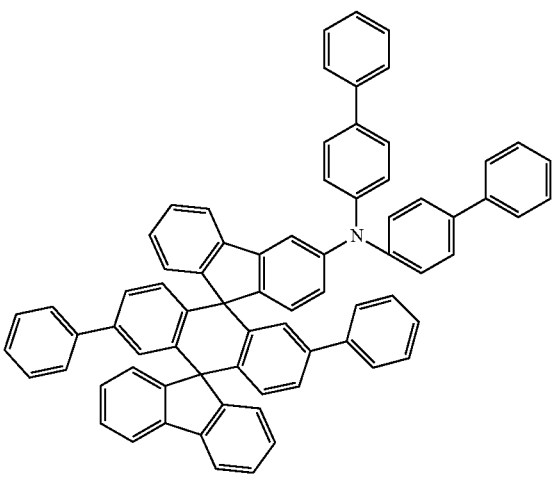
18

19
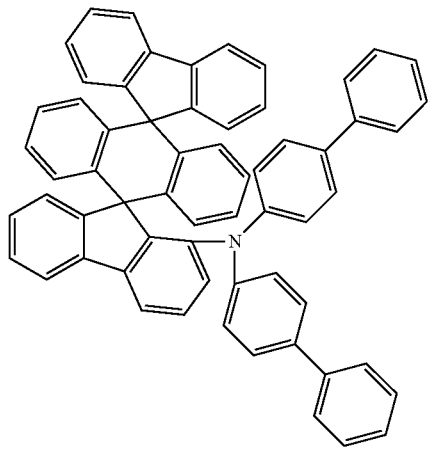
21
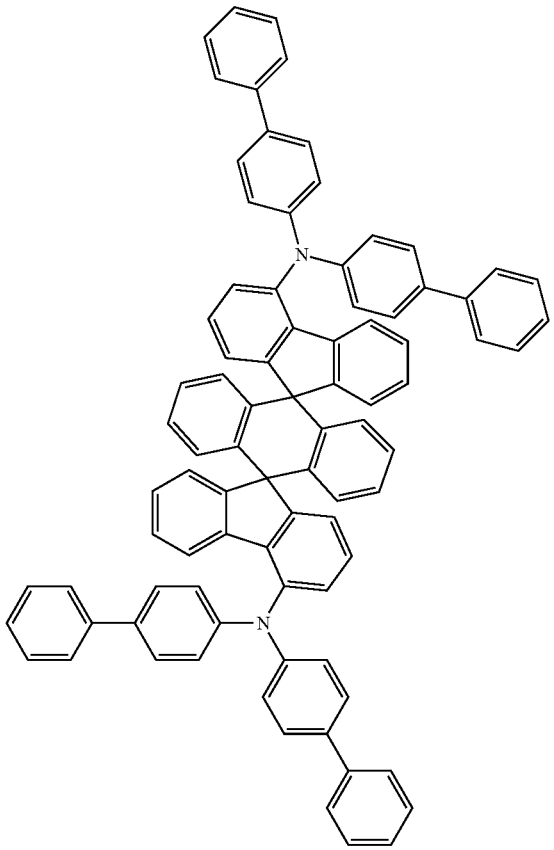
20
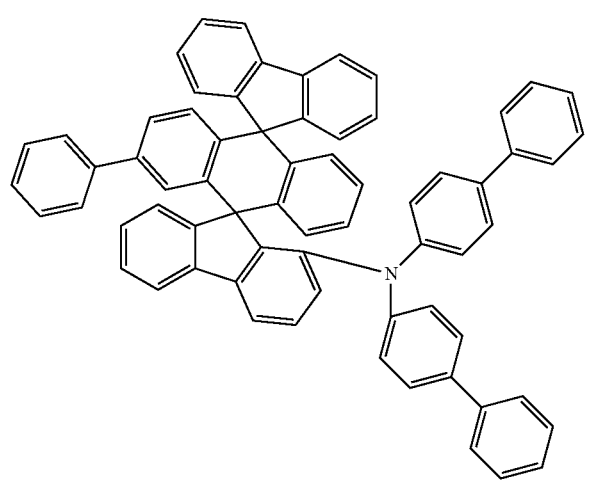
22
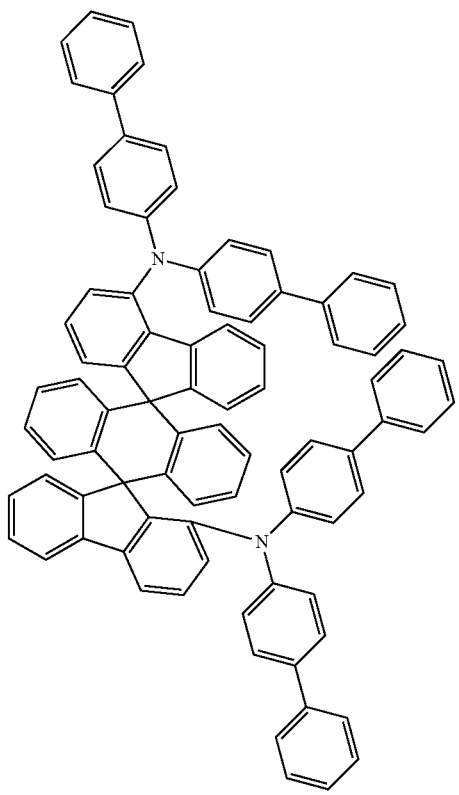

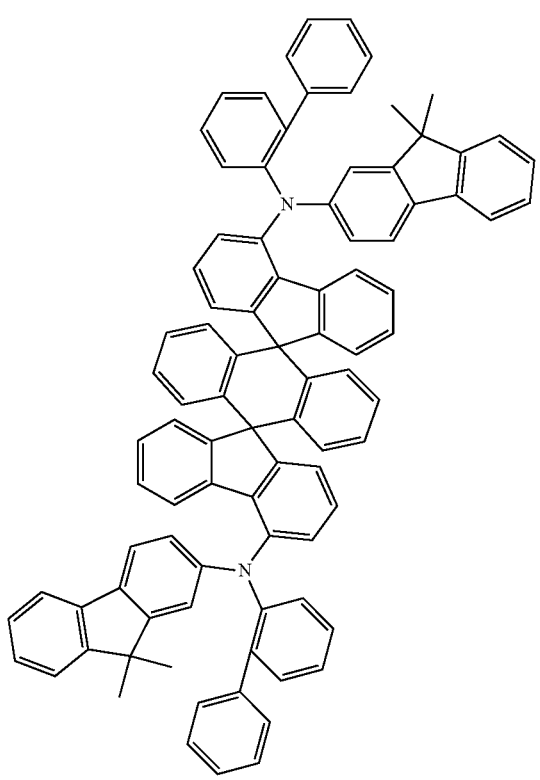
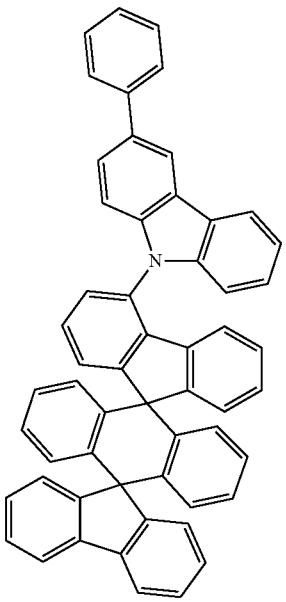

27
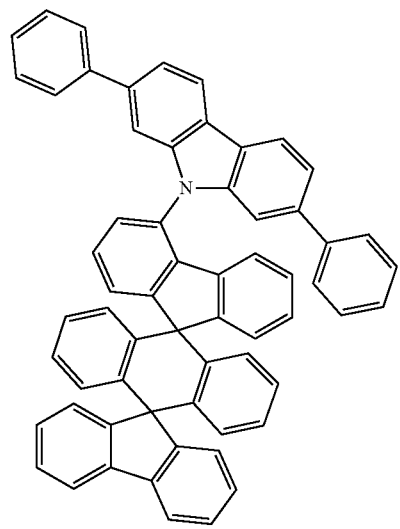
28
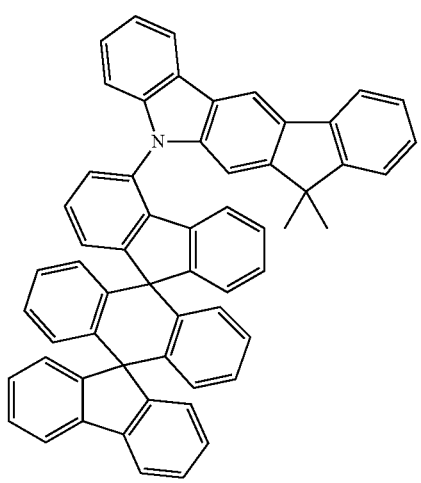
29
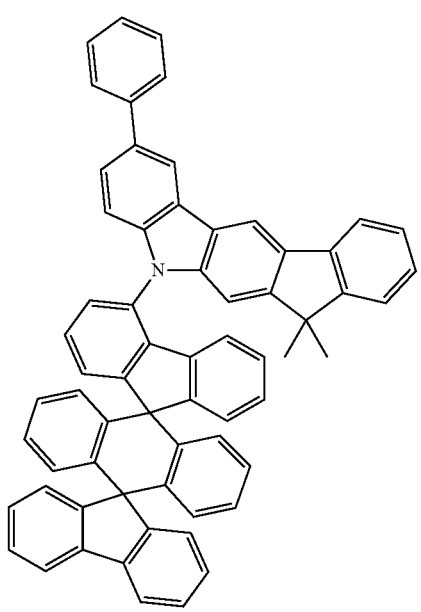
30
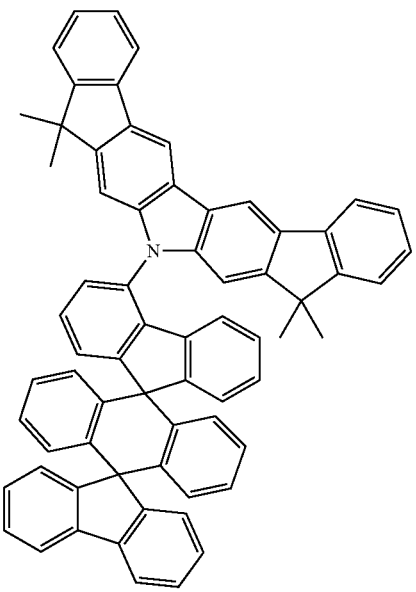
31
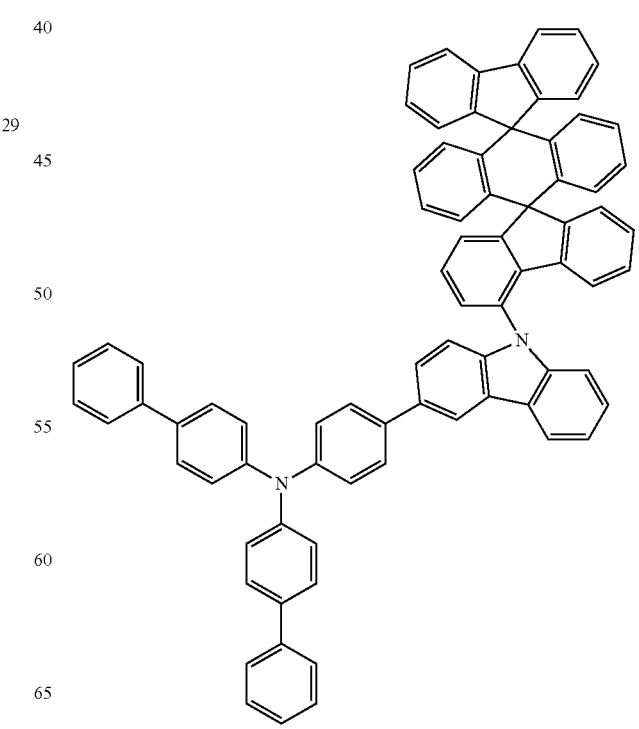

33
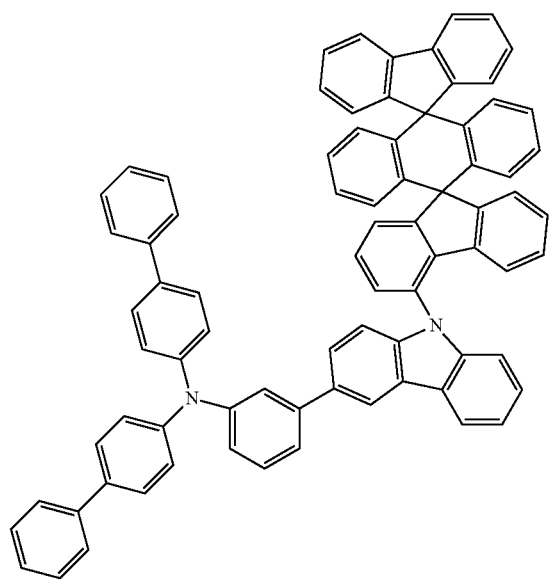
34
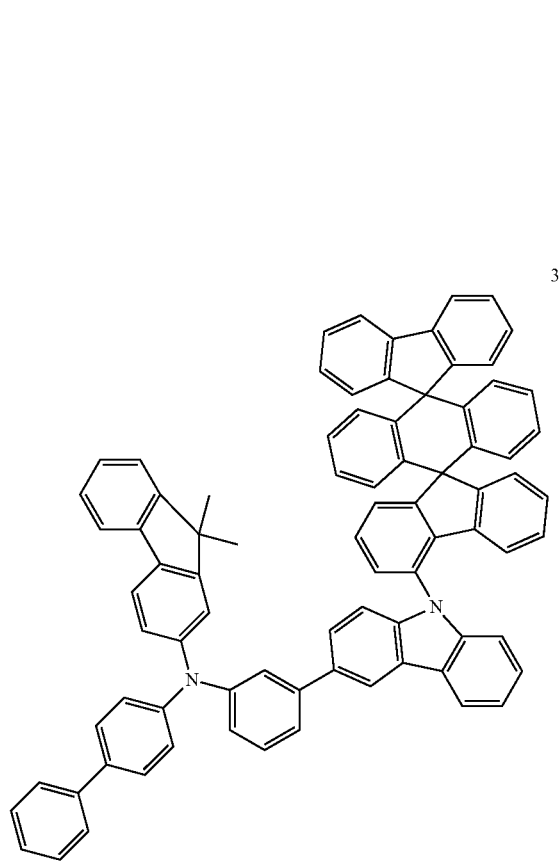
35
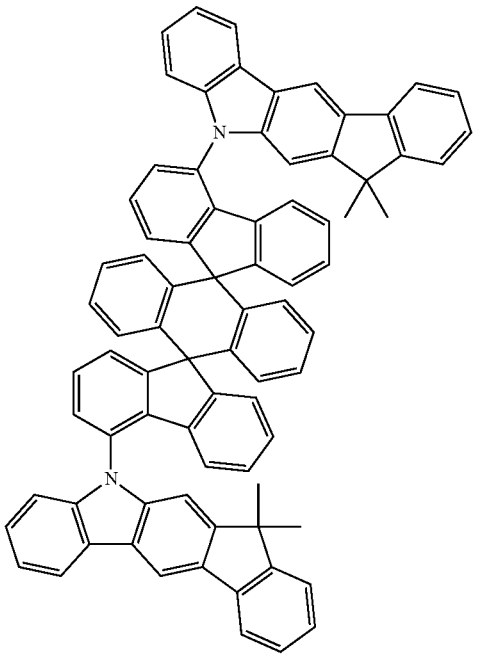
36
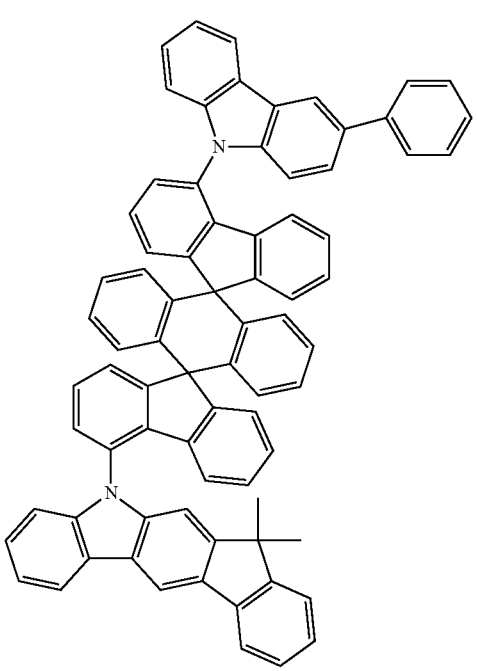

37
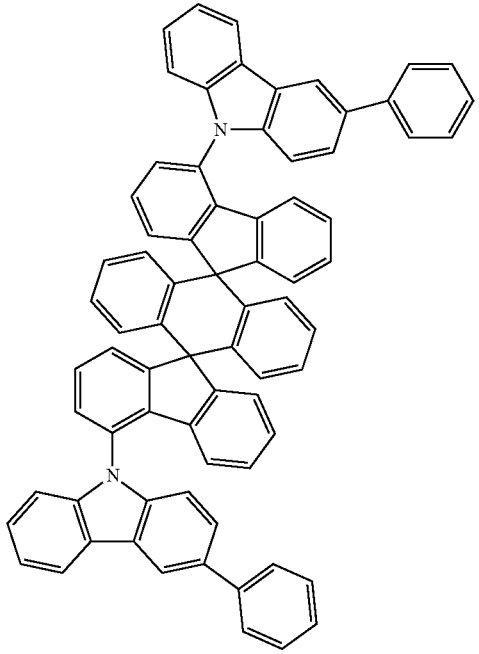
38
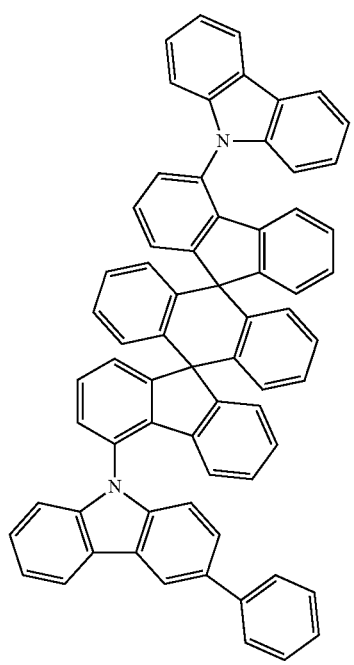
39
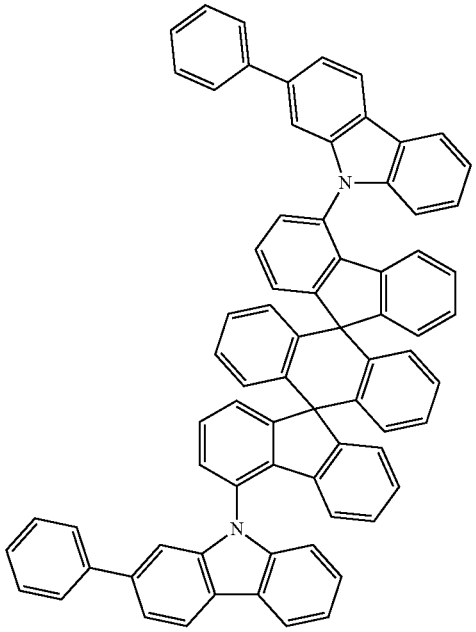
40
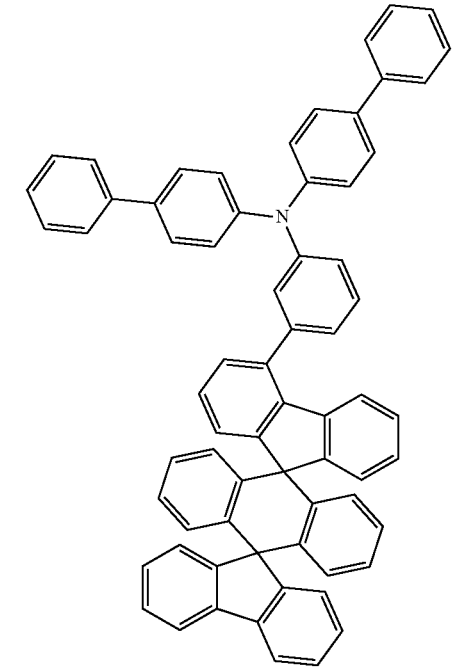

41
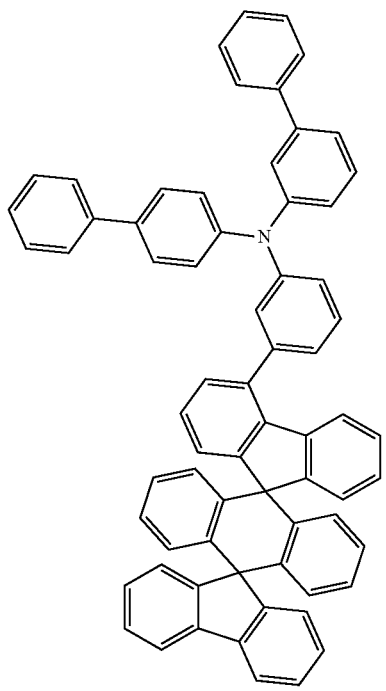
42
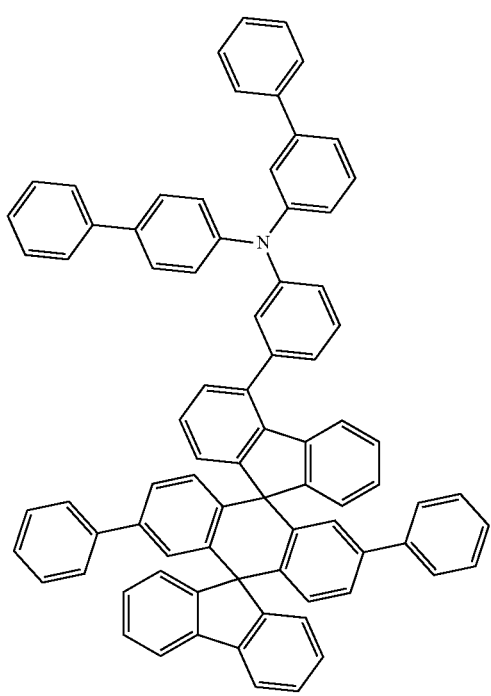
43
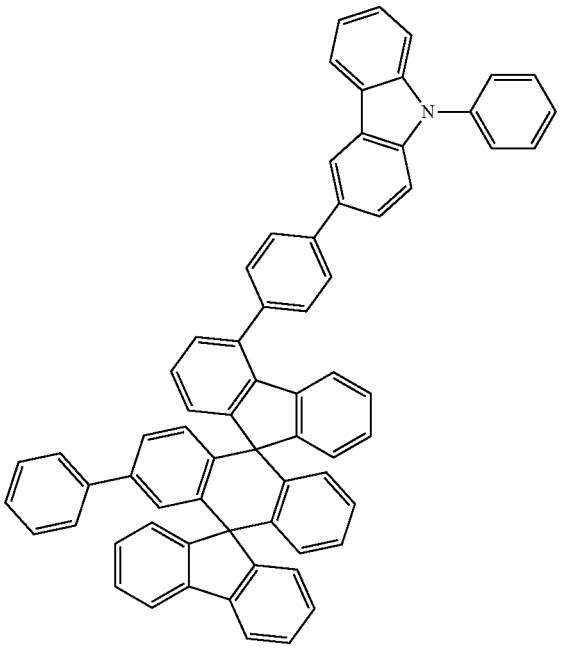
44
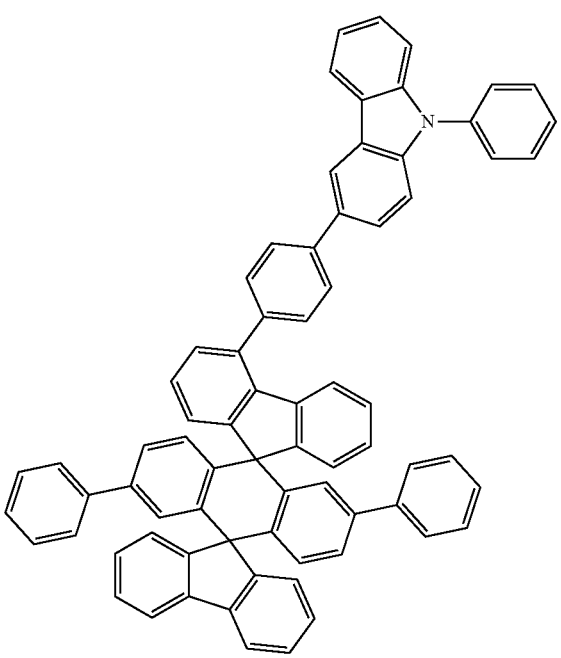

45
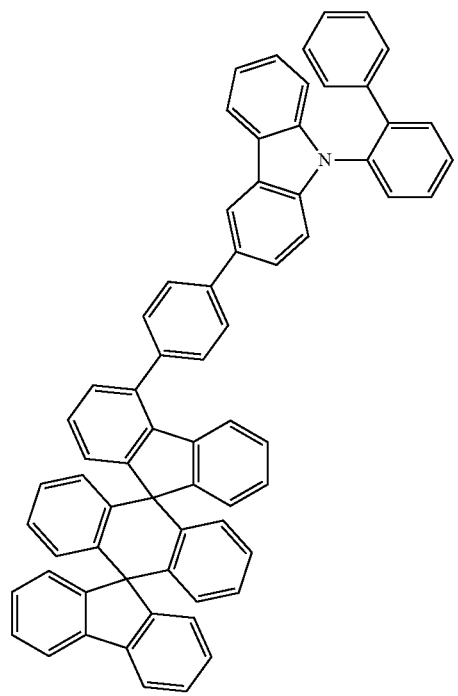
46
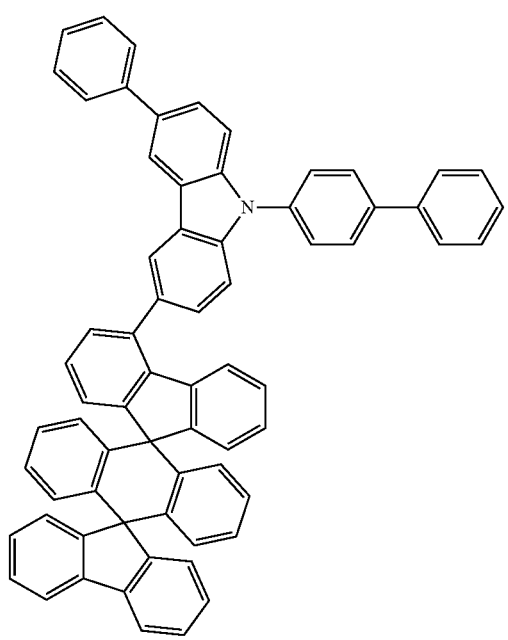
47
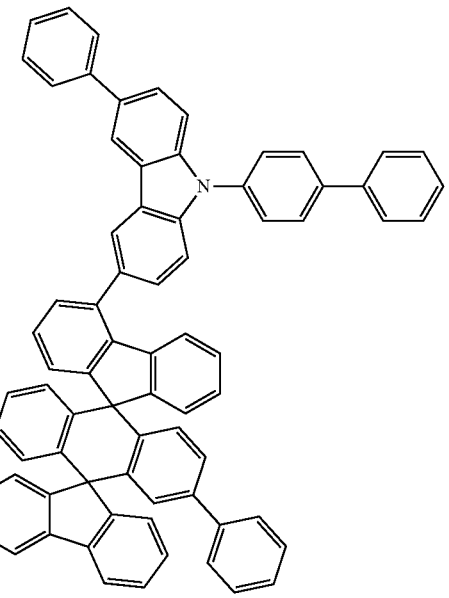
48
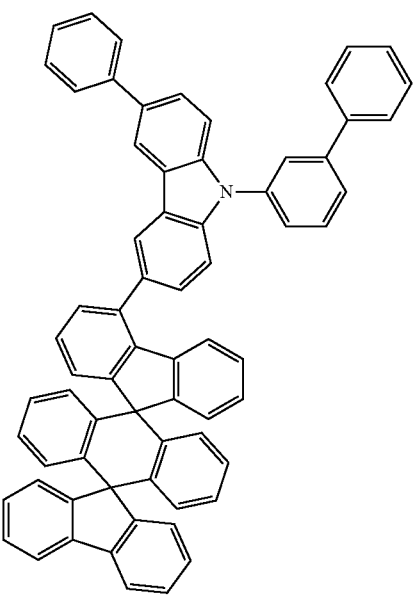

89
49
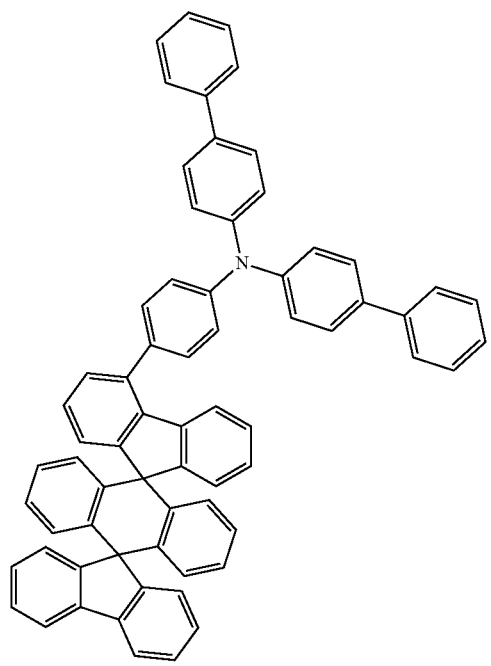
90
51
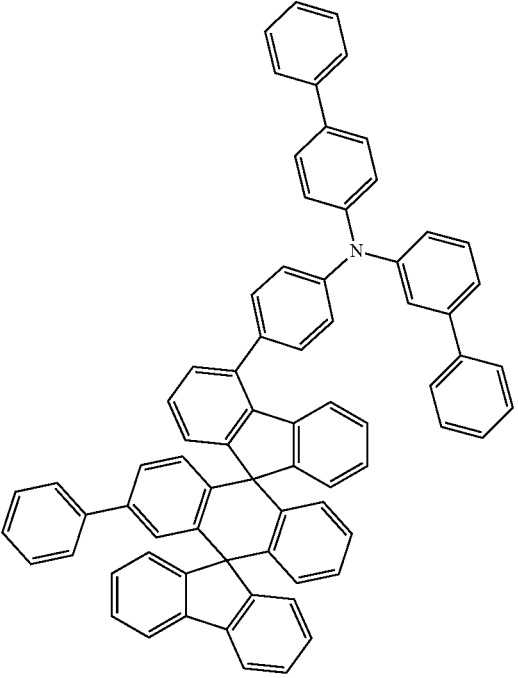
50
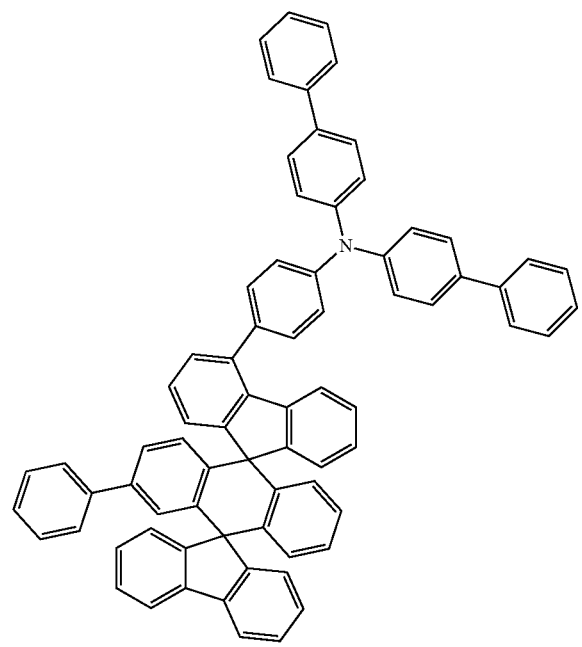
52
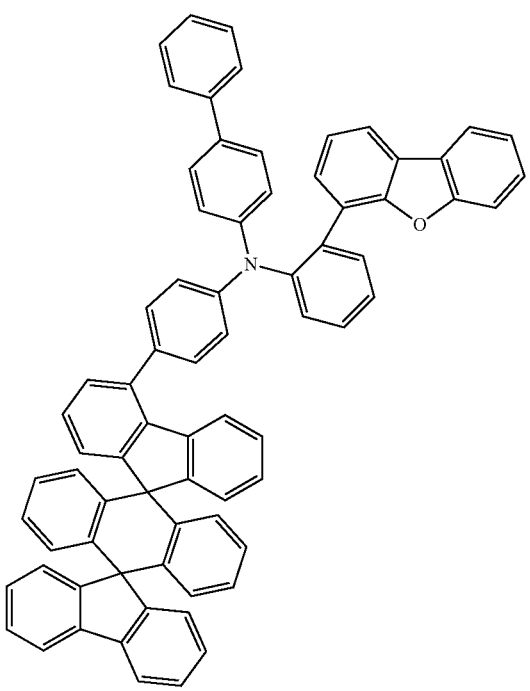

53
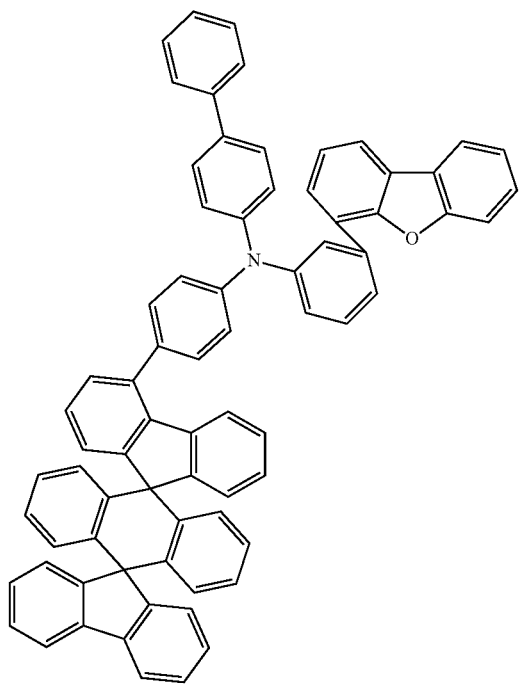
54
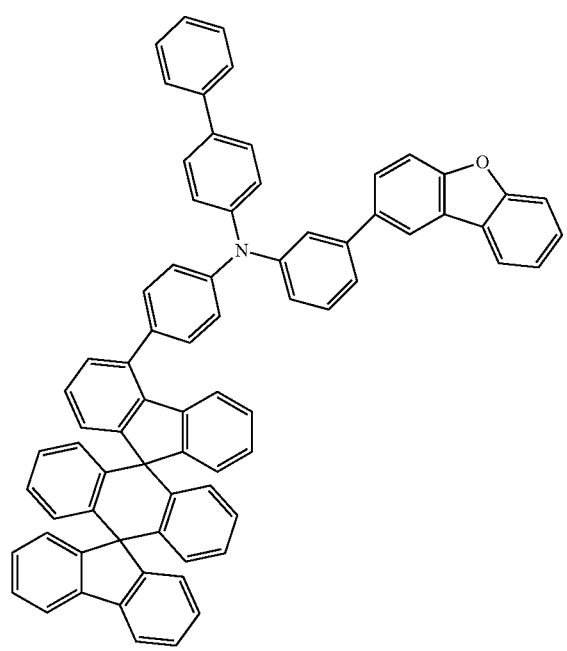
55
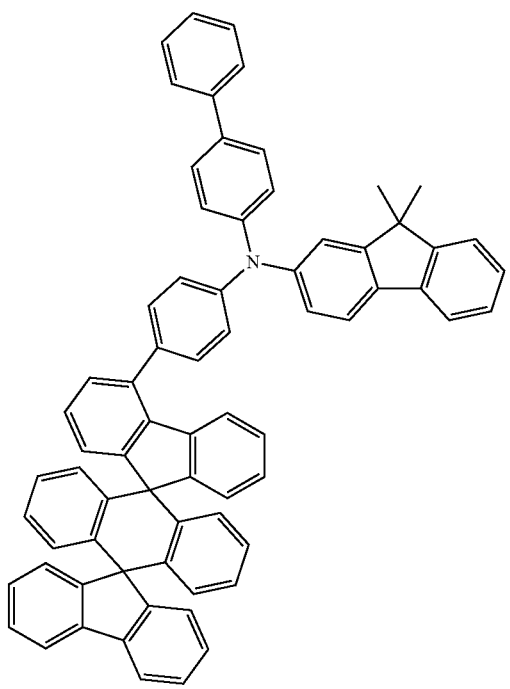
56
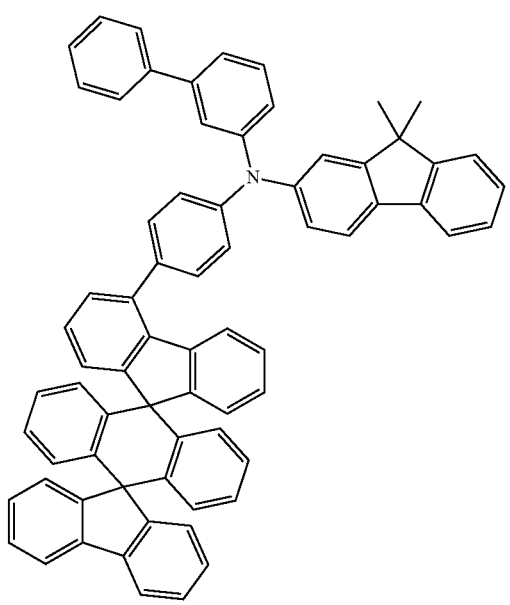

57
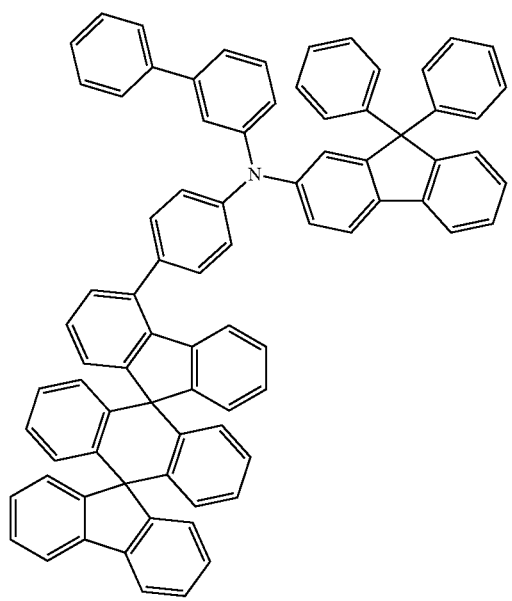
58
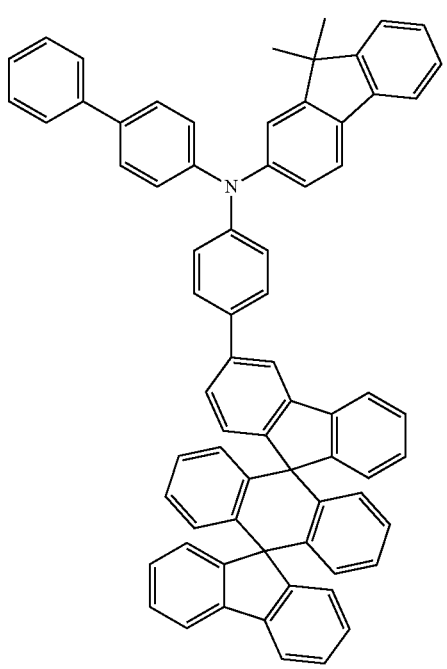
59
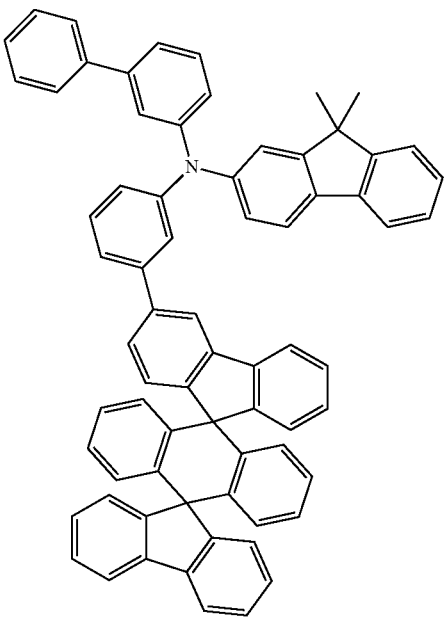
60
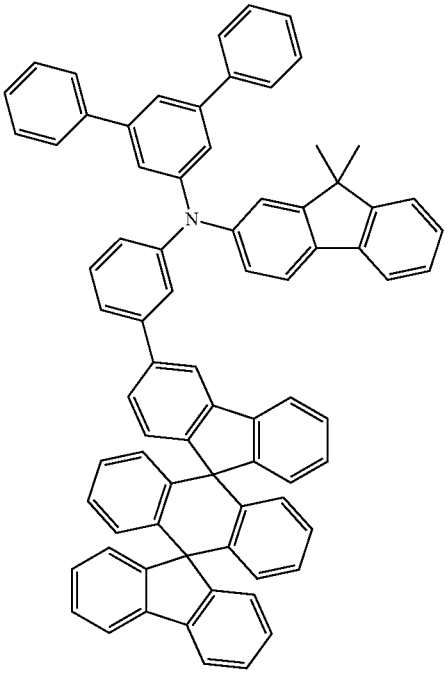

61
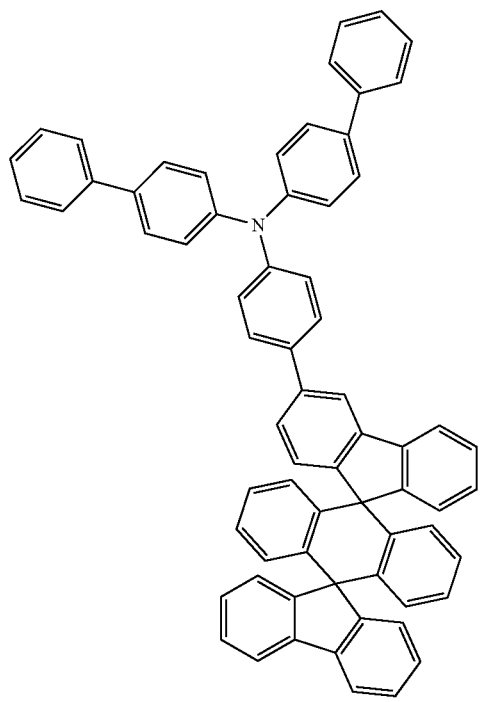
63
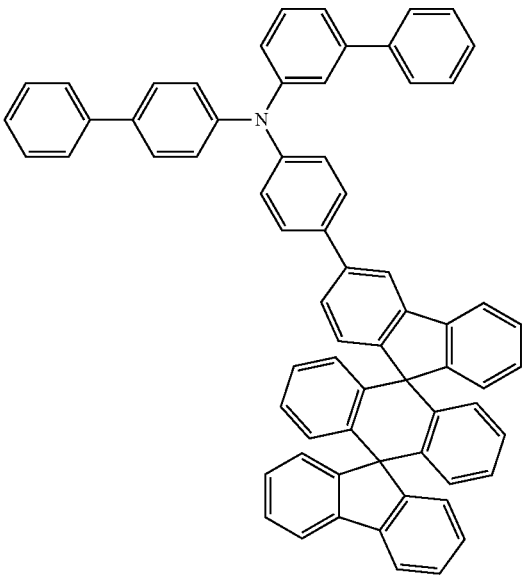
62
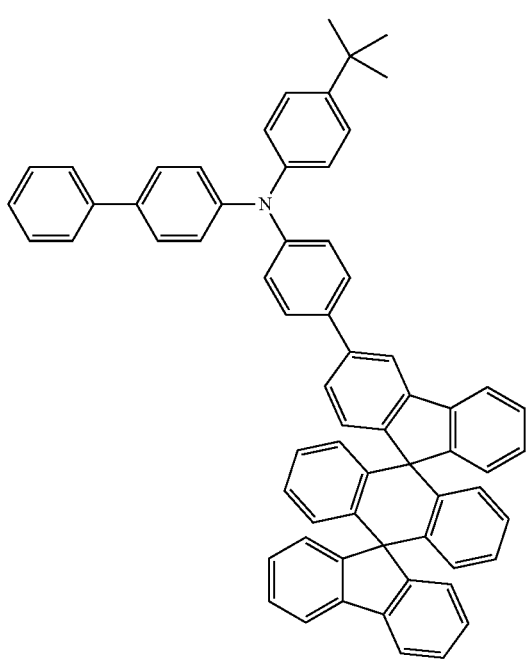
64
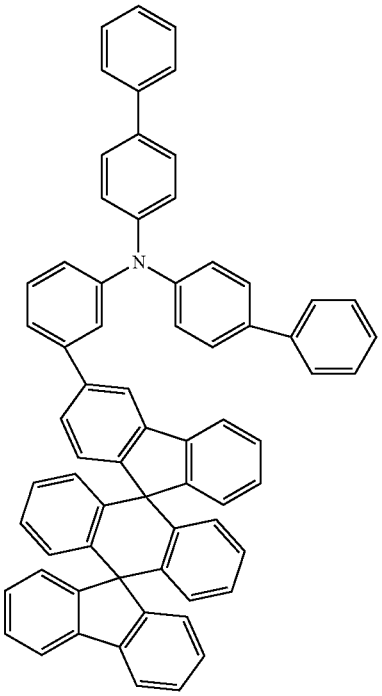

97
-continued
98
-continued
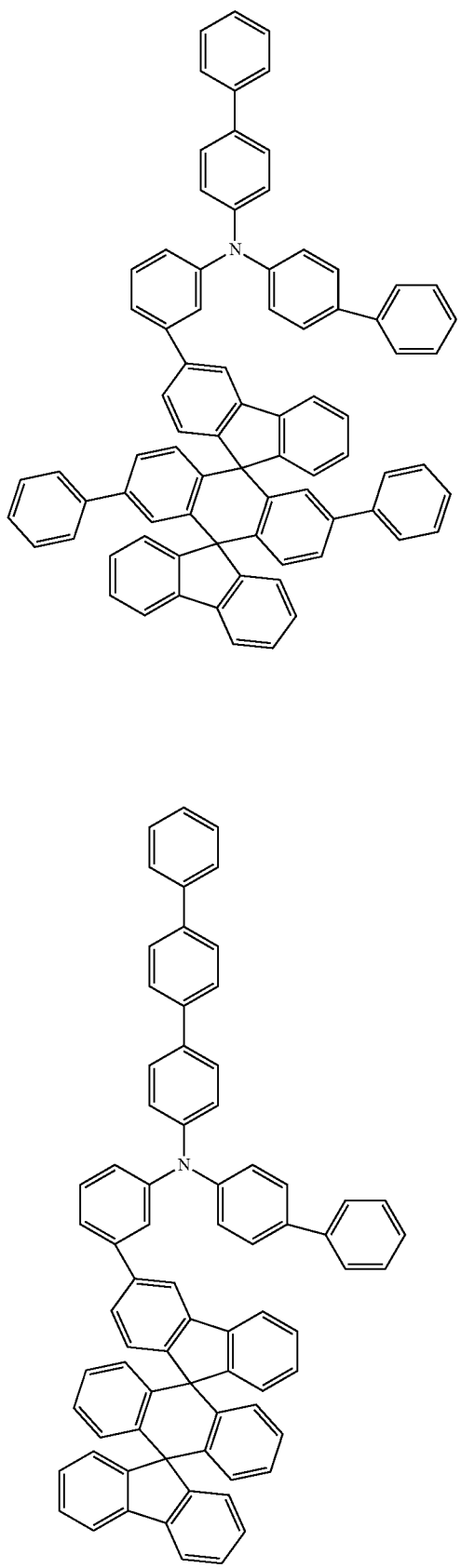
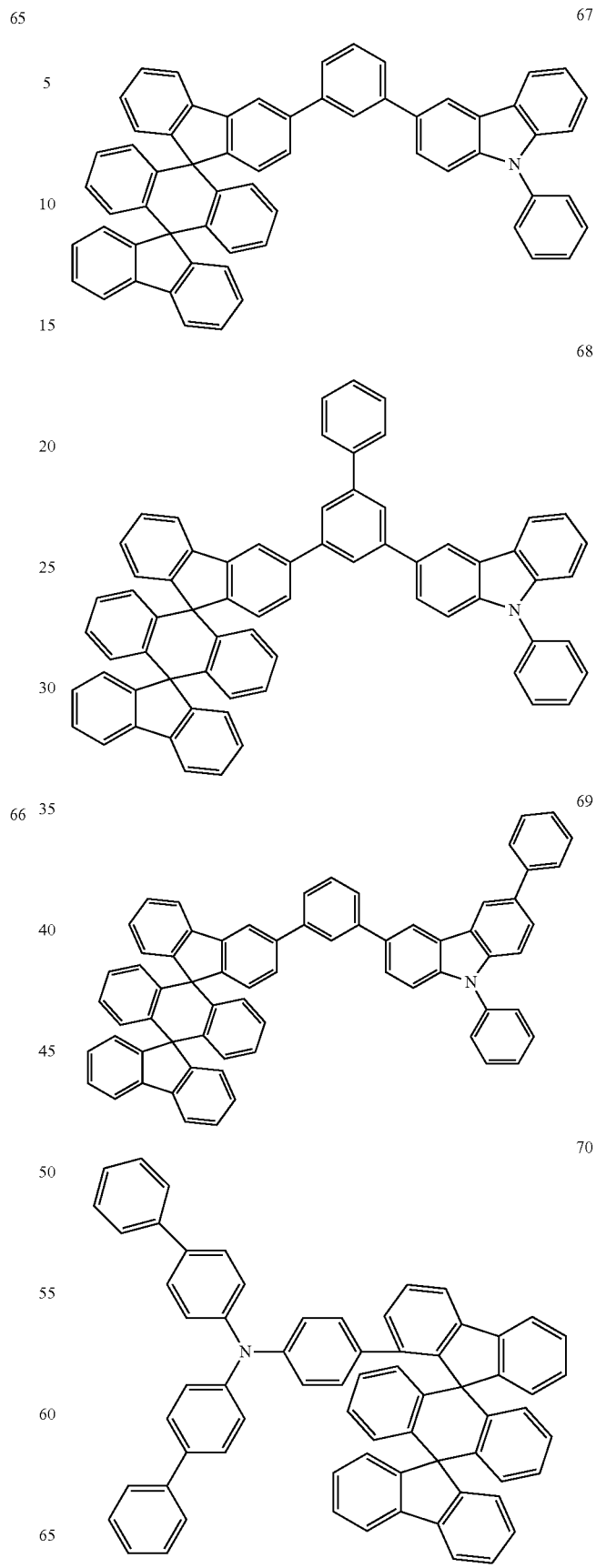

71
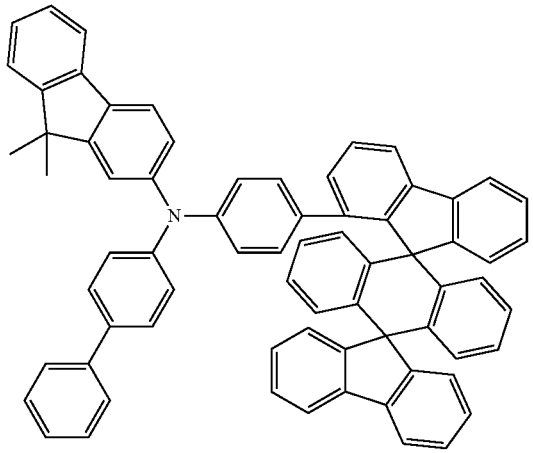
74
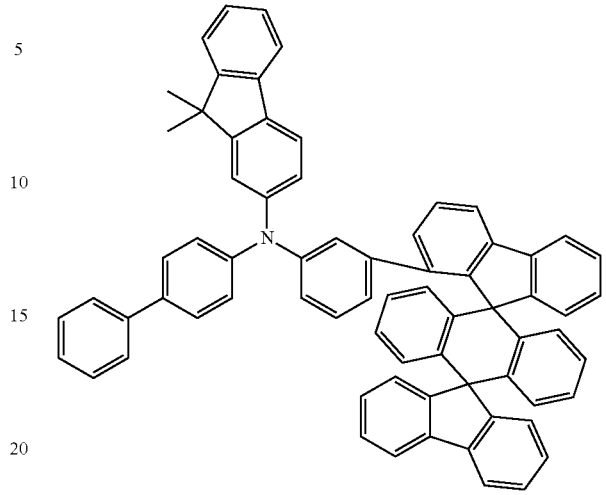
72
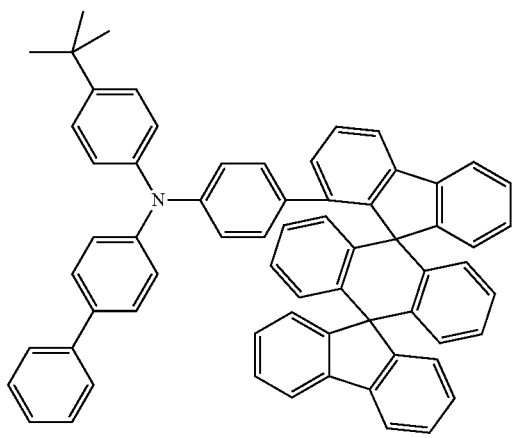
75
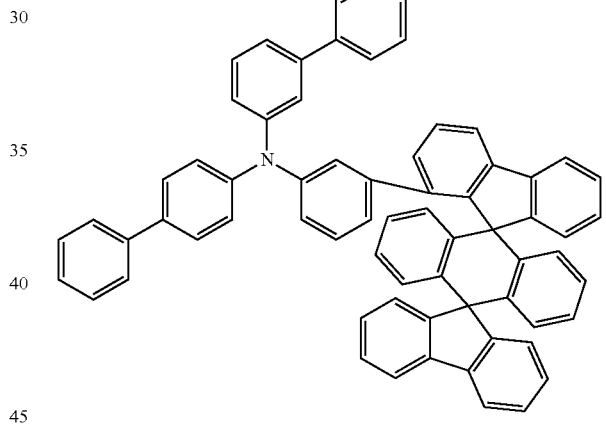
73
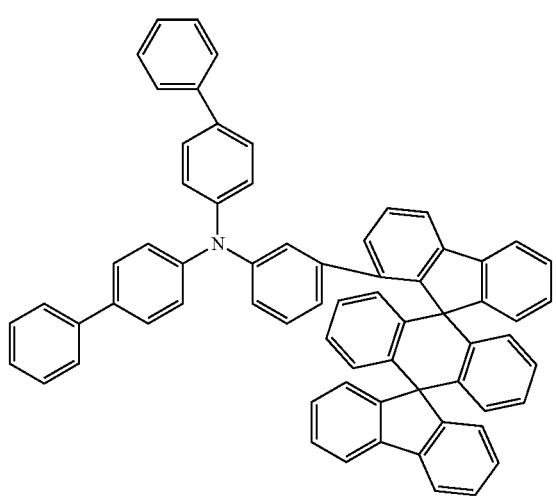
76
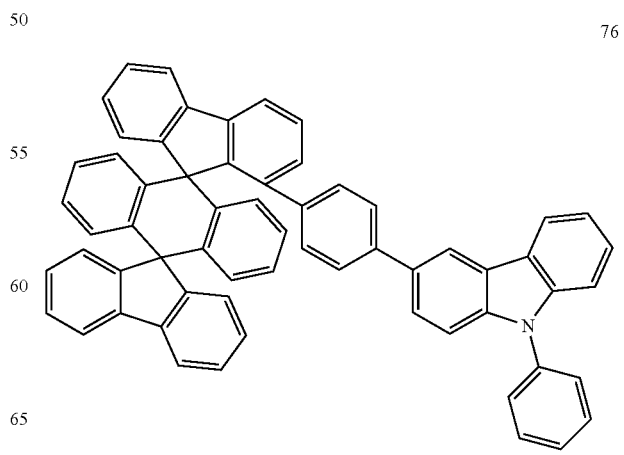

101
-continued
77
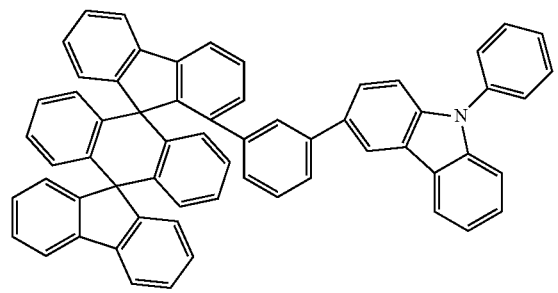
78
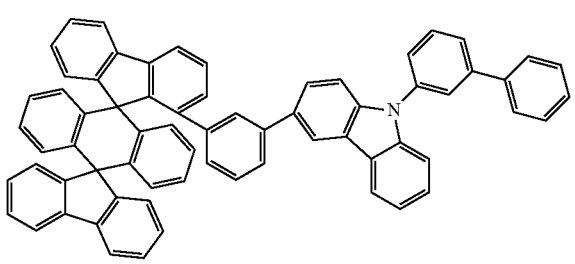
79
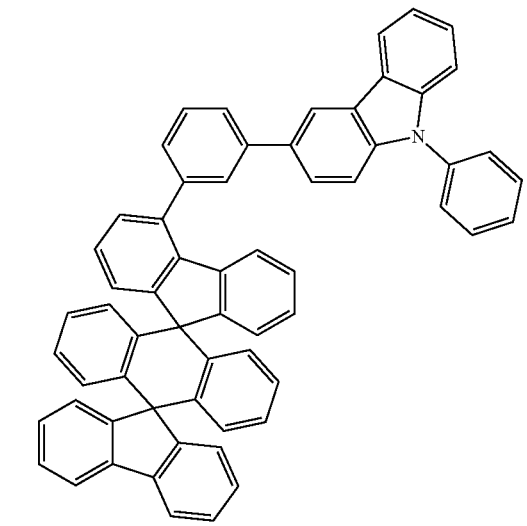
80
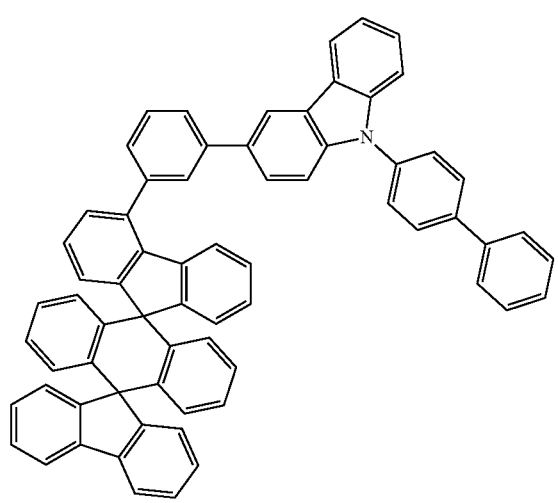
102
-continued
81
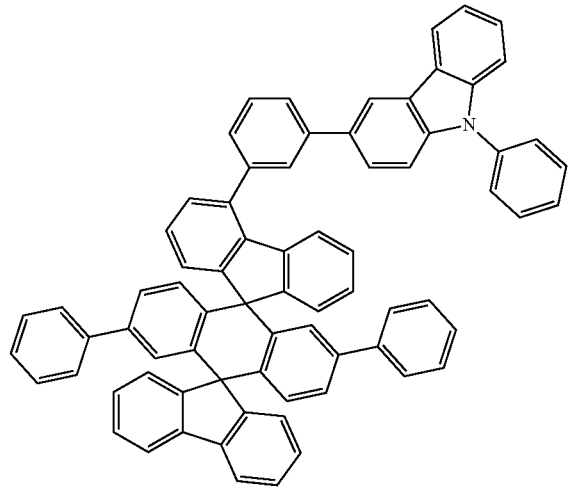
82
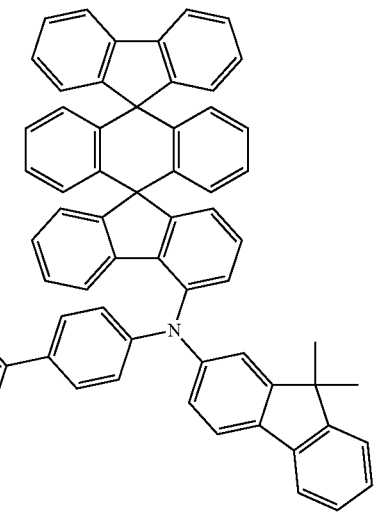
83
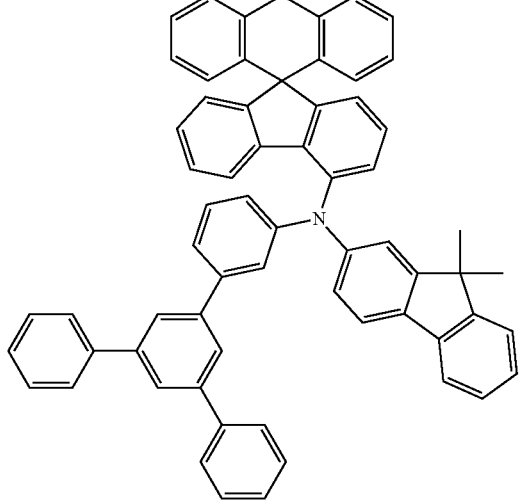

84
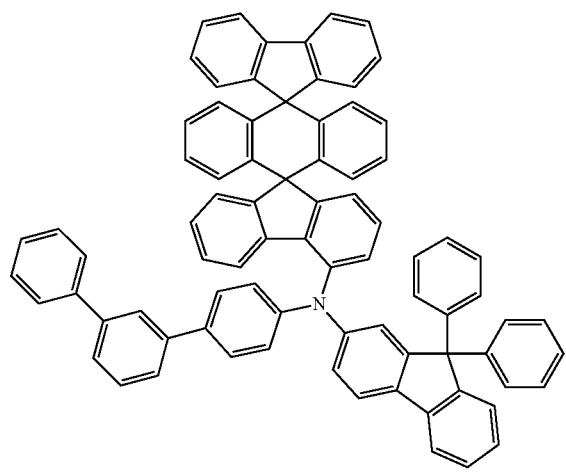
85
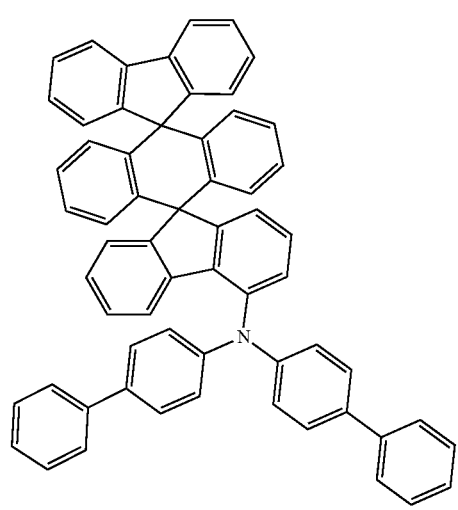
86
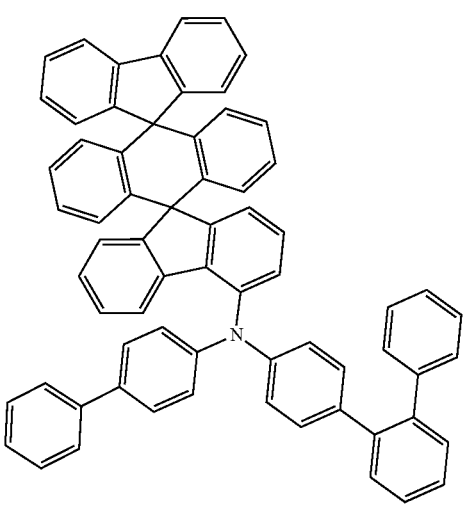
87
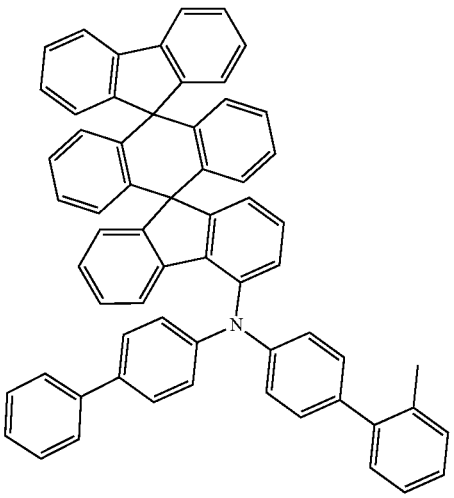
88
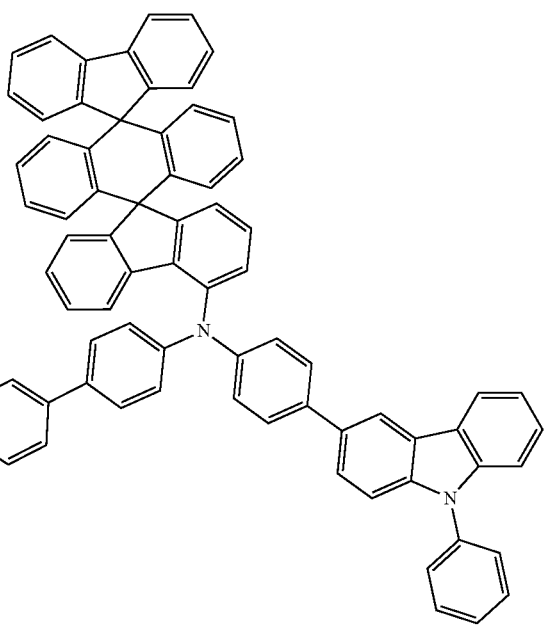

89
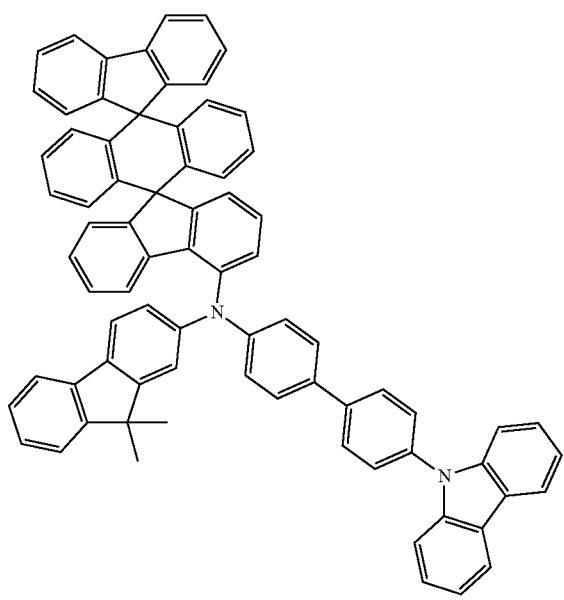
91
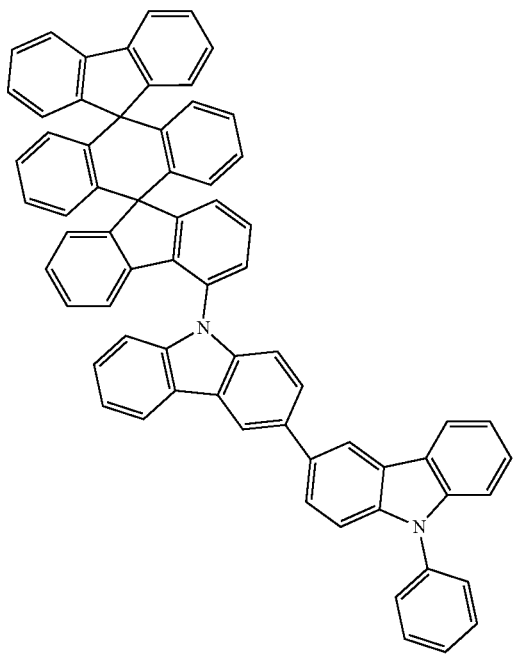
90
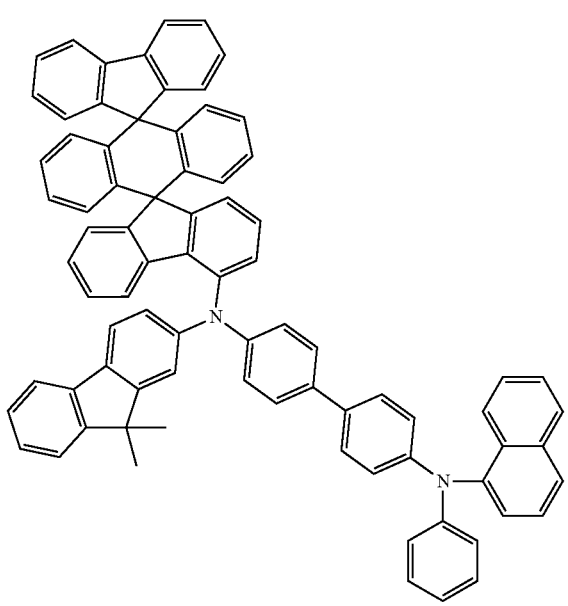
92
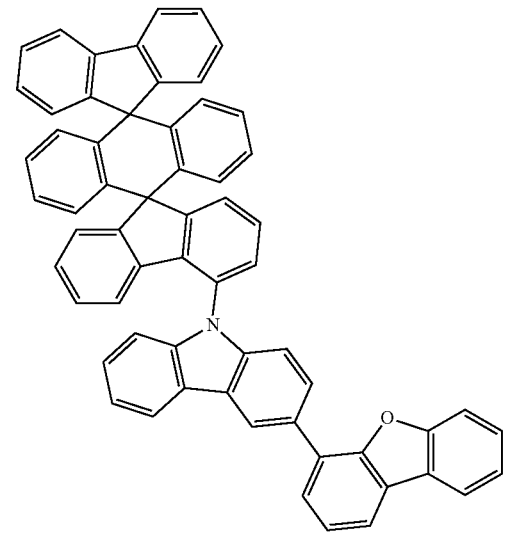

93
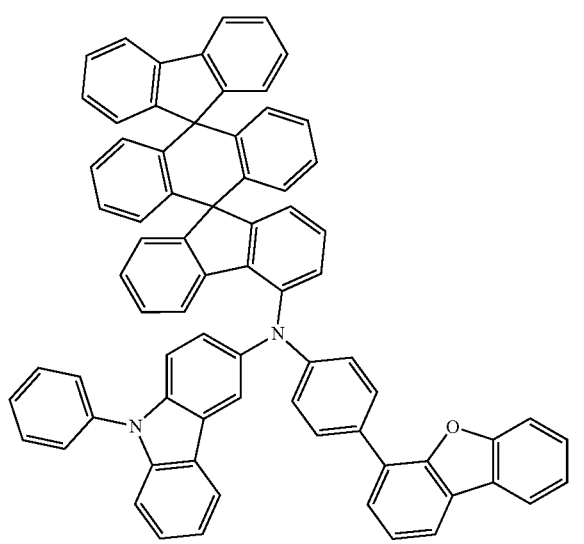
94
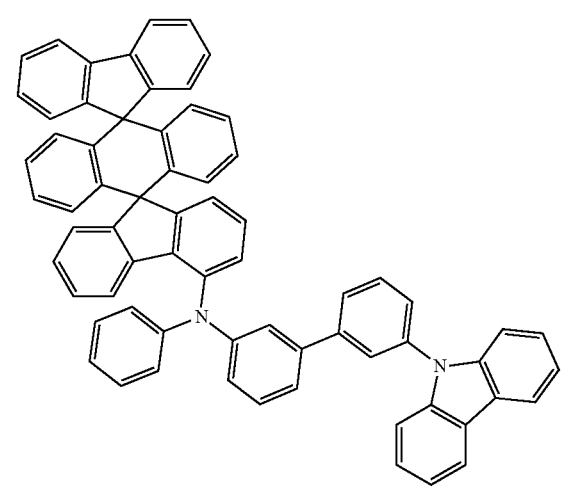
95
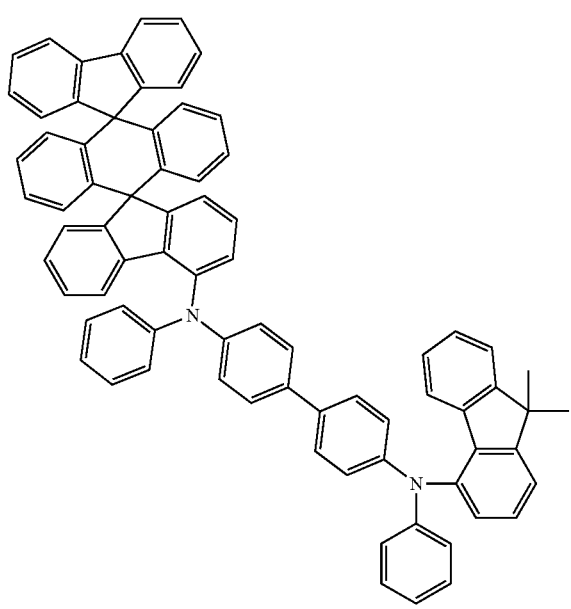
96
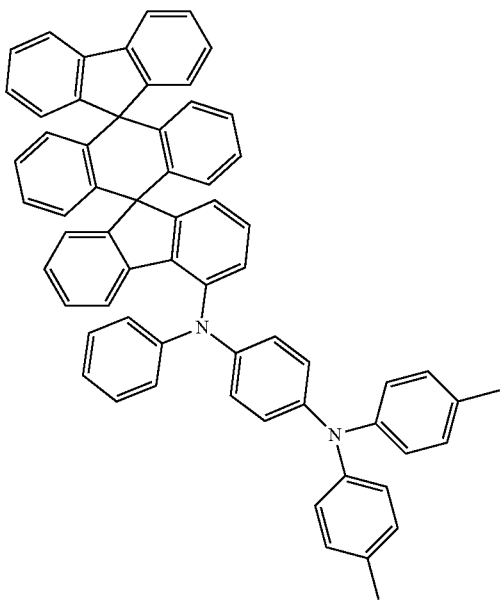
97
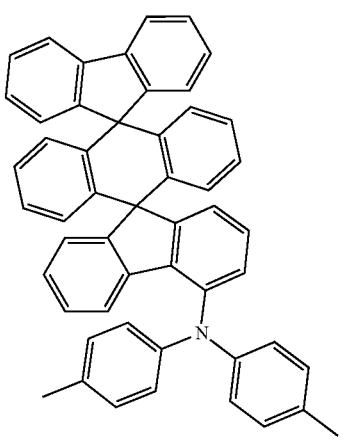
98
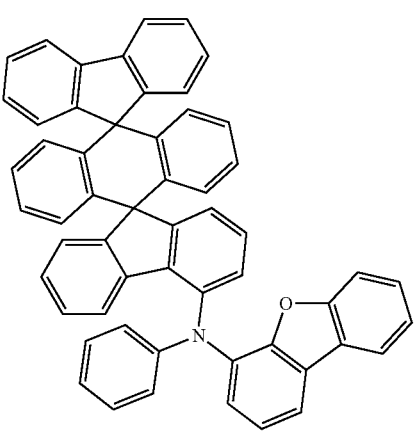

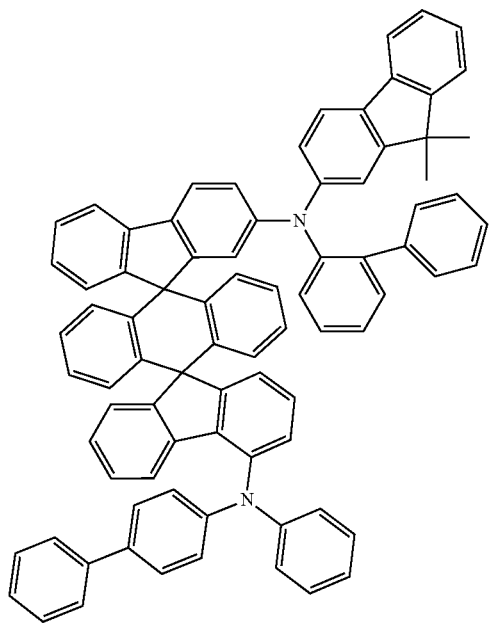
99
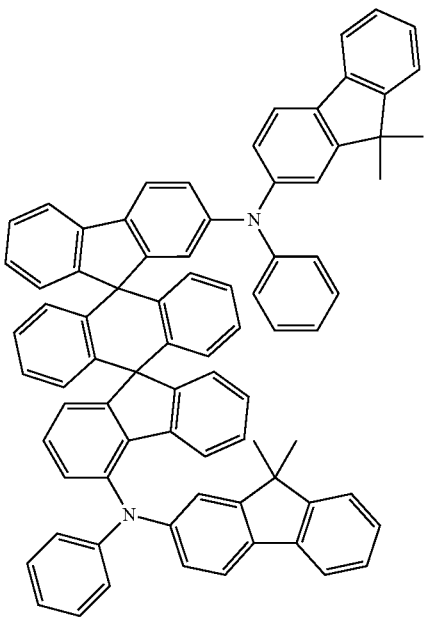
101
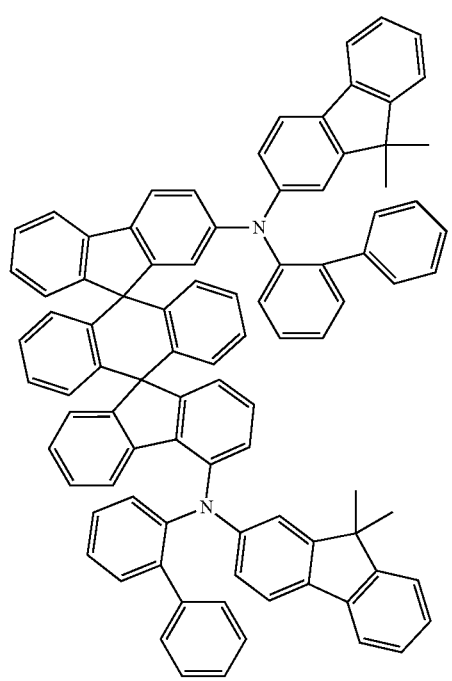
100
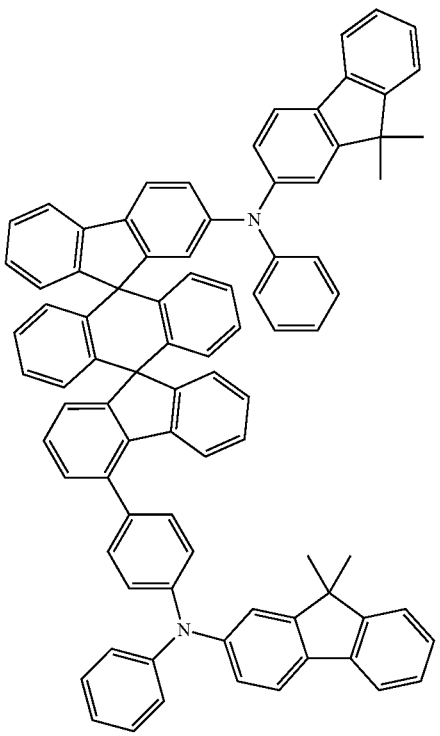
102

103

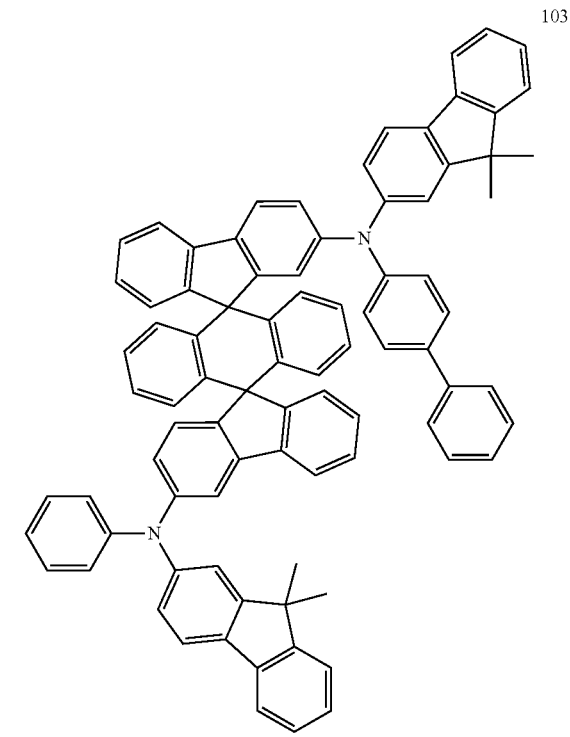

104

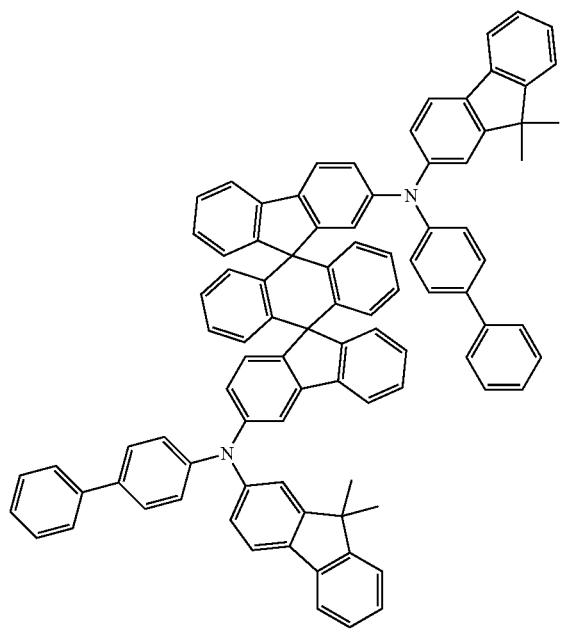

105

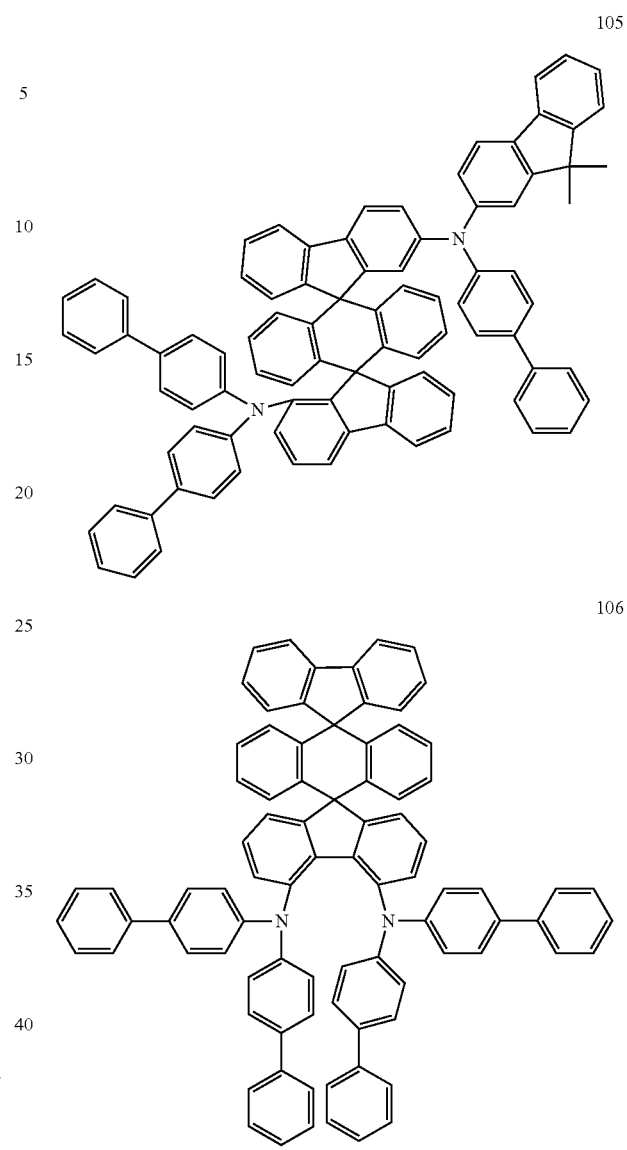

106

The synthesis of the compounds according to the invention can be carried out by processes and reaction types known from the prior art, for example bromination, Ullmann arylation, Friedel-Crafts reaction, palladium-catalysed intramolecular C—H arylation, Buchwald coupling and Suzuki coupling and Grignard reaction. In particular, the compounds can be synthesised from a correspondingly halogen-substituted basic structure by introduction of the amino group, as depicted in Scheme 1. It is either possible here firstly to introduce a primary amine with a substituent $Ar^1$ and to introduce the group $Ar^2$ in a further coupling reaction, as shown in Scheme 1 a). It is likewise possible to introduce the secondary amine $Ar^1Ar^2NH$ directly in one step, as shown in Scheme 1 b). Suitable groups X on the basic structure are reactive leaving groups, such as, for example, Cl, Br, I, triflate or tosylate. Suitable coupling reactions are, for example, Hartwig-Buchwald or Ullmann coupling reactions. The reaction conditions which can be used for these coupling reactions are known to the person skilled in the art of organic synthesis.

Scheme 1:

a)

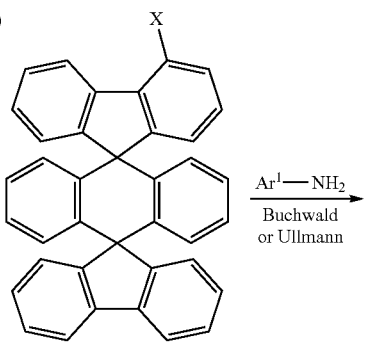

$Ar^1$—$NH_2$
Buchwald or Ullmann
→

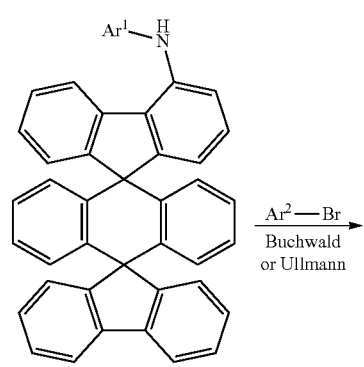

$Ar^2$—Br
Buchwald or Ullmann
→

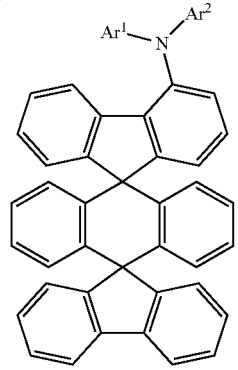

For compounds where i is equal to 1 or 2, the group $Ar^S$—$NAr^1$—$Ar^2$ can likewise be introduced via a metal-catalysed coupling reaction, for example via a Suzuki coupling or a Stille coupling.

The present invention therefore furthermore relates to a process for the preparation of a compound of the formula (1) by coupling a dispiro[fluoren-9,9'-anthracene-10',9''-fluorene]derivative which is substituted by a reactive leaving group in the 1-, 3- or 4-position to a) a primary amine, followed by coupling to a further aromatic group which is substituted by a reactive leaving group, or
b) to a secondary amine, or
c) to a triarylamine derivative.

The reactive leaving group here is preferably selected from Cl, Br, I, triflate or tosylate or, for a Suzuki coupling, also boronic acid, or a boronic acid derivative, in particular a boronic acid ester.

The coupling reaction is preferably selected from Hartwig-Buchwald couplings, from Ullmann couplings or from Suzuki couplings.

The dispiro[fluoren-9,9'-anthracene-10',9''-fluorene]skeleton is preferably built up analogously to the classical spiro synthesis.

Scheme 2:

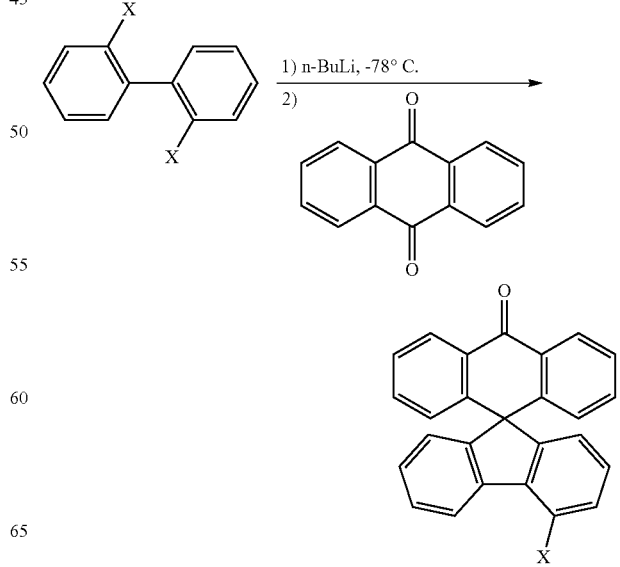

b)

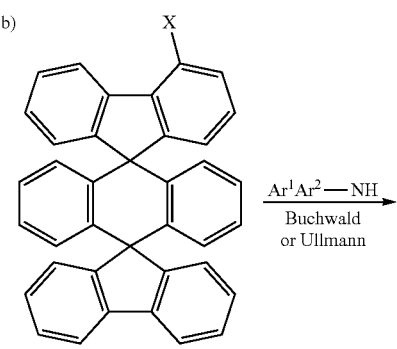

$Ar^1Ar^2$—NH
Buchwald or Ullmann
→

-continued

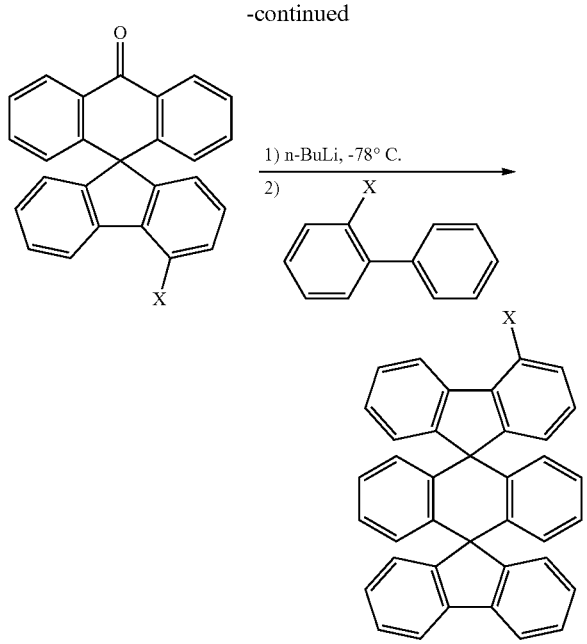

Different substitution patterns on the basic structure can be obtained here through the use of correspondingly substituted biphenyls.

In the synthesis of basic structures having more than one substituent, in particular in the case of the use of polysubstituted biphenyls, substitution isomers may form during the formation of the spirocarbons. If the compounds are not purified, they can also be employed in the form of a mixture.

The synthetic processes shown above have an illustrative character and can be modified in a suitable manner by the person skilled in the art in the area of organic synthesis if this is advantageous for the synthesis of certain embodiments of compounds according to the invention.

The compounds according to the invention described above, in particular compounds which are substituted by reactive leaving groups, such as bromine, iodine, chlorine, boronic acid or boronic acid ester, can be used as monomers for the preparation of corresponding oligomers, dendrimers or polymers. Suitable reactive leaving groups are, for example, bromine, iodine, chlorine, boronic acids, boronic acid esters, amines, alkenyl or alkynyl groups containing a terminal C—C double bond or CC triple bond respectively, oxiranes, oxetanes, groups which undergo a cycloaddition, for example a 1,3-dipolar cycloaddition, such, as, for example, dienes or azides, carboxylic acid derivatives, alcohols and silanes.

The invention therefore furthermore relates to oligomers, polymers or dendrimers comprising one or more compounds of the formula (1), where the bond(s) to the polymer, oligomer or dendrimer may be localised at any desired free positions in formula (1). Depending on the linking of the compound according to the invention, the compound is part of a side chain of the oligomer or polymer or part of the main chain.

An oligomer in the sense of this invention is taken to mean a compound which is built up from at least three monomer units. A polymer in the sense of the invention is taken to mean a compound which is built up from at least ten monomer units.

The polymers, oligomers or dendrimers according to the invention may be conjugated, partially conjugated or non-conjugated. The oligomers or polymers according to the invention may be linear, branched or dendritic.

In the structures linked in a linear manner, the units of the formula (1) may be linked directly to one another or linked to one another via a divalent group, for example via a substituted or unsubstituted alkylene group, via a heteroatom or via a divalent aromatic or heteroaromatic group.

In branched and dendritic structures, 3, 5 or more units of the formula (1) may, for example, be linked via a trivalent or polyvalent group, for example via a trivalent or polyvalent aromatic or heteroaromatic group, to give a branched or dendritic oligomer or polymer.

For the recurring units of the formula (1) in oligomers, dendrimers and polymers, the same preferences apply as described above for compounds according to the invention.

For the preparation of the oligomers or polymers, the monomers according to the invention are homopolymerised or copolymerised with further monomers. Suitable and preferred comonomers are selected from fluorenes (for example in accordance with EP 842208 or WO 2000/22026), spirobifluorenes (for example in accordance with EP 707020, EP 894107 or WO 2006/061181), para-phenylenes (for example in accordance with WO 1992/18552), carbazoles (for example in accordance with WO 2004/070772 or WO 2004/113468), thiophenes (for example in accordance with EP 1028136), dihydrophenanthrenes (for example in accordance with WO 2005/014689 or WO 2007/006383), cis- and trans-indenofluorenes (for example in accordance with WO 2004/041901 or WO 2004/113412), ketones (for example in accordance with WO 2005/040302), phenanthrenes (for example in accordance with WO 2005/104264 or WO 2007/017066) or also a plurality of these units. The polymers, oligomers and dendrimers usually also contain further units, for example emitting (fluorescent or phosphorescent) units, such as, for example, vinyltriarylamines (for example in accordance with WO 2007/068325) or phosphorescent metal complexes (for example in accordance with WO 2006/003000), and/or charge-transport units, in particular those based on triarylamines.

The polymers, oligomers and dendrimers according to the invention have advantageous properties, in particular long lifetimes, high efficiencies and good colour coordinates.

The polymers and oligomers according to the invention are generally prepared by polymerisation of one or more types of monomer, at least one monomer of which results in recurring units of the formula (1) in the polymer. Suitable polymerisation reactions are known to the person skilled in the art and are described in the literature. Particularly suitable and preferred polymerisation reactions which result in C—C or C—N links are the following:

(A) SUZUKI polymerisation;
(B) YAMAMOTO polymerisation;
(C) STILLE polymerisation; and
(D) HARTWIG-BUCHWALD polymerisation.

The way in which the polymerisation can be carried out by these methods and the way in which the polymers can then be separated off from the reaction medium and purified is known to the person skilled in the art and is described in detail in the literature, for example in WO 2003/048225, WO 2004/037887 and WO 2004/037887.

The present invention thus also relates to a process for the preparation of the polymers, oligomers and dendrimers according to the invention, which is characterised in that they are prepared by SUZUKI polymerisation, YAMAMOTO polymerisation, STILLE polymerisation or HARTWIG-BUCHWALD polymerisation. The dendrimers according to the invention can be prepared by processes known to the person skilled in the art or analogously thereto. Suitable processes are described in the literature, such as, for example, in Frechet, Jean M. J.; Hawker, Craig J., "Hyperbranched polyphenylene and hyperbranched polyesters: new soluble, three-dimensional, reactive polymers", Reactive & Functional Polymers (1995), 26(1-3), 127-36; Janssen, H. M.; Meijer, E. W., "The synthesis and characterization of dendritic molecules", Materials Science and Technology (1999), 20 (Synthesis of Polymers), 403-458; Tomalia, Donald A., "Dendrimer molecules", Scientific American (1995), 272(5), 62-6; WO 2002/067343 A1 and WO 2005/026144 A1.

For the processing of the compounds according to the invention from the liquid phase, for example by spin coating or by printing processes, formulations of the compounds according to the invention are necessary. These formulations can be, for example, solutions, dispersions or emulsions. It may be preferred to use mixtures of two or more solvents for this purpose. Suitable and preferred solvents are, for example, toluene, anisole, o-, m- or p-xylene, methyl benzoate, mesitylene, tetralin, veratrol, THF, methyl-THF, THP, chlorobenzene, dioxane, phenoxytoluene, in particular 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, methyl benzoate, NMP, p-cymene, phenetol, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane or mixtures of these solvents.

The invention therefore furthermore relates to a formulation, in particular a solution, dispersion or emulsion, comprising at least one compound of the formula (1) or at least one polymer, oligomer or dendrimer containing at least one unit of the formula (1), and at least one solvent, preferably an organic solvent. The way in which solutions of this type can be prepared is known to the person skilled in the art and is described, for example, in WO 2002/072714, WO 2003/019694 and the literature cited therein.

The compounds according to the invention are suitable for use in an electronic device. An electronic device here is taken to mean a device which comprises at least one layer which comprises at least one organic compound. However, the component may also comprise inorganic materials or also layers which are built up entirely from inorganic materials.

The invention therefore furthermore relates to the use of the compounds according to the invention in electronic devices and to electronic devices themselves which comprise one or more compounds according to the invention. The electronic devices here are preferably selected from the group consisting of organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), light-emitting electrochemical cells (LECs), organic laser diodes (O-lasers) and particularly preferably organic electroluminescent devices (OLEDs). Particular preference is given to organic electroluminescent devices comprising anode, cathode and at least one emitting layer, characterised in that at least one organic layer, which may be an emitting layer, a hole-transport layer or another layer, comprises at least one compound according to the invention.

The organic electroluminescent devices and the light-emitting electrochemical cells can be employed for various applications, for example for monochromatic or polychromatic displays, for lighting applications or for medical and/or cosmetic applications, for example in phototherapy.

Apart from cathode, anode and the emitting layer, the organic electroluminescent device may also comprise further layers. These are selected, for example, from in each case one or more hole-injection layers, hole-transport layers, hole-blocking layers, electron-transport layers, electron-injection layers, electron-blocking layers, exciton-blocking layers, interlayers, charge-generation layers (IDMC 2003, Taiwan; Session 21 OLED (5), T. Matsumoto, T. Nakada, J. Endo, K. Mori, N. Kawamura, A. Yokoi, J. Kido, *Multiphoton Organic EL Device Having Charge Generation Layer*) and/or organic or inorganic p/n junctions. However, it should be pointed out that each of these layers does not necessarily have to be present and the choice of layers is always dependent on the compounds used and in particular also on whether the electroluminescent device is fluorescent or phosphorescent.

The organic electroluminescent device may also comprise a plurality of emitting layers. In this case, these emission layers particularly preferably have in total a plurality of emission maxima between 380 nm and 750 nm, resulting overall in white emission, i.e. various emitting compounds which are able to fluoresce or phosphoresce and which emit blue, yellow, orange or red light are used in the emitting layers. Particular preference is given to three-layer systems, i.e. systems having three emitting layers, where at least one of these layers comprises at least one compound according to the invention and where the three layers exhibit blue, green and orange or red emission (for the basic structure see, for example, WO 2005/011013). The compounds according to the invention may alternatively and/or additionally also be present in the hole-transport layer and/or in an interlayer. It should be noted that, for the generation of white light, an emitter compound used individually which emits in a broad wavelength range may also be suitable instead of a plurality of emitter compounds emitting in colour. It is possible here for all emitting layers to be fluorescent or for all emitting layers to be phosphorescent or for one or more emitting layers to be fluorescent and one or more other layers to be phosphorescent.

The compound according to the invention in accordance with the embodiments indicated above can be employed in various layers, depending on the precise structure. Preference is given to an organic electroluminescent device comprising a compound of the formula (1) or the preferred embodiments as hole-transport material in a hole-transport or hole-injection or exciton-blocking layer or as matrix material for fluorescent or phosphorescent emitters, in particular for phosphorescent emitters. The preferred embodiments indicated above also apply to the use of the materials in organic electronic devices.

In a preferred embodiment of the invention, the compound of the formula (1) or the preferred embodiments are employed as hole-transport or hole-injection material in a hole-transport or hole-injection layer. The emitting layer here may be fluorescent or phosphorescent. A hole-injection layer in the sense of the present invention is a layer which is directly adjacent to the anode. A hole-transport layer in the sense of the present invention is a layer which is located between a hole-injection layer and an emitting layer. The hole-transport layer may be directly adjacent to the emission layer. If the compounds of the formula (1), or the preferred embodiments, are used as hole-transport material or as hole-injection material, it may be preferred for them to be doped with electron-acceptor compounds, for example with F4-TCNQ or with compounds as described in EP 1476881 or EP 1596445.

In a further preferred embodiment of the invention, a compound of the formula (1), or a preferred embodiment, is used as hole-transport material in combination with a hexaazatriphenylene derivative, as described in US 2007/0092755. The hexaazatriphenylene derivative is particularly preferably employed in a separate layer here.

If the compound of the formula (1), or a preferred embodiment, is employed as hole-transport material in a hole-transport layer, the compound can be employed as pure material, i.e. in a proportion of 100%, in the hole-transport layer, or it can be employed in combination with one or more further compounds in the hole-transport layer.

In still a further preferred embodiment of the invention, the compound of the formula (1), or a preferred embodiment, is employed in an electron-blocking layer. An electron-blocking layer is taken to mean a layer which is directly adjacent to an emitting layer on the anode side.

Particular preference is given to the use of the compound of the formula (1) or the preferred embodiments in a hole-transport or electron-blocking layer.

In a further preferred embodiment of the invention, the compound of the formula (1), or a preferred embodiment, is employed as matrix material for a fluorescent or phosphorescent compound, in particular for a phosphorescent compound, in an emitting layer. The organic electroluminescent device here may comprise one emitting layer, or it may comprise a plurality of emitting layers, where at least one emitting layer comprises at least one compound according to the invention as matrix material.

If the compound of the formula (1), or a preferred embodiment, is employed as matrix material for an emitting compound in an emitting layer, it is preferably employed in combination with one or more phosphorescent materials (triplet emitters). Phosphorescence in the sense of this invention is taken to mean the luminescence from an excited state having spin multiplicity >1, in particular from an excited triplet state. For the purposes of this application, all luminescent complexes with transition metals or lanthanoids, in particular all luminescent iridium, platinum and copper complexes, are to be regarded as phosphorescent compounds.

The mixture of the compound of the formula (1), or a preferred embodiment, and the emitting compound comprises between 99.9 and 1% by weight, preferably between 99 and 10% by weight, particularly preferably between 97 and 60% by weight, in particular between 95 and 80% by weight, of the compound of the formula (1), or a preferred embodiment, based on the entire mixture of emitter and matrix material. Correspondingly, the mixture comprises between 0.1 and 99% by weight, preferably between 1 and 90% by weight, particularly preferably between 3 and 40% by weight, in particular between 5 and 20% by weight, of the emitter, based on the entire mixture of emitter and matrix material. The limits indicated above apply, in particular, if the layer is applied from solution. If the layer is applied by vacuum evaporation, the same numerical values apply, where in this case the percentage is in each case indicated in % by vol.

An emitting layer of an organic electroluminescent device may also comprise systems comprising a plurality of matrix materials (mixed-matrix systems) and/or a plurality of dopants. In this case, the dopants are generally the materials whose proportion in the system is the smaller and the matrix materials are the materials whose proportion in the system is the greater. In individual cases, however, the proportion of an individual matrix material in the system may be smaller than the proportion of an individual dopant.

In a preferred embodiment of the invention, the compound of the formula (1) is used as a component of mixed-matrix systems. The mixed-matrix systems preferably comprise two or three different matrix materials, particularly preferably two different matrix materials. The two different matrix materials here may be present in a ratio of 1:10 to 1:1, preferably in a ratio of 1:4 to 1:1.

The mixed-matrix systems may comprise one or more dopants. The dopant compound or the dopant compounds together have, in accordance with the invention, the proportions indicated above for the emitter.

Mixed-matrix systems are preferably employed in phosphorescent organic electroluminescent devices.

Particularly suitable matrix materials which can be employed in combination with the compounds according to the invention as matrix components of a mixed-matrix system are aromatic ketones, aromatic phosphine oxides or aromatic sulfoxides or sulfones, for example in accordance with WO 04/013080, WO 04/093207, WO 06/005627 or WO 10/006680, triarylamines, carbazole derivatives, for example CBP (N,N-biscarbazolylbiphenyl), mCBP or the carbazole derivatives disclosed in WO 05/039246, US 2005/0069729, JP 2004/288381, EP 1205527 or WO 08/086851, indolocarbazole derivatives, for example in accordance with WO 07/063754 or WO 08/056746, indenocarbazole derivatives, for example in accordance with WO 2010/136109 or WO 2011/000455, azacarbazole derivatives, for example in accordance with EP 1617710, EP 1617711, EP 1731584, JP 2005/347160, bipolar matrix materials, for example in accordance with WO 07/137725, silanes, for example in accordance with WO 05/111172, azaboroles or boronic esters, for example in accordance with WO 06/117052, triazine derivatives, for example in accordance with WO 10/015306, WO 07/063754 or WO 08/056746, zinc complexes, for example in accordance with EP 652273 or WO 09/062578, fluorene derivatives, for example in accordance with WO 2010/054730, or bridged carbazole derivatives, for example in accordance with US 2009/0136779, WO 2010/050778, WO 2011/042107 or in accordance with the unpublished application DE 10201005697.9, diazasilole or tetraazasilole derivatives, for example in accordance with WO 10/054729, or diazaphosphole derivatives, for example in accordance with WO 10/054730. It is furthermore possible to use an electronically neutral co-host which has neither hole-transporting nor electron-transporting properties, as described, for example, in WO 2010/108579.

It is likewise possible to use two or more phosphorescent emitters in the mixture. In this case, the emitter which emits at shorter wavelength acts as co-host in the mixture.

The term phosphorescent dopants typically encompasses compounds in which the light emission takes place through a spin-forbidden transition, for example a transition from an excited triplet state or a state having a relatively high spin quantum number, for example a quintet state.

Suitable phosphorescent dopants are, in particular, compounds which emit light, preferably in the visible region, on suitable excitation and in addition contain at least one atom having an atomic number greater than 20, preferably greater than 38 and less than 84, particularly preferably greater than 56 and less than 80. The phosphorescent dopants used are preferably compounds which contain copper, molybdenum, tungsten, rhenium, ruthenium, osmium, rhodium, iridium, palladium, platinum, silver, gold or europium, in particular compounds which contain iridium, platinum or copper.

All luminescent iridium, platinum or copper complexes are regarded as phosphorescent compounds in the sense of the present invention.

Examples of phosphorescent dopants are revealed by the applications WO 2000/70655, WO 2001/41512, WO 2002/02714, WO 2002/15645, EP 1191613, EP 1191612, EP 1191614, WO 2005/033244, WO 2005/019373 and US 2005/0258742. In general, all phosphorescent complexes as are used in accordance with the prior art for phosphorescent OLEDs and as are known to the person skilled in the art in the area of organic electroluminescent devices are suitable for use in the devices according to the invention. The person skilled in the art will also be able, without inventive step, to employ further phosphorescent complexes in combination with the compounds according to the invention in OLEDs.

Explicit examples of suitable phosphorescent emitter compounds are the phosphorescent dopants depicted in the table below.

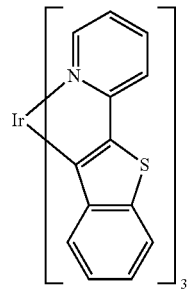

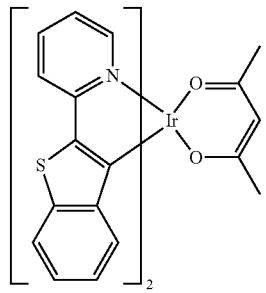

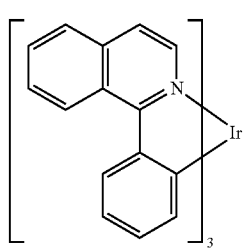

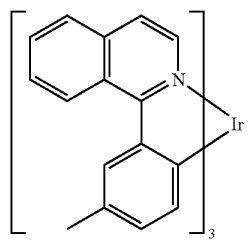

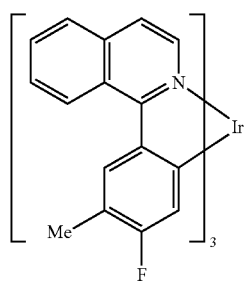

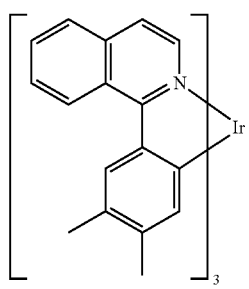

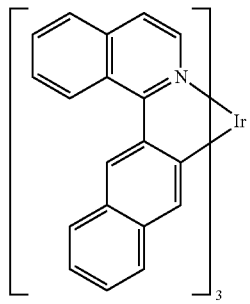

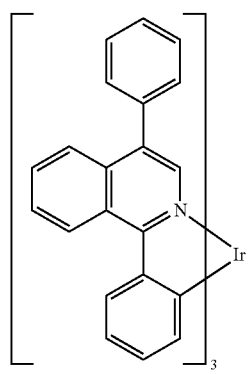

123
-continued
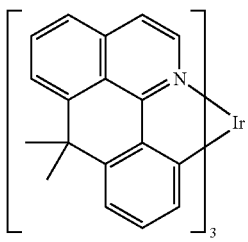
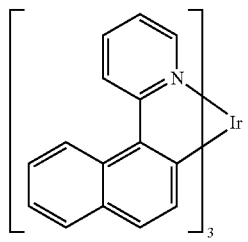
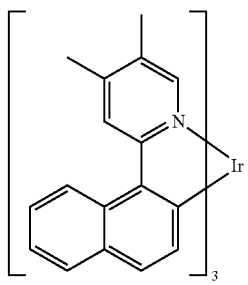
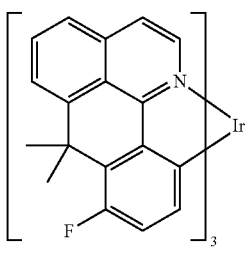
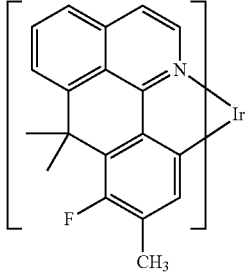
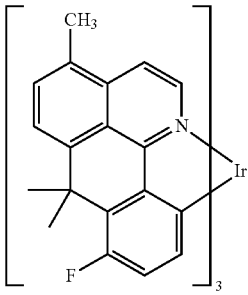
124
-continued
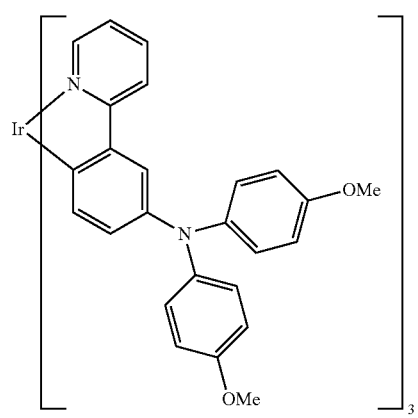
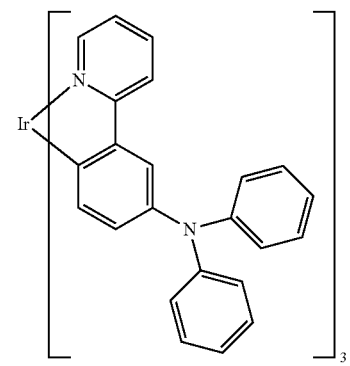
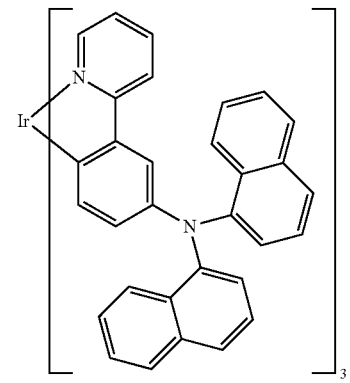
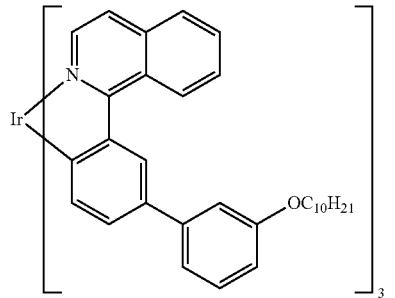

125
-continued
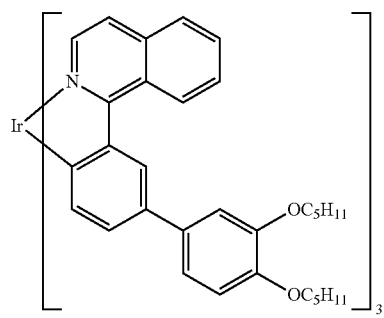
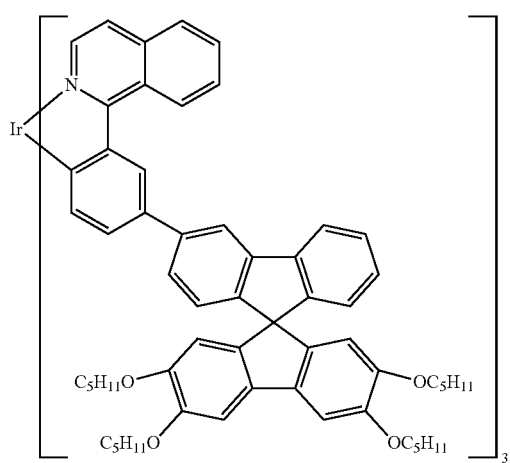
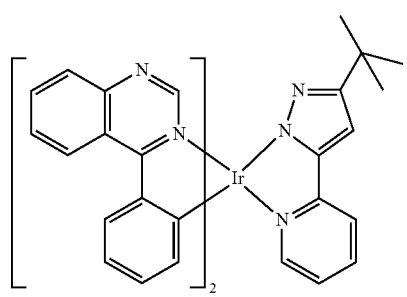
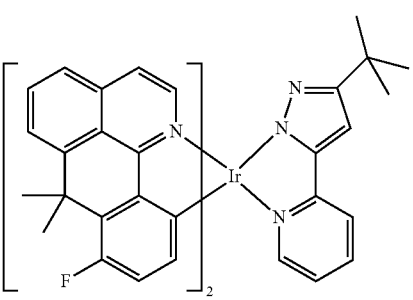
126
-continued
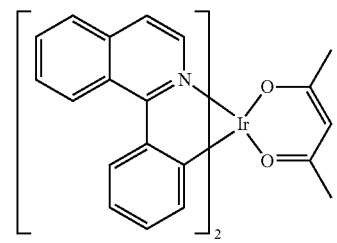
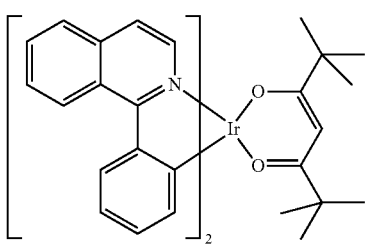
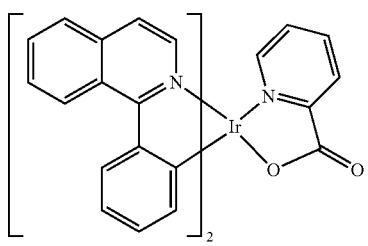
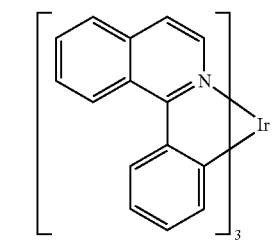
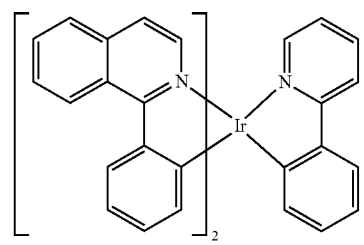

127
-continued
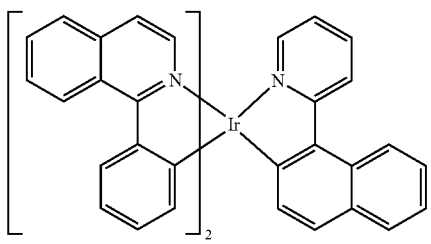
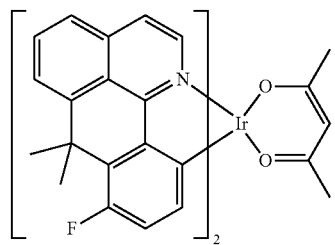
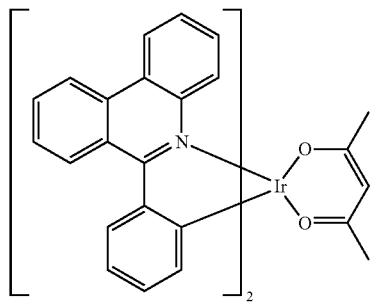
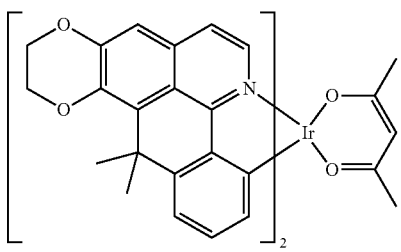
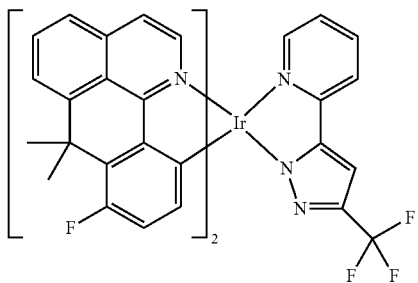
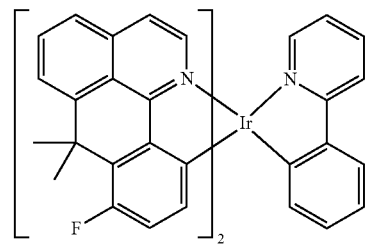
128
-continued
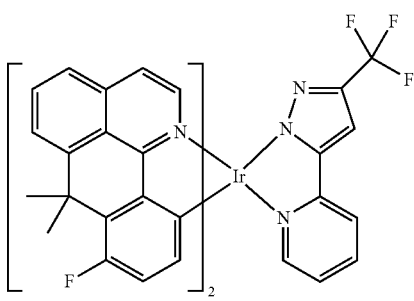
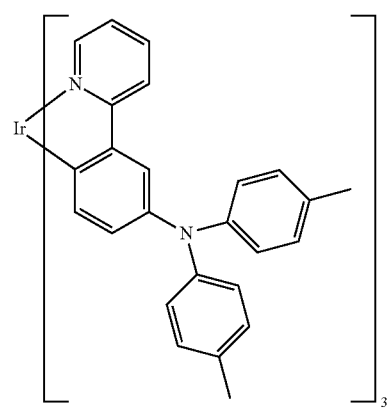
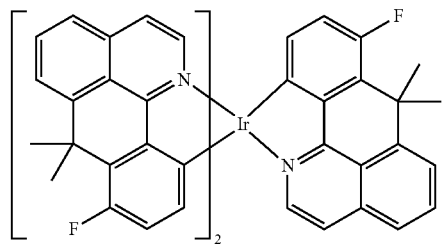
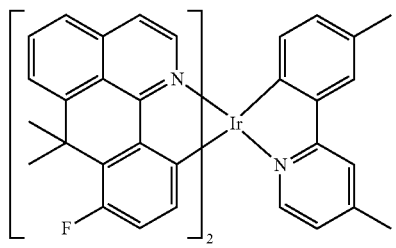
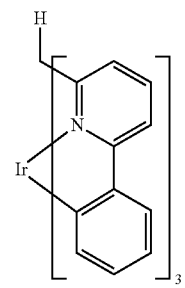

129
-continued
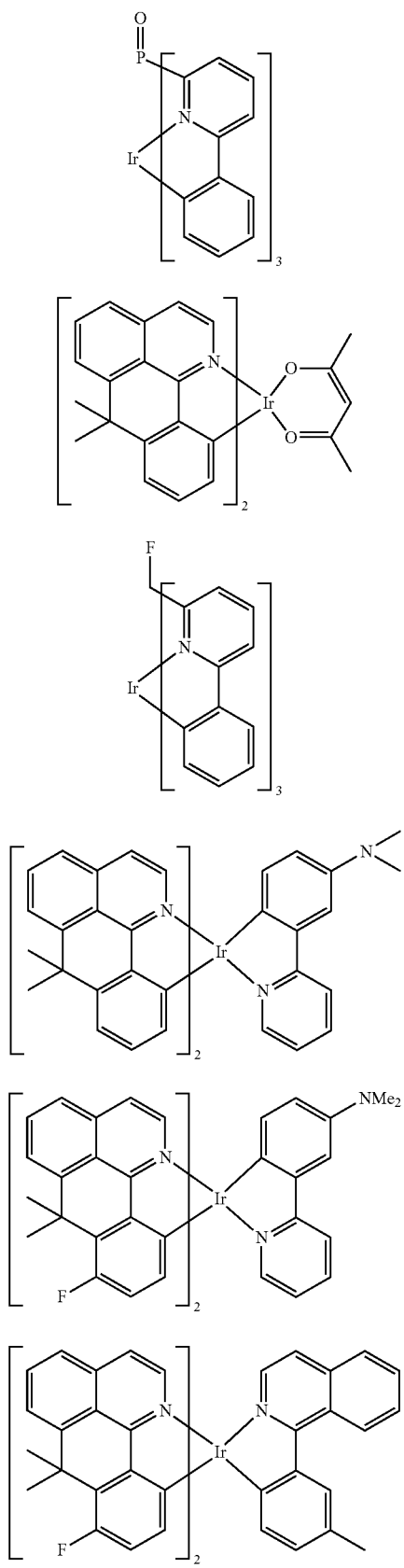
130
-continued
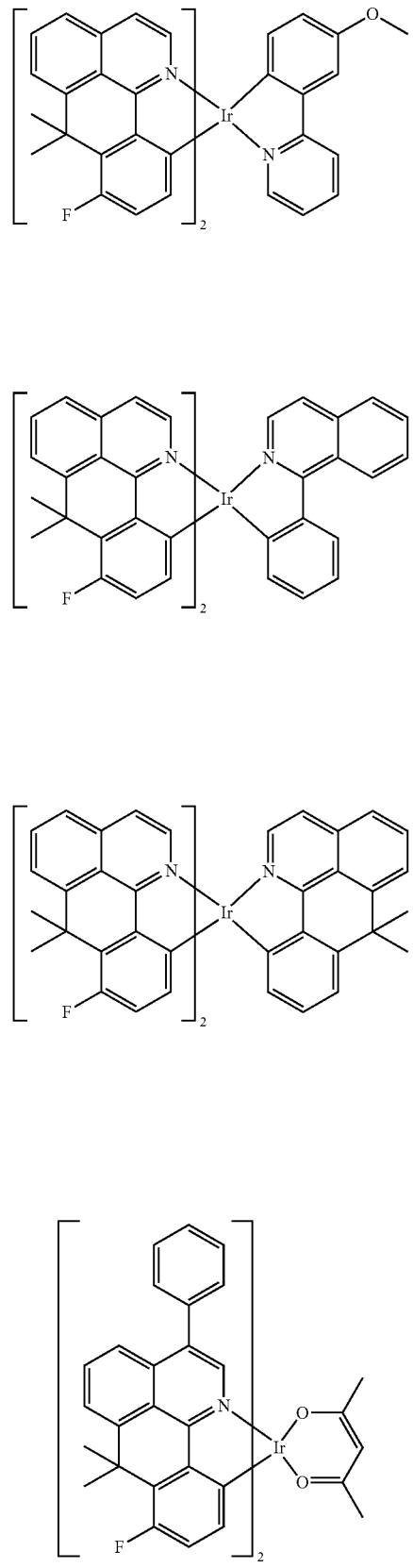

131
-continued
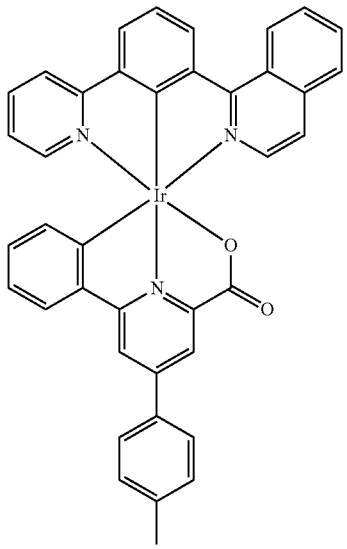
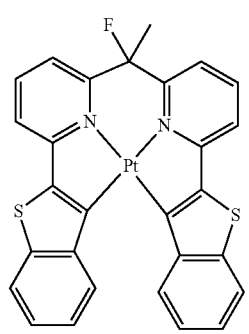
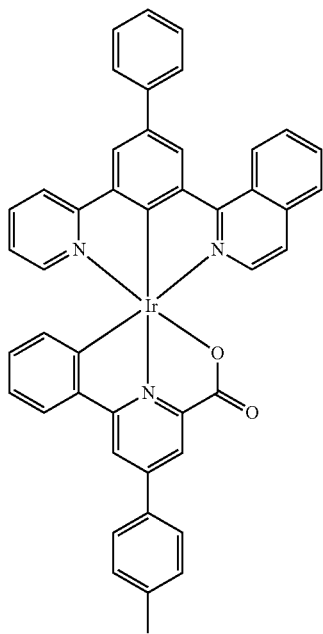
132
-continued
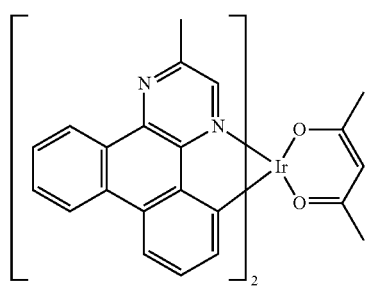
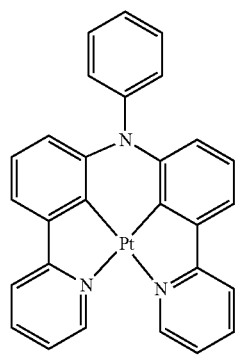
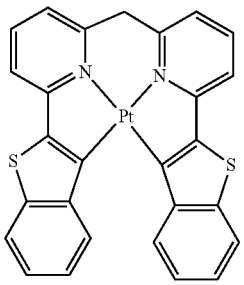
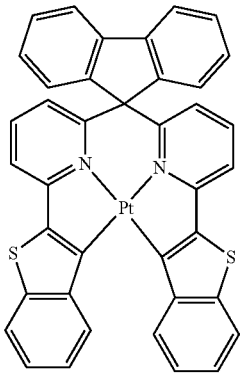
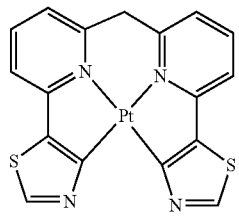

133
-continued
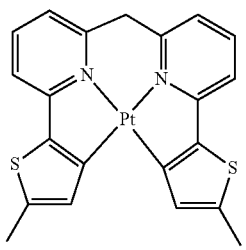
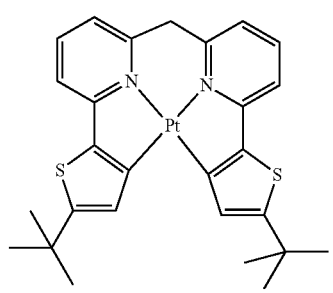
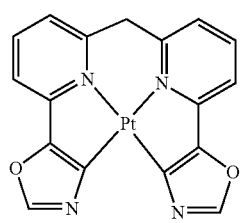
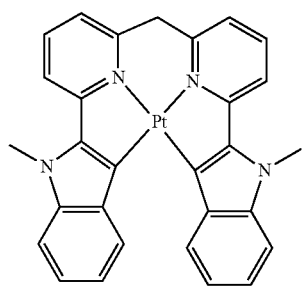
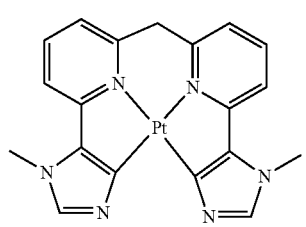
134
-continued
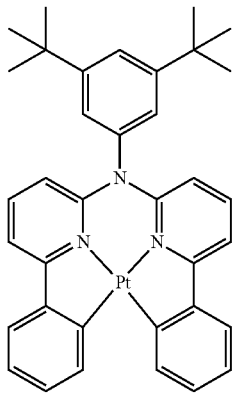
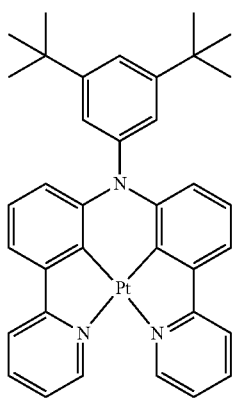
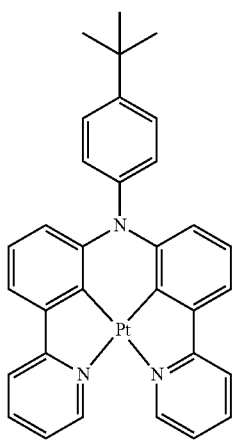
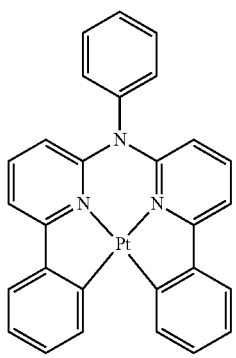

| 135 -continued | 136 -continued |
|---|---|
| 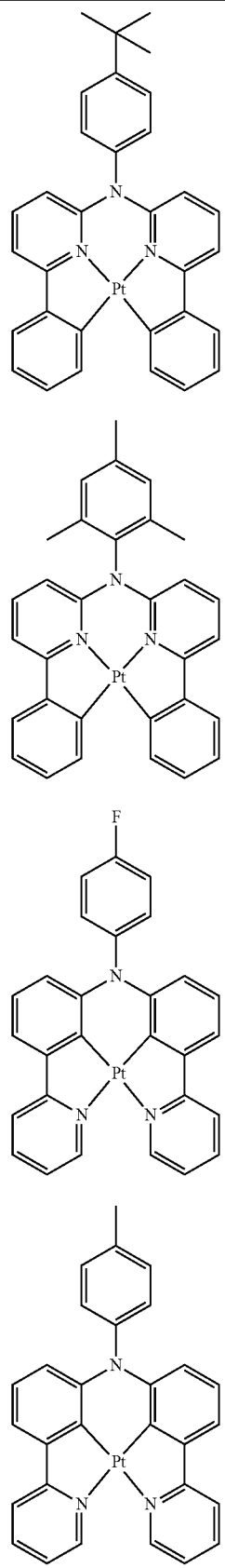 | 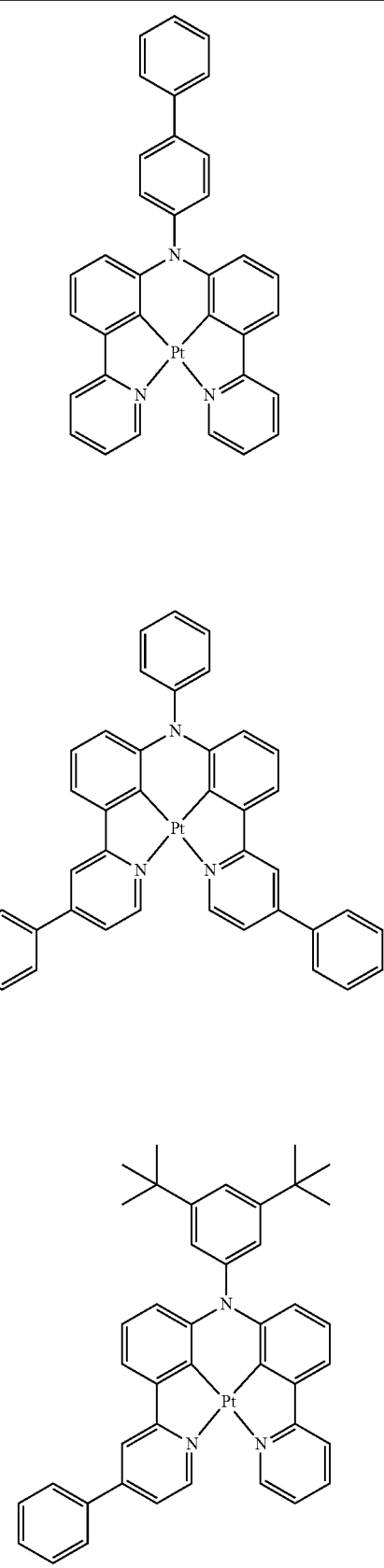 |

137
-continued
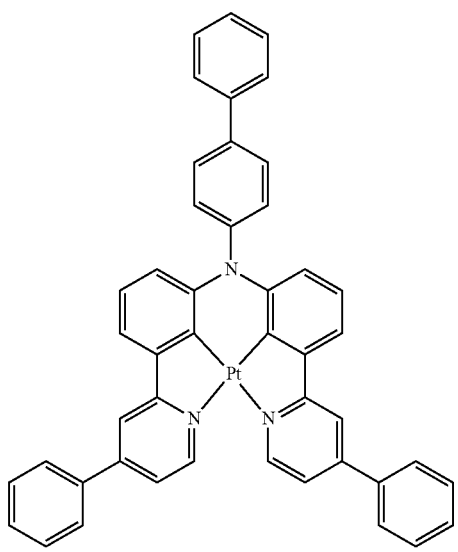
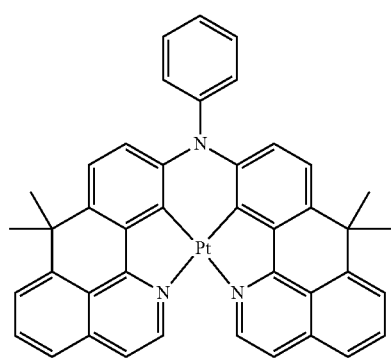
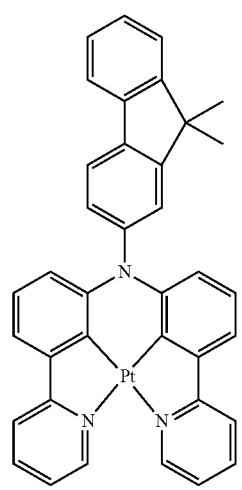
138
-continued
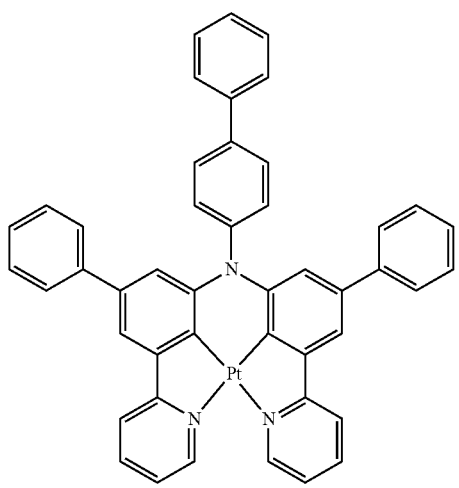
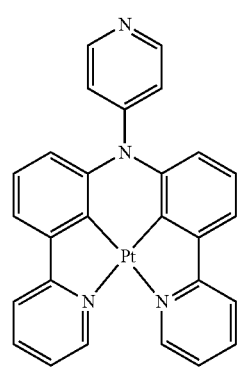
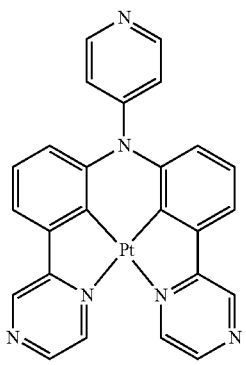
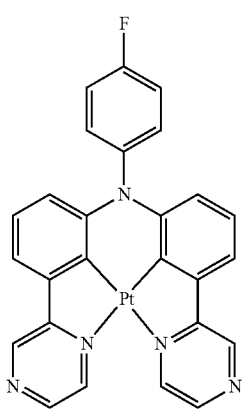

139
-continued
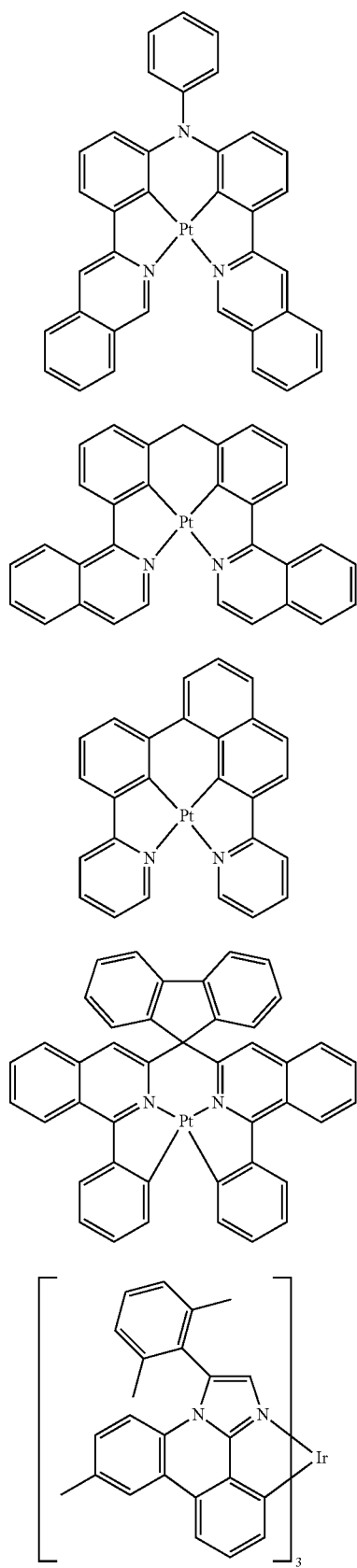
140
-continued
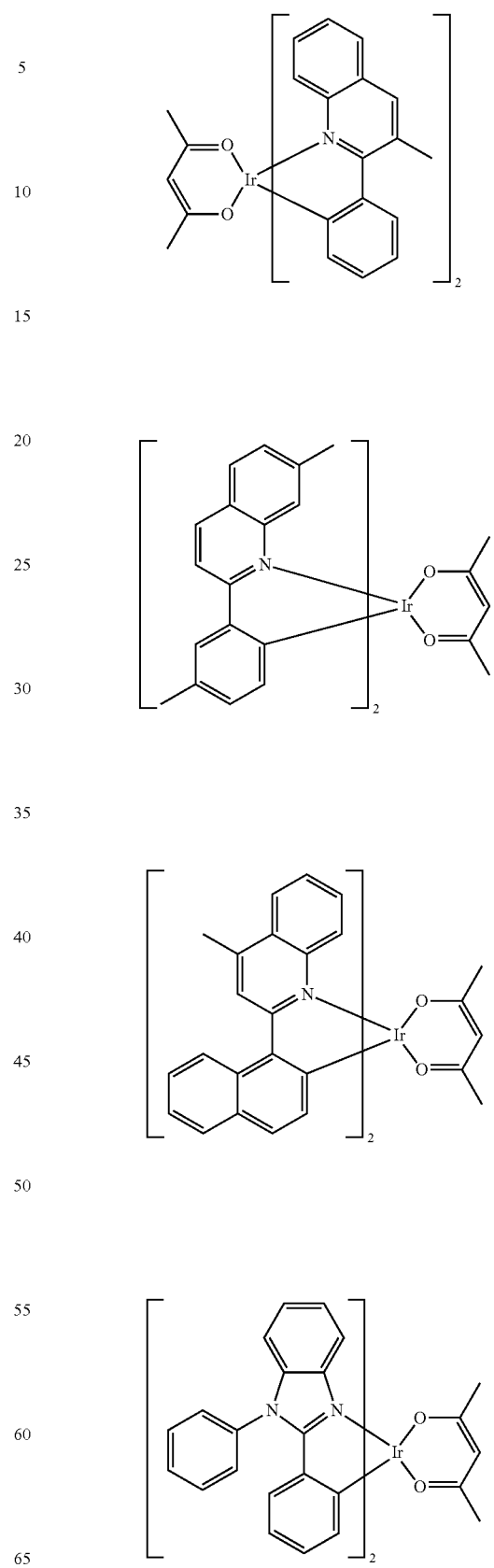

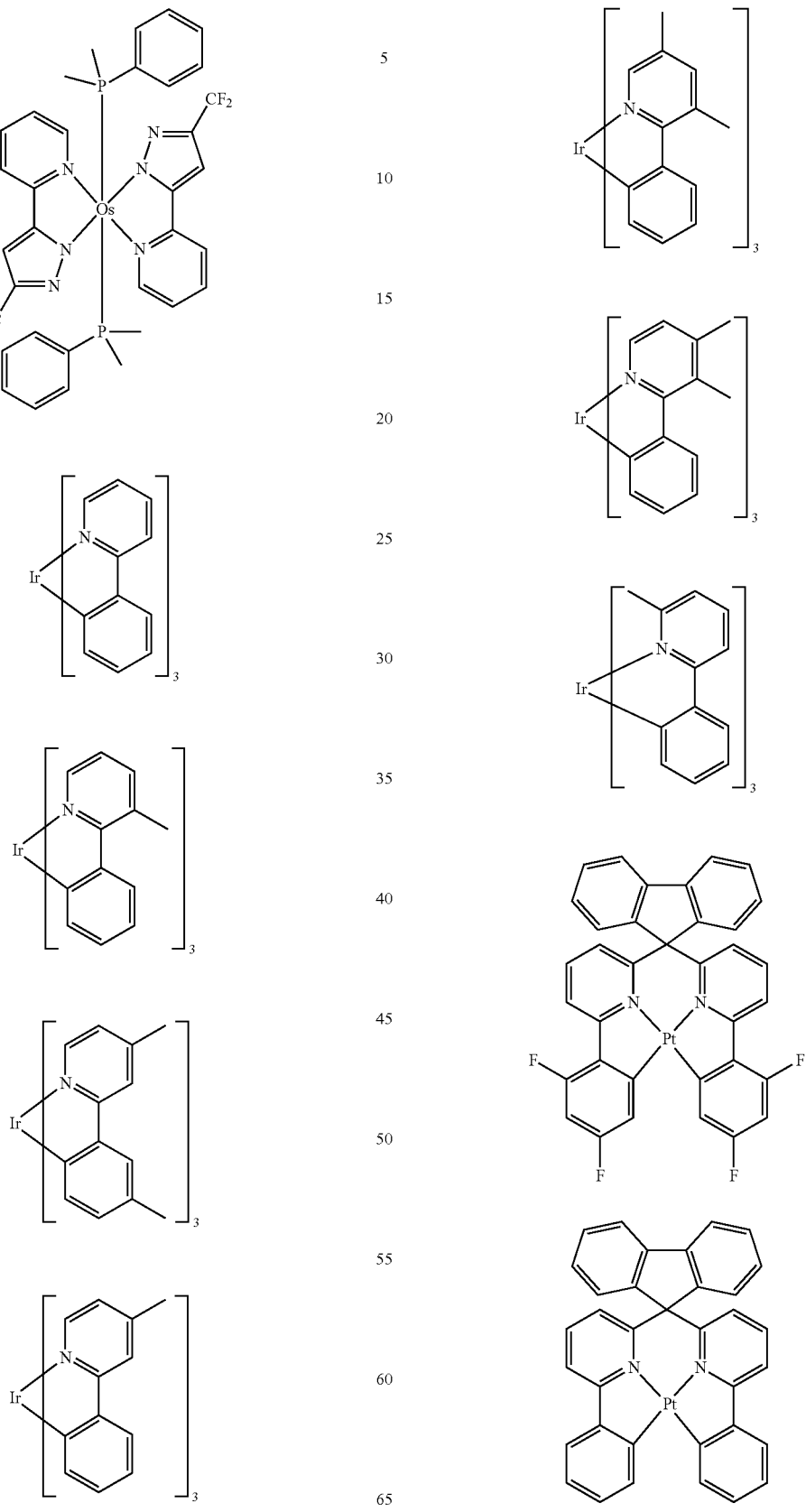

-continued
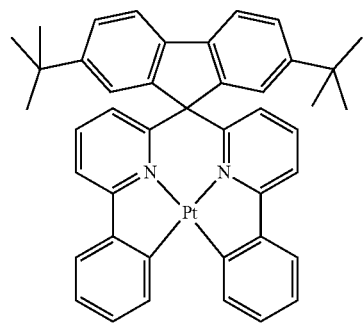
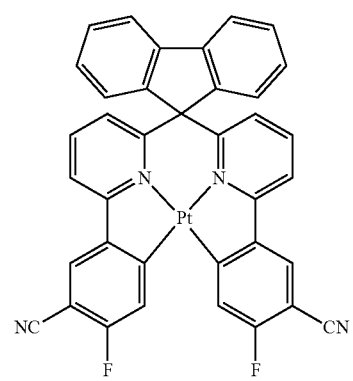
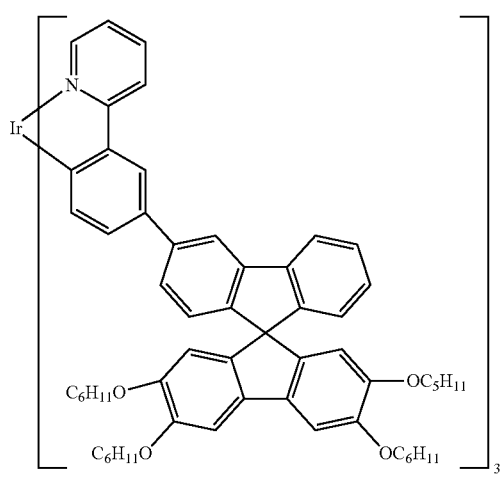
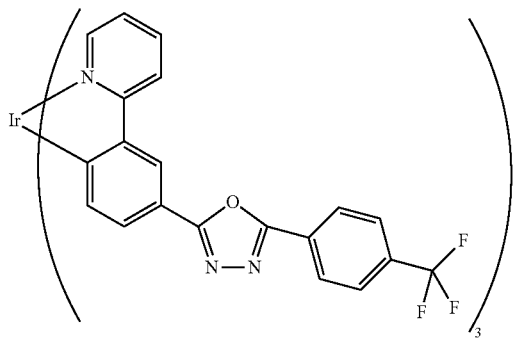
-continued
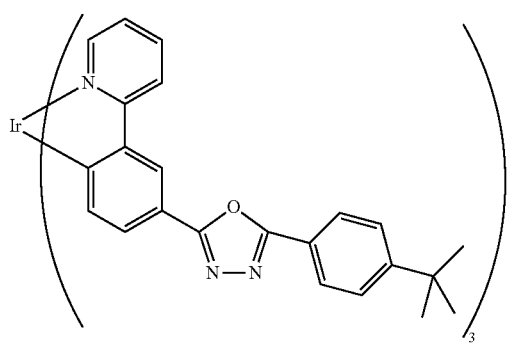
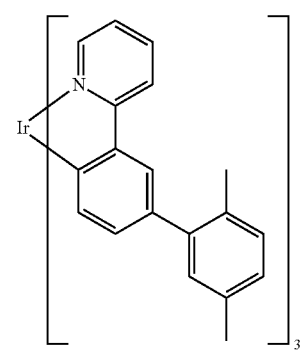
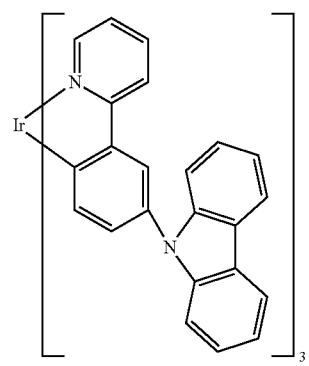
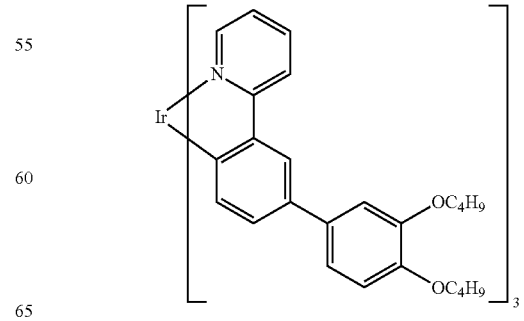

| 145 -continued | 146 -continued |
|---|---|
| 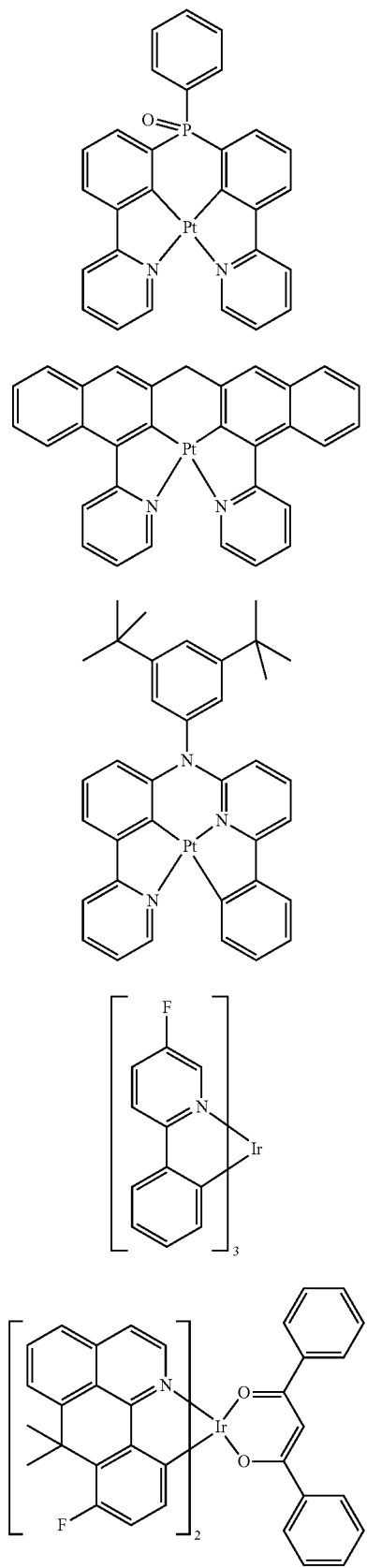 | 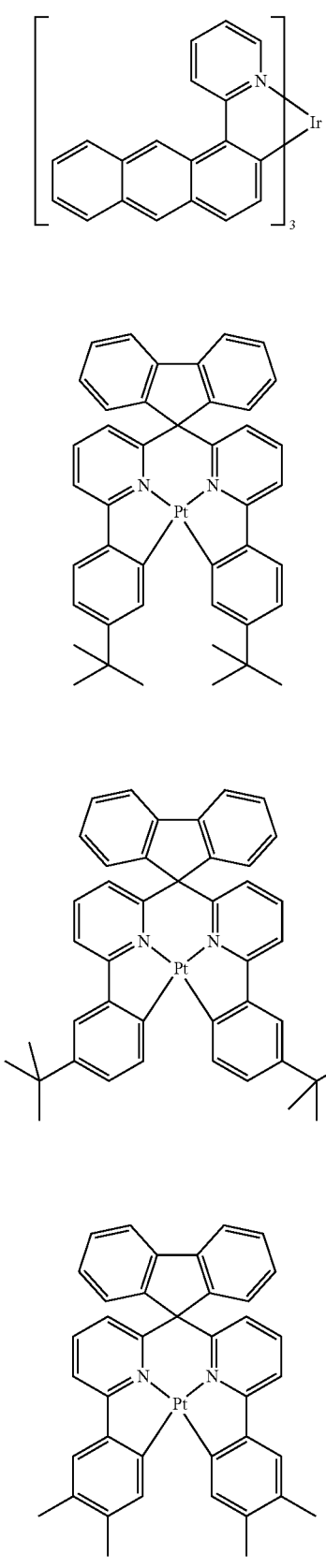 |

147
-continued
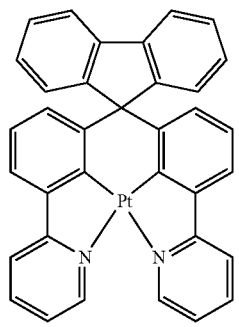
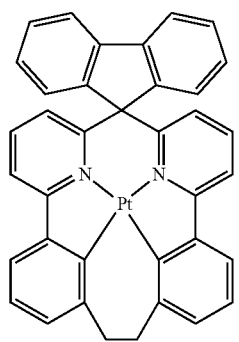
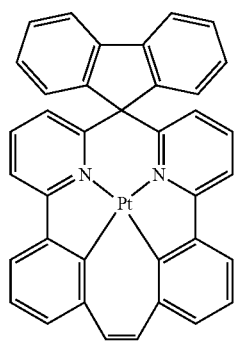
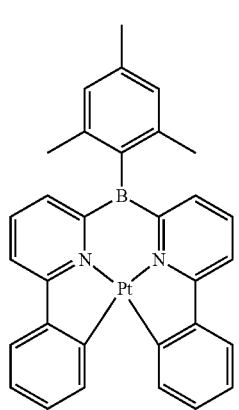
148
-continued
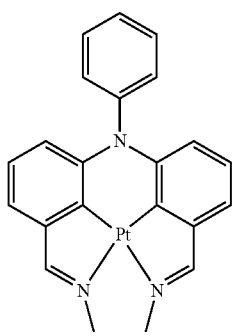
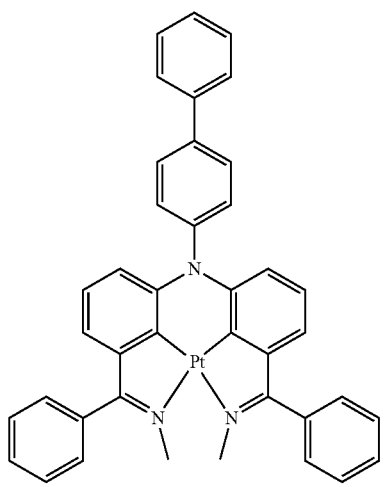
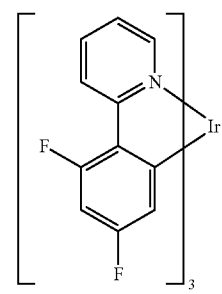
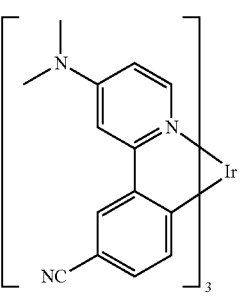

149
-continued
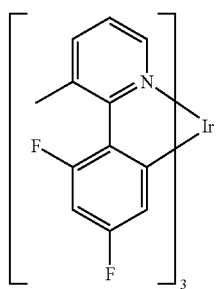
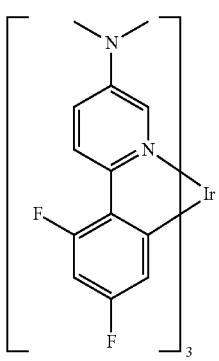
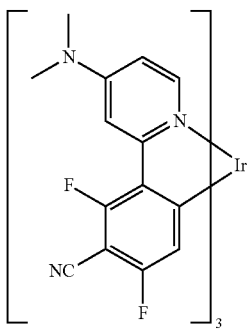
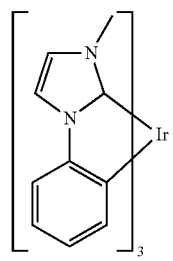
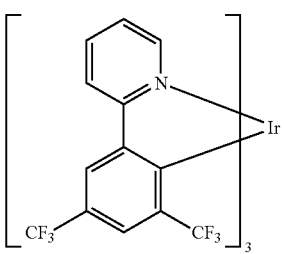
150
-continued
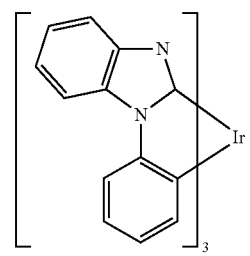
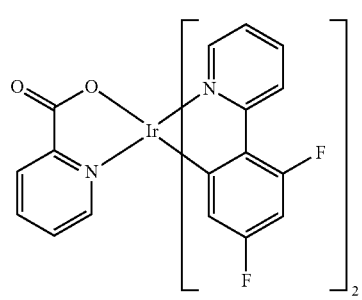
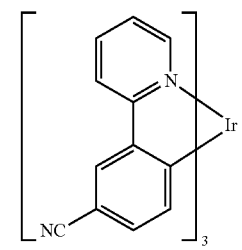
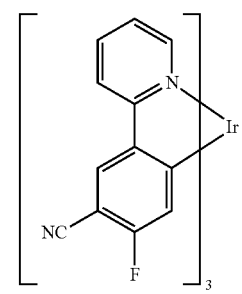
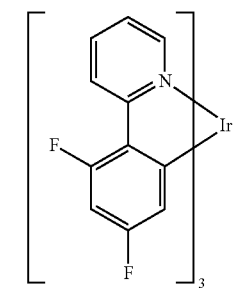

| 151 -continued | 152 -continued |
|---|---|
| 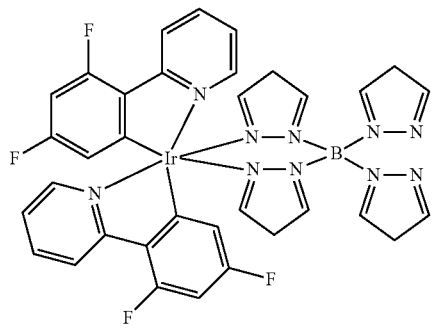 | 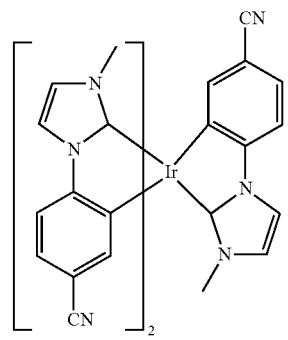 |
| 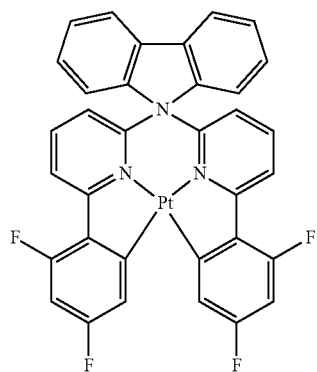 | 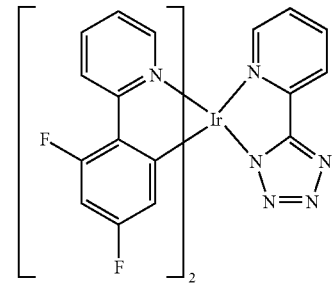 |
| 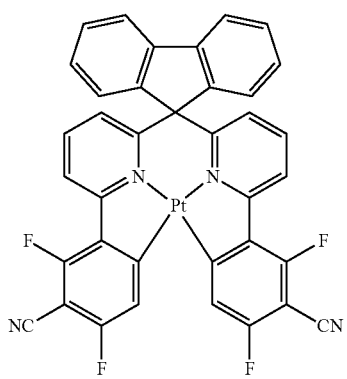 | 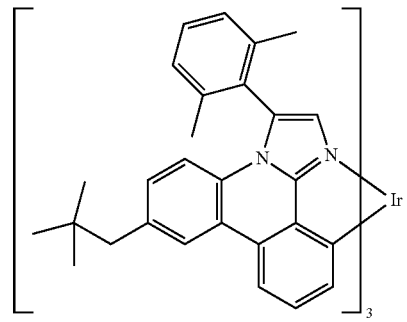 |
| 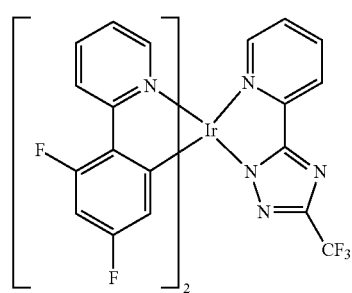 | 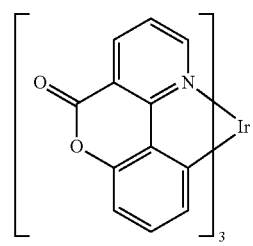 |
| | 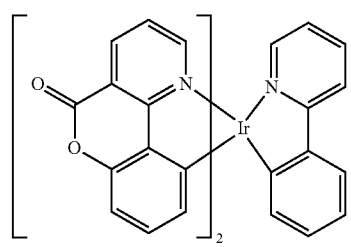 |

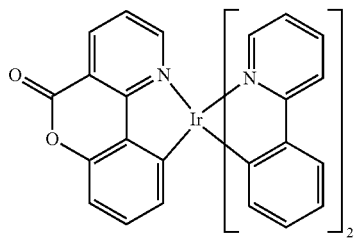

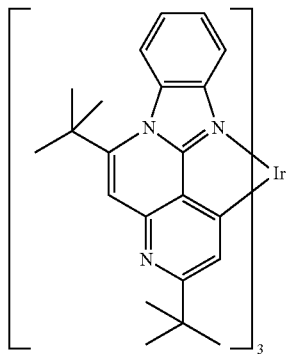

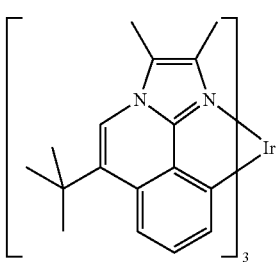

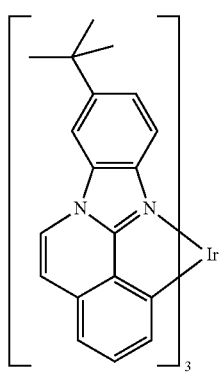

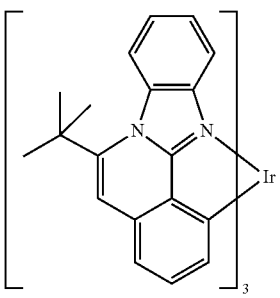

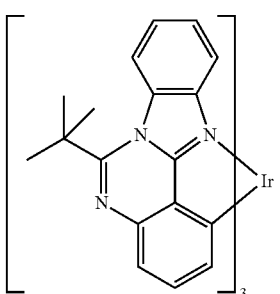

In a further embodiment of the invention, the organic electroluminescent device according to the invention does not comprise a separate hole-injection layer and/or hole-transport layer and/or hole-blocking layer and/or electron-transport layer, i.e. the emitting layer is directly adjacent to the hole-injection layer or the anode, and/or the emitting layer is directly adjacent to the electron-transport layer or the electron-injection layer or the cathode, as described, for example, in WO 2005/053051. Furthermore, it is possible to use a metal complex, which is identical or similar to the metal complex in the emitting layer, directly adjacent to the emitting layer as hole-transport or hole-injection material, as described, for example, in WO 2009/030981.

It is furthermore possible to use the compound of the formula (1) or the preferred embodiments both in a hole-transport layer or exciton-blocking layer and also as matrix in an emitting layer.

In the further layers of the organic electroluminescent device according to the invention, it is possible to use all materials as are usually employed in accordance with the prior art. The person skilled in the art will therefore be able, without inventive step, to employ all materials known for organic electroluminescent devices in combination with the compounds of the formula (1) according to the invention or the preferred embodiments.

According to a further preferred embodiment of the invention, the compounds of the formula (1), or the preferred embodiments, are employed in an interlayer. Interlayers are preferably employed in organic electroluminescent devices comprising a plurality of emitting layers, for example in white-emitting OLEDs which comprise in each case one red-emitting layer, one green-emitting layer and one blue-emitting layer. Interlayers are particularly preferably arranged between two emitting layers. In accordance with a preferred embodiment of the invention, an interlayer comprising a compound according to the invention is arranged between the blue-emitting layer and the green-emitting layer of a OLED emitting white light which comprises one red-emitting layer, one green-emitting layer and one blue-emitting layer. It is particularly preferred for the blue-emitting layer here to be a fluorescent layer and for the green-emitting layer to be a phosphorescent layer.

Preferred fluorescent dopants are selected from the class of the arylamines. An arylamine or aromatic amine in the sense of this invention is taken to mean a compound which contains three substituted or unsubstituted aromatic or heteroaromatic ring systems bonded directly to the nitrogen. At least one of these aromatic or heteroaromatic ring systems is preferably a condensed ring system, particularly preferably having at least 14 aromatic ring atoms. Preferred examples thereof are aromatic anthracenamines, aromatic anthracenediamines, aromatic pyrenamines, aromatic pyrenediamines, aromatic chrysenamines or aromatic chrysenediamines. An aromatic anthracenamine is taken to mean a compound in which one diarylamino group is bonded directly to an anthracene group, preferably in the 9-position. An aromatic anthracenediamine is taken to mean a compound in which two diarylamino groups are bonded directly to an anthracene group, preferably in the 9,10-position. Aromatic pyrenamines, pyrenediamines, chrysenamines and chrysenediamines are defined analogously thereto, where the diarylamino groups are preferably bonded to the pyrene in the 1-position or in the 1,6-position. Further preferred fluorescent dopants are selected from indenofluorenamines or indenofluorenediamines, for example in accordance with WO 2006/122630, benzoindenofluorenamines or benzoindenofluorenediamines, for example in accordance with WO 2008/006449, and dibenzoindenofluorenamines or dibenzoindenofluorenediamines, for example in accordance with WO 2007/140847. Preference is furthermore given to the condensed hydrocarbons disclosed in WO 2010/012328.

Suitable fluorescent dopants are furthermore the derivatives of these structures disclosed in JP 200600 1973, WO 2004/047499, WO 2006/098080, WO 2007/065678, US 2005/0260442 and WO 2004/092111.

Suitable matrix materials, preferably for fluorescent dopants, are materials from various classes of substance. Preferred matrix materials are selected from the classes of the oligoarylenes (for example 2,2',7,7'-tetraphenylspirobifluorene in accordance with EP 676461 or dinaphthylanthracene), in particular the oligoarylenes containing condensed aromatic groups, the oligoarylenevinylenes (for example DPVBi or spiro-DPVBi in accordance with EP 676461), the polypodal metal complexes (for example in accordance with WO 2004/081017), the hole-conducting compounds (for example in accordance with WO 2004/058911), the electron-conducting compounds, in particular ketones, phosphine oxides, sulfoxides, etc. (for example in accordance with WO 2005/084081 and WO 2005/084082), the atropisomers (for example in accordance with WO 2006/048268), the boronic acid derivatives (for example in accordance with WO 2006/117052) or the benzanthracenes (for example in accordance with WO 2008/145239). Particularly preferred matrix materials are selected from the classes of the oligoarylenes, comprising naphthalene, anthracene, benzanthracene and/or pyrene or atropisomers of these compounds, the oligoarylenevinylenes, the ketones, the phosphine oxides and the sulfoxides. Very particularly preferred matrix materials are selected from the classes of the oligoarylenes, comprising anthracene, benzanthracene, benzophenanthrene and/or pyrene or atropisomers of these compounds. An oligoarylene in the sense of this invention is intended to be taken to mean a compound in which at least three aryl or arylene groups are bonded to one another.

Suitable charge-transport materials, as can be used in the hole-injection or hole-transport layer or in the electron-transport layer of the organic electroluminescent device according to the invention, are, for example, the compounds disclosed in Y. Shirota et al., Chem. Rev. 2007, 107(4), 953-1010, or other materials as are employed in these layers in accordance with the prior art.

The cathode preferably comprises metals having a low work function, metal alloys or multilayered structures comprising various metals, such as, for example, alkaline-earth metals, alkali metals, main-group metals or lanthanoids (for example Ca, Ba, Mg, Al, In, Mg, Yb, Sm, etc.). Also suitable are alloys comprising an alkali metal or alkaline-earth metal and silver, for example an alloy comprising magnesium and silver. In the case of multilayered structures, further metals which have a relatively high work function, such as, for example, Ag or Al, can also be used in addition to the said metals, in which case combinations of the metals, such as, for example, Ca/Ag, Ba/Ag or Mg/Ag, are generally used. It may also be preferred to introduce a thin interlayer of a material having a high dielectric constant between a metallic cathode and the organic semiconductor. Suitable for this purpose are, for example, alkali metal fluorides or alkaline-earth metal fluorides, but also the corresponding oxides or carbonates (for example LiF, $Li_2O$, $BaF_2$, MgO, NaF, CsF, $Cs_2CO_3$, etc.). Furthermore, lithium quinolinate (LiQ) can be used for this purpose. The layer thickness of this layer is preferably between 0.5 and 5 nm.

The anode preferably comprises materials having a high work function. The anode preferably has a work function of greater than 4.5 eV vs. vacuum. Suitable for this purpose are on the one hand metals having a high redox potential, such as, for example, Ag, Pt or Au. On the other hand, metal/metal oxide electrodes (for example Al/Ni/NiOx, Al/PtOx) may also be preferred. For some applications, at least one of the electrodes must be transparent or partially transparent in order to facilitate either irradiation of the organic material (organic solar cells) or the coupling-out of light (OLEDs, O-lasers). Preferred anode materials here are conductive mixed metal oxides. Particular preference is given to indium tin oxide (ITO) or indium zinc oxide (IZO). Preference is furthermore given to conductive, doped organic materials, in particular conductive, doped polymers.

The device is appropriately (depending on the application) structured, provided with contacts and finally sealed, since the lifetime of the devices according to the invention is shortened in the presence of water and/or air.

In a preferred embodiment, the organic electroluminescent device according to the invention is characterised in that one or more layers are applied by means of a sublimation process, in which the materials are applied by vapour deposition in vacuum sublimation units at an initial pressure of less than $10^{-5}$ mbar, preferably less than $10^{-6}$ mbar. However, it is also possible here for the initial pressure to be even lower, for example less than $10^{-7}$ mbar.

Preference is likewise given to an organic electroluminescent device, characterised in that one or more layers are applied by means of the OVPD (organic vapour phase deposition) process or with the aid of carrier-gas sublimation, in which the materials are applied at a pressure of between $10^{-5}$ mbar and 1 bar. A special case of this process is the OVJP (organic vapour jet printing) process, in which the materials are applied directly through a nozzle and are thus structured (for example M. S. Arnold et at, *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing, nozzle printing or offset printing, but particularly preferably LITI (light induced thermal imaging, thermal transfer printing) or ink-jet printing. Soluble compounds of the formula (1), or of a preferred embodiment, are necessary for this purpose. High solubility can be achieved through suitable substitution of the compounds.

For the production of an organic electroluminescent device according to the invention, it is furthermore preferred to apply one or more layers from solution and one or more layers by a sublimation process.

Also possible are hybrid processes, in which, for example, one or more layers are applied from solution and one or more further layers are applied by vapour deposition. Thus, for example, the emitting layer can be applied from solution and the electron-transport layer can be applied by vapour deposition. These processes are generally known to the person skilled in the art and can be applied by him, without inventive step, to organic electroluminescent devices comprising the compounds according to the invention.

The present invention furthermore relates to mixtures comprising at least one compound of the formula (1) or the preferred embodiments indicated above and at least one further compound. The further compound can be, for example, a fluorescent or phosphorescent dopant if the compound according to the invention is used as matrix material. The mixture may then also additionally comprise a further material as additional matrix material.

The compounds according to the invention and the organic electroluminescent devices according to the invention are distinguished by the following surprising advantages over the prior art:

1. The compounds according to the invention are very highly suitable for use in a hole-transport or hole-injection layer in an organic electroluminescent device. They are, in particular, also suitable for use in a layer which is directly adjacent to a phosphorescent emitting layer, since the compounds according to the invention do not extinguish the luminescence.
2. The compounds according to the invention, employed as matrix material for fluorescent or phosphorescent emitters, result in very high efficiencies and in long lifetimes. This applies, in particular, if the compounds are employed as matrix material together with a further matrix material and a phosphorescent emitter.
3. The compounds according to the invention, employed in organic electroluminescent devices, result in high efficiencies and in steep current/voltage curves with low operating voltages.
4. The compounds according to the invention have high thermal stability and can be sublimed without decomposition and without a residue.
5. The compounds according to the invention have high oxidation stability, which has, in particular, a positive effect on the handling of these compounds and on the storage stability for solutions.

These above-mentioned advantages are not accompanied by an impairment of the other electronic properties.

The invention is explained in greater detail by the following examples, without wishing to restrict it thereby. The descriptions enable the person skilled in the art to carry out the invention throughout the range disclosed and to prepare further compounds according to the invention without inventive step and use them in electronic devices or to use the process according to the invention.

The invention is explained in greater detail by the following use examples, where the invention is not restricted to the scope of the examples.

WORKING EXAMPLES

The following syntheses are carried out, unless indicated otherwise, under a protective-gas atmosphere. The starting materials can be purchased from ALDRICH or ABCR (palladium(II) acetate, tri-o-tolylphosphine, inorganics, solvents).

The compounds denoted by * in the following tables may also be in the form of a mixture of substitution isomers. This may also already apply to the starting materials used.

In addition, the compounds may optionally be in the form of a mixture of enantiomers or diastereomers.

Example 0

Synthesis of Compound (0-1)

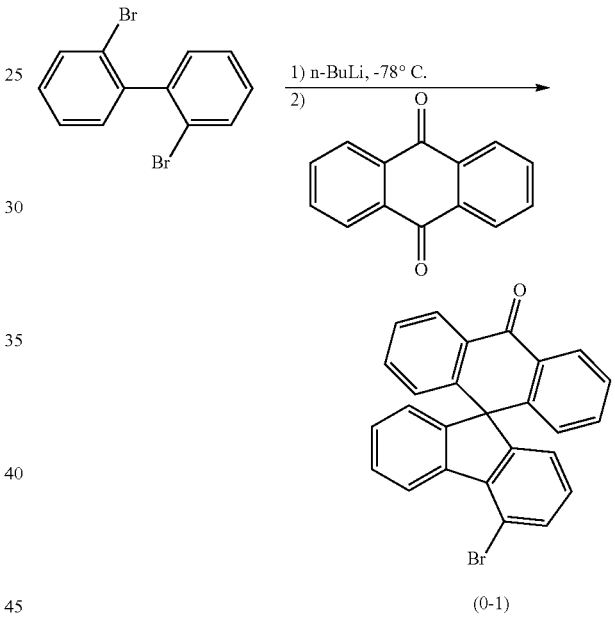

(0-1)

37.4 g (120 mmol) of 2,2'-dibromobiphenyl are dissolved in 300 ml of dried THF in a flask which has been dried by heating. The reaction mixture is cooled to −78° C. At this temperature, 75 ml of a 15% solution of n-BuLi in hexane (119 mmol) are slowly added dropwise. The batch is stirred at −70° C. for a further 1 h. 22.9 g of anthraquinone (CAS No.: 84-65-1) (110 mmol) are subsequently dissolved in 100 ml of THF and added dropwise at −70° C. When the addition is complete, the reaction mixture is slowly warmed to room temperature, quenched using NH$_4$Cl and subsequently evaporated in a rotary evaporator. 500 ml of acetic acid are carefully added to the evaporated solution, and 90 ml of fuming HCl are subsequently added. The batch is heated to 75° C. and kept at this temperature for 4 h. A white solid precipitates out during this time. The batch is then cooled to room temperature, and the solid which has precipitated out is filtered off with suction and rinsed with methanol. The residue is dried at 40° C. in vacuo. The yield is 44.4 g (105 mmol) (87.5% of theory).

The following compounds (0-2) to (0-3) are prepared analogously;

| Starting material 1 | Starting material 2 | Product | Yield |
|---|---|---|---|
| 0-2 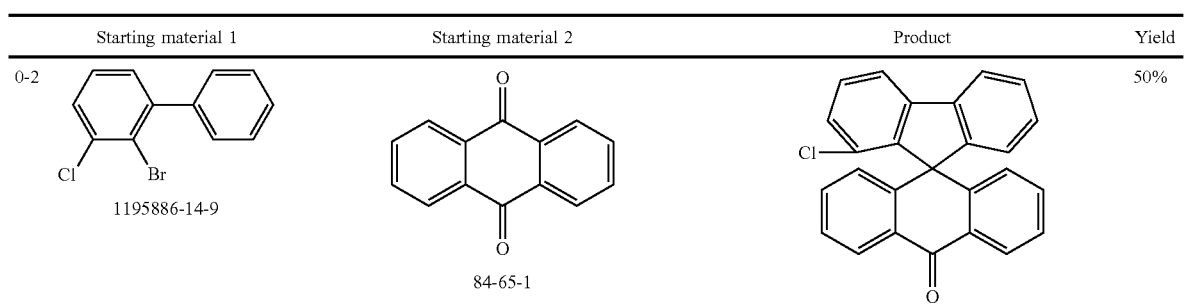 1195886-14-9 | 84-65-1 | | 50% |
| 0-3 1195886-14-9 | 131268-46-7 | | 43%* |

Example 1

Synthesis of Compound (1-1)

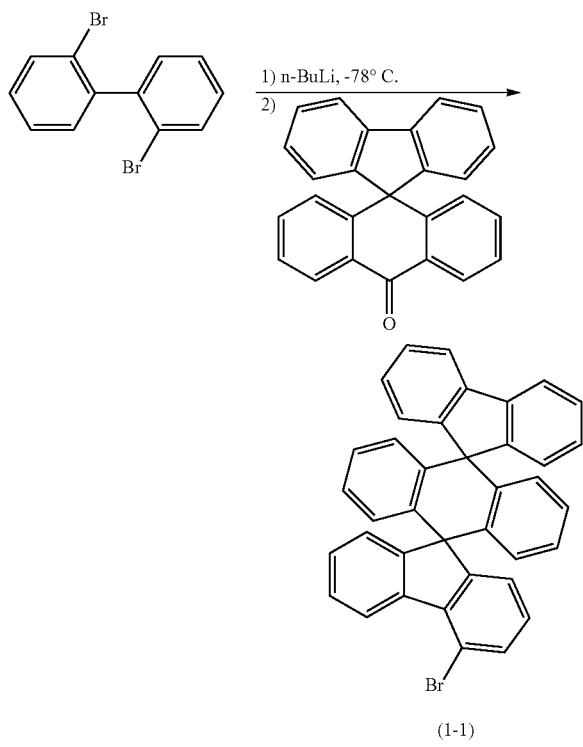

37.4 g (120 mmol) of 2,2'-dibromobiphenyl are dissolved in 300 ml of dried THF in a flask which has been dried by heating. The reaction mixture is cooled to −78° C. At this temperature, 75 ml of a 15% solution of n-BuLi in hexane (119 mmol) are slowly added dropwise. The batch is stirred at −70° C. for a further 1 h. 37.8 g of the ketone derivative (CAS No.: 717881-21-5) (110 mmol) are subsequently dissolved in 100 ml of THF and added dropwise at −70° C. When the addition is complete, the reaction mixture is slowly warmed to room temperature, quenched using NH$_4$Cl and subsequently evaporated in a rotary evaporator. 500 ml of acetic acid are carefully added to the evaporated solution, and 90 ml of fuming HCl are subsequently added. The batch is heated to 75° C. and kept at this temperature for 4 h. A white solid precipitates out during this time. The batch is then cooled to room temperature, and the solid which has precipitated out is filtered off with suction and rinsed with methanol. The residue is dried at 40° C. in vacuo. The yield is 61.4 g (81% of theory).

The following compounds (1-2) to (1-10) are prepared analogously

| Starting material 1 | Starting material 2 |
|---|---|
| 1-2 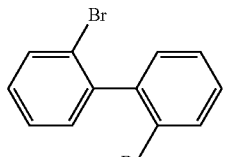 13029-09-9 | 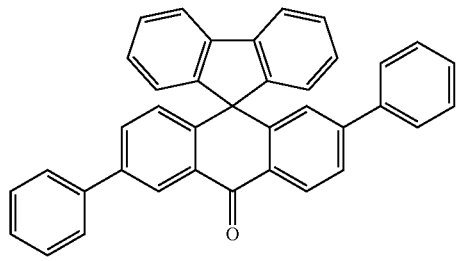 1355363-51-7 |
| 1-3 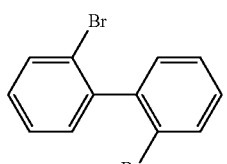 13029-09-9 | 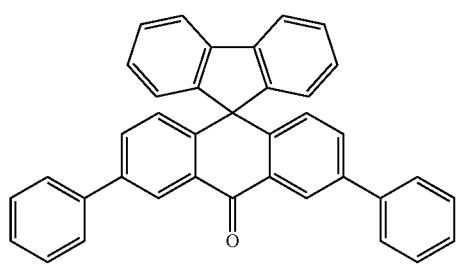 1355363-60-8 |
| 1-4 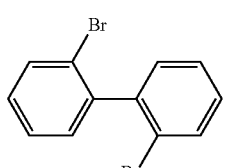 13029-09-9 | 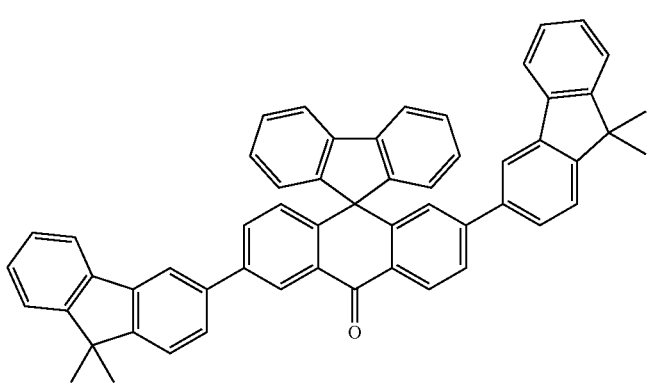 1355363-56-2 |
| 1-5 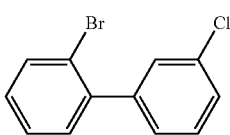 154407-17-7 | 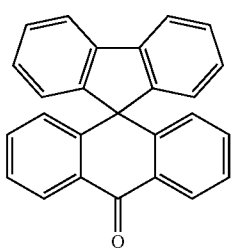 717881-21-5 |
| 1-6 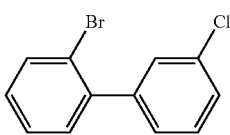 154407-17-7 | 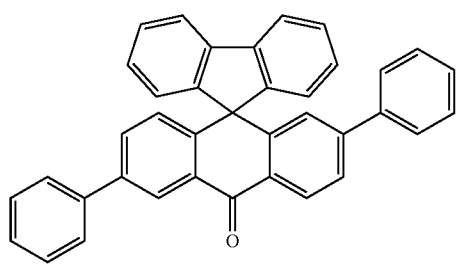 1355363-51-7 |

-continued
| | | |
|---|---|---|
| 1-7 | 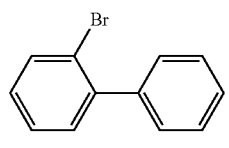<br>2052-07-5 | 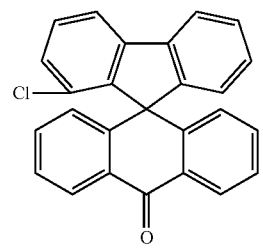 [SMILES: O=C1c2ccccc2C2(c3ccccc31)c1ccccc1-c1cccc(Cl)c12] |
| 1-8 | 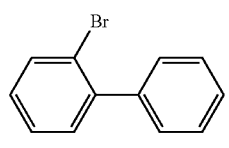<br>2052-07-5 | 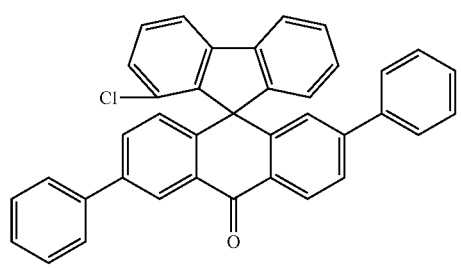 |
| 1-9 | 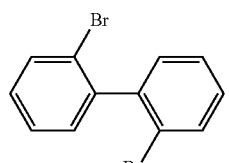<br>13029-09-9 | 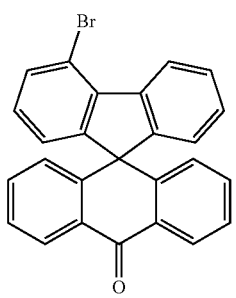 [SMILES: O=C1c2ccccc2C2(c3ccccc31)c1ccccc1-c1c(Br)cccc12] |
| 1-10 | 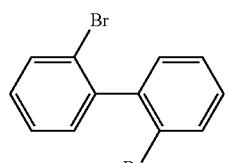<br>13029-09-9 | 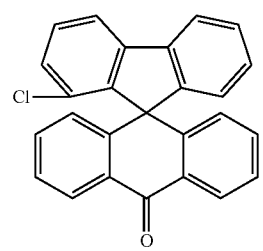 [SMILES: O=C1c2ccccc2C2(c3ccccc31)c1ccccc1-c1cccc(Cl)c12] |
| | Product | Yield |
|---|---|---|
| 1-2 | 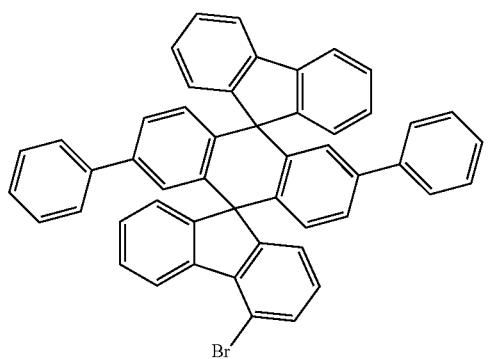 [SMILES: Brc1cccc2c1-c1ccccc1C21c2ccc(-c3ccccc3)cc2C2(c3ccccc3-c3ccccc32)c2ccc(-c3ccccc3)cc21] | 75%* |

-continued
| | | |
|---|---|---|
| 1-3 | 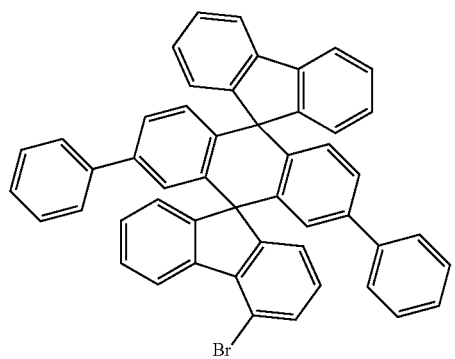 [SMILES: Brc1cccc2c1-c1ccccc1C21c2cc(-c3ccccc3)ccc2C2(c3ccccc3-c3ccccc32)c2ccc(-c3ccccc3)cc21] | 72% |
| 1-4 | 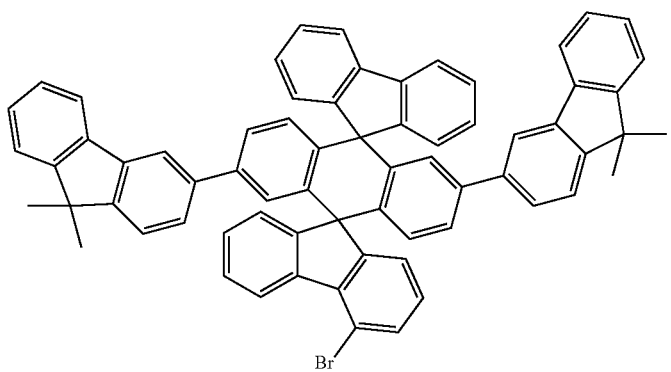 [SMILES: CC1(C)c2ccccc2-c2cc(-c3ccc4c(c3)C3(c5ccccc5-c5ccccc53)c3ccc(-c5ccc6c(c5)-c5ccccc5C6(C)C)cc3C43c4ccccc4-c4c(Br)cccc43)ccc21] | 65%* |
| 1-5 | 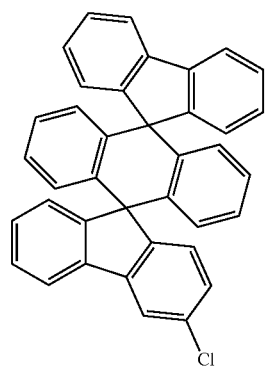 [SMILES: Clc1ccc2c(c1)-c1ccccc1C21c2ccccc2C2(c3ccccc3-c3ccccc32)c2ccccc21] | 47% |
| 1-6 | 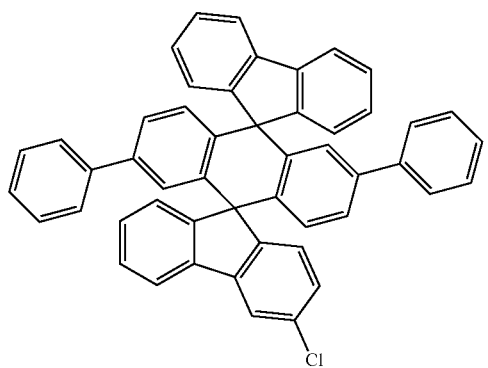 [SMILES: Clc1ccc2c(c1)-c1ccccc1C21c2ccc(-c3ccccc3)cc2C2(c3ccccc3-c3ccccc32)c2ccc(-c3ccccc3)cc21] | 43%* |

| | | |
|---|---|---|
| 1-7 | 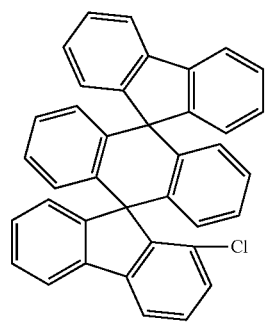 [SMILES: Clc1cccc2c1C1(c3ccccc3-2)c2ccccc2C2(c3ccccc3-c3ccccc32)c2ccccc21] | 45% |
| 1-8 | 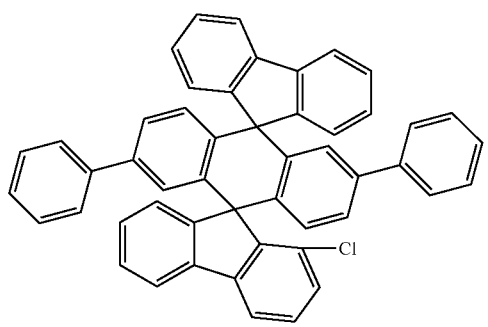 [SMILES: Clc1cccc2c1C1(c3ccccc3-2)c2ccc(-c3ccccc3)cc2C2(c3ccccc3-c3ccccc32)c2ccc(-c3ccccc3)cc21] | 35%* |
| 1-9 | 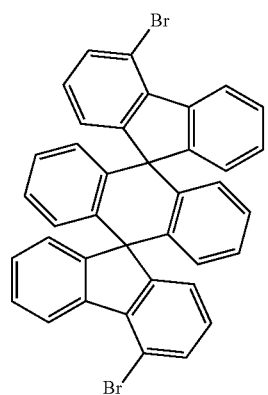 [SMILES: Brc1cccc2c1-c1ccccc1C21c2ccccc2C2(c3ccccc3-c3c(Br)cccc32)c2ccccc21] | 56%* |
| 1-10 | 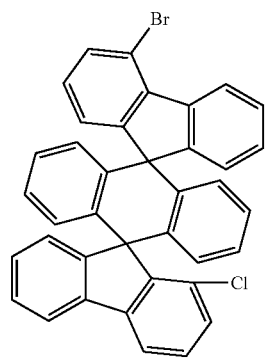 | 48%* |

Example 2

Synthesis of Compound (2-1)

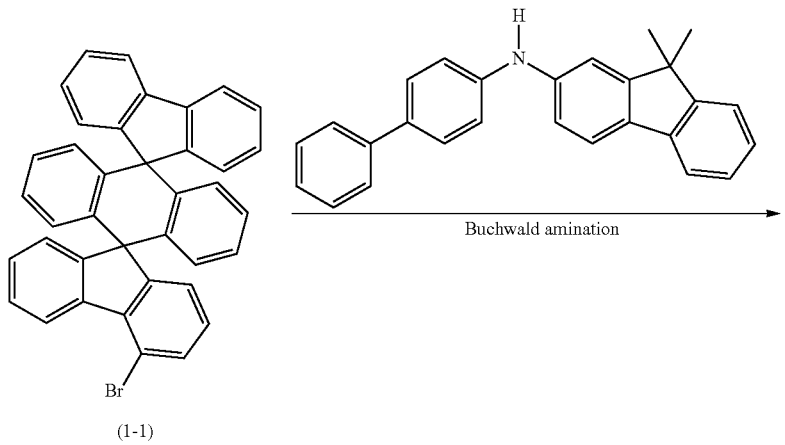

(1-1)

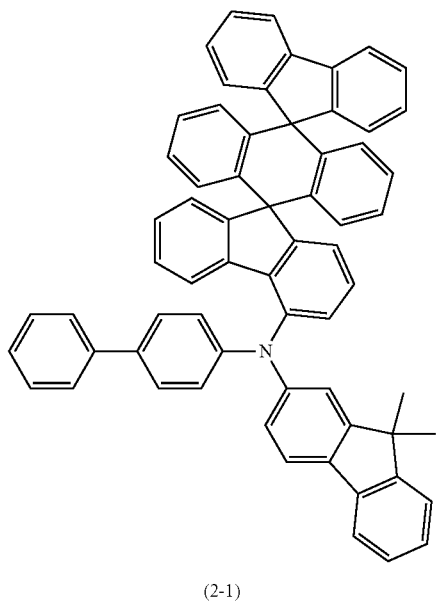

(2-1)

12.9 g of biphenyl-4-yl-(9,9-dimethyl-9H-fluoren-2-yl)amine (36 mmol) and 20 g of the bromine derivative (1-1) (36 mmol) are dissolved in 600 ml of toluene. The solution is degassed and saturated with $N_2$. 3.6 ml (3.6 mmol) of a 1 M tri-tert-butylphosphine solution and 0.4 g (1.79 mmol) of palladium(II) acetate are then added. 8.59 g of sodium tert-butoxide (89.4 mmol) are subsequently added. The reaction mixture is heated at the boil under a protective atmosphere for 7 h. The mixture is subsequently partitioned between toluene and water, and the organic phase is washed three times with water, dried over $Na_2SO_4$ and evaporated in a rotary evaporator. After filtration of the crude product through silica gel with toluene, the residue which remains is recrystallised from heptane/toluene and finally sublimed in a high vacuum. The purity is 99.9%. The yield is 25 g (85% of theory).

The following compounds (2-2) to (2-23) are prepared analogously:

| Starting material 1 | Starting material 2 |
|---|---|
| 2-2 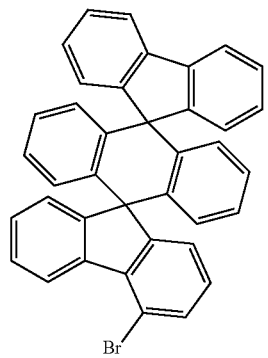 [SMILES: Brc1cccc2c1-c1ccccc1C21c2ccccc2C2(c3ccccc3-c3ccccc32)c2ccccc21] | 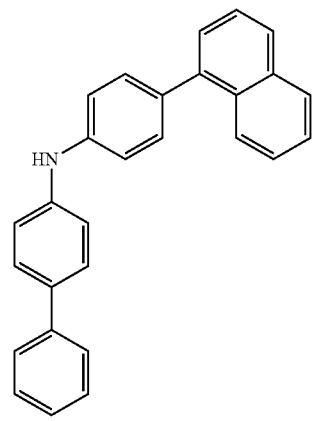<br>897921-59-4 |
| 2-3 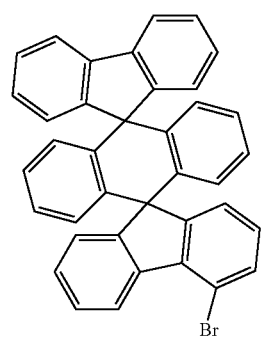 [SMILES: Brc1cccc2c1-c1ccccc1C21c2ccccc2C2(c3ccccc3-c3ccccc32)c2ccccc21] | 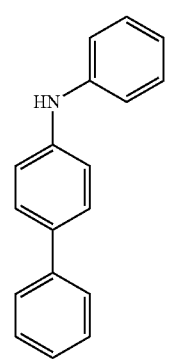<br>32228-99-2 |
| 2-4 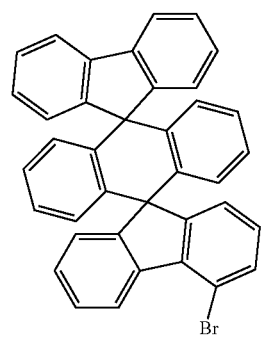 [SMILES: Brc1cccc2c1-c1ccccc1C21c2ccccc2C2(c3ccccc3-c3ccccc32)c2ccccc21] | 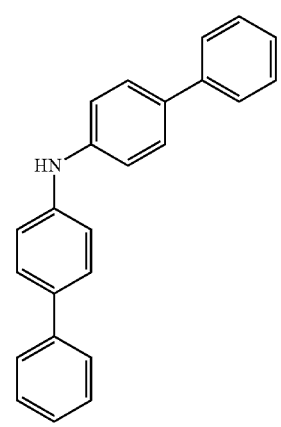<br>102113-98-4 |

-continued
2-5
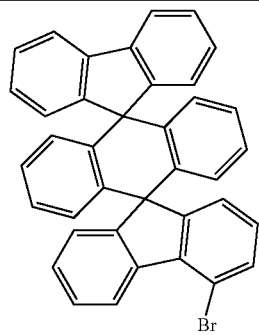
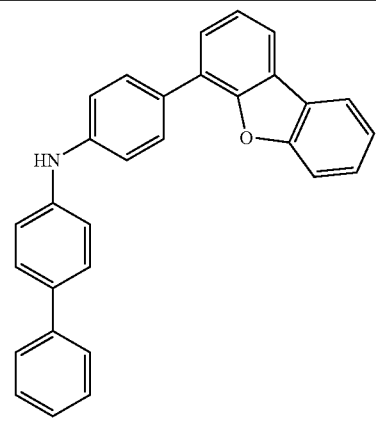
955959-89-4
2-6
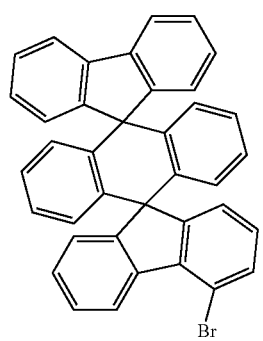 [SMILES: Brc1cccc2c1-c1ccccc1C21c2ccccc2C2(c3ccccc3-c3ccccc32)c2ccccc21]
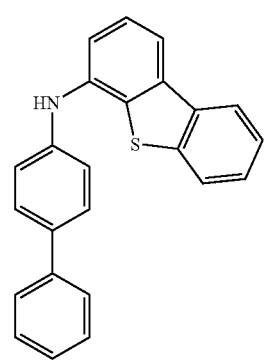
1448185-87-2
2-7
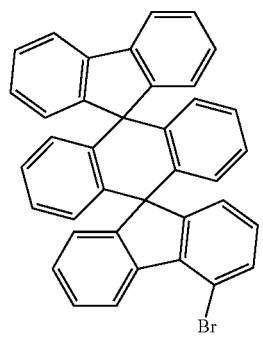 [SMILES: Brc1cccc2c1-c1ccccc1C21c2ccccc2C2(c3ccccc3-c3ccccc32)c2ccccc21]
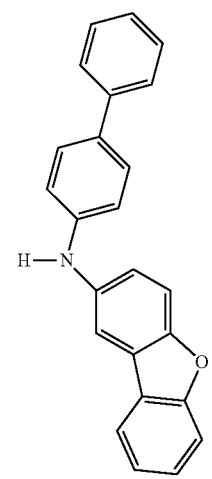
1300028-94-7

-continued
| | | |
|---|---|---|
| 2-8 | 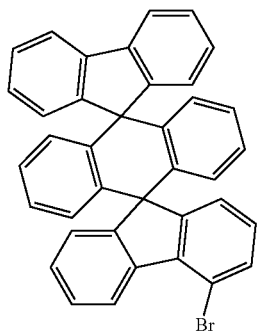 [SMILES: Brc1cccc2c1-c1ccccc1C21c2ccccc2C2(c3ccccc3-c3ccccc32)c2ccccc21] | 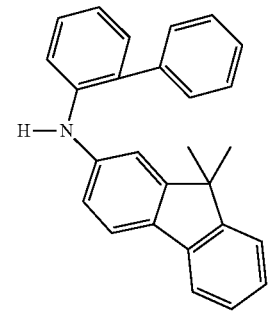
1198395-24-2 |
| 2-9 | 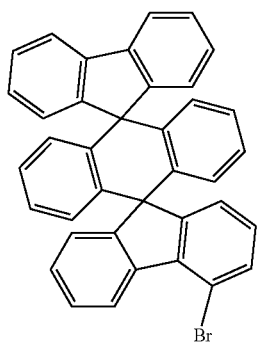 [SMILES: Brc1cccc2c1-c1ccccc1C21c2ccccc2C2(c3ccccc3-c3ccccc32)c2ccccc21] | 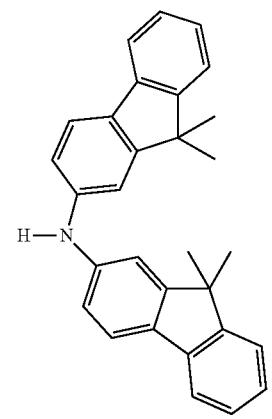
500717-23-7 |
| 2-10 | 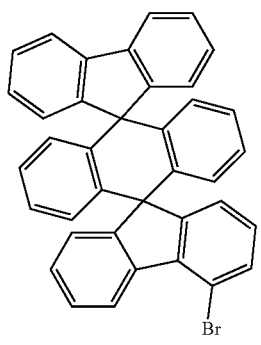 [SMILES: Brc1cccc2c1-c1ccccc1C21c2ccccc2C2(c3ccccc3-c3ccccc32)c2ccccc21] | 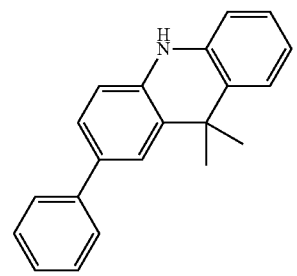 [SMILES: CC1(C)c2ccccc2Nc2ccc(-c3ccccc3)cc21] |
| 2-11 | 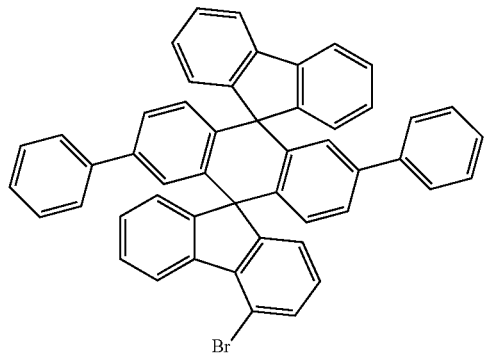 [SMILES: Brc1cccc2c1-c1ccccc1C21c2ccc(-c3ccccc3)cc2C2(c3ccccc3-c3ccccc32)c2ccc(-c3ccccc3)cc21] | 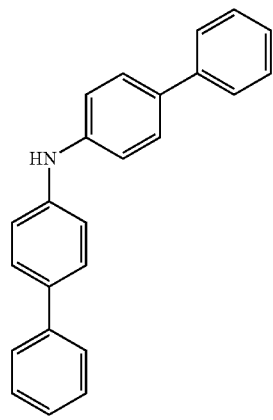
102113-98-4 |

2-12 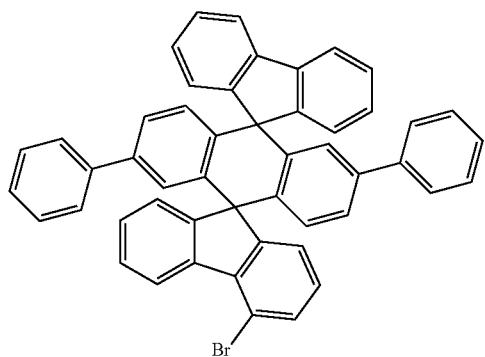 [SMILES: Brc1cccc2c1-c1ccccc1C21c2ccc(-c3ccccc3)cc2C2(c3ccccc3-c3ccccc32)c2ccc(-c3ccccc3)cc21] 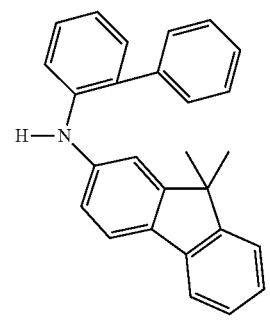
1198395-24-2
2-13 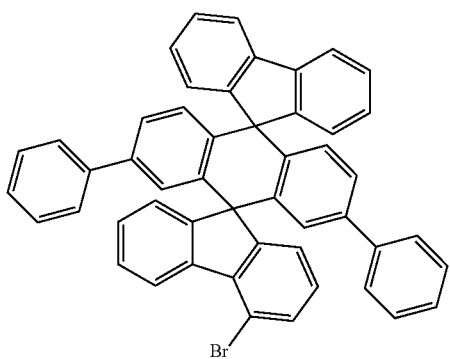 [SMILES: Brc1cccc2c1-c1ccccc1C21c2cc(-c3ccccc3)ccc2C2(c3ccccc3-c3ccccc32)c2ccc(-c3ccccc3)cc21] 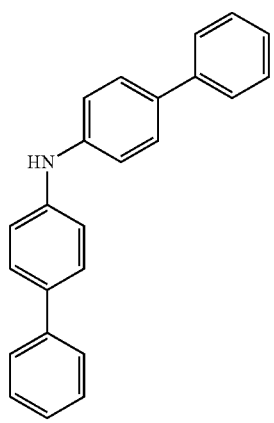
102113-98-4
2-14 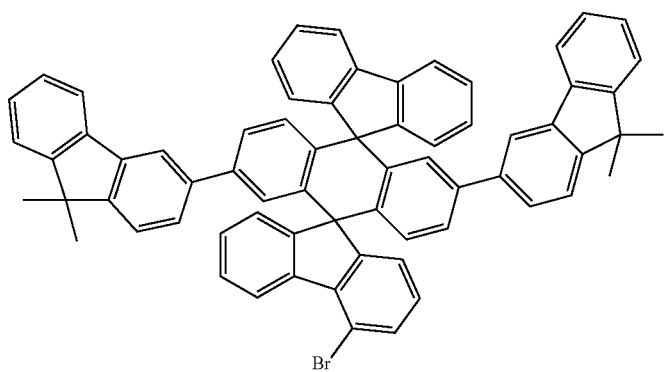 [SMILES: CC1(C)c2ccccc2-c2cc(-c3ccc4c(c3)C3(c5ccccc5-c5ccccc53)c3ccc(-c5ccc6c(c5)-c5ccccc5C6(C)C)cc3C43c4ccccc4-c4c(Br)cccc43)ccc21] 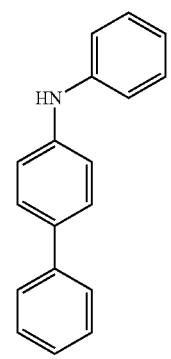
32228-99-2

2-15 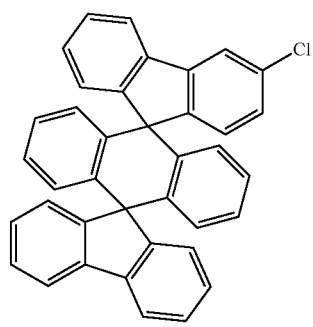 [SMILES: Clc1ccc2c(c1)-c1ccccc1C21c2ccccc2C2(c3ccccc3-c3ccccc32)c2ccccc21] 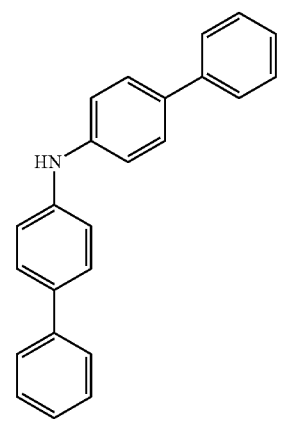
102113-98-4
2-16 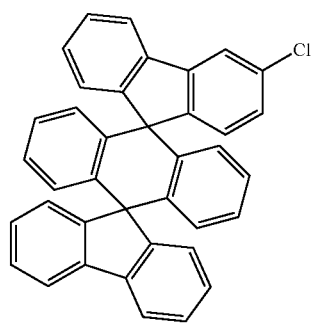 [SMILES: Clc1ccc2c(c1)-c1ccccc1C21c2ccccc2C2(c3ccccc3-c3ccccc32)c2ccccc21] 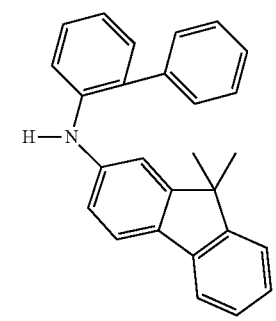
1198395-24-2
2-17 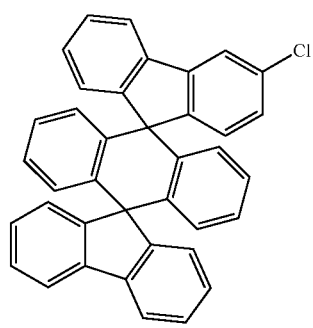 [SMILES: Clc1ccc2c(c1)-c1ccccc1C21c2ccccc2C2(c3ccccc3-c3ccccc32)c2ccccc21] 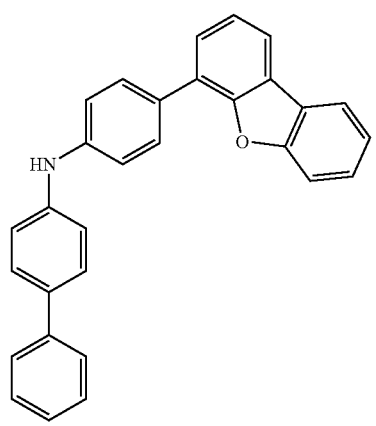
955959-89-4

2-18 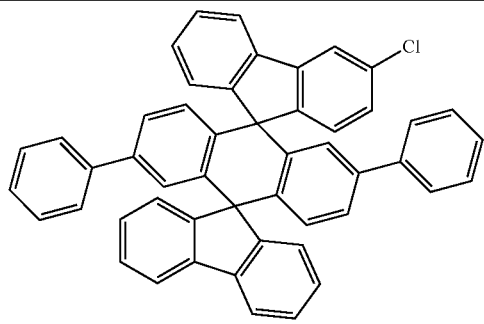 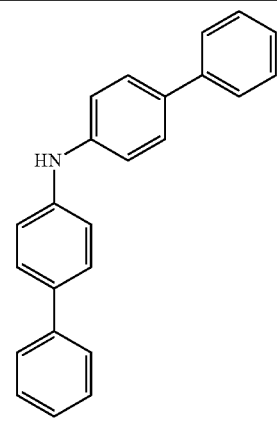
102113-98-4
2-19 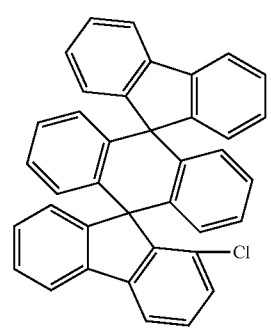 [SMILES: Clc1cccc2c1C1(c3ccccc3-2)c2ccccc2C2(c3ccccc3-c3ccccc32)c2ccccc21] 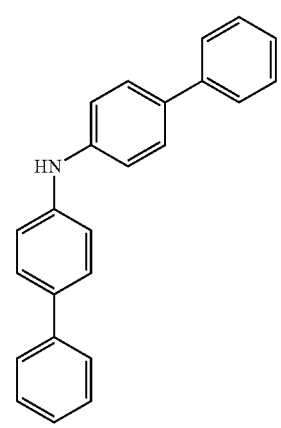
102113-98-4
2-20 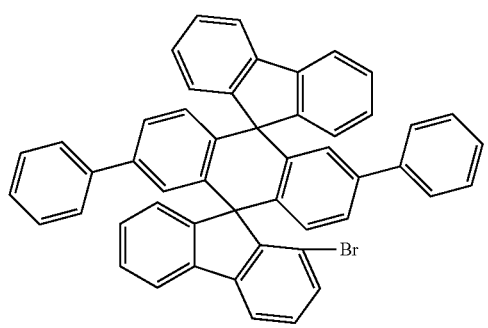 [SMILES: Brc1cccc2c1C1(c3ccccc3-2)c2ccc(-c3ccccc3)cc2C2(c3ccccc3-c3ccccc32)c2ccc(-c3ccccc3)cc21] 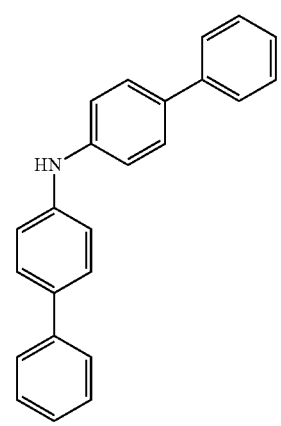
102113-98-4

-continued
| | | |
|---|---|---|
| 2-21 | 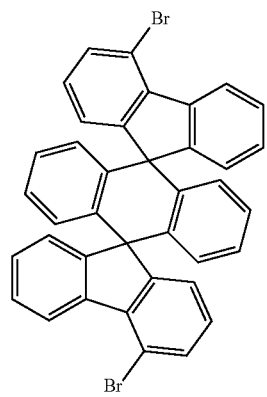 [SMILES: Brc1cccc2c1-c1ccccc1C21c2ccccc2C2(c3ccccc3-c3c(Br)cccc32)c2ccccc21] | 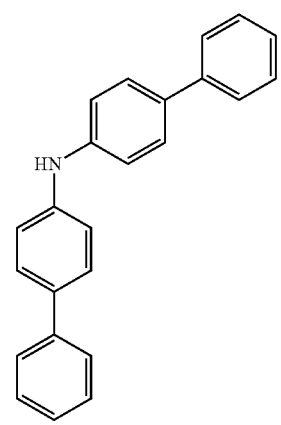
102113-98-4
2 eq. |
| 2-22 | 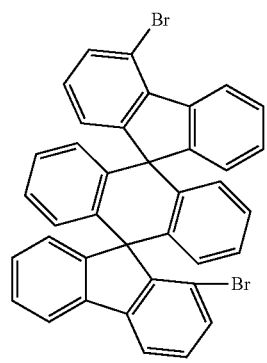 [SMILES: Brc1cccc2c1-c1ccccc1C21c2ccccc2C2(c3ccccc3-c3cccc(Br)c32)c2ccccc21] | 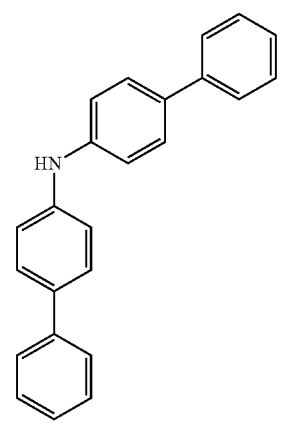
102113-98-4
2 eq. |
| 2-23 | 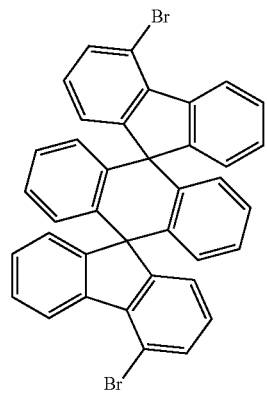 [SMILES: Brc1cccc2c1-c1ccccc1C21c2ccccc2C2(c3ccccc3-c3c(Br)cccc32)c2ccccc21] | 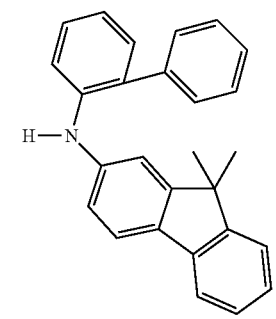
1198395-24-2
2 eq. |

| Product | Yield |
|---|---|
| 2-2 | 78% |
| 2-3 | 83% |
| 2-4 | 92% |

| | | |
|---|---|---|
| 2-5 | 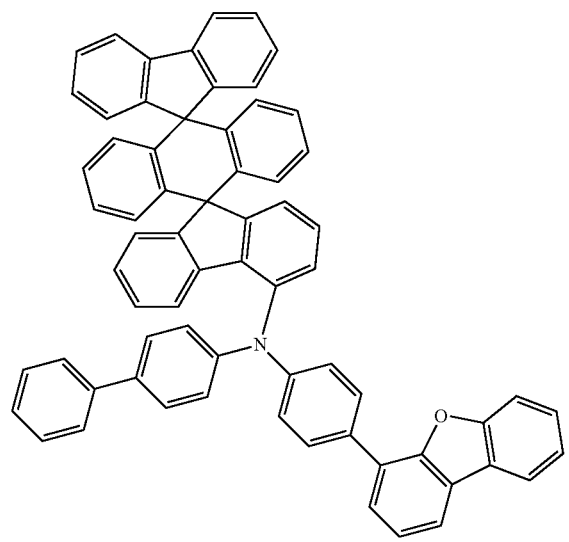 [SMILES: c1ccc(-c2ccc(N(c3ccc(-c4cccc5c4oc4ccccc45)cc3)c3cccc4c3-c3ccccc3C43c4ccccc4C4(c5ccccc5-c5ccccc54)c4ccccc43)cc2)cc1] | 88% |
| 2-6 | 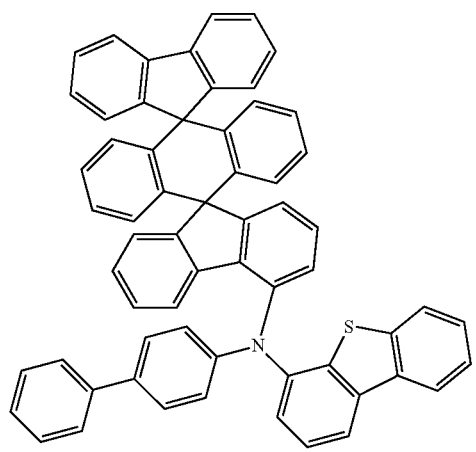 [SMILES: c1ccc(-c2ccc(N(c3cccc4c3-c3ccccc3C43c4ccccc4C4(c5ccccc5-c5ccccc54)c4ccccc43)c3cccc4c3sc3ccccc34)cc2)cc1] | 77% |
| 2-7 | 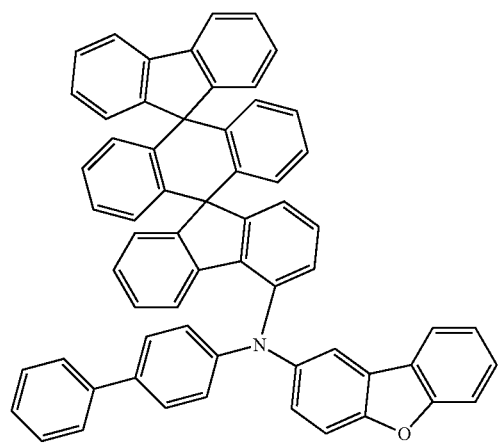 [SMILES: c1ccc(-c2ccc(N(c3ccc4oc5ccccc5c4c3)c3cccc4c3-c3ccccc3C43c4ccccc4C4(c5ccccc5-c5ccccc54)c4ccccc43)cc2)cc1] | 76% |

| | | |
|---|---|---|
| 2-8 | 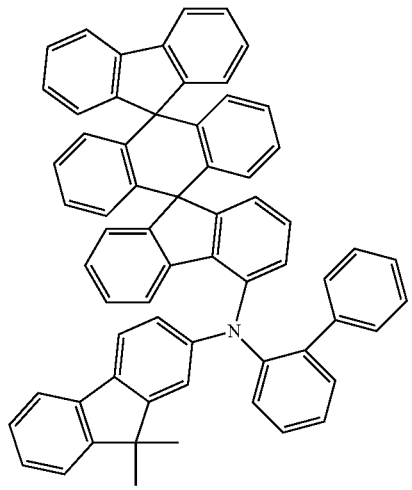 [SMILES: CC1(C)c2ccccc2-c2ccc(N(c3ccccc3-c3ccccc3)c3cccc4c3-c3ccccc3C43c4ccccc4C4(c5ccccc5-c5ccccc54)c4ccccc43)cc21] | 69% |
| 2-9 | 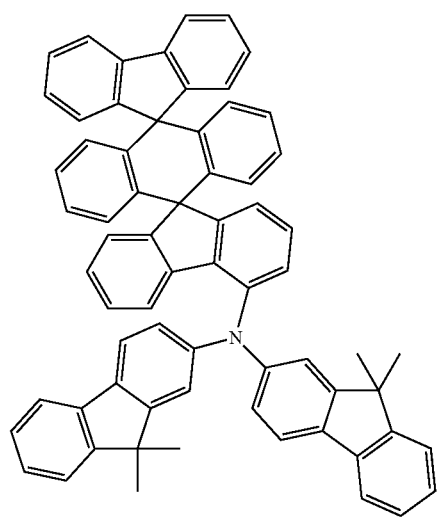 [SMILES: CC1(C)c2ccccc2-c2ccc(N(c3ccc4c(c3)C(C)(C)c3ccccc3-4)c3cccc4c3-c3ccccc3C43c4ccccc4C4(c5ccccc5-c5ccccc54)c4ccccc43)cc21] | 72% |
| 2-10 | 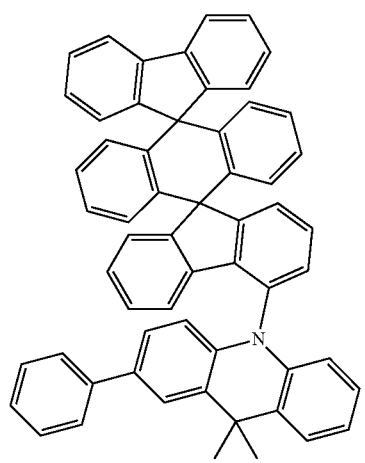 [SMILES: CC1(C)c2ccccc2N(c2cccc3c2-c2ccccc2C32c3ccccc3C3(c4ccccc4-c4ccccc43)c3ccccc32)c2ccc(-c3ccccc3)cc21] | 75% |

| | | |
|---|---|---|
| 2-11 | 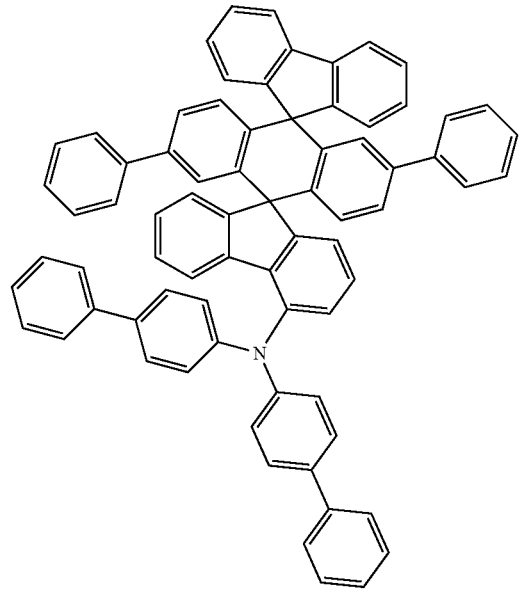 [SMILES: c1ccc(-c2ccc(N(c3ccc(-c4ccccc4)cc3)c3cccc4c3-c3ccccc3C43c4ccc(-c5ccccc5)cc4C4(c5ccccc5-c5ccccc54)c4ccc(-c5ccccc5)cc43)cc2)cc1] | 68%* |
| 2-12 | 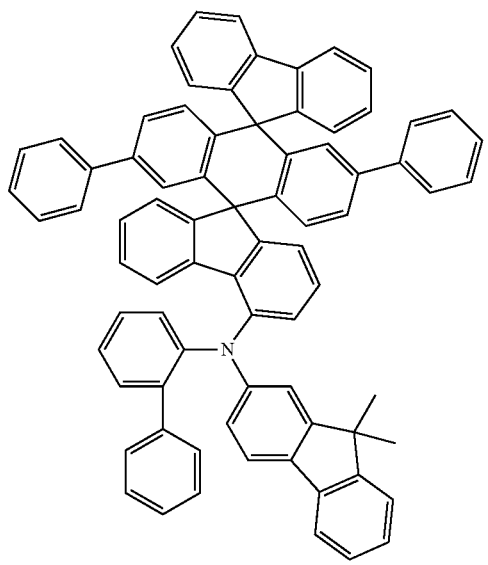 [SMILES: CC1(C)c2ccccc2-c2ccc(N(c3ccccc3-c3ccccc3)c3cccc4c3-c3ccccc3C43c4ccc(-c5ccccc5)cc4C4(c5ccccc5-c5ccccc54)c4ccc(-c5ccccc5)cc43)cc21] | 68%* |

| | | |
|---|---|---|
| 2-13 | 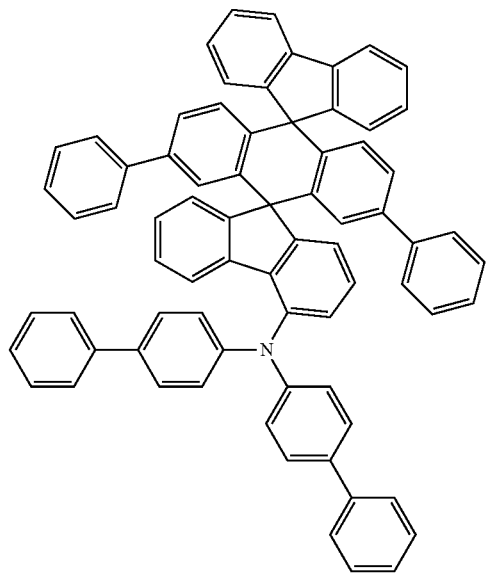 [SMILES: c1ccc(-c2ccc(N(c3ccc(-c4ccccc4)cc3)c3cccc4c3-c3ccccc3C43c4cc(-c5ccccc5)ccc4C4(c5ccccc5-c5ccccc54)c4ccc(-c5ccccc5)cc43)cc2)cc1] | 70% |
| 2-14 | 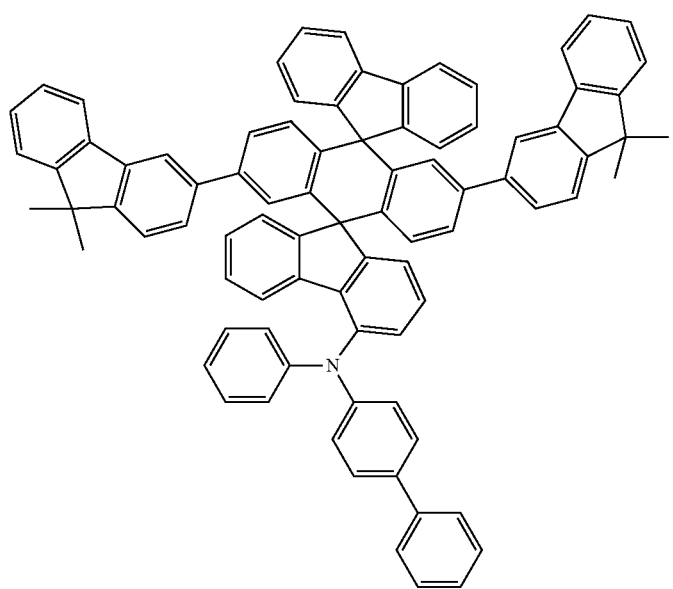 [SMILES: CC1(C)c2ccccc2-c2cc(-c3ccc4c(c3)C3(c5ccccc5-c5ccccc53)c3ccc(-c5ccc6c(c5)-c5ccccc5C6(C)C)cc3C43c4ccccc4-c4c(N(c5ccccc5)c5ccc(-c6ccccc6)cc5)cccc43)ccc21] | 65%* |
| 2-15 | 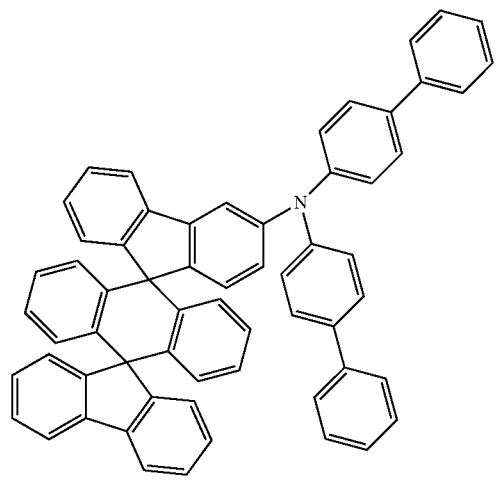 [SMILES: c1ccc(-c2ccc(N(c3ccc(-c4ccccc4)cc3)c3ccc4c(c3)-c3ccccc3C43c4ccccc4C4(c5ccccc5-c5ccccc54)c4ccccc43)cc2)cc1] | 80% |

| | | |
|---|---|---|
| 2-16 | 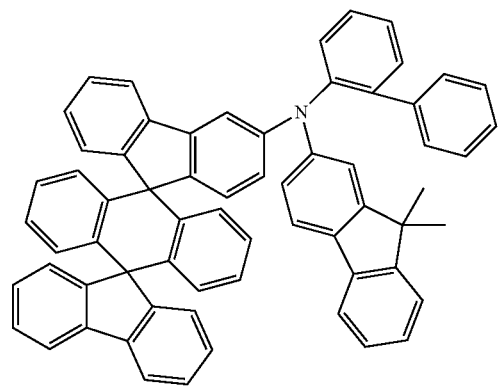 [SMILES: CC1(C)c2ccccc2-c2ccc(N(c3ccc4c(c3)-c3ccccc3C43c4ccccc4C4(c5ccccc5-c5ccccc54)c4ccccc43)c3ccccc3-c3ccccc3)cc21] | 85% |
| 2-17 | 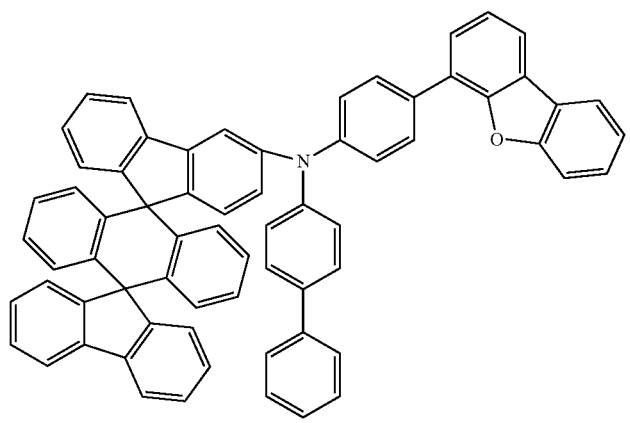 [SMILES: c1ccc(-c2ccc(N(c3ccc(-c4cccc5c4oc4ccccc45)cc3)c3ccc4c(c3)-c3ccccc3C43c4ccccc4C4(c5ccccc5-c5ccccc54)c4ccccc43)cc2)cc1] | 82% |
| 2-18 | 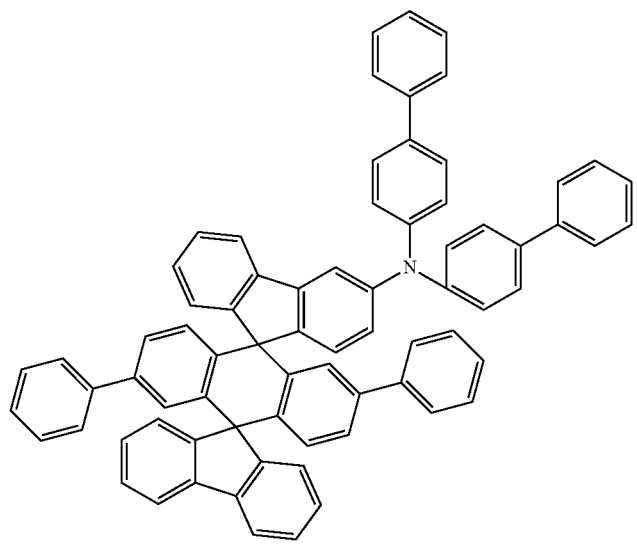 [SMILES: c1ccc(-c2ccc(N(c3ccc(-c4ccccc4)cc3)c3ccc4c(c3)-c3ccccc3C43c4ccc(-c5ccccc5)cc4C4(c5ccccc5-c5ccccc54)c4ccc(-c5ccccc5)cc43)cc2)cc1] | 70%* |

| | | |
|---|---|---|
| 2-19 | 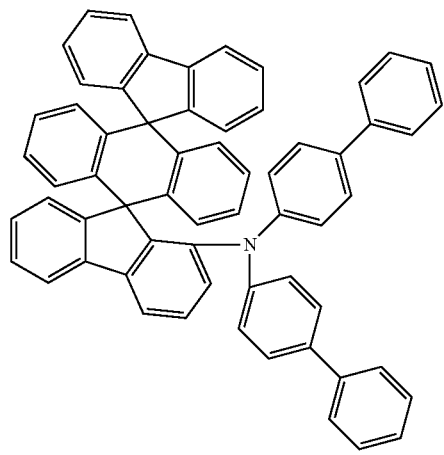 [SMILES: c1ccc(-c2ccc(N(c3ccc(-c4ccccc4)cc3)c3cccc4c3C3(c5ccccc5-4)c4ccccc4C4(c5ccccc5-c5ccccc54)c4ccccc43)cc2)cc1] | 30% |
| 2-20 | 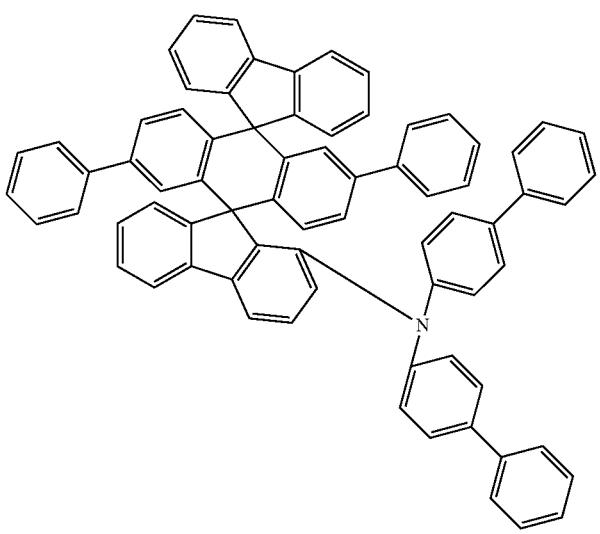 [SMILES: c1ccc(-c2ccc(N(c3ccc(-c4ccccc4)cc3)c3cccc4c3C3(c5ccccc5-4)c4ccc(-c5ccccc5)cc4C4(c5ccccc5-c5ccccc54)c4ccc(-c5ccccc5)cc43)cc2)cc1] | 25%* |
| 2-21 | 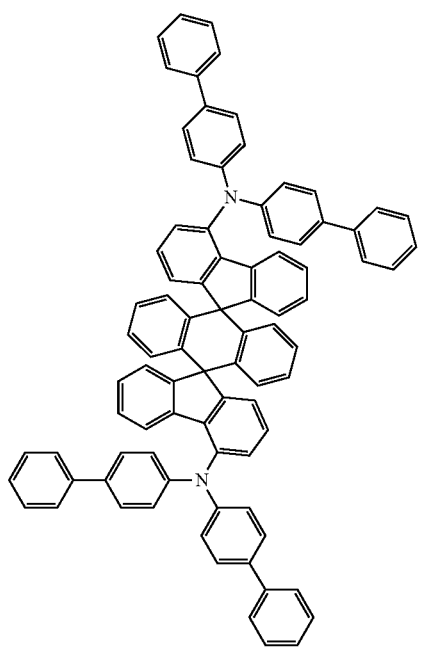 [SMILES: c1ccc(-c2ccc(N(c3ccc(-c4ccccc4)cc3)c3cccc4c3-c3ccccc3C43c4ccccc4C4(c5ccccc5-c5c(N(c6ccc(-c7ccccc7)cc6)c6ccc(-c7ccccc7)cc6)cccc54)c4ccccc43)cc2)cc1] | 60%* |

| 2-22 | 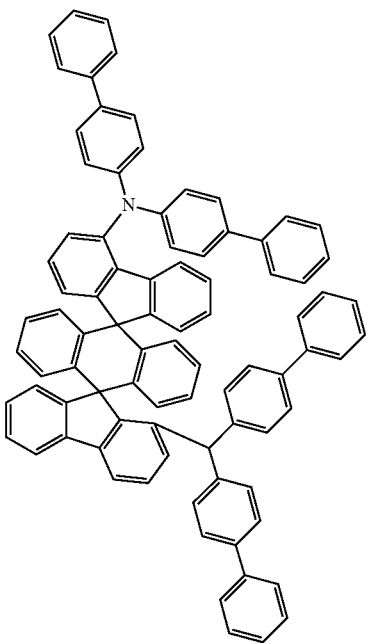 [SMILES: c1ccc(-c2ccc(C(c3ccc(-c4ccccc4)cc3)c3cccc4c3C3(c5ccccc5-4)c4ccccc4C4(c5ccccc5-c5c(N(c6ccc(-c7ccccc7)cc6)c6ccc(-c7ccccc7)cc6)cccc54)c4ccccc43)cc2)cc1] | 30%* |
|---|---|---|
| 2-23 | 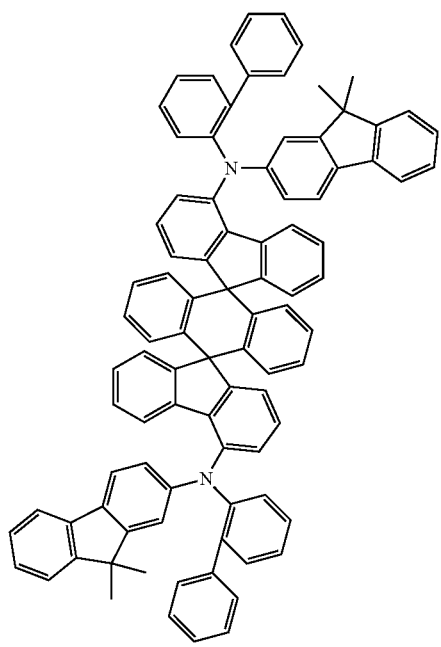 [SMILES: CC1(C)c2ccccc2-c2ccc(N(c3ccccc3-c3ccccc3)c3cccc4c3-c3ccccc3C43c4ccccc4C4(c5ccccc5-c5c(N(c6ccc7c(c6)C(C)(C)c6ccccc6-7)c6ccccc6-c6ccccc6)cccc54)c4ccccc43)cc21] | 65%* |

Example 3

Synthesis of Compound 3-1

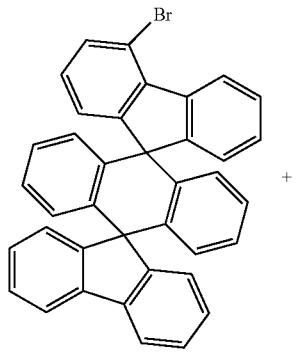

+

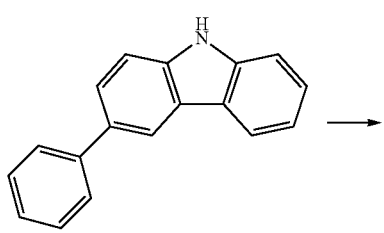

→

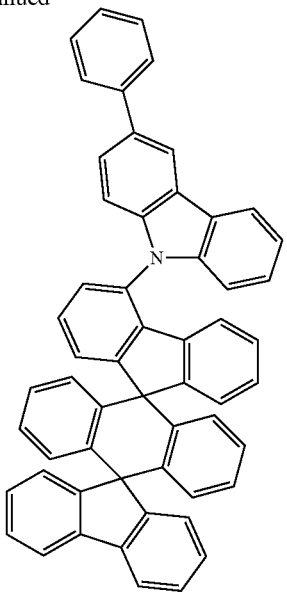

(3-1)

26.3 g (47 mmol) of compound (1-1), 15 g (47 mmol) of 3,6-diphenyl-9H-carbazole and 29.2 g of $Rb_2CO_3$ are suspended in 250 ml of p-xylene. 0.95 g (4.2 mmol) of $Pd(OAc)_2$ and 12.6 ml of a 1M tri-tert-butylphosphine solution are added to this suspension. The reaction mixture is heated under reflux for 24 h. After cooling, the organic phase is separated off, washed three times with 150 ml of water and subsequently evaporated to dryness. The residue is extracted with hot toluene, recrystallised three times from toluene/heptane and finally sublimed in a high vacuum, giving 18.5 g (25.6 mmol), corresponding to 54.5% of theory. The purity is 99.9%.

The following compounds (3-2) to (3-5) are prepared analogously.

| | Starting material 1 | Starting material 2 |
|---|---|---|
| 3-2 | (spirobifluorene-Br structure) | (dimethyl-indenocarbazole structure) 1257220-47-5 |

-continued
3-3 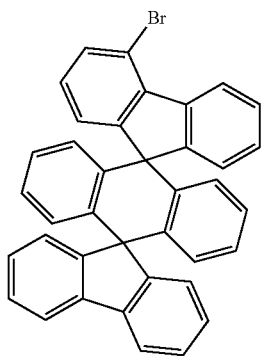 [SMILES: Brc1cccc2c1-c1ccccc1C21c2ccccc2C2(c3ccccc3-c3ccccc32)c2ccccc21] 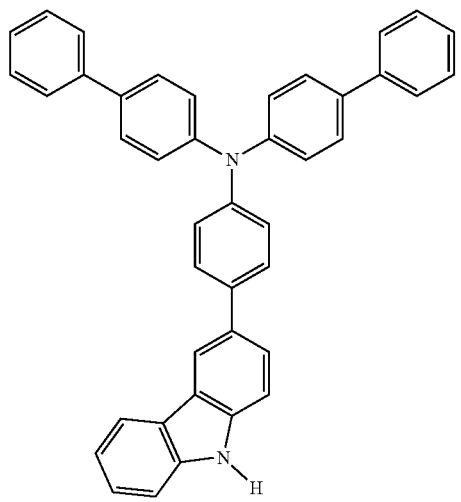
1221495-66-4
3-4 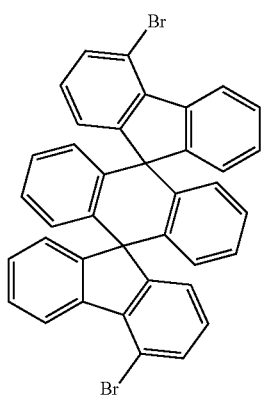 [SMILES: Brc1cccc2c1-c1ccccc1C21c2ccccc2C2(c3ccccc3-c3c(Br)cccc32)c2ccccc21] 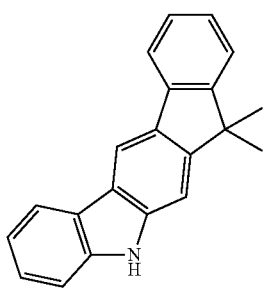
1257220-47-5
2 eq.
3-5 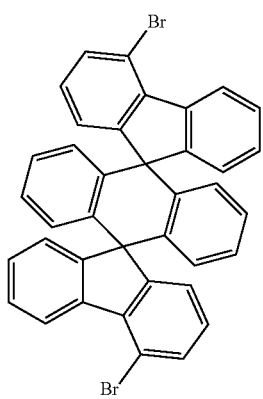 [SMILES: Brc1cccc2c1-c1ccccc1C21c2ccccc2C2(c3ccccc3-c3c(Br)cccc32)c2ccccc21] 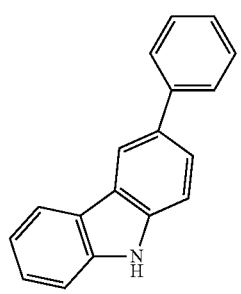
103012-26-6
2 eq.

-continued
| Product | Yield |
|---|---|
| 3-2 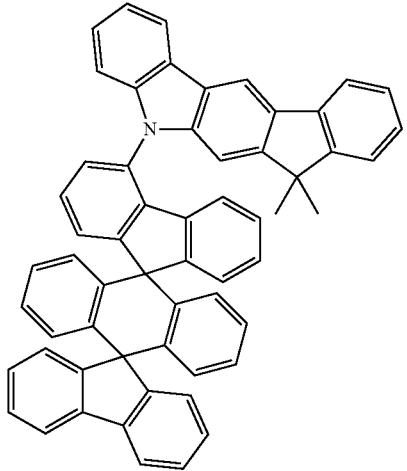 [SMILES: CC1(C)c2ccccc2-c2cc3c4ccccc4n(-c4cccc5c4-c4ccccc4C54c5ccccc5C5(c6ccccc6-c6ccccc65)c5ccccc54)c3cc21] | 60% |
| 3-3 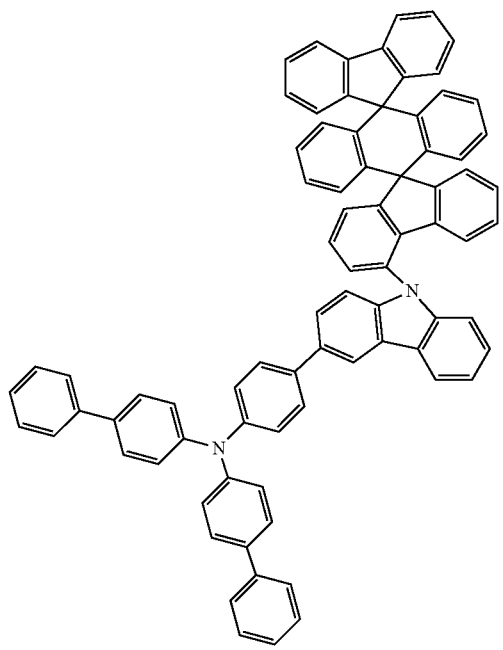 [SMILES: c1ccc(-c2ccc(N(c3ccc(-c4ccccc4)cc3)c3ccc(-c4ccc5c(c4)c4ccccc4n5-c4cccc5c4-c4ccccc4C54c5ccccc5C5(c6ccccc6-c6ccccc65)c5ccccc54)cc3)cc2)cc1] | 40% |

-continued
| | | |
|---|---|---|
| 3-4 | 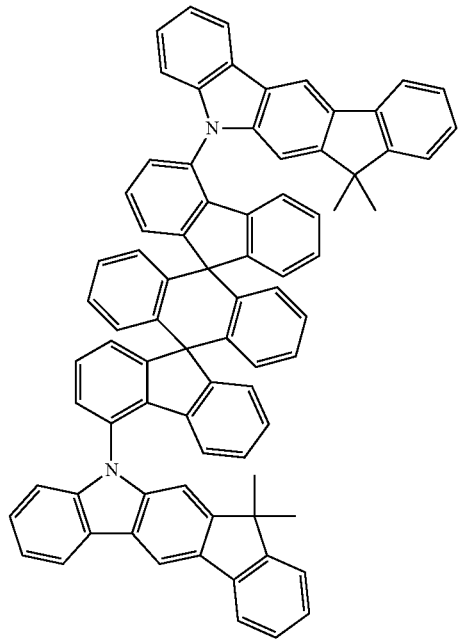 [SMILES: CC1(C)c2ccccc2-c2cc3c4ccccc4n(-c4cccc5c4-c4ccccc4C54c5ccccc5C5(c6ccccc6-c6c(-n7c8ccccc8c8cc9c(cc87)C(C)(C)c7ccccc7-9)cccc65)c5ccccc54)c3cc21] | 35%* |
| 3-5 | 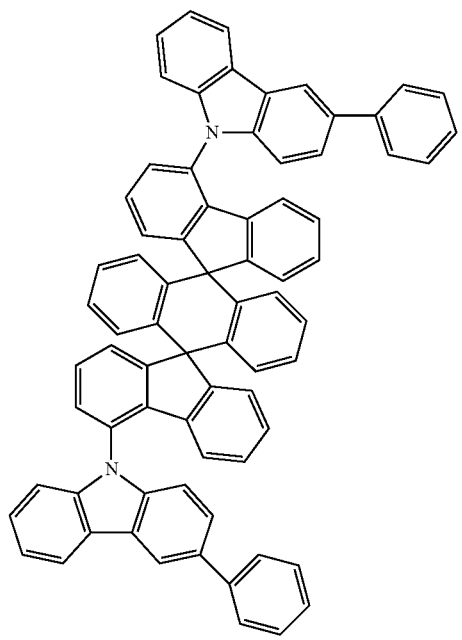 [SMILES: c1ccc(-c2ccc3c(c2)c2ccccc2n3-c2cccc3c2-c2ccccc2C32c3ccccc3C3(c4ccccc4-c4c(-n5c6ccccc6c6cc(-c7ccccc7)ccc65)cccc43)c3ccccc32)cc1] | 35%* |

Example 4

Synthesis of Compound 4-1

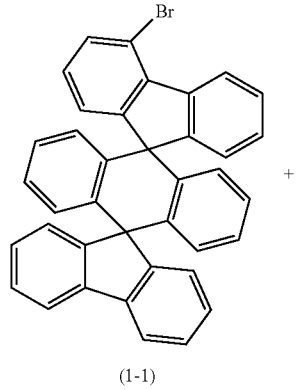

(1-1)

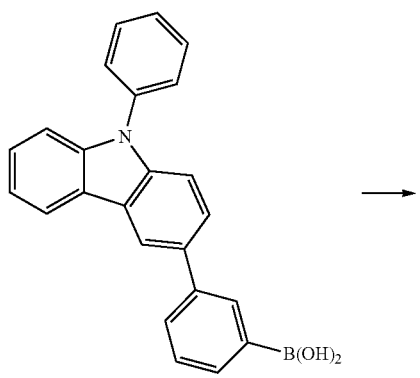

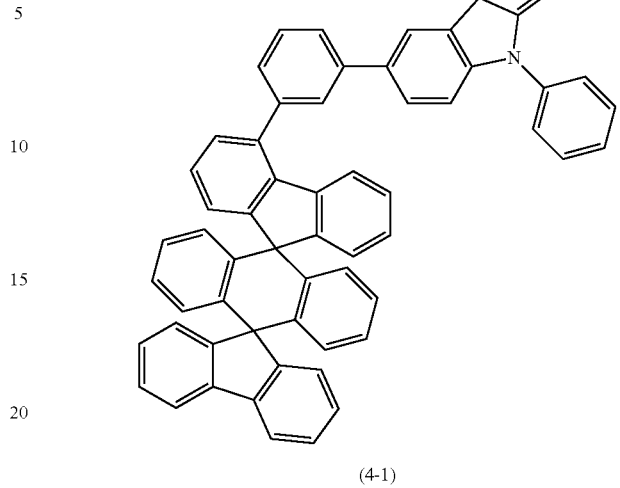

(4-1)

16.8 g (30 mmol) of compound (1-1) and 10 g (30 mmol) of carbazoleboronic acid are suspended in 300 ml of dioxane and 9.1 g of caesium fluoride (60 mmol). 2.2 g (3 mmol) of bis(tricyclohexylphosphine)palladium dichloride are added to this suspension, and the reaction mixture is heated under reflux for 18 h. After cooling, the organic phase is separated off, filtered through silica gel, washed three times with 80 ml of water and subsequently evaporated to dryness. The residue is extracted with hot toluene, recrystallised three times from toluene/heptane and finally sublimed in a high vacuum, giving 15.9 g, corresponding to 66.4% of theory. The purity is 99.9%.

The following compounds (4-2) to (4-14) are prepared analogously:

| | Starting material 1 | Starting material 2 | Product | Yield |
|---|---|---|---|---|
| 4-2 | | | | 68% |

US 10,158,083 B2
-continued
| | Starting material 1 | Starting material 2 | Product | Yield |
|---|---|---|---|---|
| 4-3 | 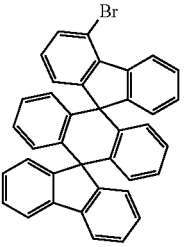 [SMILES: Brc1cccc2c1-c1ccccc1C21c2ccccc2C2(c3ccccc3-c3ccccc32)c2ccccc21] | 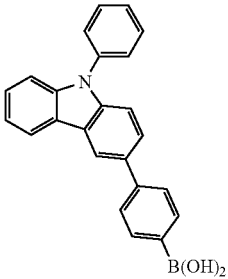 [SMILES: OB(O)c1ccc(-c2ccc3c(c2)c2ccccc2n3-c2ccccc2)cc1]
40963-55-6 | 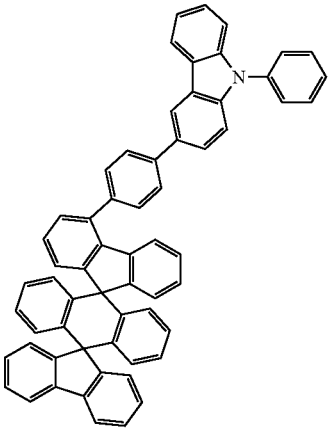 [SMILES: c1ccc(-n2c3ccccc3c3cc(-c4ccc(-c5cccc6c5-c5ccccc5C65c6ccccc6C6(c7ccccc7-c7ccccc76)c6ccccc65)cc4)ccc32)cc1] | 70% |
| 4-4 | 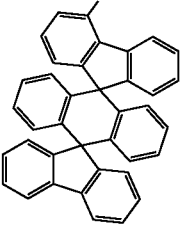 | 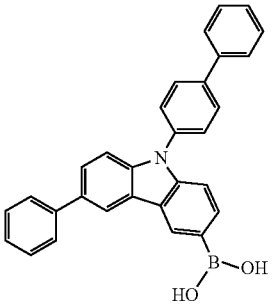 [SMILES: OB(O)c1ccc2c(c1)c1cc(-c3ccccc3)ccc1n2-c1ccc(-c2ccccc2)cc1]
1316311-18-8 | 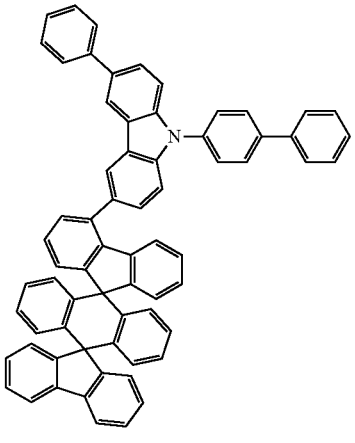 [SMILES: c1ccc(-c2ccc(-n3c4ccc(-c5ccccc5)cc4c4cc(-c5cccc6c5-c5ccccc5C65c6ccccc6C6(c7ccccc7-c7ccccc76)c6ccccc65)ccc43)cc2)cc1] | 72% |
| 4-5 | 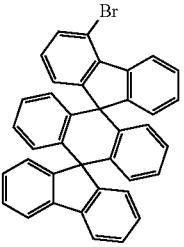 [SMILES: Brc1cccc2c1-c1ccccc1C21c2ccccc2C2(c3ccccc3-c3ccccc32)c2ccccc21] | 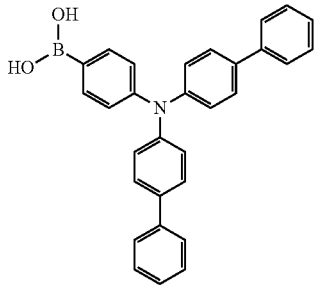 [SMILES: OB(O)c1ccc(N(c2ccc(-c3ccccc3)cc2)c2ccc(-c3ccccc3)cc2)cc1]
943836-24-6 | 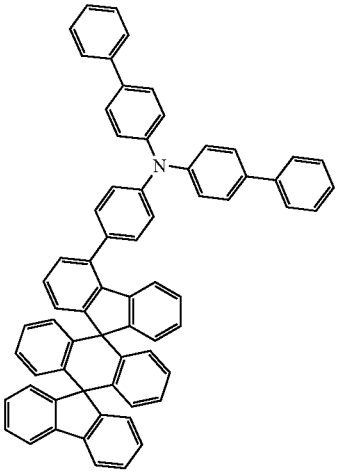 [SMILES: c1ccc(-c2ccc(N(c3ccc(-c4ccccc4)cc3)c3ccc(-c4cccc5c4-c4ccccc4C54c5ccccc5C5(c6ccccc6-c6ccccc65)c5ccccc54)cc3)cc2)cc1] | 75% |

-continued
| | Starting material 1 | Starting material 2 | Product | Yield |
|---|---|---|---|---|
| 4-6 |  | 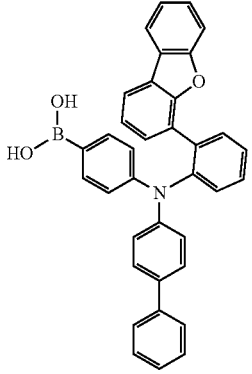 [SMILES: OB(O)c1ccc(N(c2ccc(-c3ccccc3)cc2)c2ccccc2-c2cccc3c2oc2ccccc23)cc1] | 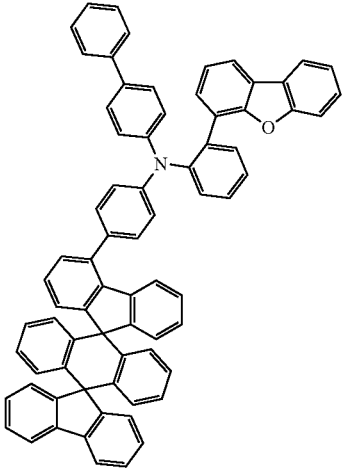 [SMILES: c1ccc(-c2ccc(N(c3ccc(-c4cccc5c4-c4ccccc4C54c5ccccc5C5(c6ccccc6-c6ccccc65)c5ccccc54)cc3)c3ccccc3-c3cccc4c3oc3ccccc34)cc2)cc1] | 77% |
| 4-7 | 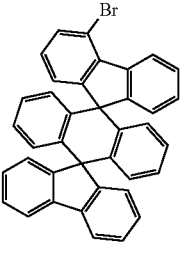 [SMILES: Brc1cccc2c1-c1ccccc1C21c2ccccc2C2(c3ccccc3-c3ccccc32)c2ccccc21] | 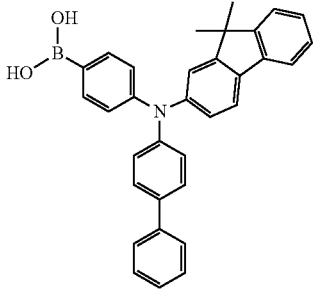 [SMILES: CC1(C)c2ccccc2-c2ccc(N(c3ccc(B(O)O)cc3)c3ccc(-c4ccccc4)cc3)cc21]
1265177-27-2 | 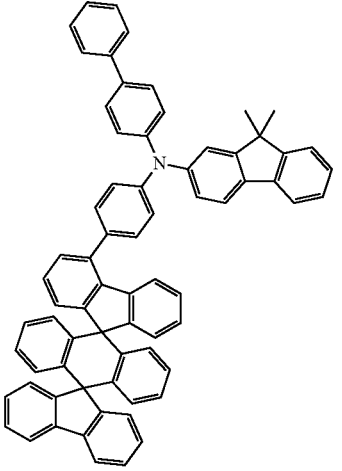 [SMILES: CC1(C)c2ccccc2-c2ccc(N(c3ccc(-c4ccccc4)cc3)c3ccc(-c4cccc5c4-c4ccccc4C54c5ccccc5C5(c6ccccc6-c6ccccc65)c5ccccc54)cc3)cc21] | 81% |
| 4-8 | 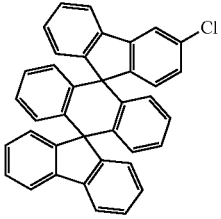 [SMILES: Clc1ccc2c(c1)-c1ccccc1C21c2ccccc2C2(c3ccccc3-c3ccccc32)c2ccccc21] | 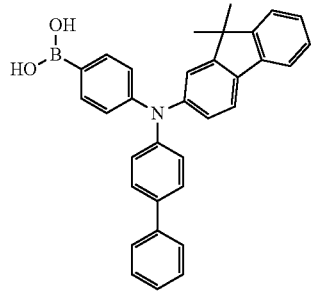 [SMILES: CC1(C)c2ccccc2-c2ccc(N(c3ccc(B(O)O)cc3)c3ccc(-c4ccccc4)cc3)cc21]
1565177-27-2 | 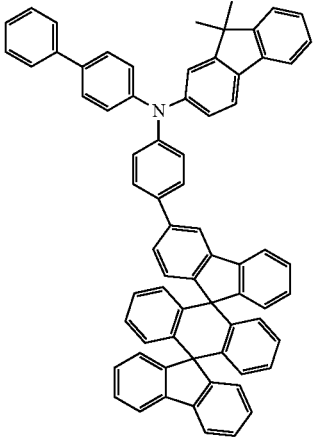 [SMILES: CC1(C)c2ccccc2-c2ccc(N(c3ccc(-c4ccccc4)cc3)c3ccc(-c4ccc5c(c4)-c4ccccc4C54c5ccccc5C5(c6ccccc6-c6ccccc65)c5ccccc54)cc3)cc21] | 82% |

-continued

| | Starting material 1 | Starting material 2 | Product | Yield |
|---|---|---|---|---|
| 4-9 | | 943836-24-6 | | 79% |
| 4-10 | | | | 75% |
| 4-11 | | 854952-60-6 | | 81% |
| 4-12 | | 943836-24-6 | | 51% |

| | Starting material 1 | Starting material 2 | Product | Yield |
|---|---|---|---|---|
| 4-13 | | | | 46% |
| 4-14 | | | 854952-60-6 | 48% |

Part B: Production of the OLEDs

OLEDs according to the invention and OLEDs in accordance with the prior art are produced by a general process in accordance with WO 04/058911, which is adapted to the circumstances described here (layer-thickness variation, materials).

The data of various OLEDs are presented in the following Inventive Examples E1 to E9 and in Reference Example V1. The substrates used are glass plates coated with structured ITO (indium tin oxide) in a thickness of 50 nm. The OLEDs have in principle the following layer structure: substrate/p-doped hole-transport layer A' (HIL1)/hole-transport layer A (HTL)/p-doped hole-transport layer B (HIL2)/hole-transport layer C (EBL)/emission layer (EML)/electron-transport layer (ETL)/electron-injection layer (EIL) and finally a cathode. The cathode is formed by an aluminium layer with a thickness of 100 nm. The materials required for the production of the OLEDs are shown in Table 1, the structure of the various electronic devices produced is shown in Table 2.

All materials are applied by thermal vapour deposition in a vacuum chamber. The emission layer here always consists of at least one matrix material (host material) and an emitting dopant (emitter), which is admixed with the matrix material or matrix materials in a certain proportion by volume by coevaporation. An expression such as H1:SEB (5%) here means that material H1 is present in the layer in a proportion by volume of 95% and SEB is present in the layer in a proportion of 5%. Analogously, the electron-transport layer or the hole-injection layers may also consist of a mixture of two materials. An expression such as H2:H3 (60%):TEG (10%) here means that material H2 is present in the layer in a proportion by volume of 30%, H3 is present in the layer in a proportion by volume of 60% and TEG is present in the layer in a proportion of 10%.

The OLEDs are characterised by standard methods. For this purpose, the electroluminescence spectra, the current efficiency (measured in cd/A), the power efficiency (measured in lm/W) and the external quantum efficiency (EQE, measured in percent) as a function of the luminous density, calculated from current/voltage/luminous density characteristic lines (IUL characteristic lines) assuming Lambert emission characteristics, and the lifetime are determined. The electroluminescence spectra are determined at a luminous density of 1000 cd/m², and the CIE 1931 x and y colour coordinates are calculated therefrom. The term EQE @2 mA/cm² denotes the external quantum efficiency at a current density of 2 mA/cm². LT80 @50 mA/cm² is the lifetime by which the OLED has dropped to 80% of the initial intensity at constant current.

TABLE 1

Structures of the materials used

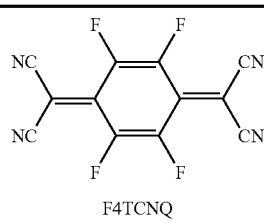

F4TCNQ

TABLE 1-continued
Structures of the materials used
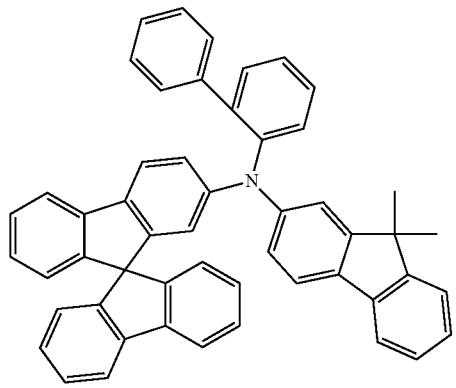
HIM
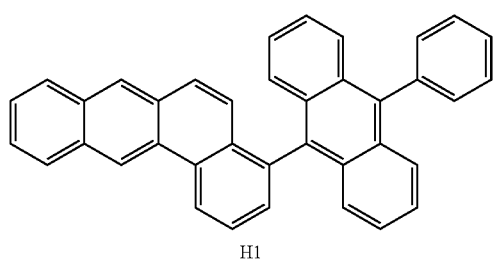
H1
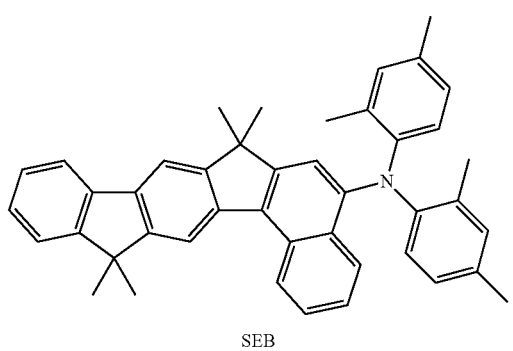 [SMILES: Cc1ccc(N(c2ccc(C)cc2C)c2cc3c(c4ccccc24)-c2cc4c(cc2C3(C)C)-c2ccccc2C4(C)C)c(C)c1]
SEB
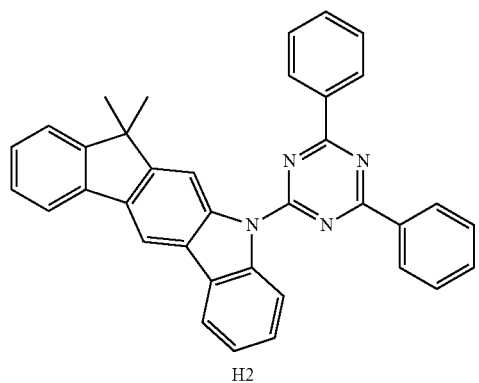
H2
TABLE 1-continued
Structures of the materials used
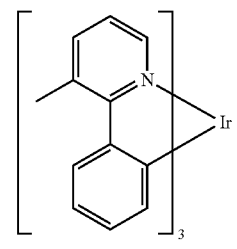
TEG
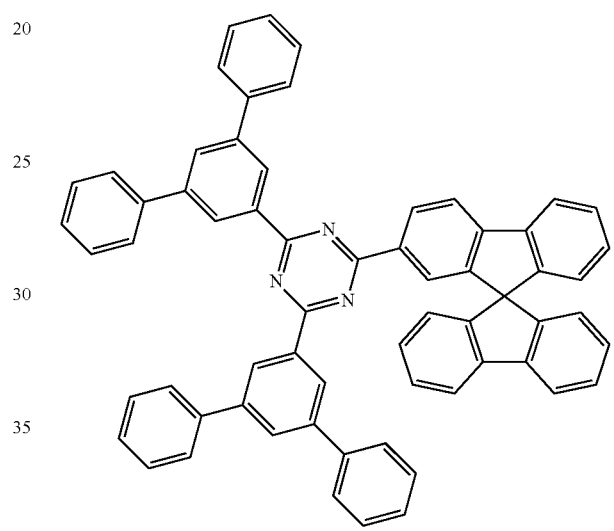
ETM
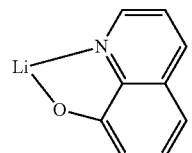
LiQ
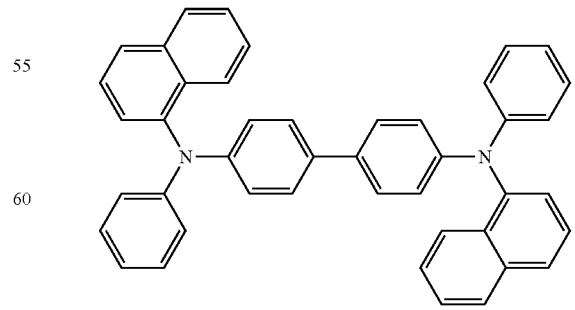
NPB TABLE 1-continued
Structures of the materials used
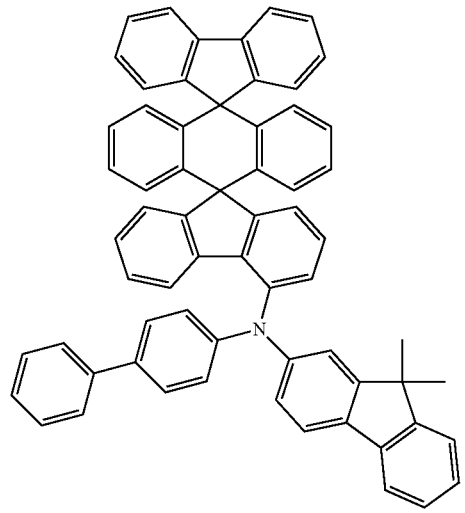
HTM1
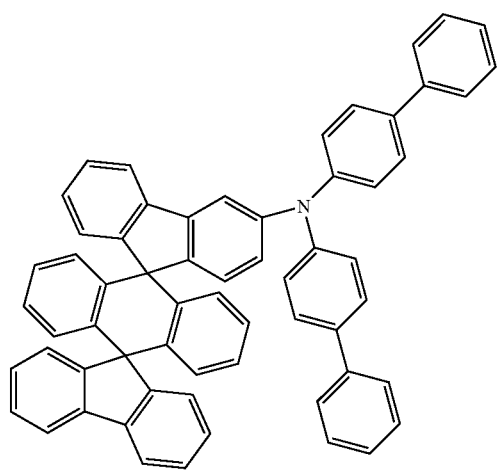
HTM2
TABLE 1-continued
Structures of the materials used
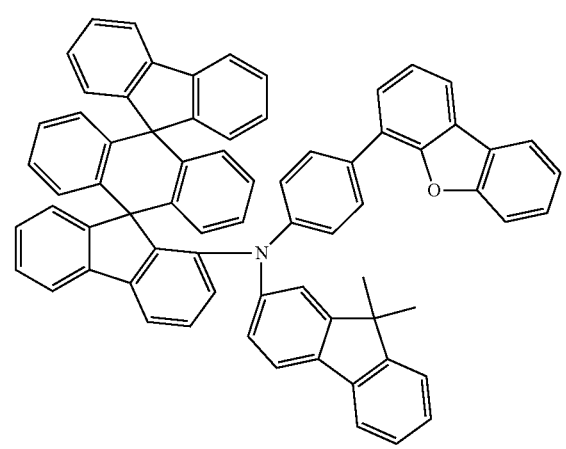
HTM3
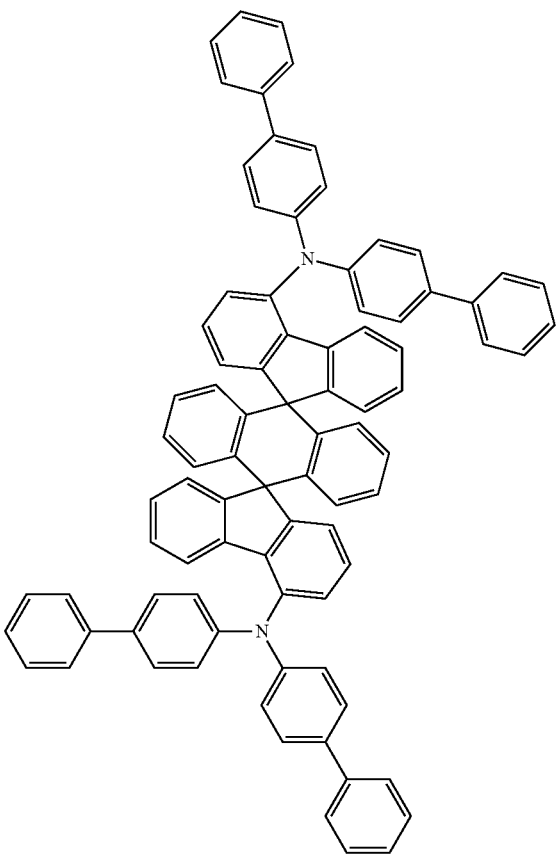
HTM4

TABLE 1-continued
Structures of the materials used
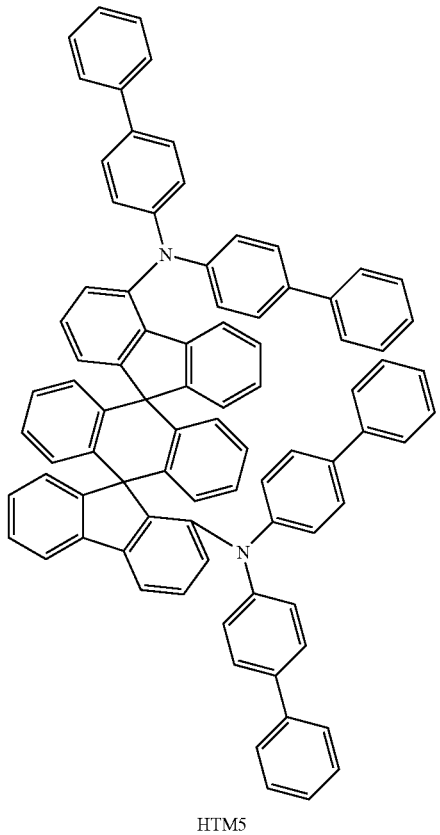
HTM5
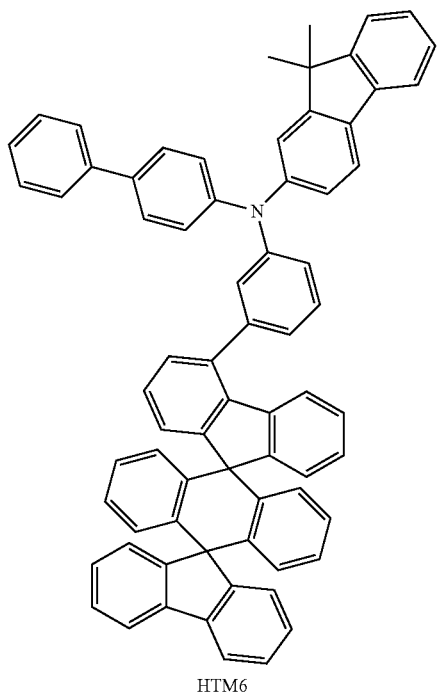
HTM6
TABLE 1-continued
Structures of the materials used
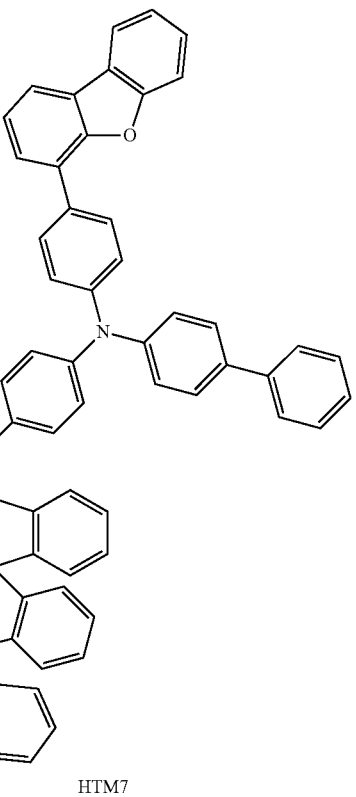
HTM7
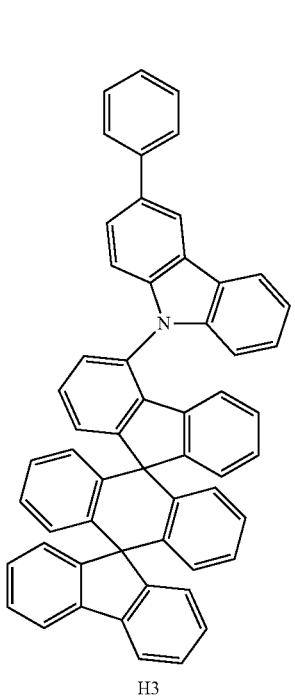
H3

TABLE 1-continued

Structures of the materials used

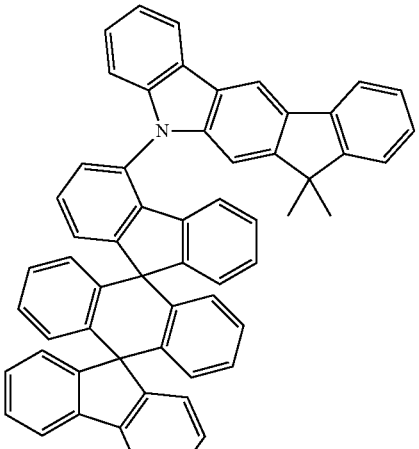

H4

Example 1

In an OLED with blue singlet emission, samples E1 (6.6%), E2 (7.6%), E3 (8.5%), E4 (7.5%), E5 (7.5%), E6 (7.3%) and E7 (7.1%) according to the invention exhibit higher quantum efficiencies at 10 mA/cm$^2$ compared with reference sample V1 (6.2%). The lifetime LT80 at 50 mA/cm$^2$ is also significantly better in the case of samples E1 (390 h), E2 (370 h), E3 (380 h), E4 (305 h), E5 (220 h), E6 (300 h) and E7 (440 h) according to the invention than in the case of reference sample V1 (135 h).

Example 2

A green-phosphorescent reference sample V2 was produced and compared with samples E8 and E9 according to the invention. Reference sample V2 has an external quantum efficiency of 19.8% and a lifetime (LT80 @ 20 mA/cm$^2$) of 135 h at a current density of 2 mA/cm$^2$. By comparison, samples E8 (19.2%) and E9 (19.3%) according to the invention have comparable quantum efficiencies and significantly better lifetimes of 310 h (E8) and 270 h (E9).

TABLE 2

Structure of the OLEDs

| Ex. | HIL1 Thickness/nm | HTL Thickness/nm | HIL2 Thickness/nm | EBL Thickness/nm | EML Thickness/nm | ETL Thickness/nm | EIL Thickness/nm |
|---|---|---|---|---|---|---|---|
| V1 | HIM1:F4TCNQ (3%) 20 nm | HIM1 155 nm | NPB:F4TCNQ (3%) 20 nm | NPB 20 nm | H1:SEB(5%) 20 nm | ETM(50%):LiQ (50%) 30 nm | LiQ 1 nm |
| E1 | HIM1:F4TCNQ (3%) 20 nm | HIM1 155 nm | HTM1:F4TCNQ (3%) 20 nm | HTM1 20 nm | H1:SEB(5%) 20 nm | ETM(50%):LiQ (50%) 30 nm | LiQ 1 nm |
| E2 | HIM1:F4TCNQ (3%) 20 nm | HIM1 155 nm | HTM2:F4TCNQ (3%) 20 nm | HTM2 20 nm | H1:SEB(5%) 20 nm | ETM(50%):LiQ (50%) 30 nm | LiQ 1 nm |
| E3 | HIM1:F4TCNQ (3%) 20 nm | HIM1 155 nm | HTM3:F4TCNQ (3%) 20 nm | HTM3 20 nm | H1:SEB(5%) 20 nm | ETM(50%):LiQ (50%) 30 nm | LiQ 1 nm |
| E4 | HIM1:F4TCNQ (3%) 20 nm | HIM1 155 nm | HTM4:F4TCNQ (3%) 20 nm | HTM4 20 nm | H1:SEB(5%) 20 nm | ETM(50%):LiQ (50%) 30 nm | LiQ 1 nm |
| E5 | HIM1:F4TCNQ (3%) 20 nm | HIM1 155 nm | HTM5:F4TCNQ (3%) 20 nm | HTM5 20 nm | H1:SEB(5%) 20 nm | ETM(50%):LiQ (50%) 30 nm | LiQ 1 nm |
| E6 | HIM1:F4TCNQ (3%) 20 nm | HIM1 155 nm | HTM6:F4TCNQ (3%) 20 nm | HTM6 20 nm | H1:SEB(5%) 20 nm | ETM(50%):LiQ (50%) 30 nm | LiQ 1 nm |
| E7 | HIM1:F4TCNQ (3%) 20 nm | HIM1 155 nm | HTM7:F4TCNQ (3%) 20 nm | HTM7 20 nm | H1:SEB(5%) 20 nm | ETM(50%):LiQ (50%) 30 nm | LiQ 1 nm |
| V2 | HIM1:F4TCNQ (3%) 20 nm | HIM1 210 nm | HIM1:F4TCNQ (3%) 20 nm | HIM1 20 nm | H2:TEG(10%) 30 nm | ETM(50%):LiQ (50%) 40 nm | LiQ 1 nm |
| E8 | HIM1:F4TCNQ (3%) 20 nm | HIM1 210 nm | HIM1:F4TCNQ (3%) 20 nm | HIM1 20 nm | H2:H3(60%):TEG (10%) 30 nm | ETM(50%):LiQ (50%) 40 nm | LiQ 1 nm |
| E9 | HIM1:F4TCNQ (3%) 20 nm | HIM1 210 nm | HIM1:F4TCNQ (3%) 20 nm | HIM1 20 nm | H2:H4(60%):TEG (10%) 30 nm | ETM(50%):LiQ (50%) 40 nm | LiQ 1 nm |

The invention claimed is:

1. A compound of the formula (2), (3), (4) or (5)

formula (2)
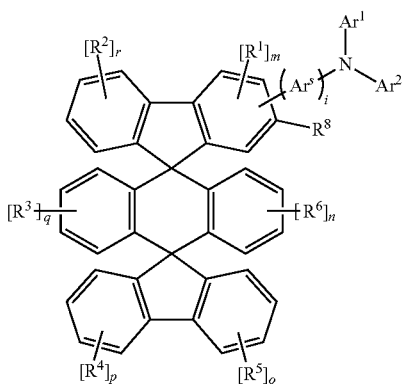

formula (3)
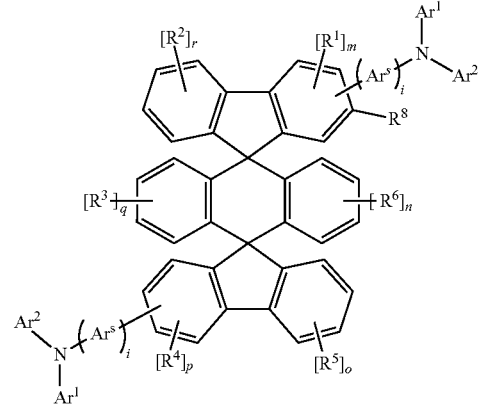

formula (4)
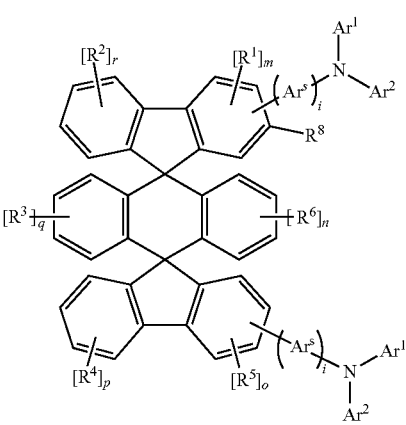

formula (5)
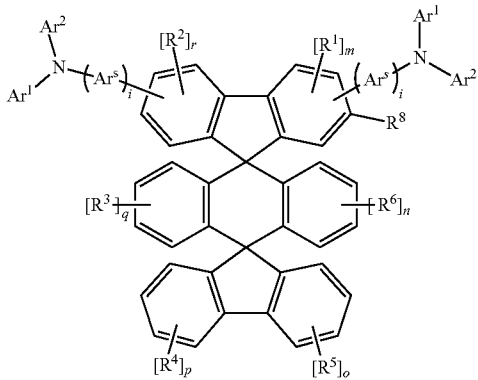

where the following applies to the symbols and indices occurring:

$Ar^S$ is, identically or differently on each occurrence, an aromatic or heteroaromatic ring system having 6 to 60 C atoms, which may in each case also be substituted by one or more radicals $R^7$;

$Ar^1$, $Ar^2$ are selected, identically or differently on each occurrence, selected from the groups of the formulae (Ar-2) to (Ar-33)

formula (Ar-2)
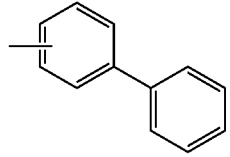

formula (Ar-3)
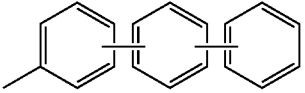

formula (Ar-4)
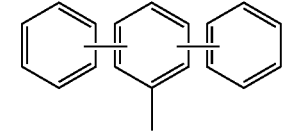

formula (Ar-5)
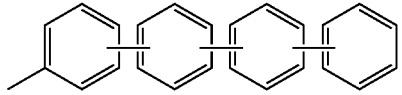

formula (Ar-6)
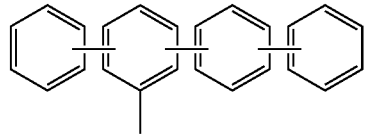

formula (Ar-7)
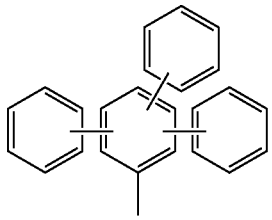

formula (Ar-8)
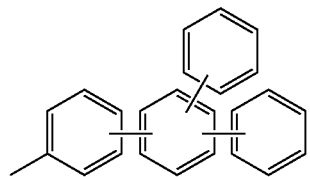
formula (Ar-9)
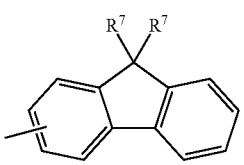
formula (Ar-10)
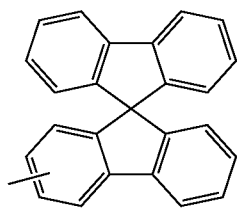
formula (Ar-11)
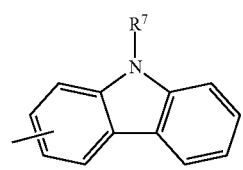
formula (Ar-12)
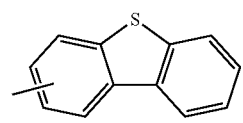
formula (Ar-13)
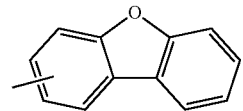
formula (Ar-14)
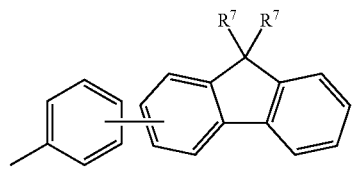
formula (Ar-15)
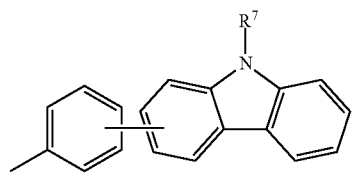
formula (Ar-16)
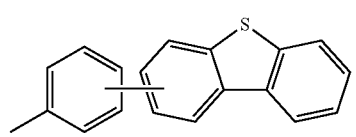
formula (Ar-17)
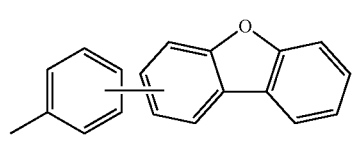
formula (Ar-18)
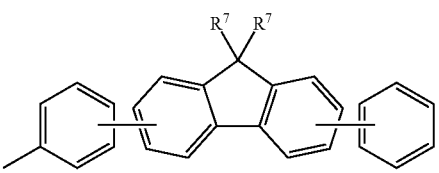
formula (Ar-19)
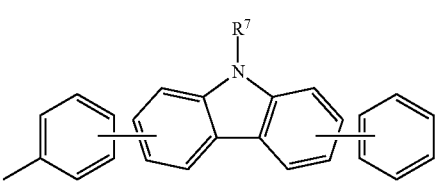
formula (Ar-20)
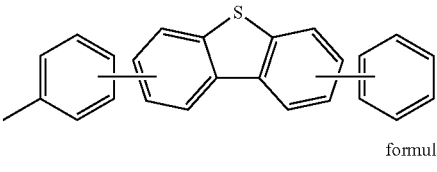
formula (Ar-21)
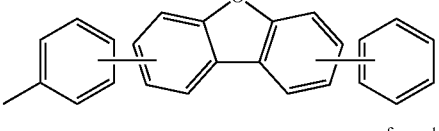
formula (Ar-22)
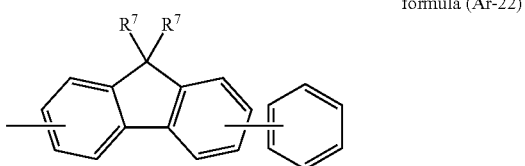
formula (Ar-23)
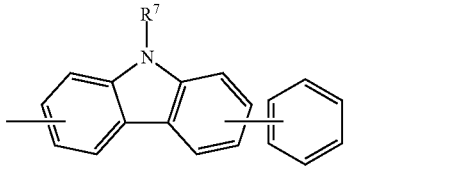
formula (Ar-24)
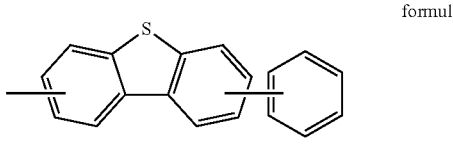
formula (Ar-25)
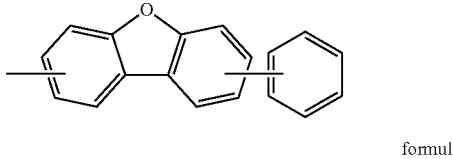
formula (Ar-26)
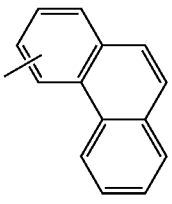

formula (Ar-27)

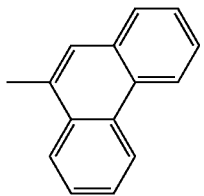

formula (Ar-28)

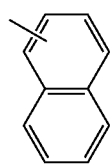

formula (Ar-29)

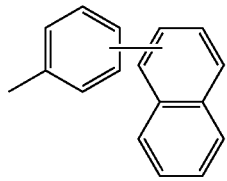

formula (Ar-30)

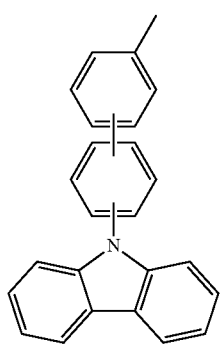

formula (Ar-31)

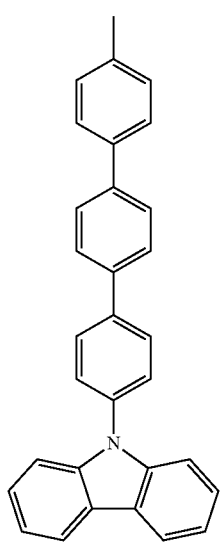

formula (Ar-32)

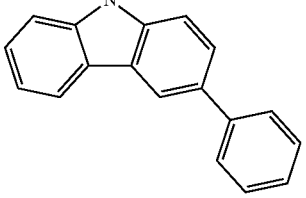

formula (Ar-33)

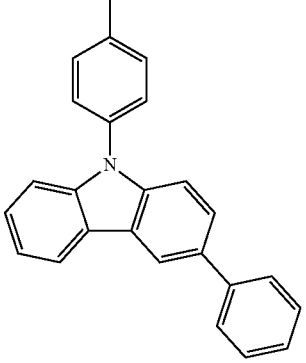

which are optionally substituted at the free positions by $R^7$;

$R^1$, $R^2$, $R^3$, $R^4$, $R^5$, $R^6$, $R^7$, $R^8$ are selected on each occurrence, identically or differently, from the group consisting of H, D, a straight-chain alkyl group having 1 to 10 C atoms or a branched or cyclic alkyl group having 3 to 10 C atoms, each of which is optionally substituted by one or more radicals $R^9$, an aromatic ring system having 6 to 60 C atoms, which may in each case be substituted by one or more radicals $R^9$;

$R^9$ is selected on each occurrence, identically or differently, from the group consisting of H, D, F, Cl, Br, I, $Si(R^{10})_3$, a straight-chain alkyl, alkoxy or thioalkyl group having 1 to 40 C atoms or a branched or cyclic alkyl, alkoxy or thioalkyl group having 3 to 40 C atoms, each of which is optionally substituted by one or more radicals $R^{10}$, where one or more non-adjacent $CH_2$ groups is optionally replaced by $Si(R^{10})_2$, $C=NR^{10}$, $P(=O)(R^{10})$, SO, $SO_2$, $NR^{10}$, O, S or $CONR^{10}$ and where one or more H atoms is optionally replaced by D, F, Cl, Br or I, an aromatic or heteroaromatic ring system having 6 to 60 aromatic ring atoms, which may in each case be substituted by one or more radicals $R^{10}$, an aryloxy group or heteroaryloxy group having 5 to 60 aromatic ring atoms, which is optionally substituted by one or more radicals $R^{10}$, or an aralkyl group or heteroaralkyl group having 5 to 60 aromatic or heteroaromatic ring atoms, which is optionally substituted by one or more radicals $R^{10}$, where two or more adjacent substituents $R^9$ may optionally form a mono- or polycyclic, aliphatic ring system, which is optionally substituted by one or more radicals $R^{10}$;

$R^{10}$ is selected from the group consisting of H, D, F, an aliphatic hydrocarbon radical having 1 to 20 C atoms, an aromatic ring system having 6 to 30 C atoms, in which one or more H atoms is optionally replaced by D or F, where two or more adjacent substituents $R^{10}$ may form a mono- or polycyclic, aliphatic ring system with one another;

i is on each occurrence 0, 1 or 2;

m is 0, 1 or 2;

n, o, p, q, r are on each occurrence, identically or differently, 0, 1, 2, 3 or 4;

wherein p is 0, 1, 2 or 3 for formula (3), wherein o is 0, 1, 2 or 3 for formula (4), and wherein r is 0, 1, 2 or 3 for formula (5).

2. The compound according to claim 1, wherein the group $Ar^S$ stands for a group of one of the following formulae (Ar3-1) to (Ar3-12):

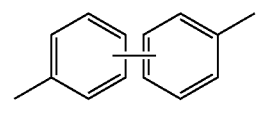

formula (Ar3-1)

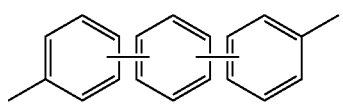

formula (Ar3-2)

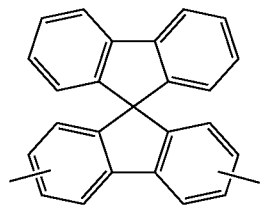

formula (Ar3-3)

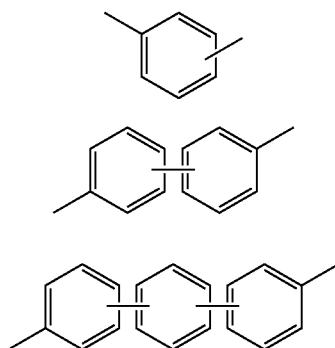

formula (Ar3-4)

formula (Ar3-5)

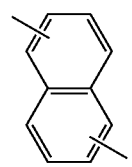

formula (Ar3-6)

-continued

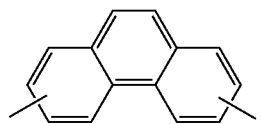

formula (Ar3-7)

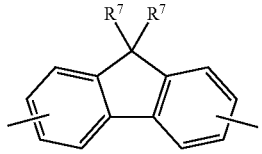

formula (Ar3-8)

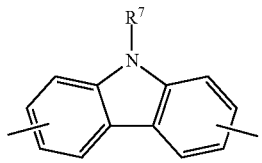

formula (Ar3-9)

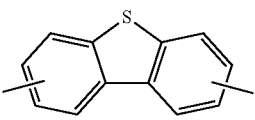

formula (Ar3-10)

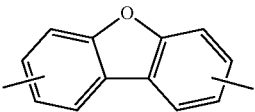

formula (Ar3-11)

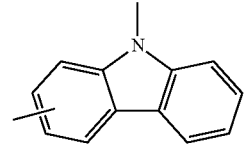

formula (Ar3-12)

where the symbols used have the meanings given in claim 1 and the two bond lines dashed bonds represent the bonds to the adjacent groups and the groups is optionally substituted by $R^7$ at the free positions.

3. The compound according to claim 1 for which:

$Ar^S$ is, identically or differently on each occurrence, an aromatic or heteroaromatic ring system, where, for i=1 or 2, $Ar^S$ is selected from the groups of the formulae (Ar3-1) to (Ar3-12),

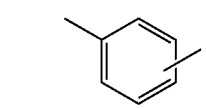

formula (Ar3-1)

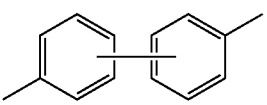

formula (Ar3-2)

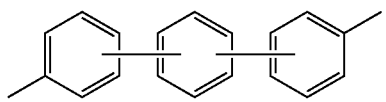

formula (Ar3-3)

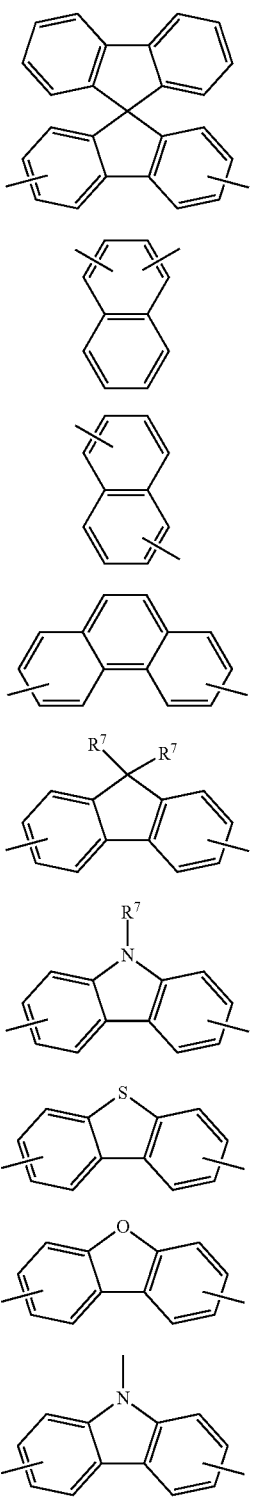

formula (Ar3-4)

formula (Ar3-5)

formula (Ar3-6)

formula (Ar3-7)

formula (Ar3-8)

formula (Ar3-9)

formula (Ar3-10)

formula (Ar3-11)

formula (Ar3-12)

where
R$^9$ is selected, identically or differently on each occurrence, from the group consisting of H, D, F, a straight-chain alkyl group having 1 to 10 C atoms or a branched or cyclic alkyl group having 3 to 10 C atoms or an aromatic ring system having 6 to 30 C atoms, each of which is optionally substituted by one or more radicals R$^{10}$, where two or more adjacent substituents R$^9$ may form a mono- or polycyclic, aliphatic ring system with one another;

R$^{10}$ is selected from the group consisting of H, D, F, an aliphatic hydrocarbon radical having 1 to 20 C atoms, an aromatic ring system having 6 to 30 C atoms, in which one or more H atoms is optionally replaced by D or F, where two or more adjacent substituents R$^{10}$ may form a mono- or polycyclic, aliphatic ring system with one another;

i is on each occurrence 0, 1 or 2;

m is 0 or 1;

o, p, r are on each occurrence, identically or differently, 0, 1 or 2;

n, q are on each occurrence, identically or differently, 0, 1 or 2.

4. The compound according to claim 1, wherein the compound is of the formula (3).

5. The compound according to claim 1, wherein the compound is of the formula (4).

6. The compound according to claim 1, wherein the compound is of the formula (5).

7. A process for the preparation of a compound according to claim 1 which comprises coupling a dispiro[fluoren-9,9'-anthracene-10',9"-fluorene] derivative which is substituted by a reactive leaving group in the 1-, 3- or 4-position to
  a) a primary amine, followed by coupling to a further aromatic group which is substituted by a reactive leaving group, or
  b) to a secondary amine, or
  c) to a triarylamine derivative.

8. A formulation comprising at least one compound according to claim 1 and at least one solvent.

9. An electronic device comprising at least one compound according to claim 1.

10. An electronic device comprising at least one formulation according to claim 8.

11. The electronic device according to claim 10, wherein the device is selected from the group consisting of organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), light-emitting electrochemical cells (LECs), organic laser diodes (O-lasers) and organic electroluminescent devices (OLEDs).

12. An organic electroluminescent device (OLED) comprising the compound according to claim 1 wherein the compound is present as
  (1) a hole-transport material in a hole-transport or hole-injection layer,
  (2) an electron-blocking layer,
  (3) an exciton-blocking layer,
  (4) an emitter for fluorescent emission layers or
  (5) a matrix material in an emitting layer.

13. An organic electroluminescent devices (OLEDs) comprising at least one formulation according to claim 8, where the formulation is employed as hole-transport material in a hole-transport or hole-injection layer, or as electron-blocking layer, or as exciton-blocking layer or as emitter for fluorescent emission layers or as matrix material in an emitting layer.

* * * * *